US012714346B2

(12) United States Patent
Hatakeyama

(10) Patent No.: US 12,714,346 B2
(45) Date of Patent: Aug. 25, 2026

(54) BIO-ELECTRODE AND METHOD FOR MANUFACTURING BIO-ELECTRODE

(71) Applicant: SHIN-ETSU CHEMICAL CO., LTD., Tokyo (JP)

(72) Inventor: Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 372 days.

(21) Appl. No.: 18/427,617

(22) Filed: Jan. 30, 2024

(65) Prior Publication Data

US 2024/0285211 A1 Aug. 29, 2024

(30) Foreign Application Priority Data

Feb. 2, 2023 (JP) .................................. 2023-14756

(51) Int. Cl.
*A61B 5/268* (2021.01)
*C09D 5/24* (2006.01)
(Continued)

(52) U.S. Cl.
CPC ................ *A61B 5/268* (2021.01); *C09D 5/24* (2013.01); *C09D 7/65* (2018.01); *C09D 125/18* (2013.01);
(Continued)

(58) Field of Classification Search
CPC ........... A61B 5/25; A61B 5/263; A61B 5/268; A61B 2562/125
See application file for complete search history.

(56) References Cited

U.S. PATENT DOCUMENTS

2015/0340118 A1 11/2015 Nagasawa et al.
2016/0064112 A1 3/2016 Hatakeyama et al.
(Continued)

FOREIGN PATENT DOCUMENTS

CN 103762014 A * 4/2014 ............... B82B 1/00
JP 2015100673 A 6/2015
(Continued)

OTHER PUBLICATIONS

Korean Office Action in application No. 10-2024-0012138 issued on Nov. 19, 2025.
(Continued)

*Primary Examiner* — Khanh T Nguyen
(74) *Attorney, Agent, or Firm* — Harness, Dickey & Pierce, P.L.C.

(57) ABSTRACT

The present invention is a bio-electrode includes an electro-conductive polymer composite layer, an electro-conductive layer (C), and a substrate (D). The electro-conductive polymer composite layer consists of an electro-conductive polymer composite which includes (A) a π-conjugated polymer and (B) a dopant polymer. The substrate (D) has a transmittance of 20% or more at a wavelength of 600 nm and is yellow-red (YR) with a value in the range of 1 to 9 and a chroma in the range of 1 to 12 in the Munsell color system. This provides: a bioelectrode which is thin film, highly transparent, slightly different from the skin in color, highly sensitive to biological signals, excellent in biocompatibility, light-weight, manufacturable at low cost, capable of preventing significant reduction in the sensitivity to biological signals when wetted with water or dried and when attached on the skin for a long time; and a method for manufacturing the bio-electrode.

18 Claims, 8 Drawing Sheets

(51) Int. Cl.
*C09D 7/65* (2018.01)
*C09D 125/18* (2006.01)
*C09D 133/16* (2006.01)

(52) U.S. Cl.
CPC ...... *C09D 133/16* (2013.01); *A61B 2562/125* (2013.01)

(56) References Cited

U.S. PATENT DOCUMENTS

| | | | |
|---|---|---|---|
| 2016/0064113 | A1 | 3/2016 | Hatakeyama et al. |
| 2016/0067702 | A1 | 3/2016 | Hatakeyama et al. |
| 2017/0062089 | A1 | 3/2017 | Hatakeyama et al. |
| 2017/0233596 | A1 | 8/2017 | Hatakeyama et al. |
| 2018/0072930 | A1 | 3/2018 | Hatakeyama et al. |
| 2018/0086948 | A1 | 3/2018 | Hatakeyama et al. |
| 2018/0229024 | A1 | 8/2018 | Hatakeyama et al. |
| 2018/0240564 | A1 | 8/2018 | Hatakeyama et al. |
| 2020/0207952 | A1 | 7/2020 | Hatakeyama |
| 2022/0157484 | A1 | 5/2022 | Nonaka et al. |
| 2022/0220313 | A1 | 7/2022 | Ikeda et al. |

FOREIGN PATENT DOCUMENTS

| | | | |
|---|---|---|---|
| JP | 6271378 | B2 | 1/2018 |
| JP | 2018044147 | A | 3/2018 |
| JP | 2018059050 | A | 4/2018 |
| JP | 2018059052 | A | 4/2018 |
| JP | 6335138 | B2 | 5/2018 |
| JP | 2018130534 | A | 8/2018 |
| JP | 6407107 | B2 | 10/2018 |
| JP | 6438348 | B2 | 12/2018 |
| JP | 6450661 | B2 | 1/2019 |
| JP | 6483518 | B2 | 3/2019 |
| JP | 6496258 | B2 | 4/2019 |
| JP | 6661212 | B2 | 3/2020 |
| JP | 2020107875 | A | 7/2020 |
| JP | 2022078861 | A | 5/2022 |
| KR | 10-2022-0099904 | A | 7/2022 |
| WO | 2013039151 | A1 | 3/2013 |

OTHER PUBLICATIONS

Zhang, Chengpeng, et al. Fabrication of flexible silvernanowireconductive films and transmittance improvement based onmoth-eye nanostructure array. Journalof Micromechanics and Microengineering, 2017, 27.7.

Collier, Graham S., et al. Exploring isomeric effects onopticaland electrochemical properties of red/orangeelectrochromic polymers. Macromolecules, 2021,54.4: pp. 1677-1692.

Araki, et al.; Non-contact Laser Printing of Ag Nanowire-based Electrode with Photodegradable Polymers; Journal of Photopolymer Science and Technology, vol. 32, No. 3 (2019) 429-434; published Jun. 24, 2019.

Trulove, et al.; Ionic Liquids in Synthesis, Chapter 3.6; Electrochemical Properties of Ionic Liquids; published Feb. 26, 2023.

Yang, et al.; Facile fabrication of stretchable Ag nanowire/polyurethane electrodes using high intensity pulsed light; Nano Research 2016, 9(2):401-414, DOI 10.1007/s12274-015-0921-9; published Jan. 7, 2016.

* cited by examiner

[FIG. 1]
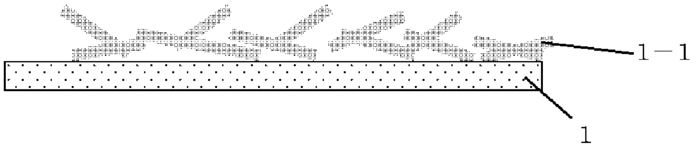
[FIG. 2]
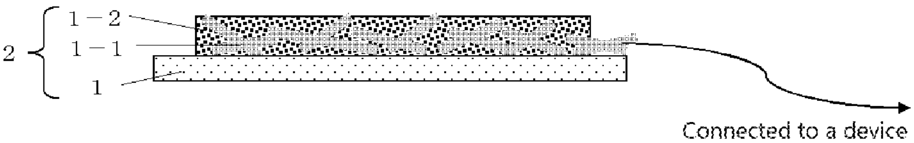
[FIG. 3]
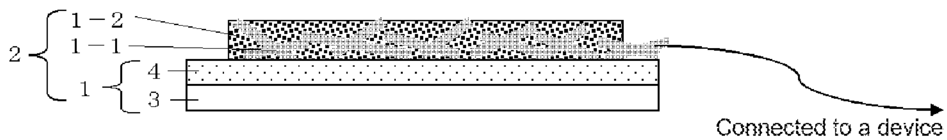
[FIG. 4]
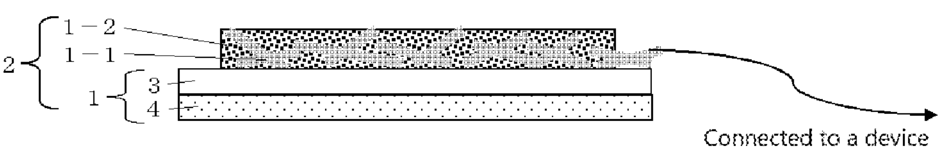
[FIG. 5]
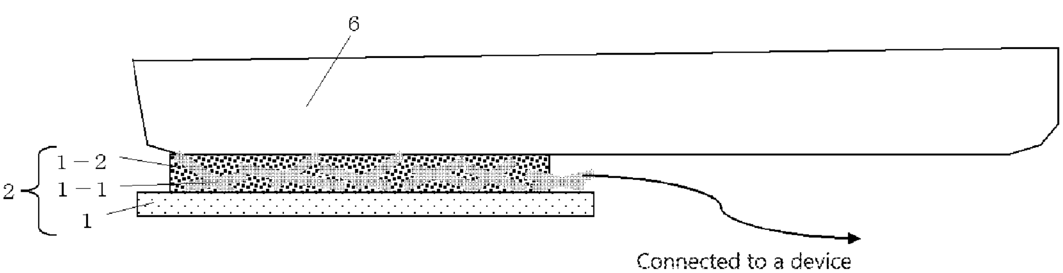
[FIG. 6]
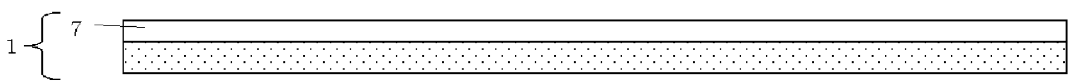

[FIG. 7]
[FIG. 8]
[FIG. 9]
[FIG. 10]
[FIG. 11]
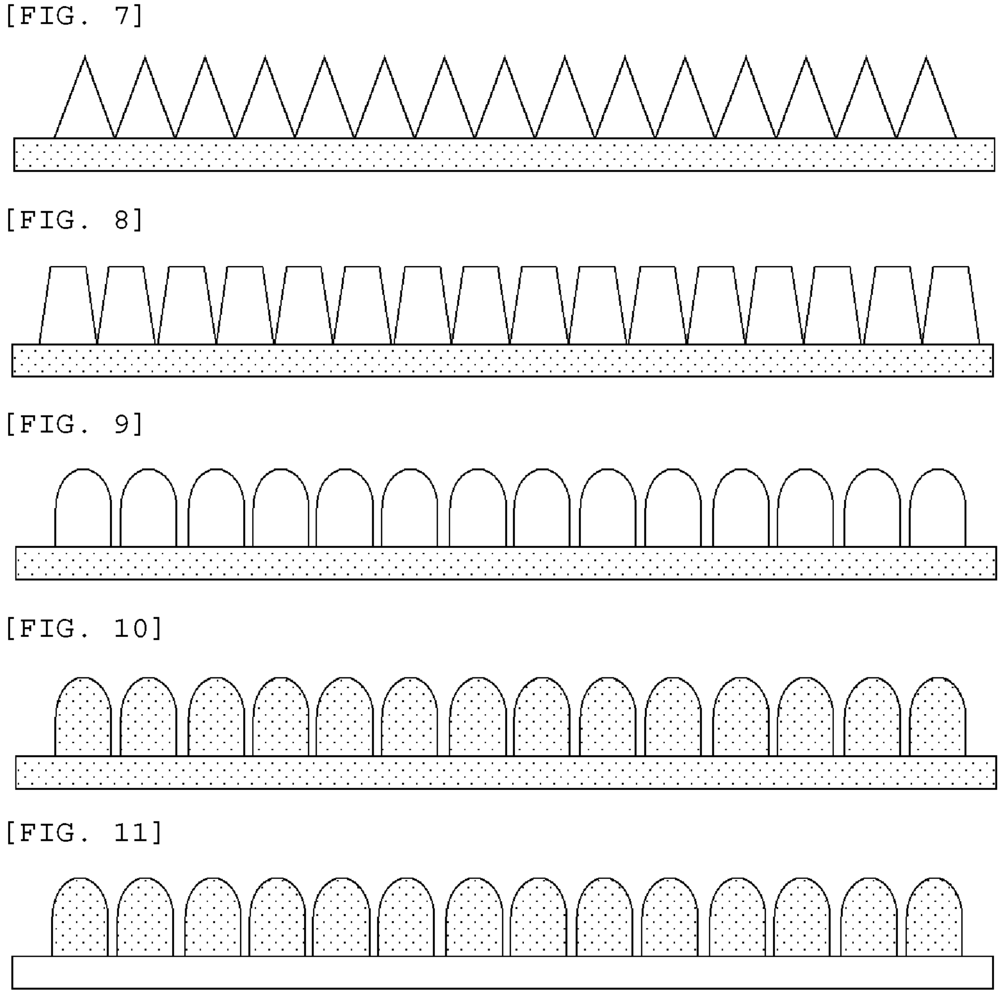

[FIG. 12]
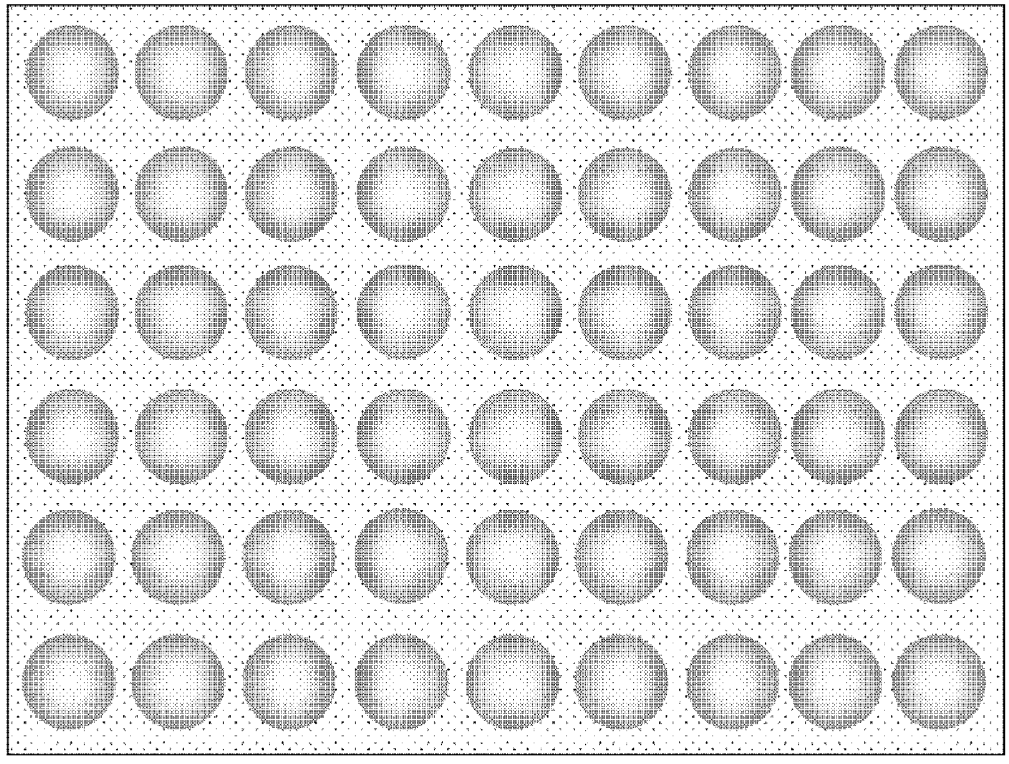
[FIG. 13]
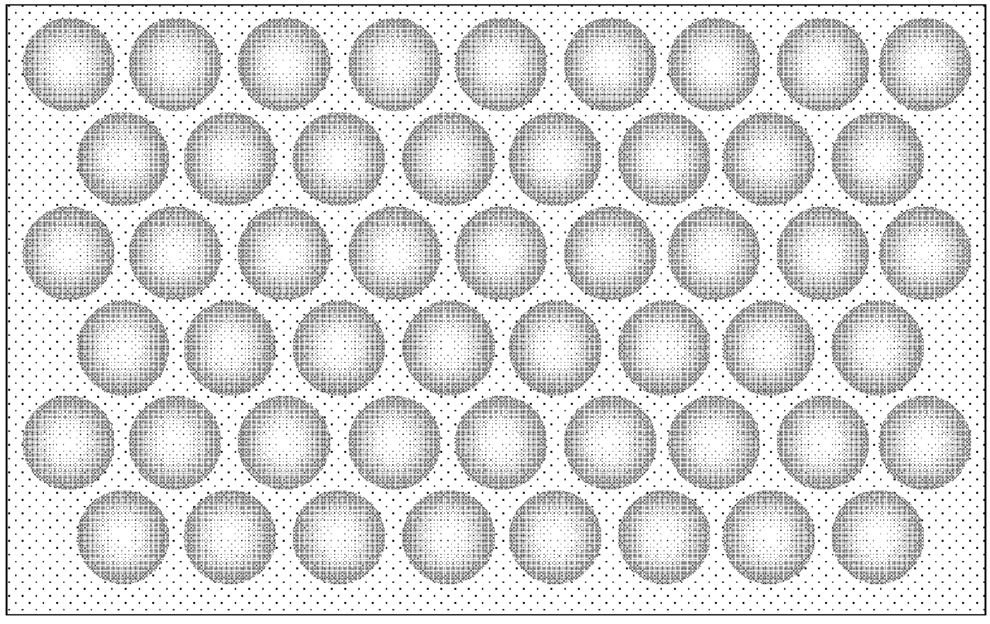

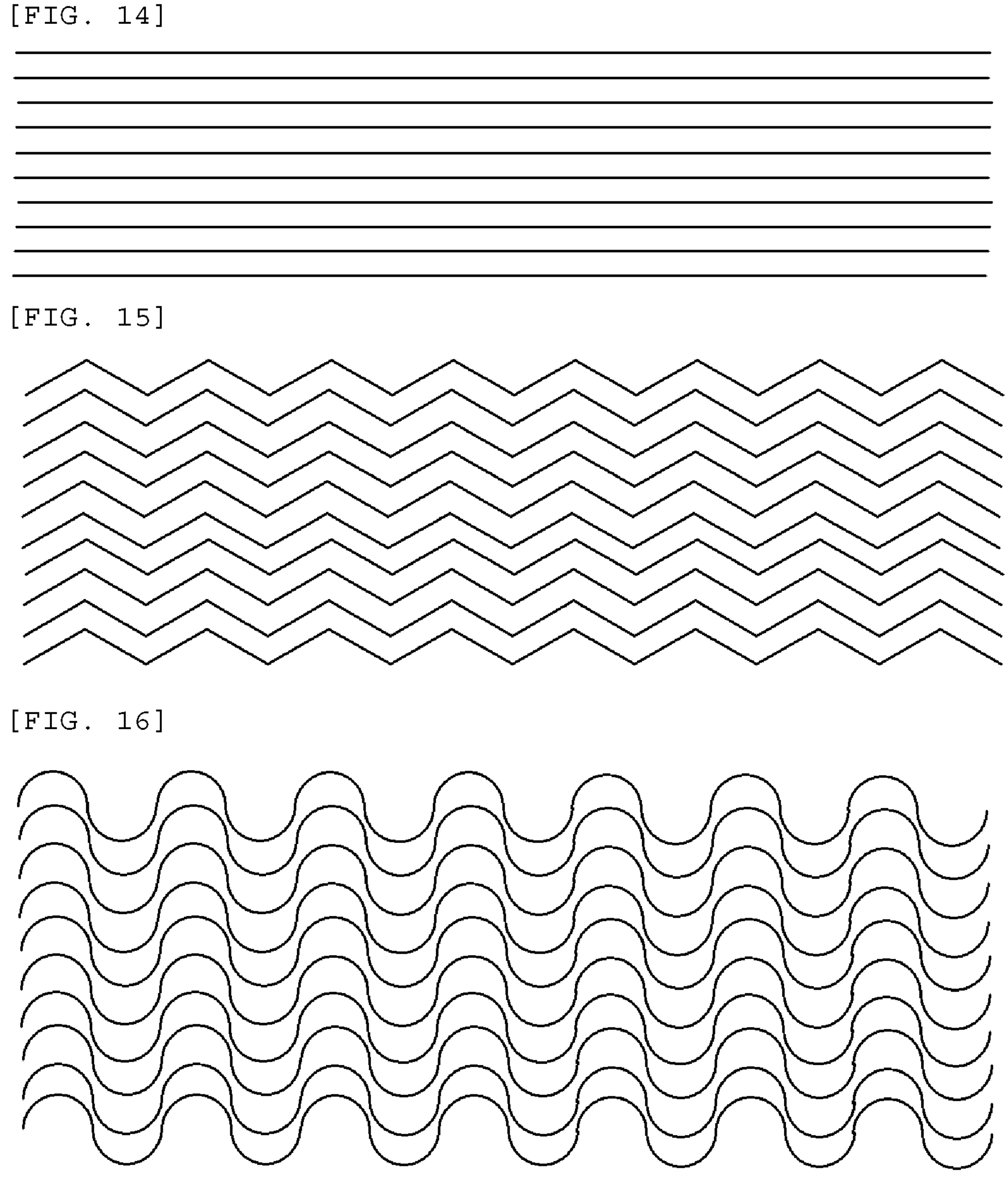
[FIG. 14]
[FIG. 15]
[FIG. 16]
[FIG. 17]
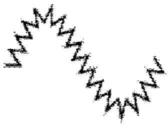

[FIG. 18]
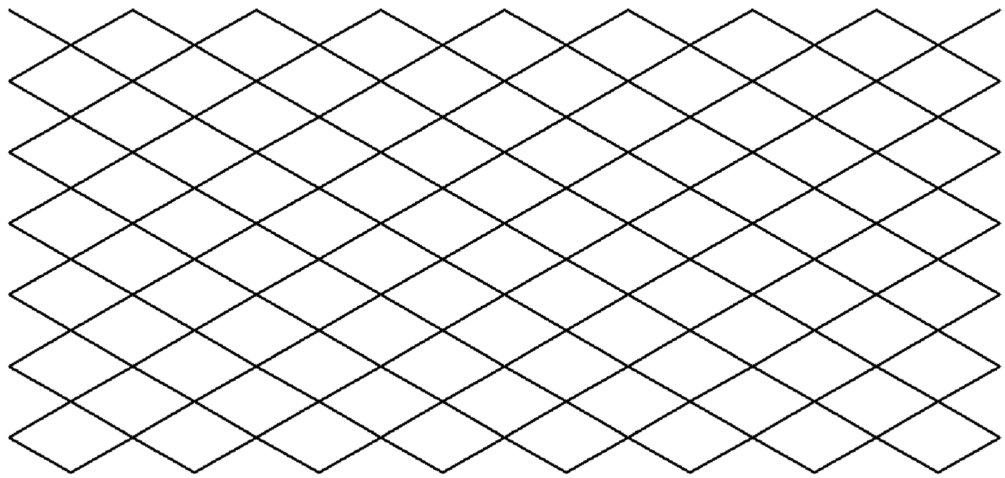
[FIG. 19]
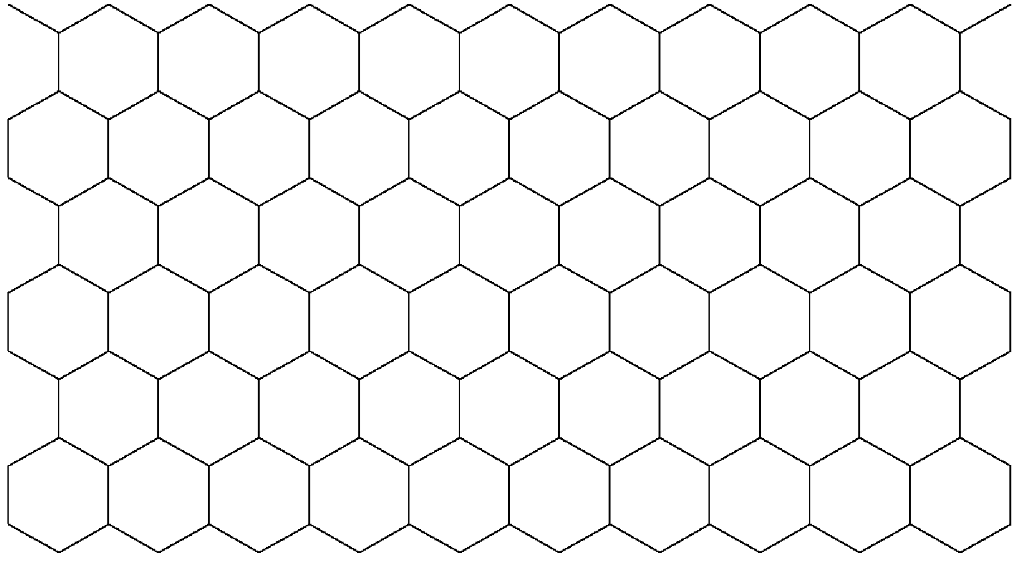

[FIG. 20]
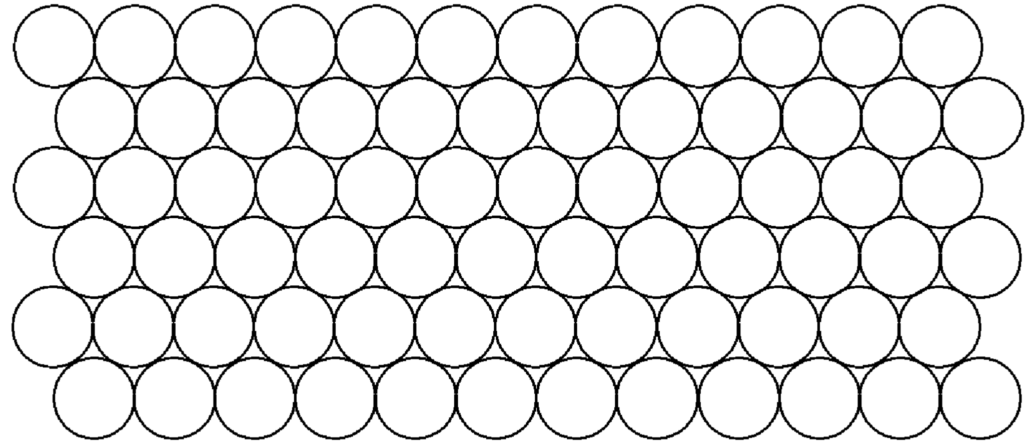
[FIG. 21]
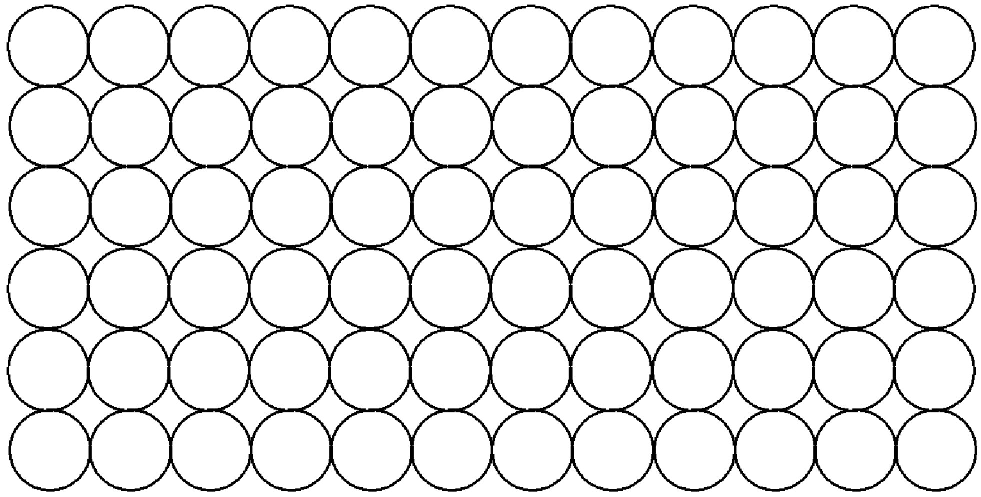

[FIG. 22]
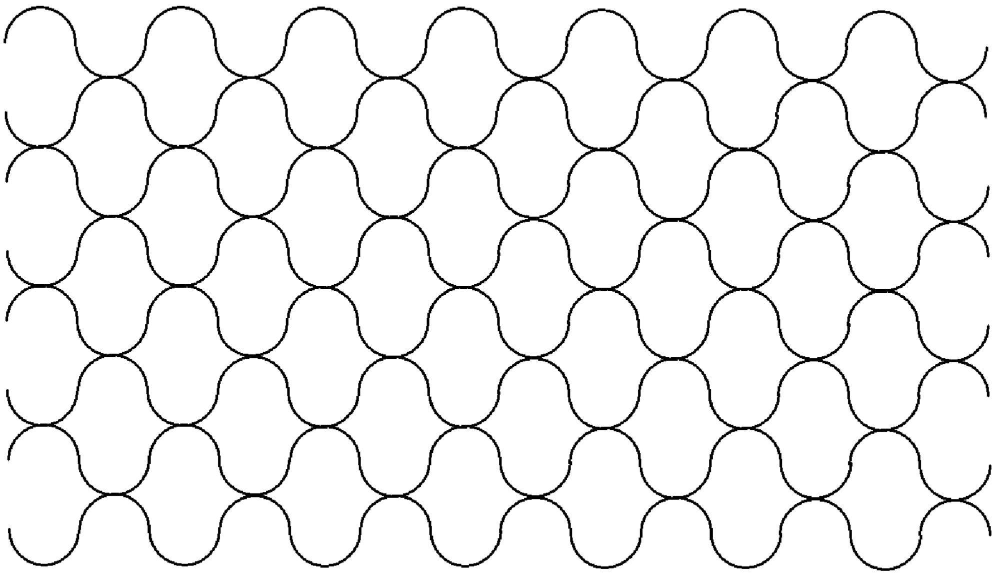
[FIG. 23]
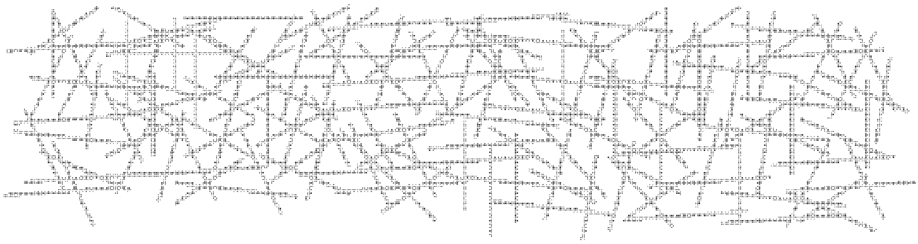
[FIG. 24]
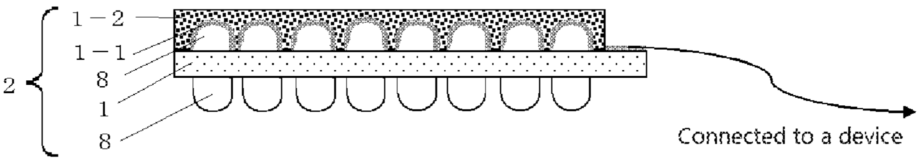

[FIG. 25]
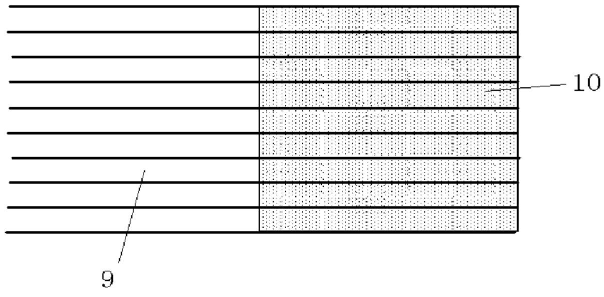
[FIG. 26]
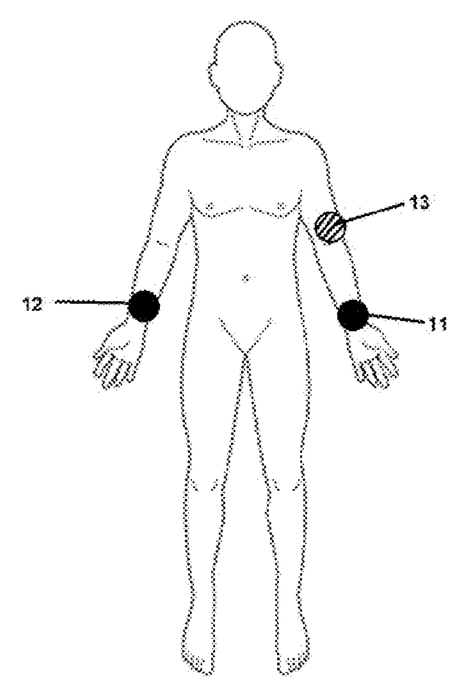

BIO-ELECTRODE AND METHOD FOR MANUFACTURING BIO-ELECTRODE

TECHNICAL FIELD

The present invention relates to a bio-electrode and a method for manufacturing a bio-electrode.

BACKGROUND ART

The recent growing popularity of IoT (Internet of Things) has accelerated the development of wearable devices. In the fields of medicine and sports, wearable devices for constantly monitoring the user's physical state are demanded, and such technological development is expected to be further encouraged. In particular, because the global spread of the new coronavirus (COVID-19) causes a serious burden on medical care, home medical care for people who are not infected with the virus is strongly needed and its accelerated development is desired.

In the field of medicine, wearable devices for monitoring the state of human organs by sensing an extremely weak current are sold, for example, like electrocardiogram measuring which detects the motion of the heart by electric signals. The electrocardiogram measurement is performed by attaching electrodes coated with a hydrated gel to the body, but this is a single, short-time measurement. In contrast to this, development of the above medical wearable device is aimed at devices for continuously monitoring the health condition for a few weeks. Accordingly, the bio-electrode used for the medical wearable device is required to be able to collect biological signals, not to cause an itchiness or a skin allergy, and to be used comfortably, even over extended periods of use in daily life which involves showering, bathing, sweating, etc. In addition to these, the bio-electrode is also required to be light-weight and thin to give no feeling when attached, and to be manufacturable with good productivity at low cost.

It is possible to measure an electrocardiogram with a watch-type device represented by Apple Watch or non-contact sensing using Rader. However, accurate electrocardiogram measuring for medical use needs an electrocardiogramonitor which requires to attach bio-electrodes on several locations on the body.

Medical wearable devices are classified into two types: one type is attached to the body, and another type is incorporated into clothing. For the attached type, for example, the bio-electrode using the aforementioned hydrated gel such as hydrophilic gel containing water and electrolytes disclosed in patent document 1 is widely used. The hydrophilic gel contains sodium, potassium, and calcium as electrolytes in a hydrophilic polymer for retaining water, and converts a change in ion concentration from the skin into an electric signal by a reductive reaction of silver chloride in contact with the hydrophilic gel. The bio-electrode has problems: a bio-electrode loses electric conductivity and consequently a function as an electrode when its gel gets dry; it swells during bathing or showering and falls off.

Meanwhile, for the electrode incorporated into closing, patent document 2 proposes a method to use fabric as an electrode, in which an electro-conductive polymer such as PEDOT-PSS (Poly-3,4-ethylenedioxythiophene-Polystyrenesulfonate) or silver paste is incorporated in fibers.

A bio-electrode sheet with a stretchability and high electric conductivity is under development (Non Patent Document 1). In the development, silver nanowires are coated on a polyurethane film, and are heated to 500° C. or higher on its surface instantaneously by a flash lamp anneal treatment to be made into fusion splicing with each other.

A bio-electrode using gold thin film, high concentrations of silver nanowires, or anything else is in metal color and not transparent. If a transparent bio-electrode through which the skin can be observed in a see-through manner is developed, it produces an advantage that there is no incongruity in appearance when the bio-electrode is attached on the skin.

For a transparent electro-conductive film for organic EL as a substitute for ITO, PEDOT-PSS has been studied. A combination of a silver nanowire and PEDOT-PSS is also studied (Non Patent Document 2). However, PEDOT-PSS is colored in blue, and is quite different in color from the skin. In order to increase transparency to lighten the blue color, Patent Documents 3 to 10 disclose application of polythiophene combined with fluorine-introduced dopant to a transparent electro-conductive film.

CITATION LIST

Patent Literature

Patent Document 1: WO 2013/039151 A1
Patent Document 2: JP 2015-100673 A
Patent Document 3: JP 6661212 B2
Patent Document 4: JP 6450661 B2
Patent Document 5: JP 6335138 B2
Patent Document 6: JP 6271378 B2
Patent Document 7: JP 6407107 B2
Patent Document 8: JP 6496258 B2
Patent Document 9: JP 6483518 B2
Patent Document 10: JP 6438348 B2

Non Patent Literature

Non Patent Document 1: Nano Res. 9, 401 (2016)
Non Patent Document 2: J. Photopolymer Sci. and Tech. Vol. 32 No. 3 p 429 (2019)

SUMMARY OF INVENTION

Technical Problem

The present invention has been made to solve the problems, and has an object to provide; a bio-electrode which is thin film, highly transparent, slightly different from the skin in color, highly sensitive to biological signals, excellent in biocompatibility, light-weight, manufacturable at low cost, capable of preventing significant reduction in the sensitivity to biological signals even when wetted with water or dried and when attached on the skin for a long time, and comfortable without itching, reddening, or rash of the skin; and a method for manufacturing the bio-electrode.

Solution to Problem

To solve the above problems, the present invention provides a bio-electrode comprising an electro-conductive polymer composite layer, an electro-conductive layer (C), and a substrate (D), wherein the electro-conductive polymer composite layer consisting of an electro-conductive polymer composite comprises (A) a π-conjugated polymer and (B) a dopant polymer which contains a repeating unit "a" having one or more compounds selected from the group consisting of sulfonic acid, fluorosulfonic acid, fluorosulfonimide, and N-carbonylfluorosulfonamide, and has a weight-average molecular weight of 1,000 to 500,000, and the substrate (D) has a transmittance of 20% or more at a wavelength of 600 nm and is in a yellow-red (YR) color with a value (brightness) in the range of 1 to 9 and a chroma (saturation) in the range of 1 to 12 in the Munsell color system.

Such an electrode is thin film, highly transparent, slightly different from the skin in color, highly sensitive to biological signals, excellent in biocompatibility, light-weight, manufacturable at low cost, capable of preventing significant reduction in the sensitivity to biological signals even when wetted with water or dried and when attached on the skin for a long time, and comfortable without itching, reddening, or rash of the skin.

Further, in the present invention, the electro-conductive layer (C) preferably comprises one or more kinds of substances selected from the group consisting of gold, silver, silver chloride, platinum, aluminum, magnesium, tin, tungsten, iron, copper, nickel, stainless steel, chromium, titanium, and carbon.

The electro-conductive layer (C) can contain such atoms.

Further, in the present invention, the bio-electrode the repeating unit "a" preferably has any of partial structure represented by the following general formulae (1)-1 to (1)-4.

(1)-1

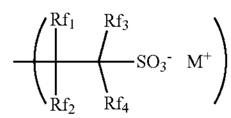

(1)-2

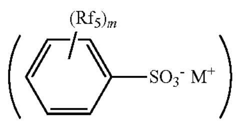

(1)-3

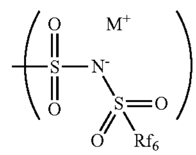

(1)-4

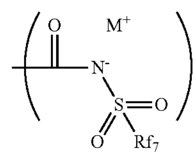

In the general formula (1)-1, $Rf_1$ and $Rf_2$ each represent a hydrogen atom, a fluorine atom, an oxygen atom, a methyl group, or a trifluoromethyl group. When $Rf_1$ and $Rf_2$ represent an oxygen atom, $Rf_1$ and $Rf_2$ represent a single oxygen atom bonded to a single carbon atom to form a carbonyl group; $Rf_3$ and $Rf_4$ each represent a hydrogen atom, a fluorine atom, or a trifluoromethyl group; at least one of $Rf_1$ to $Rf_4$ is a fluorine atom or a trifluoromethyl group. In the general formula (1)-2, $Rf_5$ represents a hydrogen atom, a fluorine atom, a trifluoromethyl group or a linear or branched alkyl group having 1 to 4 carbon atoms, and "m" represents an integer of 1 to 4. In the general formulae (1)-3 and (1)-4, $Rf_6$ and $Rf_7$ each represent a fluorine atom, a trifluoromethyl group or a linear or branched alkyl group having 1 to 4 carbon atoms and at least one fluorine atom. In the general formulae (1)-1 to (1)-4, $M^+$ represents an ion selected from the group consisting of a hydrogen ion, an ammonium ion, a sodium ion, and a potassium ion.

When the repeating unit "a" has such a structure, the electrode is further excellent in electro-conductivity and bio-compatibility.

In this event, the repeating unit "a" preferably has one or more kinds of repeating units selected from the group consisting of A1 to A7 represented by the following general formulae (2).

(2)

A1

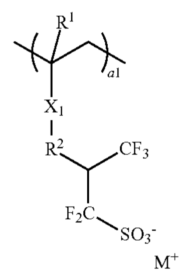

A2

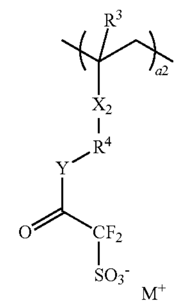

A3

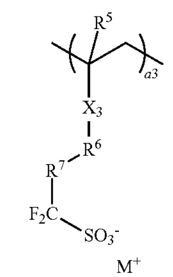

A4

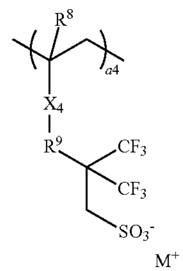

-continued

A5

A6

A7

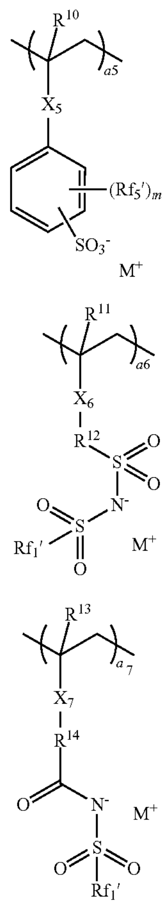

In general formula (2), $R^1$, $R^3$, $R^5$, $R^8$, $R^{10}$, $R^{11}$, and $R^{13}$ each independently represent a hydrogen atom or a methyl group, and $R^2$, $R^4$, $R^6$, $R^9$, $R^{12}$, and $R^{14}$ each independently represent a single bond or a linear, branched, or cyclic hydrocarbon group having 1 to 13 carbon atoms. The hydrocarbon group may optionally have either or both of an ester group and an ether group. $R^7$ represents a linear or branched alkylene group having 1 to 4 carbon atoms, and one or two hydrogen atoms in $R^7$ may optionally be substituted with a fluorine atom. $X_1$, $X_2$, $X_3$, $X_4$, $X_6$, and $X_7$ each independently represent a single bond, a phenylene group, a naphthylene group, an ether group, an ester group, or an amide group. $X_5$ represents a single bond, an ether group, or an ester group. Y represents an oxygen atom or an $—NR^{19}—$ group. $R^{19}$ represents a hydrogen atom, a linear, branched, or cyclic alkyl group having 1 to 12 carbon atoms, or a phenyl group, and optionally may have one or more kinds of groups selected from the group consisting of an ether group, a carbonyl group, an ester group, and an amide group. Y may optionally form a ring together with $R^4$. $Rf_1'$ and $Rf_5'$ each represent a fluorine atom, a trifluoromethyl group, or a linear or branched alkyl group having 1 to 4 carbon atoms, and have at least one fluorine atom. "m" represents an integer of 1 to 4. a1, a2, a3, a4, a5, a6, and a7 satisfy $0\leq a1\leq 1.0$, $0\leq a2\leq 1.0$, $0\leq a3\leq 1.0$, $0\leq a4\leq 1.0$, $0\leq a5\leq 1.0$, $0\leq a6\leq 1.0$, $0\leq a7\leq 1.0$, and $0<a1+a2+a3+a4+a5+a6+a7\leq 1.0$. $M^+$ represents an ion selected from the group consisting of a hydrogen ion, an ammonium ion, a sodium ion, and a potassium ion.

When the repeating unit "a" has such a structure, the electrode is further excellent in electro-conductivity and bio-compatibility.

In this event, the repeating unit "a" preferably contains an ammonium ion represented by the following general formula (3), as an ammonium ion for forming an ammonium salt.

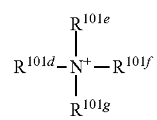

(3)

In the general formula (3), $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, and may optionally have one or more kinds selected from the group consisting of an ether group, a carbonyl group, an ester group, a hydroxy group, a carboxy group, an amino group, a nitro group, a sulfonyl group, a sulfinyl group, a halogen atom, and a sulfur atom. $R^{101d}$ and $R^{101e}$, or $R^{101d}$, $R^{101e}$, and $R^{101f}$ may optionally form a ring together with a nitrogen atom bonded to $R^{101d}$ and $R^{101e}$, or $R^{101d}$, $R^{101e}$, and $R^{101f}$. When a ring is formed, $R^{101d}$ and $R^{101e}$, or $R^{101d}$, $R^{101e}$, and $R^{101f}$ form an alkylene group having 3 to 10 carbon atoms or a heteroaromatic ring having, in the ring, nitrogen atom in the general formula (3).

When including a polymer containing such an ammonium ion, the electrode is further excellent in electro-conductivity and bio-compatibility.

Further, in the present invention, the electro-conductive polymer composite preferably contains, in addition to the components (A) and (B), one or more kinds of resin (E) selected from the group consisting of (meth)acrylate resin, (meth)acrylamide resin, urethane resin, polyvinyl alcohol, polyvinylpyrrolidone, polyoxazoline, polyglycerin, polyglycerin-modified silicone, cellulose, polyethylene glycol, and polypropylene glycol.

The electro-conductive polymer composite can contain such a resin (E).

Further, in the present invention, the substrate (D) preferably has a transmittance of 30% or more at a wavelength of 600 nm and a yellow-red (YR) color with a value in the range of 1 to 9 and a chroma in the range of 1 to 12 in the Munsell color system.

Such an electrode has further less difference in color from the skin, and is preferable.

Further, in the present invention, the substrate (D) is preferably attached, on either or both of the sides on which the bio-electrode contacts with the skin and on the opposite side, with a film having a transmittance of 30% or more at a wavelength of 600 nm and being in a yellow-red (YR) color with a value in the range of 1 to 9 and a chroma in the range of 1 to 12 in the Munsell color system.

Such an electrode is preferable because the electrode can be manufactured easily and has less difference in color from the skin.

Further, in the present invention, the substrate (D) preferably has an anti-reflective structure, on a surface of the opposite side of the side on which the bio-electrode contacts with the skin.

Such an electrode is preferable, because the electrode suppresses reflection of light, and has high transparency.

Further, the present invention provides a method of manufacturing of the bio-electrode described in the above. The method comprises forming the electro-conductive layer (C) by applying a solution containing a metal nanowire or by printing electro-conductive paste containing an electro-conductive particle on the substrate (D) having a transmittance of 20% or more at a wavelength of 600 nm and being in a yellow-red (YR) color with a value in the range of 1 to 9 and a chroma in the range of 1 to 12 in the Munsell color system, to form the electro-conductive polymer composite layer by applying the electro-conductive polymer composite on the electro-conductive layer (C).

On the basis of such a method for manufacturing a bio-electrode, it is possible to manufacture a bio-electrode which is thin film, highly transparent, slightly different from the skin in color, highly sensitive to biological signals, excellent in biocompatibility, light-weight, manufacturable at low cost, capable of preventing significant reduction in the sensitivity to biological signals even when wetted with water or dried and when attached on the skin for a long time, and comfortable without itching, reddening, or rash of the skin.

Advantageous Effects of Invention

As described above, the present inventive can provide bio-electrode which has small color difference from the skin when attached on the skin, and is highly sensitive to biological signals, excellent in biocompatibility, thin film, light-weight, highly transparent, manufacturable at low cost, capable of preventing significant reduction in the sensitivity to biological signals even when wetted with water or dried and when attached on the skin for a long time, and comfortable without itching, reddening, or rash of the skin. Further the present invention can provide a method for manufacturing the bio-electrode.

BRIEF DESCRIPTION OF DRAWINGS

FIG. 1 is a schematic sectional view after an electro-conductive layer is formed on a yellow-red (YR) substrate.

FIG. 2 is a schematic sectional view showing the inventive bio-electrode after an electro-conductive composite layer is formed on the electro-conductive layer on the yellow-red (YR) substrate.

FIG. 3 is a schematic sectional view of an example which shows that the substrate of the inventive bio-electrode is a complex of a yellow-red (YR) film and a transparent base material.

FIG. 4 is a schematic sectional view of another example which shows that the substrate of the inventive bio-electrode is a complex of a yellow-red (YR) film and a transparent base material.

FIG. 5 is a schematic sectional view when the inventive bio-electrode is attached on the skin to measure a biological signal.

FIG. 6 is a schematic sectional view of a substrate having an anti-reflective structure on its upper side.

FIG. 7 is a schematic sectional view of an example of a substrate having a moth-eye typed anti-reflective structure on its upper side.

FIG. 8 is a schematic sectional view of another example of a substrate having a moth-eye typed anti-reflective structure on its upper side.

FIG. 9 is a schematic sectional view of yet another example of a substrate having a moth-eye typed anti-reflective structure on its upper side.

FIG. 10 is a schematic sectional view of a substrate in which a moth-eye typed anti-reflective structure is also in yellow-red color as well as the substrate.

FIG. 11 is a schematic sectional view of a substrate having a yellow-red moth-eye typed anti-reflective structure on a transparent substrate.

FIG. 12 is a schematic top view of an example of the moth-eye typed anti-reflective structure.

FIG. 13 is a schematic top view of another example of the moth-eye typed anti-reflective structure.

FIG. 14 is a schematic top view of electro-conductive wiring formed in the shape of straight lines having a width of 200 μm or less by printing.

FIG. 15 is a schematic top view of electro-conductive wiring formed in the shape of zigzag lines having a width of 200 μm or less by printing.

FIG. 16 is a schematic top view of electro-conductive wiring formed in the shape of wave lines having a width of 200 μm or less by printing.

FIG. 17 is a schematic top view of electro-conductive wiring formed in the shape of a small zigzag line on a large zigzag line having a width of 200 μm or less by printing.

FIG. 18 is a schematic top view of electro-conductive wiring formed in an aslant lattice pattern with lines having a width of 200 μm or less by printing.

FIG. 19 is a schematic top view of electro-conductive wiring formed in the shape of Kikkou (hexagonal pattern) with lines having a width of 200 μm or less by printing.

FIG. 20 is a schematic top view of electro-conductive wiring formed in arrayed repeating circles with lines having a width of 200 μm or less by printing.

FIG. 21 is a schematic top view of electro-conductive wiring formed in arrayed repeating circles in another way with lines having a width of 200 μm or less by printing.

FIG. 22 is a schematic top view of electro-conductive wiring formed in a mesh pattern with lines having a width of 200 μm or less by printing.

FIG. 23 is a schematic top view of electro-conductive wiring formed by applying a solution containing a metal nanowire.

FIG. 24 is a schematic sectional view of the inventive bio-electrode after forming an electro-conductive polymer composite layer on an electro conductive layer formed on a substrate having moth-eye typed anti-reflective structure on its both sides.

FIG. 25 shows a shape of a bio-electrode used in Examples.

FIG. 26 shows locations where bio-electrodes were attached in measuring biological signals in Examples.

DESCRIPTION OF EMBODIMENTS

As described above, it is desired to develop a bio-electrode which assimilates to the skin in terms of color when attached on the skin, and is highly electro-conductive enough to show biological signals with high sensitivity and low noise, excellent in biocompatibility, manufacturable at low cost, capable of measuring biological signals even when wetted with water or dried, not causing skin damage or itching even when attached on the skin for a long time, light-weight, and thin film. As a result of diligent study of the above problems, the inventor found a bioelectrode of the following configuration and a method for manufacturing the bio-electrode, and have completed the present invention.

That is, the present invention relates to a bio-electrode including an electro-conductive polymer composite layer, an electro-conductive layer (C), and a substrate (D), wherein the electro-conductive polymer composite layer consisting of an electro-conductive polymer composite includes (A) a π-conjugated polymer and (B) a dopant polymer which contains a repeating unit "a" having one or more compounds selected from the group consisting of sulfonic acid, fluorosulfonic acid, fluorosulfonimide, and N-carbonylfluorosulfonamide, and has a weight-average molecular weight of 1,000 to 500,000, and the substrate (D) has a transmittance of 20% or more at a wavelength of 600 nm and is in a yellow-red (YR) color with a value (brightness) in the range of 1 to 9 and a chroma (saturation) in the range of 1 to 12 in the Munsell color system.

Hereinafter, the present invention will be described in detail, but the present invention is not limited thereto.

<Bio-Electrode>

The inventive bio-electrode includes an electro-conductive polymer composite layer, an electro-conductive layer (C), and a substrate (D). The electro-conductive polymer composite layer consists of an electro-conductive polymer composite, which includes a π-conjugated polymer (A) and a dopant polymer (B) which contains a repeating unit "a" having one or more compounds selected from the group consisting of sulfonic acid, fluorosulfonic acid, fluorosulfonimide, and N-carbonylfluorosulfonamide and has a weight-average molecular weight of 1,000 to 500,000. The substrate (D) has a transmittance of 20% or more at a wavelength of 600 nm and is in a yellow-red (YR) color with a value in the range of 1 to 9 and a chroma in the range of 1 to 12 in the Munsell color system.

Such an electrode is thin film, highly transparent, slightly different from the skin in color, highly sensitive to biological signals, excellent in biocompatibility, light-weight, manufacturable at low cost, capable of preventing significant reduction in the sensitivity to biological signals even when wetted with water or dried and when attached on the skin for a long time, and comfortable without itching, reddening, or rash of the skin.

In order to assimilates a bio-electrode to the skin in terms of color when attached on the skin, it is conceivable to make color of a substrate the same as the skin color of the person to whom the bio-electrode is attached. However, the color of human skin varies by race, age, gender, and individual, so it is difficult to have a bio-electrode of exactly the same color.

Electro-conductive polymer film using a polythiophene-based compound is colored in light-blue. Especially, PEDOT-PSS using polystyrene sulfonic acid for a dopant has a prominent blue color. A bio-electrode coated with PEDOT-PSS is blue even when both of electro-conductive film and substrate are transparent, and thus there is incongruity in appearance when the bio-electrode is attached on the skin.

[(D) Substrate]

For example, skin color of 5YR 8/5 in the Munsell color system can be obtain by mixing light-orange color (yellow-red (YR)) having higher value than this with small amount of blue color. When orange color is mixed with blue color, value and chroma of the mixture are decreased, and this allows skin color to be expressed. In the present invention, skin color is produced by combination of a blue color of polythiophene-based compound and a light-orange color.

That is, in the present invention, a substrate (D) has a transmittance of 20% or more at a wavelength of 600 nm and is in a yellow-red (YR) color with a value in the range of 1 to 9 and a chroma in the range of 1 to 12 in the Munsell color system. When a transmittance of at a wavelength of 600 nm is less than 20%, the bio-electrode has big color difference from the skin and not preferable. When value is outside the above range, the bio-electrode has big color difference from the skin and not preferable. When chroma is outside the above range, the bio-electrode has big color difference from the skin and not preferable. By setting low value and low chroma within the above ranges, skin color in black or brown can be expressed. By setting high value and high chroma within the above ranges, skin color in white can be expressed. Note that the transmittance is measured by a transmissometer.

For a constitution of the present invention, it is preferable to use a light-orange substrate, have a transparent electro-conductive layer on the substrate, and have a light-blue electro-conductive polymer composite layer on the transparent electro-conductive layer.

The substrate (D) itself may be in a light-orange color, or may be a transparent base material with a light-orange film attached. The side attached with an orange film may be a skin side or the opposite side.

That is, the substrate (D) preferably has a transmittance of 30% or more at a wavelength of 600 nm and is in a yellow-red (YR) color with a value in the range of 1 to 9 and a chroma in the range of 1 to 12 in the Munsell color system, the substrate (D) is attached, on either or both of the sides on which the bio-electrode contacts with the skin and on the opposite side, with a film having a transmittance of 30% or more at a wavelength of 600 nm and being in a yellow-red (YR) color with a value in the range of 1 to 9 and a chroma in the range of 1 to 12 in the Munsell color system.

Further, in order to accommodate a variety of skin color, it is preferable that transparency of a bio-electrode is increased and that the skin can be seen through the bio-electrode. By this, incongruity of the bio-electrode decreases even when color of the bioelectrode is slightly different from one of the skin in appearance when the bio-electrode is attached to the skin.

In some cases, a substrate has light reflection on its surface of the opposite side of the side attached to the skin. The light reflection on a bio-electrode is preferably reduced because the light reflection on the skin is less especially in blue region. One way to reduce the light reflection is to provide antireflection structure on the surface of the substrate. That is, the substrate (D) preferably has antireflection structure on a surface of the opposite side of the side on which a bio-electrode gets contact with the skin. FIG. 6 shows an antireflection structure of a laminated type. In a substrate, it is provided with a layer having a lower refractive index than the antireflection structure. In FIG. 6, there is one antireflection structure layer, but it is possible to enhance the effect of antireflection by having a plurality of antireflection structure layers in which the closer to an air layer a layer is located the lower its refractive index is stepwise.

It is also possible to have a moth-eye typed anti-reflective structure as shown in a schematic sectional view in FIGS. 7 to 9. The moth-eye type can produce higher antireflection effect than the laminate type.

It is possible to have not only a flat substrate but also a moth-eye typed anti-reflective structure in an orange color, as shown in a sectional view in FIG. 10. It is also possible to have a moth-eye typed anti-reflective structure in an orange color on a transparent substrate, as shown in a sectional view in FIG. 11.

Ions of sodium, potassium, and calcium are released from the surface of the skin, in accordance with heartbeats. A bio-electrode has to convert the increase and decrease of ions released from the skin to electric signals. Accordingly, the bio-electrode requires a material that is excellent in ionic conductivity to transmit the increase and decrease of ions. In accordance with heartbeats, electric potential on the surface of the skin also fluctuates. This fluctuation in electric potential is slight, and electron conductivity for conducting an extremely weak current to a device is also necessary.

A hydrophilic gel containing sodium chloride or potassium chloride has high ionic conductivity and electron conductivity, but loses conductivity if the water dries. Conductivity is degraded also by the sodium chloride or potassium chloride being eluted out of the bio-electrode due to bathing or a shower.

A bio-electrode using a metal such as gold or silver detects only an extremely weak current, and has low ionic conductivity, and therefore, has low sensitivity as a bio-electrode. Carbon has electron conductivity like metal, but has lower electron conductivity than metal, and therefore, has even lower sensitivity as a bio-electrode than metal.

Electro-conductive polymers represented by PEDOT-PSS, have both electron conductivity and ionic conductivity, but their ionic conductivity is low because of low polarization. In addition, a layer coated with PEDOT-PSS has absorption in a red region, and therefore, shows a blue color, which is the complementary color of the red. A bio-electrode in combination of an orange substrate and a layer coated with PEDOT-PSS is in slightly brownish wheat-color.

When a π-conjugated polymer and a dopant polymer containing fluorine are combined, the obtained film has high transparency in visible light, and is blue which is lighter than PEDOT-PSS. By a combination of this film and a light-orange substrate, the electrode can be applied to whiter skin. Further, with a combination of an orange color having low value and chroma, it is possible to reproduce skin color such as wheat-color or brown, and thus be applied to a variety of skin color.

Salts of sulfonic acid, fluorosulfonic acid, fluorosulfonimide, and N-carbonyl-fluorosulfonamide have high polarizability, and high ionic conductivity. By compounding these dopant polymers with a π-conjugated polymer such as polythiophene, it is possible to realize both high ionic conductivity and electron conductivity.

The main solvent for the composite (electro-conductive polymer composite) of the π-conjugated polymer and the dopant polymer is water. However, the composite is not dissolved in water, but dispersed in water as particles. Therefore, electro-conductive polymer composite layer which is made by coating, baking, and drying the composite does not dissolve in water and has high resistance to water. Accordingly, it is possible to take a shower, bathe, and swim with the inventive bio-electrode attached.

[(C) Electro-Conductive Layer]

An electro-conductive polymer composite layer contacts with an electro-conductive layer (C), and the electro-conductive layer (C) carries the signal to a device. In the present invention, the electro-conductive layer (C) is not particularly limited but preferably contains one or more selected from the group consisting of gold, silver, silver chloride, platinum, aluminum, magnesium, tin, tungsten, iron, copper, nickel, stainless steel, chromium, titanium, and carbon.

Further, an electro-conductive layer (C) is preferably transparent and preferably has a form in which electro-conductive wiring having a width of 200 μm or less preferably are connected to each other. The electro-conductive wiring having a width of 200 μm or less is preferably a printed pattern formed by an electro-conductive paste containing a particle of gold, silver, copper, or nickel, or by a fusion layer of metal nanowires containing gold, silver, copper, nickel, or alloy thereof.

When the electro-conductive wiring having a width of 200 μm or less is formed by printing, electro-conductive paste including a particle of gold, silver, copper, or nickel can be used. The electro-conductive paste is preferably mixed with an organic solvent or a resin besides an electro-conductive particle such as a particle of gold, silver, copper, or nickel. The electro-conductive particle is particularly preferably made of silver. Compositions of the electro-conductive paste are disclosed specifically in JP 2022-078861 A.

The metal nanowire preferably includes gold, silver, copper, nickel, or alloy thereof. The size of the metal nanowire is preferably in the range of 1 to 200 nm in diameter and in the range of 0.1 to 500 μm in length. The electro-conductive layer is preferably formed by coating and fusing a solution containing a metal nanowire, which is dispersed in an organic solvent such as alcohol.

The inventive bio-electrode can be attached anywhere on the skin of the body. Places to be attached on can include, for example, the chest, abdomen, shoulders, arms, legs, face, scalp, etc., and the inventive bio-electrode can measure not only electrocardiograms, but also electromyograms, electroencephalograms, and respiratory rate. Furthermore, it is possible not only to measure signals released from the skin but also to convey signals to muscles or control brainwaves by giving electric signals to the skin. For example, the bio-electrode is considered to be applied for enhancing performance, stimulating muscles to reduce fatigue during swimming, and enhancing relaxation in bathing.

For constituting a high-sensitivity bio-electrode, it is necessary not only high ionic conductivity but also high electron conductivity. The electron conductivity is ensured by the π-conjugated polymer, but for further enhancing the electron conductivity, it is effective to add a metal powder or a carbon powder in addition to the electro-conductive polymer composite.

<Electro-Conductive Polymer Composite>

Hereinafter, each component of the electro-conductive polymer composite, which forms the electro-conductive polymer composite layer of the inventive electrode, is described further in detail.

[(A) π-Conjugated Polymer]

The component (A) of the electro-conductive polymer composite for forming the electro-conductive polymer layer included in the inventive bio-electrode, may be a polymer (π-conjugated polymer) of a precursor monomer (organic monomer molecule) forming a n-conjugated chain (a structure in which a single bond and a double bond are alternately continued).

Examples of such a precursor monomer can include thiophenes for example, and a homopolymer or a copolymer of these monomers can be used as the component (A).

In addition, the component (A) can give sufficient conductivity even when the monomer constituting the n-conjugated polymer is not substituted, but for giving higher conductivity, a monomer substituted with an alkyl group, a carboxy group, a sulfo group, an alkoxy group, a hydroxy group, a cyano group, a halogen atom, or the like, may be used.

Specific examples of thiophenes can include thiophene, 3-methylthiophene, 3-ethylthiophene, 3-propylthiophene, 3-butylthiophene, 3-hexylthiophene, 3-heptylthiophene, 3-octylthiophene, 3-decylthiophene, 3-dodecylthiophene, 3-octadecyl thiophene, 3-bromothiophene, 3-chlorothiophene, 3-iodothiophene, 3-cyanothiophene, 3-phenylthiophene, 3,4-dimethylthiophene, 3,4-dibutylthiophene, 3-hydroxythiophene, 3-methoxythiophene, 3-ethoxythiophene, 3-butoxythiophene, 3-hexyloxythiophene, 3-heptyloxythiophene, 3-octyloxythiophene, 3-decyloxythiophene, 3-dodecyloxythiophene, 3-octadecyloxythiophene, 3,4-dihydroxythiophene, 3,4-dimethoxythiophene, 3,4-diethoxythiophene, 3,4-dipropoxythiophen, 3,4-dibutoxythiophene, 3,4-dihexyloxythiophene, 3,4-diheptyloxythiophene, 3,4-dioctyloxythiophene, 3,4-didecyloxythiophene, 3,4-didodecyloxythiophene, 3,4-ethylenedioxythiophene, 3,4-propylenedioxythiophene, 3,4-butenedioxythiophene, 3-methyl-4-methoxythiophene, 3-methyl-4-ethoxythiophene, 3-carboxythiophene, 3-methyl-4-carboxythiophene, 3-methyl-4-carboxyethylthiophene, 3-methyl-4-carboxybutylthiophene, etc.

In particular, a (co)polymer of one or two kinds selected from the group consisting of 3-methylthiophene, 3-methoxythiophene, and 3,4-ethylenedioxythiophene is suitably used from the viewpoints of a resistance value and reactivity.

For practical reasons, the number of these repeating units (precursor monomers) in the component (A) is preferably 2 to 20, more preferably 6 to 15.

The molecular weight of the component (A) is preferably about 130 to 5,000. The molecular weight is the weight-average molecular weight (Mw) measured in terms of polystyrene by gel permeation chromatography (GPC).

[(B) Dopant Polymer (Salt)]

The dopant polymer (B), which is contained in the electro-conductive polymer composite to form the electro-conductive polymer composite layer making up the inventive electrode, includes a repeating unit "a" having one or more kinds selected from the group consisting of sulfonic acid, fluorosulfonimide, and N-carbonyl-fluorosulfonamide and has a weight-average molecular weight of 1,000 to 500,000. Further, the dopant polymer can contain a polymer having an ionic repeating unit "a" selected from the group consisting of ammonium salts, lithium salts, sodium salts, and potassium salts of any of sulfonic acid, fluorosulfonimide, and N-carbonyl-fluorosulfonamide.

Specific examples of monomers for obtaining the repeating unit "a" containing sulfonic acid or the ionic repeating unit "a" selected from the group consisting of ammonium salts, sodium salts, and potassium salts of sulfonic acid.

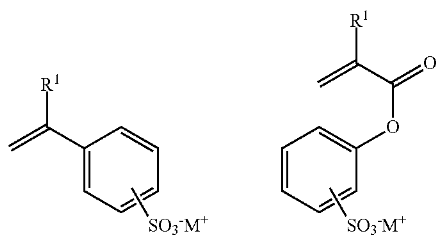

-continued

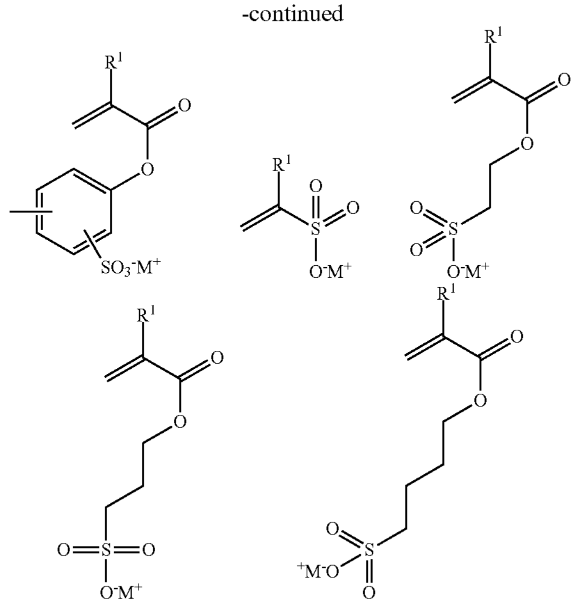

In the formulae, $R^1$ represent a hydrogen atom or a methyl group, and M represents an ion selected from the group consisting of a hydrogen ion, an ammonium ion, a sodium ion, and a potassium ion.

The repeating unit "a" can have a partial structure represented by the following general formulae (1)-1 to (1)-4.

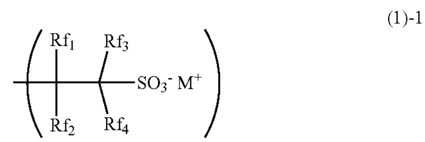

(1)-1

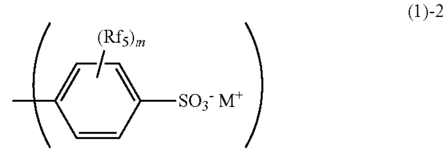

(1)-2

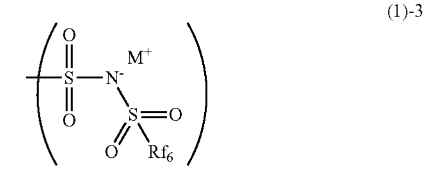

(1)-3

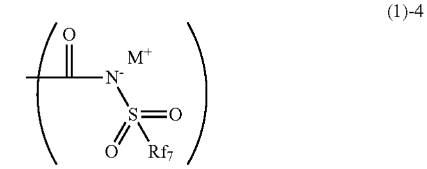

(1)-4

In the general formula (1)-1, $Rf_1$ and $Rf_2$ represent a hydrogen atom, a fluorine atom, an oxygen atom, a methyl group, or a trifluoromethyl group. When $Rf_1$ and $Rf_2$ represent an oxygen atom, $Rf_1$ and $Rf_2$ are a single oxygen atom bonded to a single carbon atom to form a carbonyl group; $Rf_3$ and $Rf_4$ represent a hydrogen atom, a fluorine atom, or a trifluoromethyl group; at least one of $Rf_1$ to $Rf_4$ is a fluorine atom or a trifluoromethyl group. In the general formula (1)-2, $Rf_5$ represents a hydrogen atom, a fluorine atom, or a trifluoromethyl group, or a linear or branched alkyl group having 1 to 4 carbon atoms, and "m" represents an integer of 1 to 4. In the general formulae (1)-3, and (1)-4, $Rf_6$ and $Rf_7$ each represent a fluorine atom, a trifluoromethyl group, or a linear or branched alkyl group having 1 to 4 carbon atoms and at least one fluorine atom. In the general formulae (1)-1 to (1)-4, $M^+$ represents an ion selected from the group consisting of a hydrogen ion, an ammonium ion, a sodium ion, and a potassium ion. In the general formula (1)-2, "m" represents an integer of 1 to 4.

The repeating unit "a" preferably has one or more repeating units selected from the repeating units-A1 to -A7 represented by the following general formulae (2).

(2)

A1

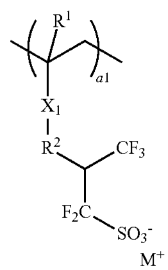

A2

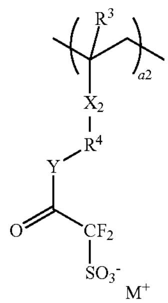

A3

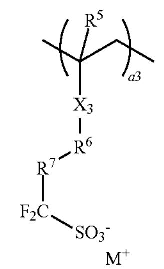

A4

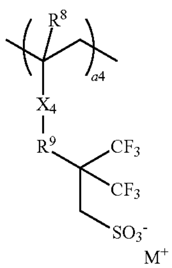

-continued

A5

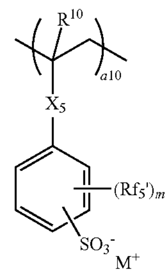

A6

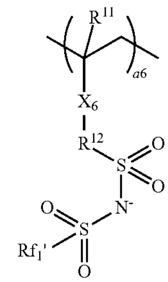

A7

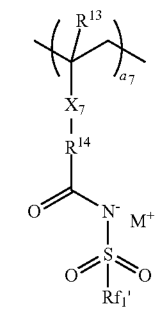

In the general formulae (2), $R^1$, $R^3$, $R^5$, $R^8$, $R^{10}$, $R^{11}$, and $R^{13}$ each independently represent a hydrogen atom or a methyl group. $R^2$, $R^4$, $R^6$, $R^9$, $R^{12}$, and $R^{14}$ each independently represent a single bond or a linear, branched, or cyclic hydrocarbon group having 1 to 13 carbon atoms, and the hydrocarbon group may contain either or both of an ester group and an ether group. $R^7$ represents a linear or branched alkylene group having 1 to 4 carbon atoms, and one or two hydrogen atoms in $R^7$ may optionally be substituted with a fluorine atom. $X_1$, $X_2$, $X_3$, $X_4$, $X_6$, and $X_7$ each independently represent a single bond, a phenylene group, a naphthylene group, an ether group, an ester group, or an amide group. $X_5$ represents a single bond, an ether group, or an ester group. Y represents an oxygen atom or an —$NR^{19}$— group. $R^{19}$ represents a hydrogen atom, a linear, branched, or cyclic alkyl or phenyl group having 1 to 12 carbon atoms, and may have one or more groups selected from the group consisting of an ether group, a carbonyl group, an ester group, and an amide group. Y may form a ring together with $R^4$. $Rf_1'$ and $Rf_5'$ each represent a fluorine atom, a trifluoromethyl group, or a linear or branched alkyl group having 1 to 4 carbon atoms and at least one fluorine atom. "m" represents an integer of 1 to 4. a1, a2, a3, a4, a5, a6, and a7 satisfy $0 \le a1 \le 1.0$, $0 \le a2 \le 1.0$, $0 \le a3 \le 1.0$, $0 \le a4 \le 1.0$, $0 \le a5 \le 1.0$, $0 \le a6 \le 1.0$, $0 \le a7 \le 1.0$, and $0 < a1+a2+a3+a4+a5+a6+a7 \le 1.0$. $M^+$ represents an ion selected from the group consisting of a hydrogen ion, an ammonium ion, a sodium ion, and a potassium ion.

In the general formulae (2), a1 to a7 are the proportions of the repeating units-A1 to -A7 respectively.

(Repeating Units A)
Specific examples of fluorosulfonic acid monomers and fluorosulfonic acid salt monomers for obtaining the repeating units-A1 to -A5 among the repeating units-A1 to -A7 represented by the general formulae (2) can include the following.
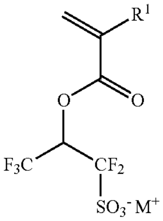
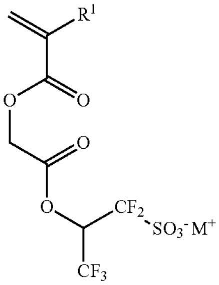
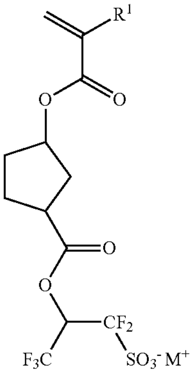
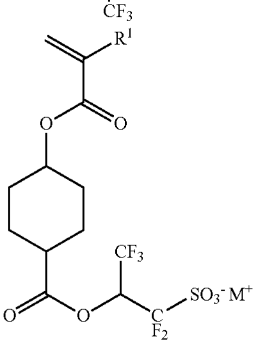
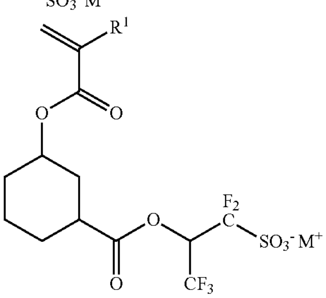
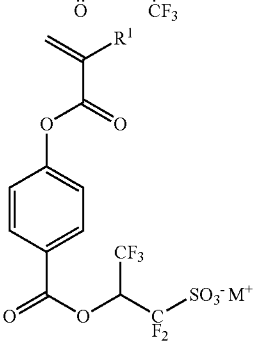
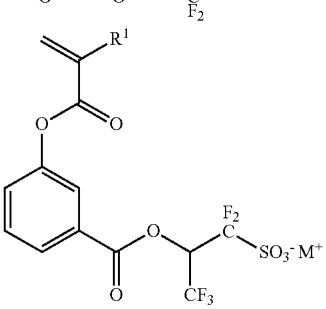
-continued
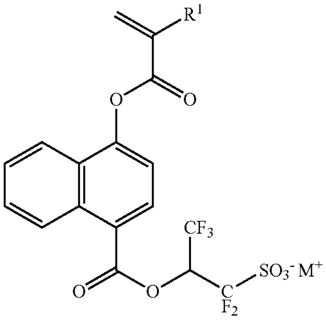
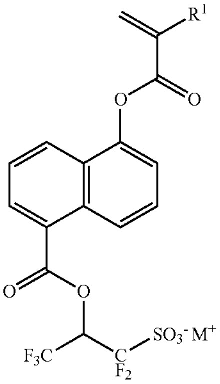
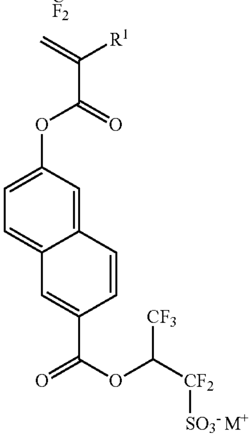
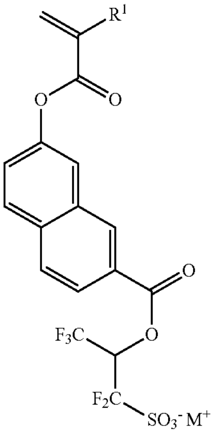
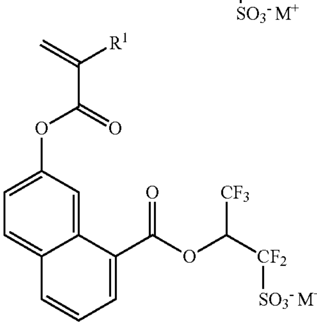
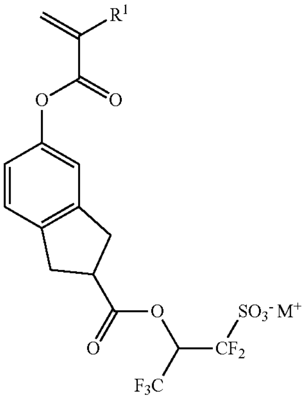
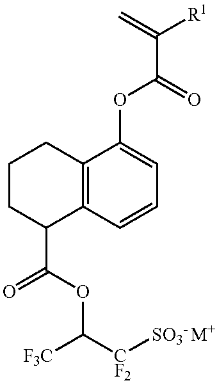

-continued
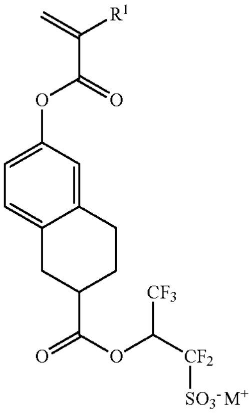
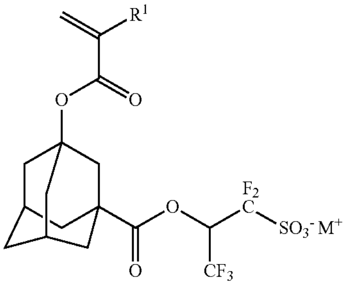
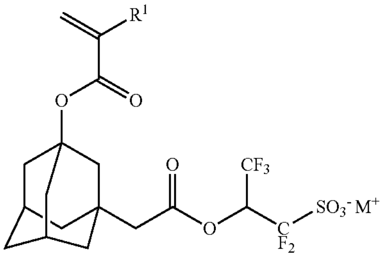
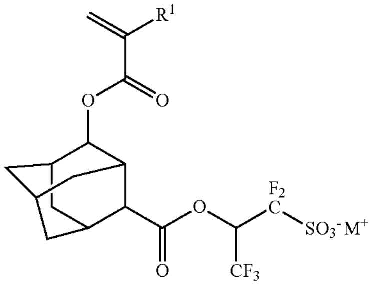
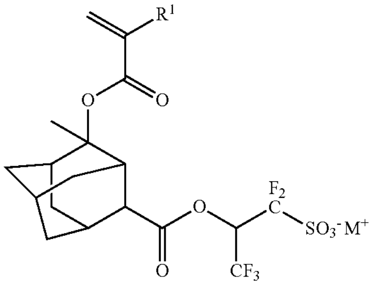
-continued
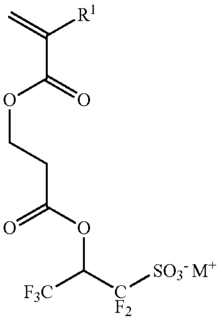
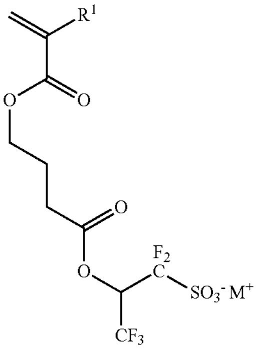
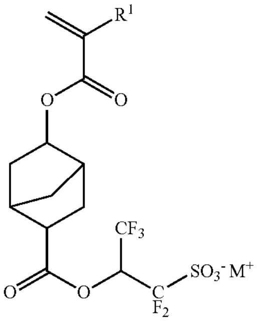
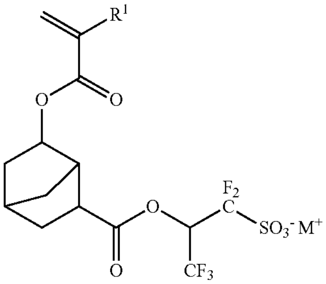
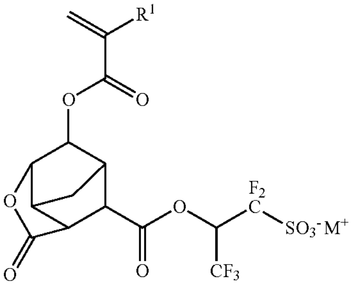
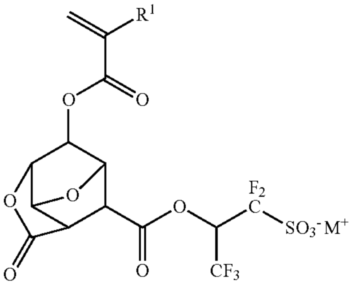

-continued
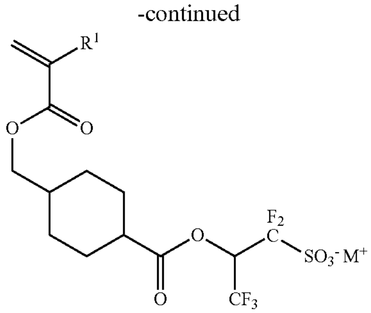
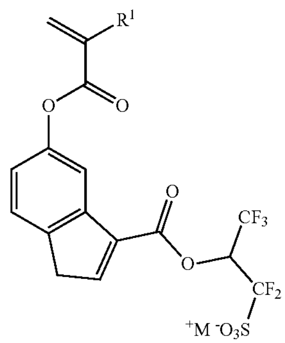
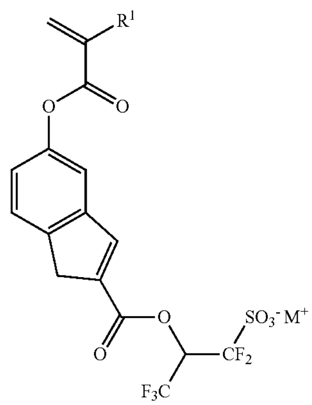
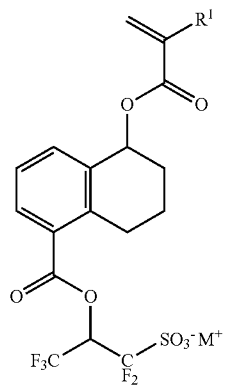
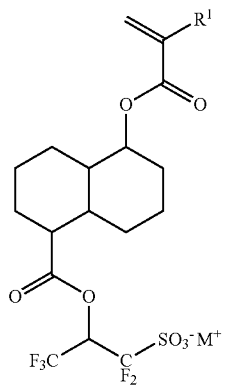
-continued
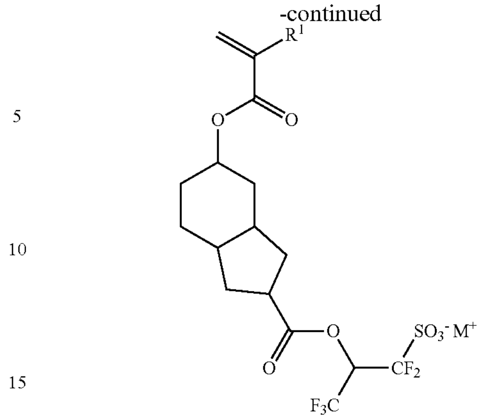
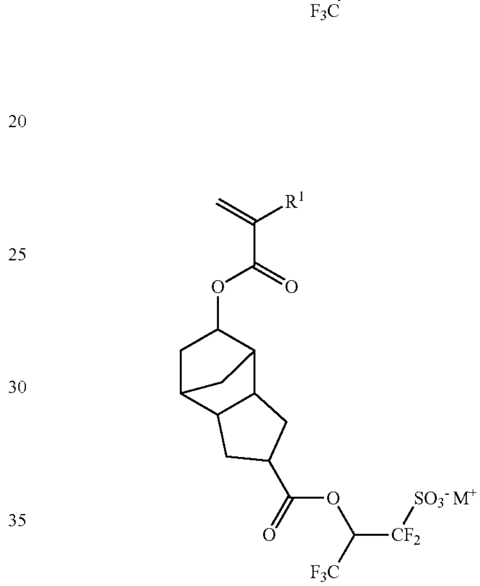
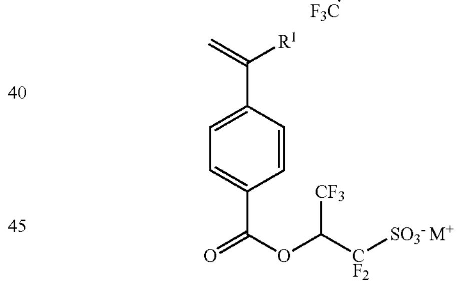
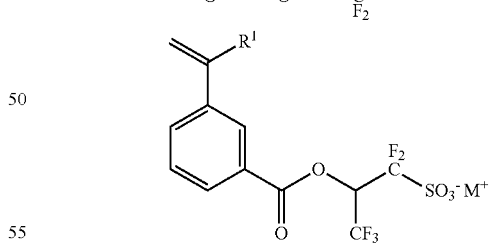
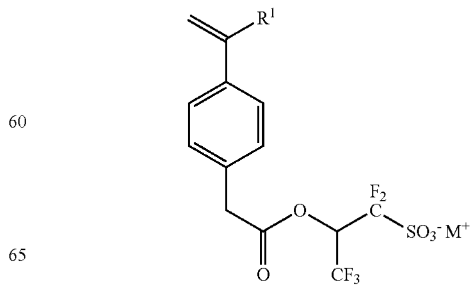

-continued
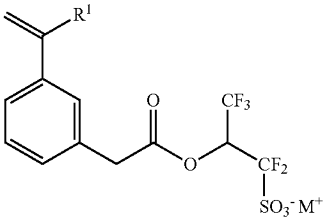
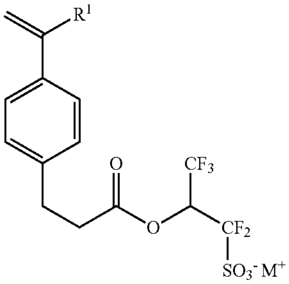
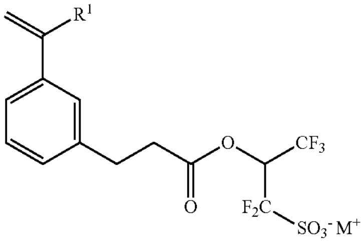
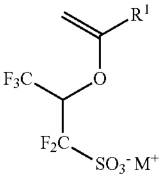
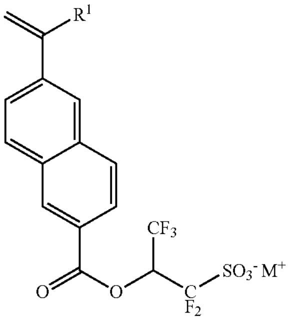
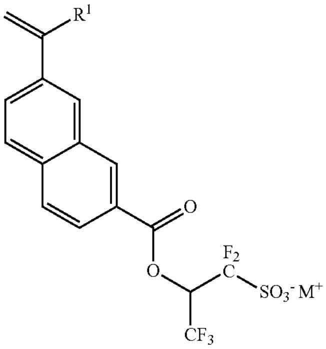
-continued
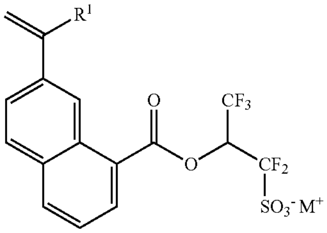
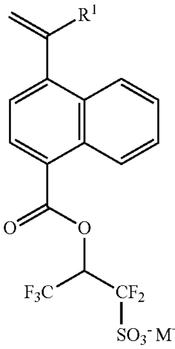
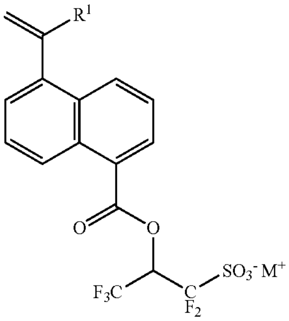
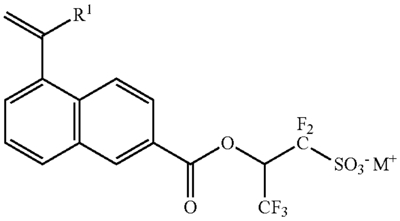
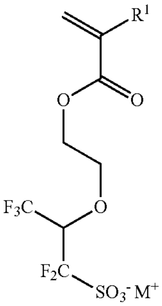
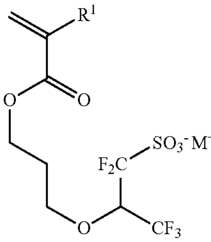
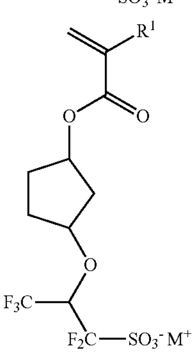
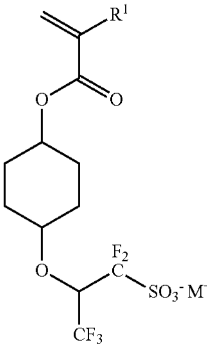

-continued
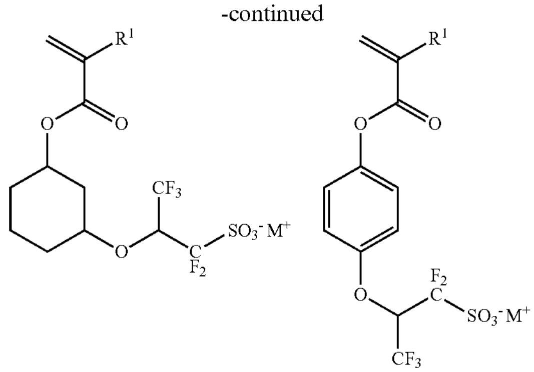
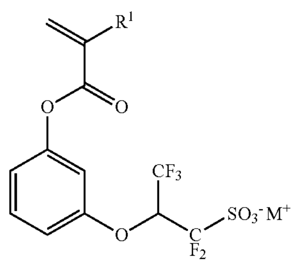
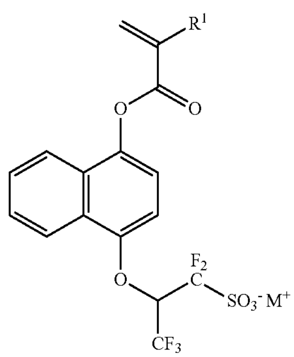
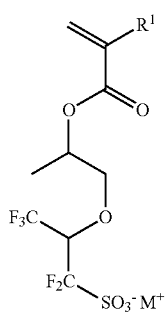
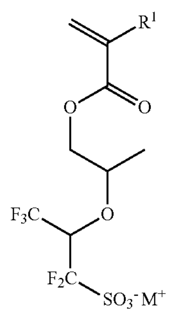
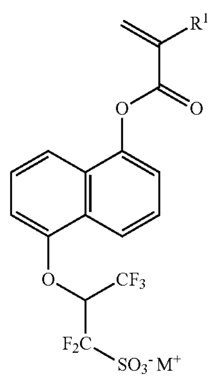
-continued
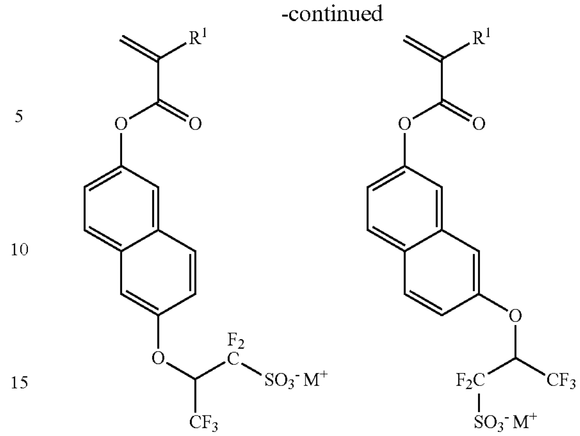
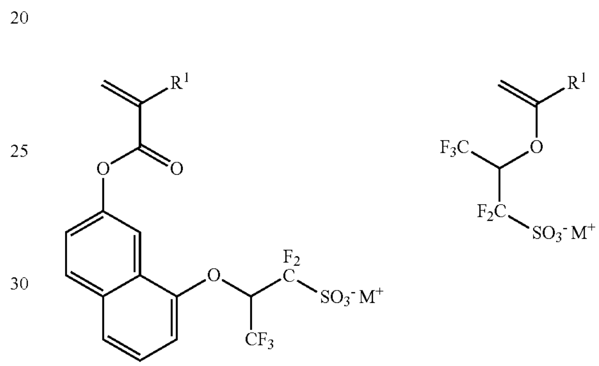
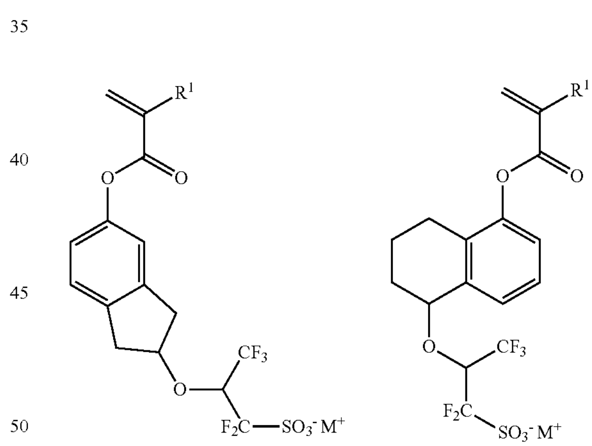
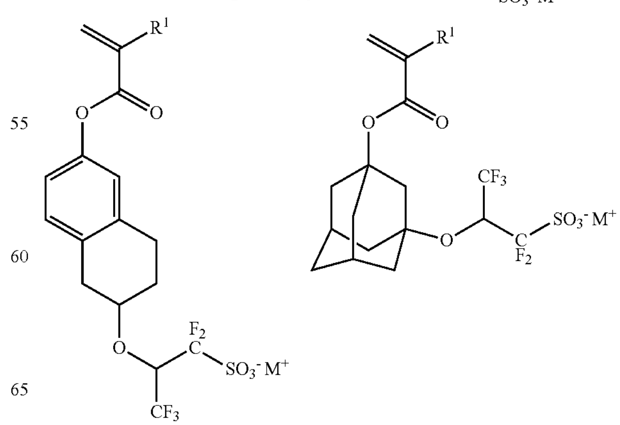

-continued
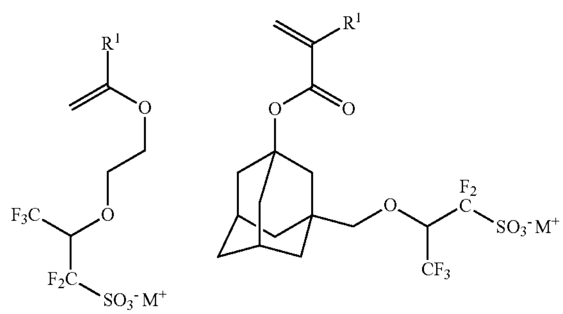
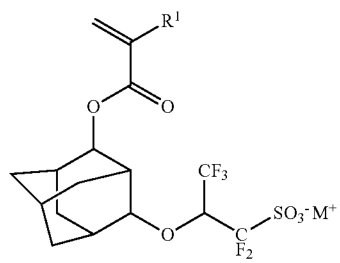
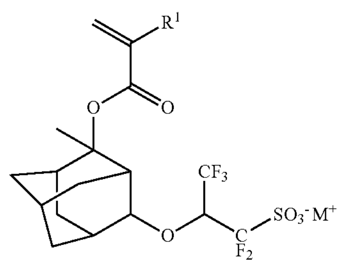
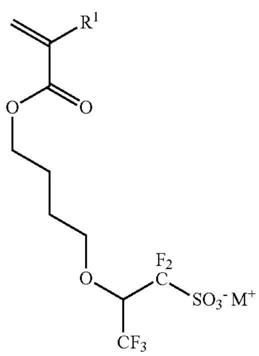
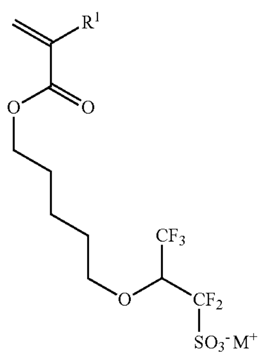
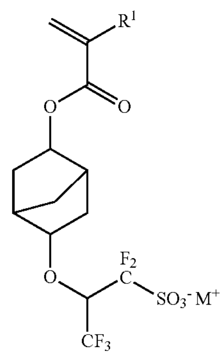
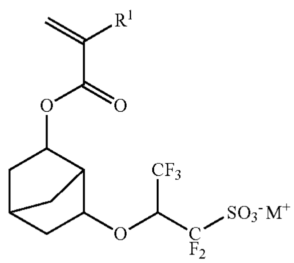
-continued
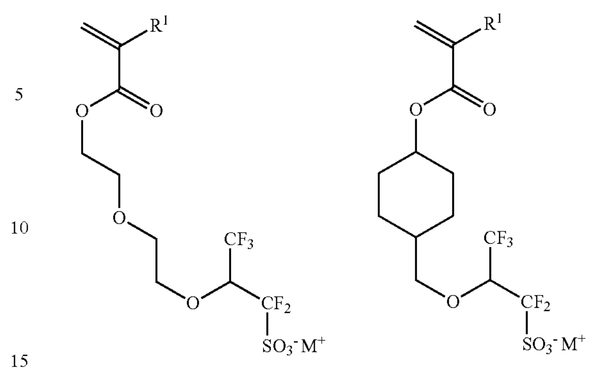
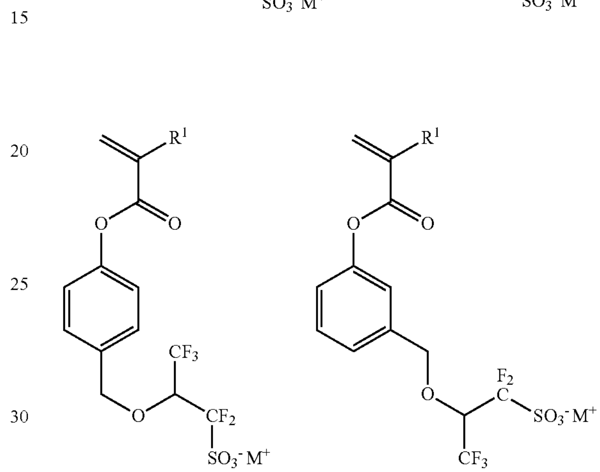
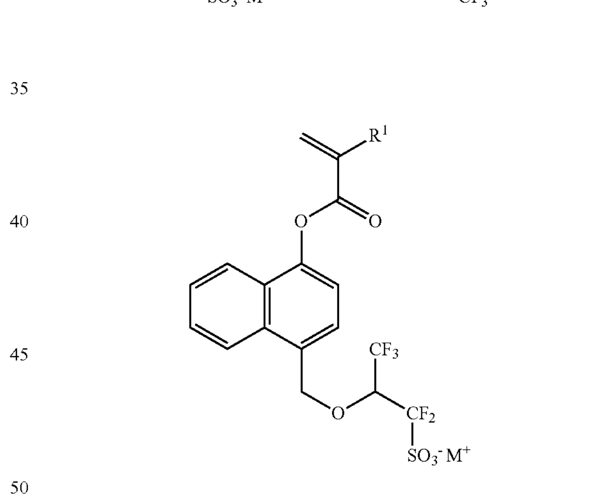
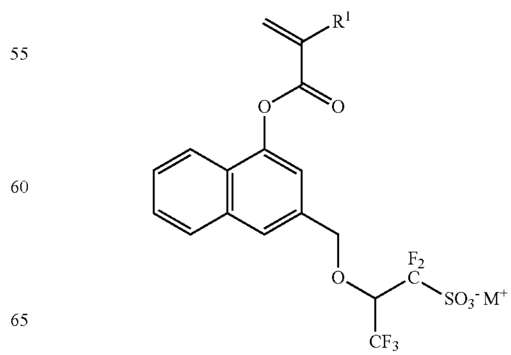

-continued
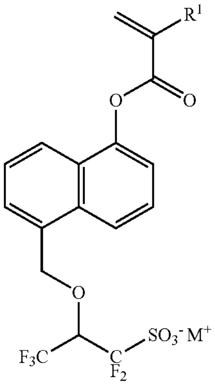
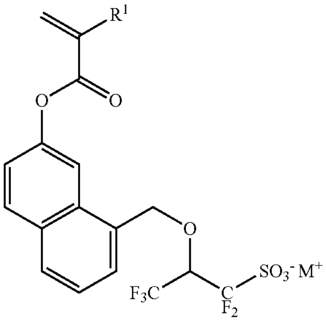
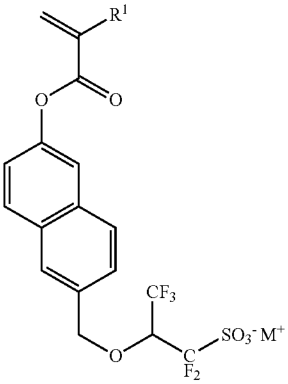
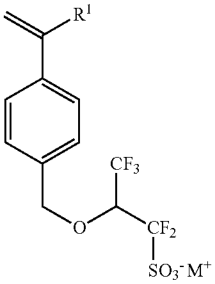
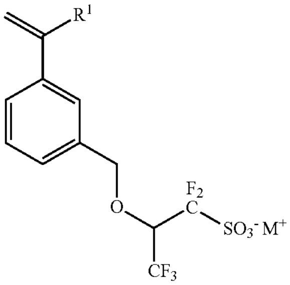
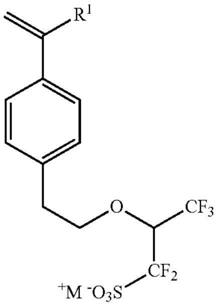
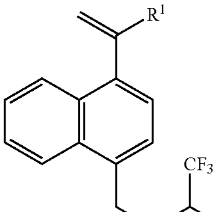
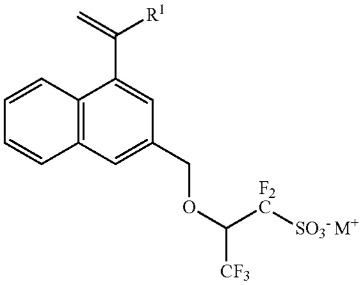
-continued
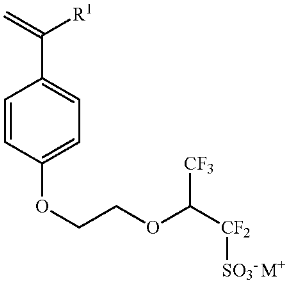
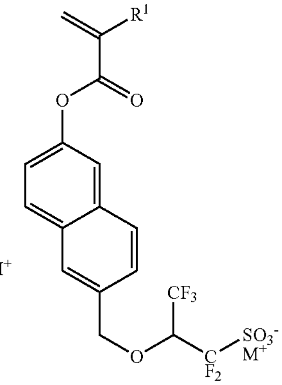
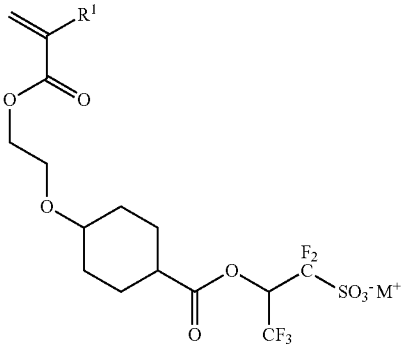
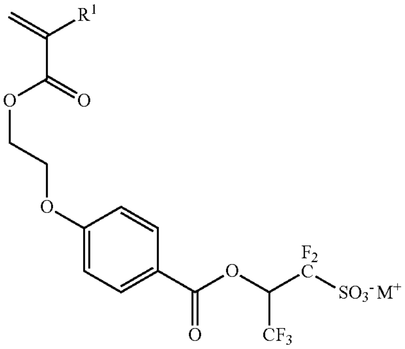
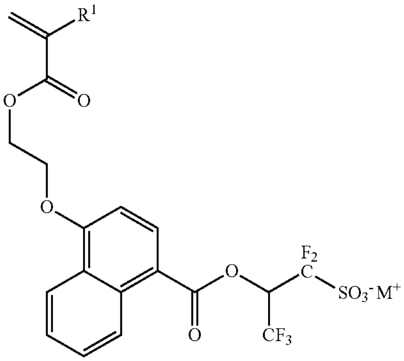

-continued
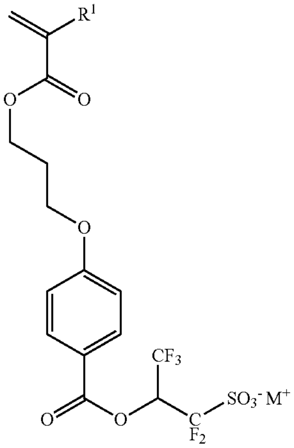
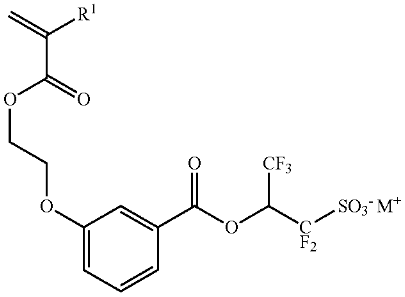
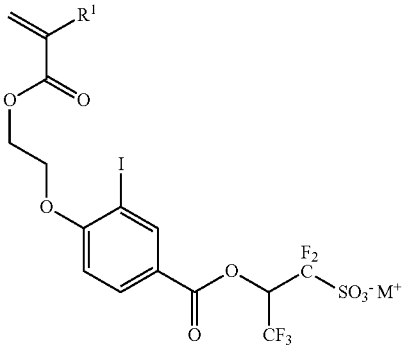
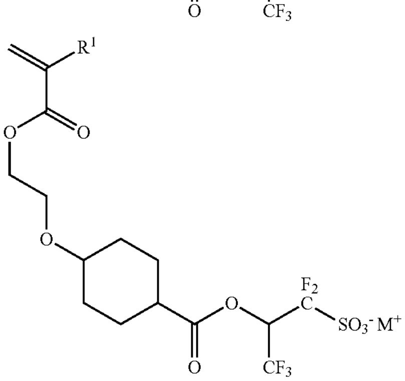
-continued
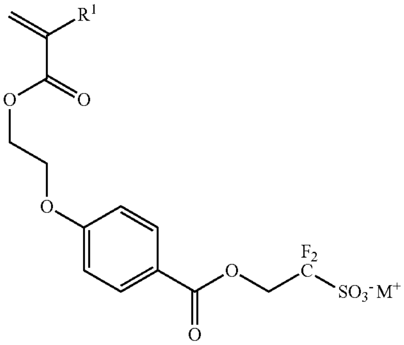
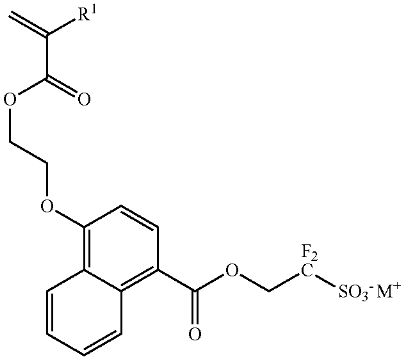
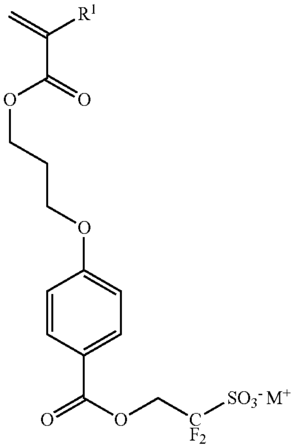
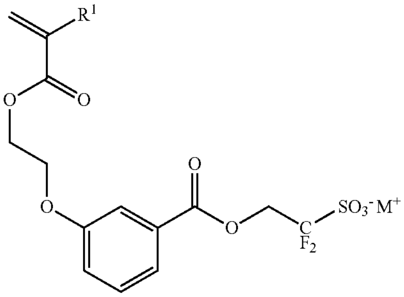

-continued
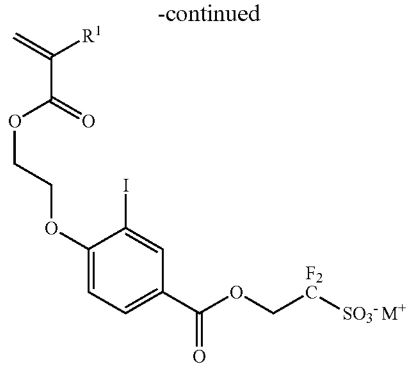
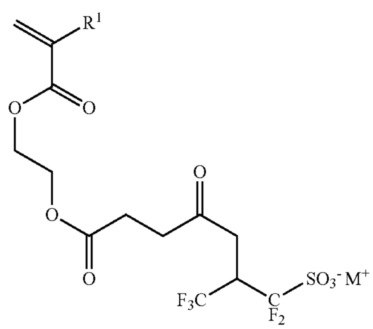
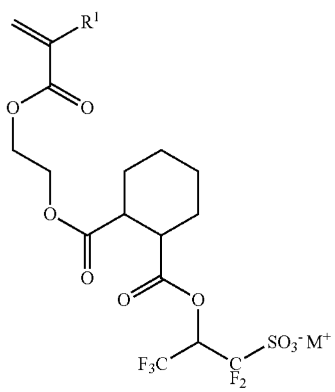
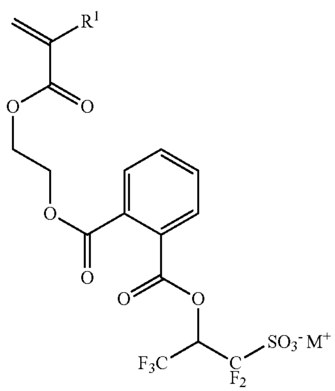
-continued
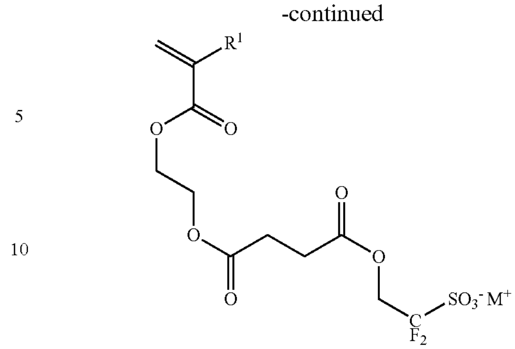
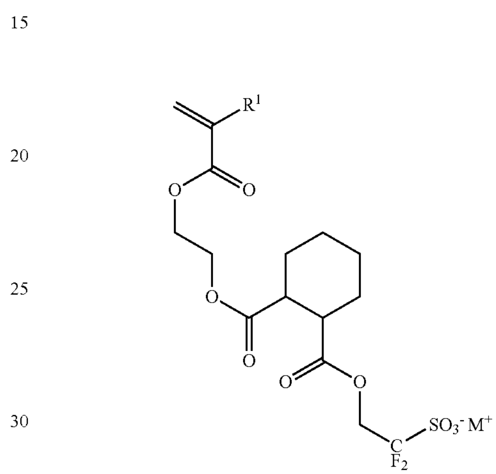
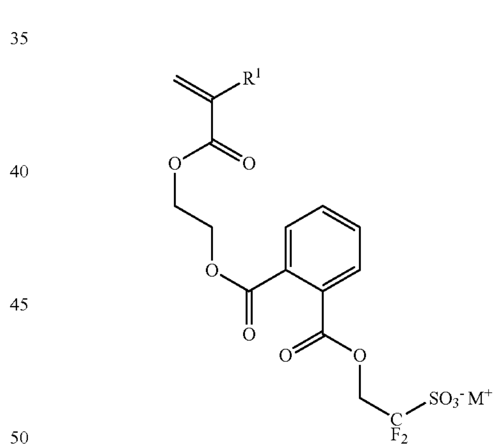
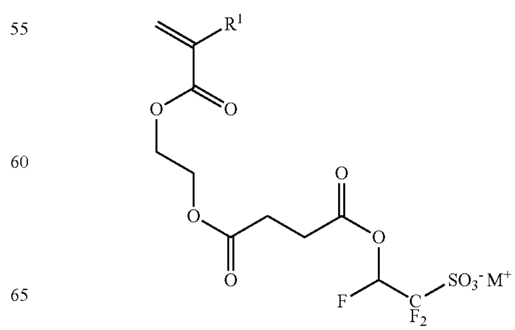

-continued
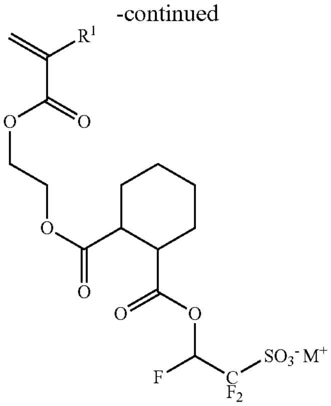
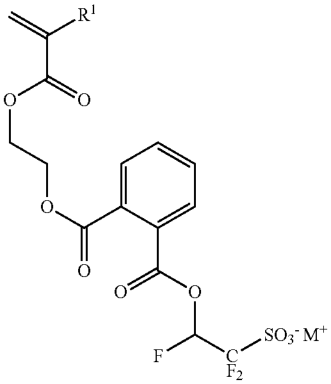
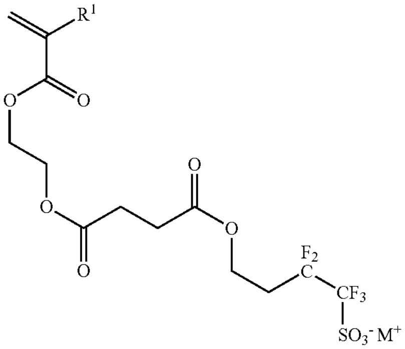
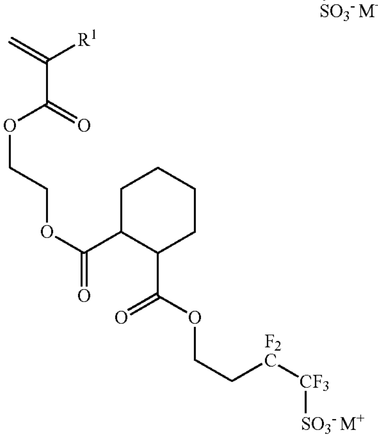
-continued
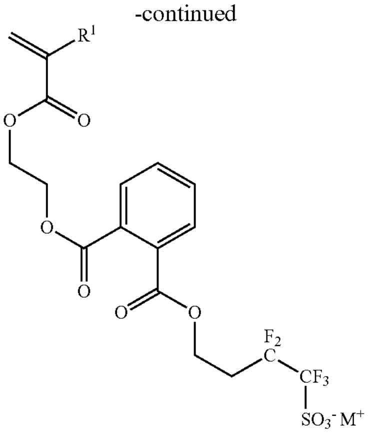
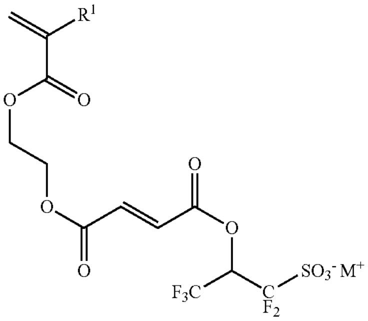
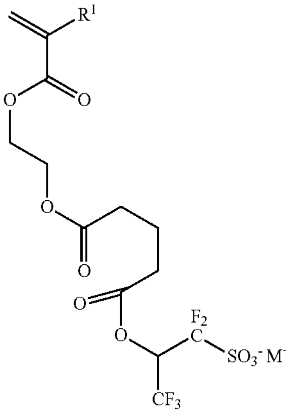
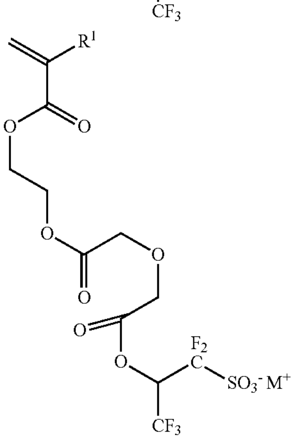

-continued
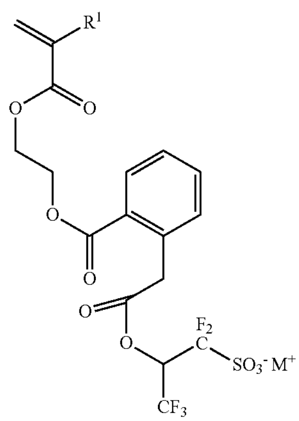
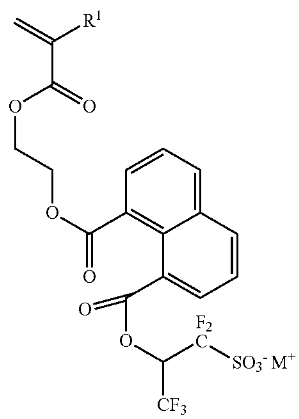
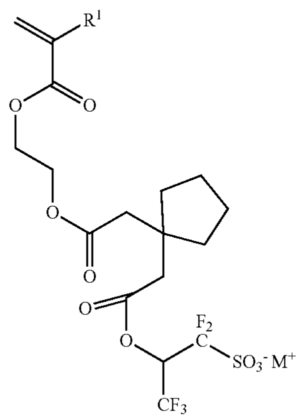
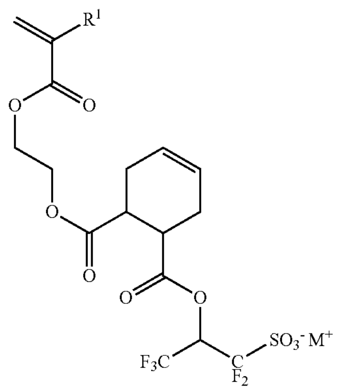
-continued
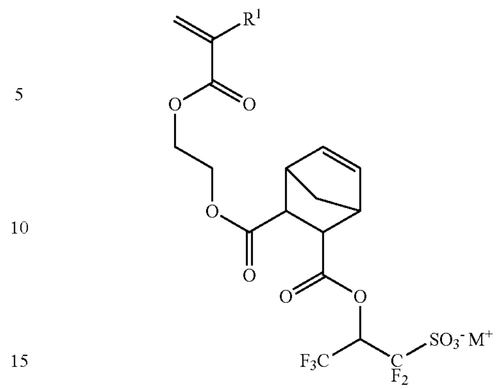
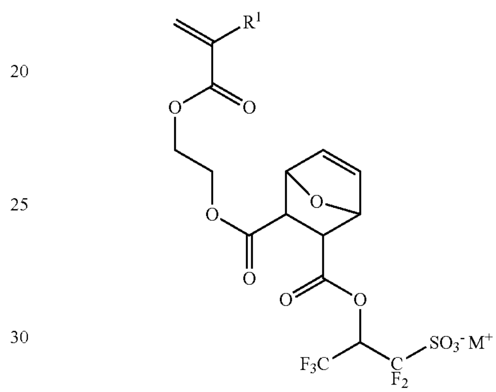
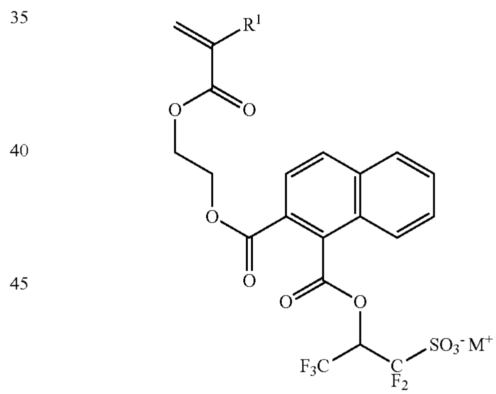
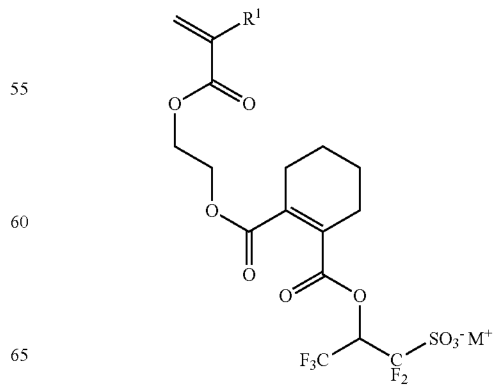

-continued
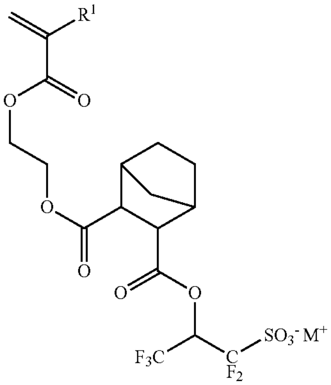
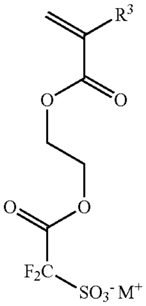
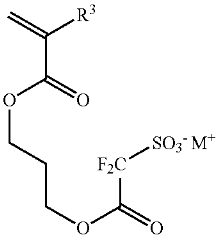
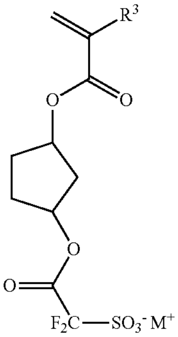
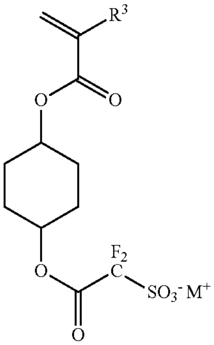
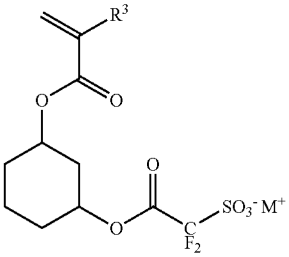
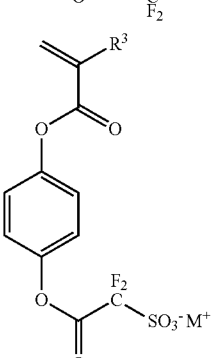
-continued
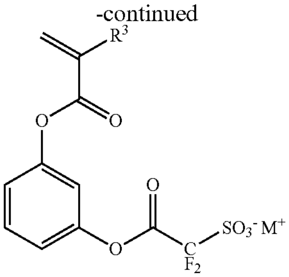
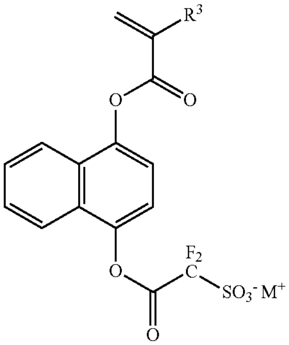
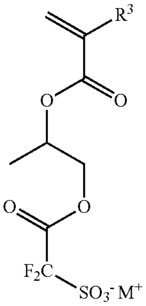
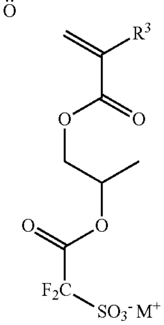
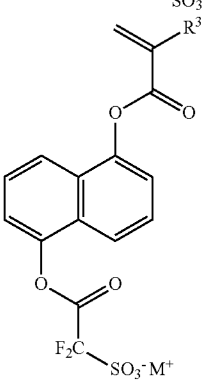
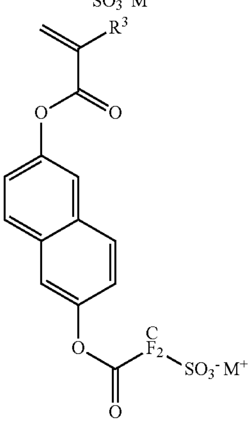
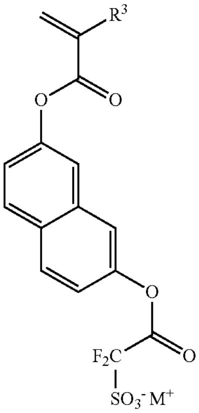
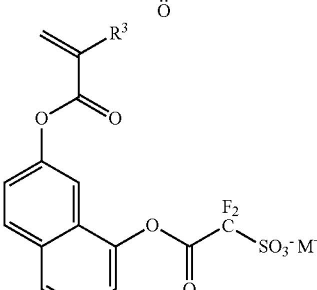

-continued
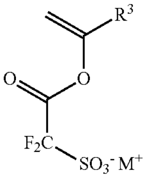
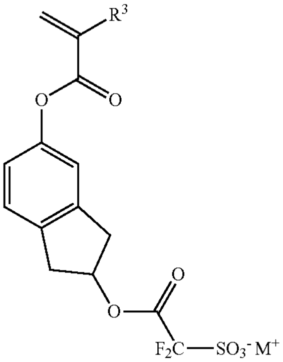
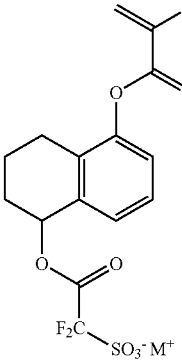
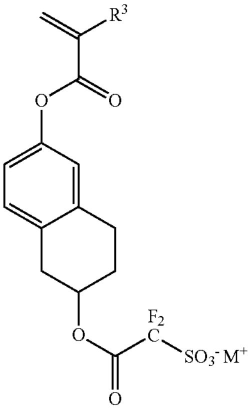
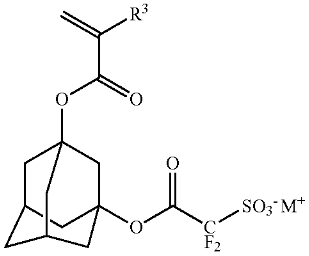
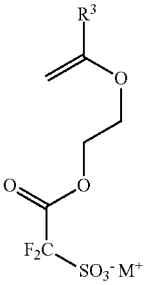
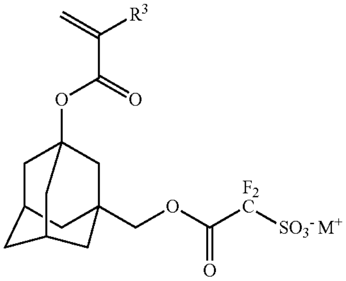
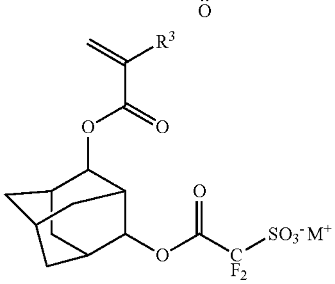
-continued
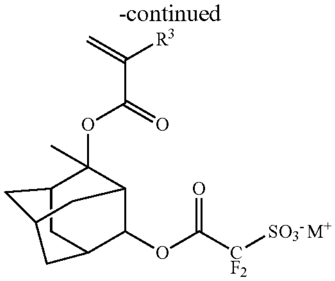
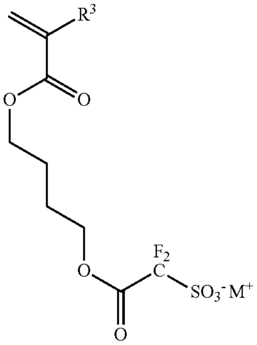
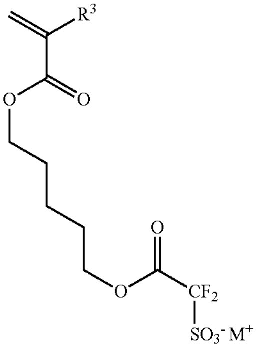
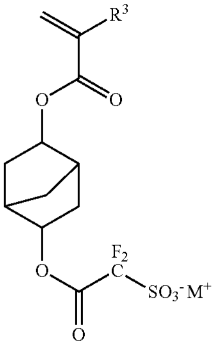
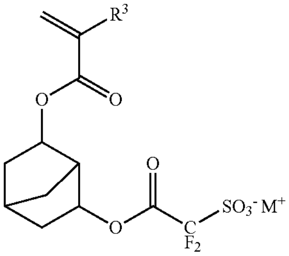
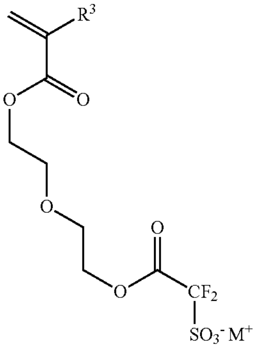
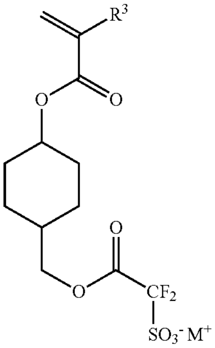

-continued
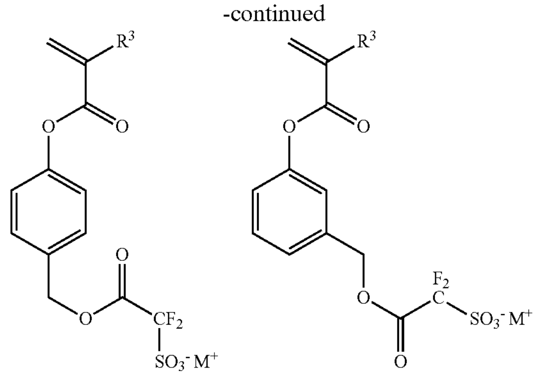
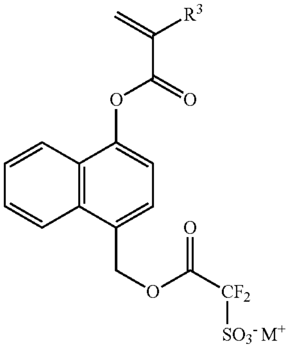
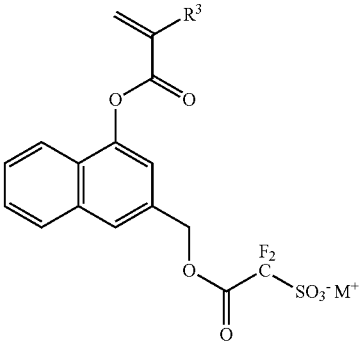
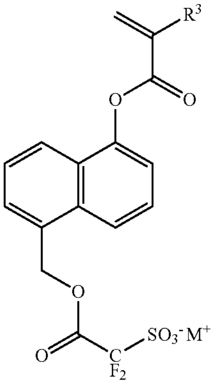
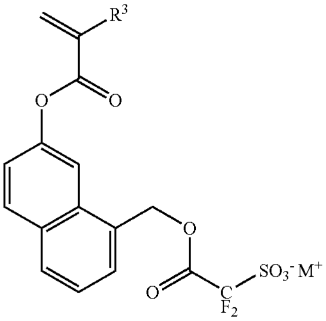
-continued
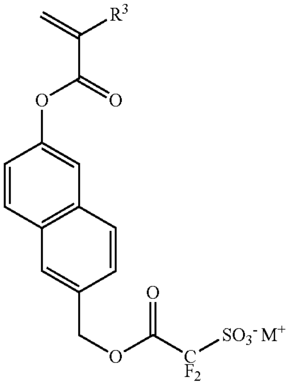
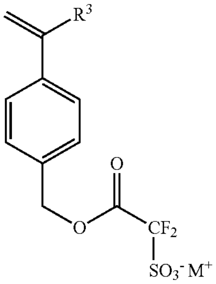
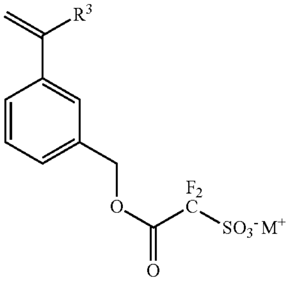
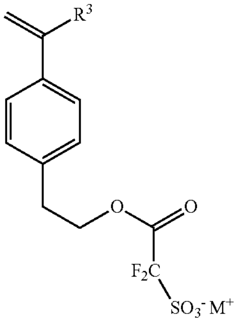
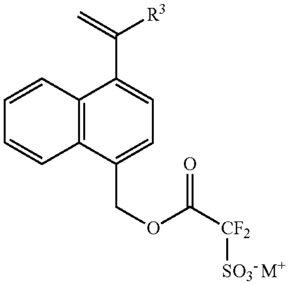
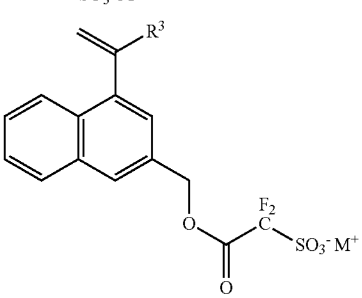
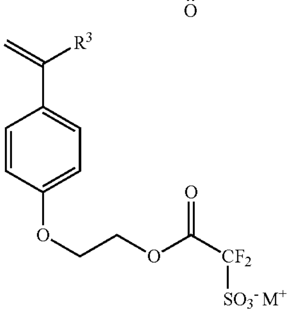

-continued
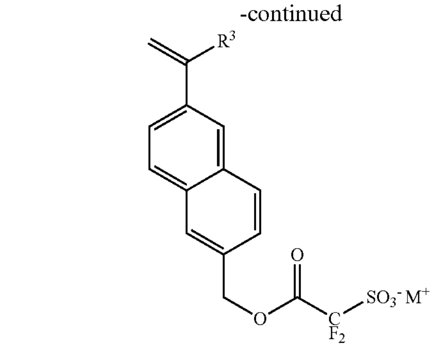
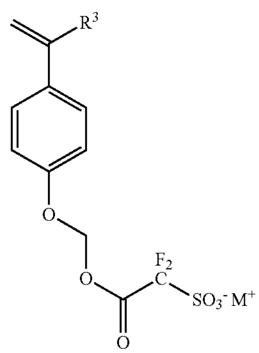
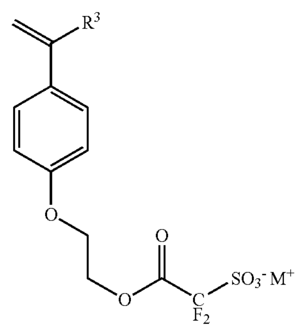
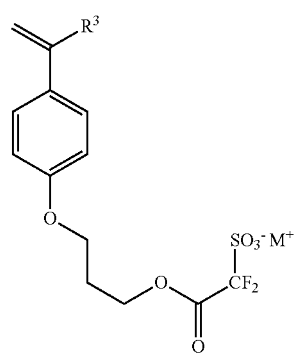
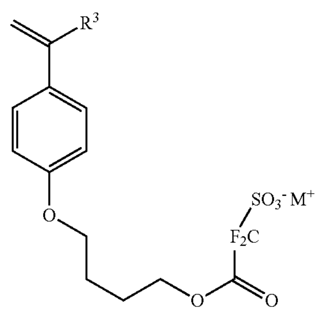
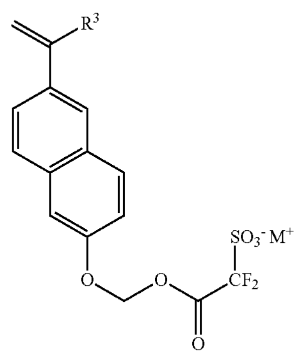
-continued
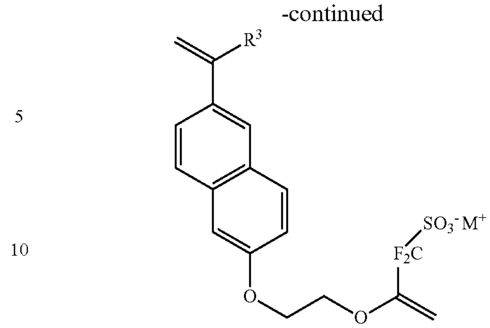
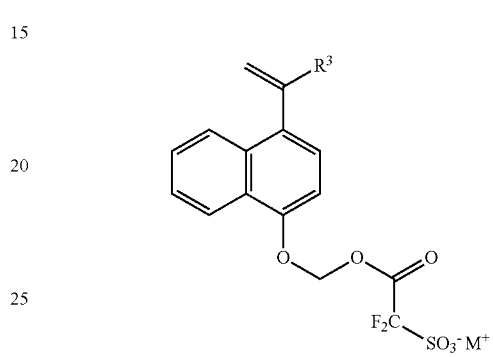
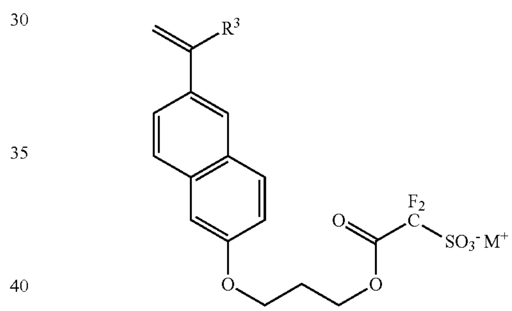
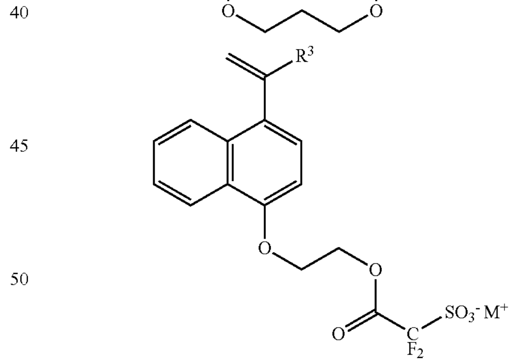
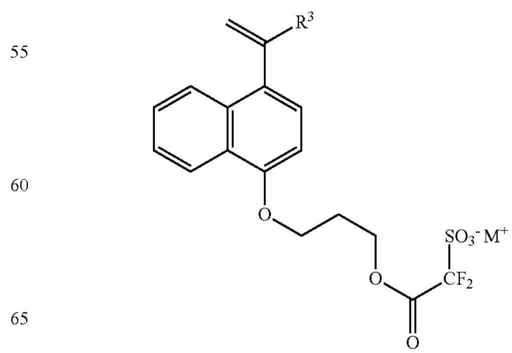

-continued
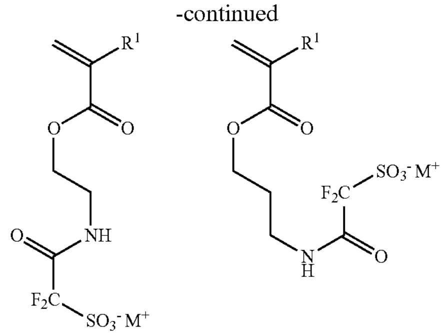
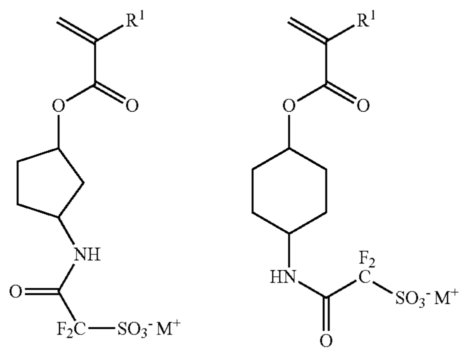
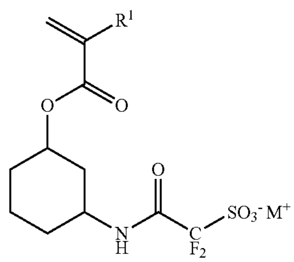
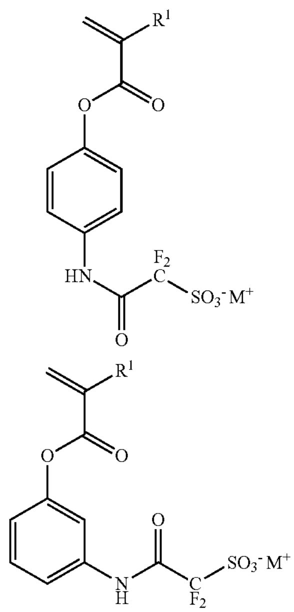
-continued
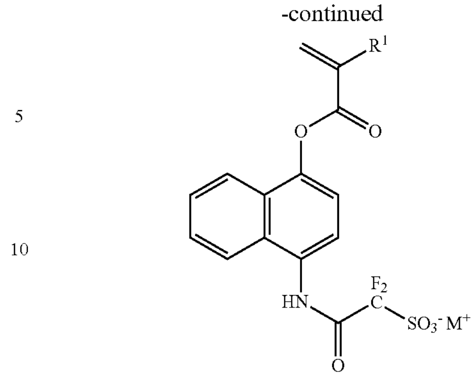
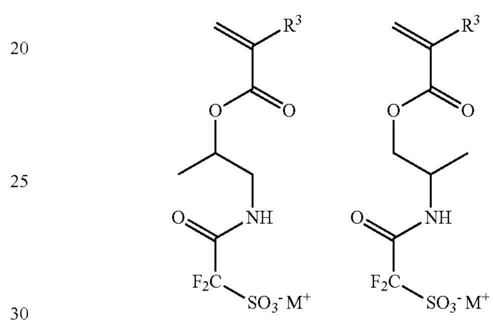
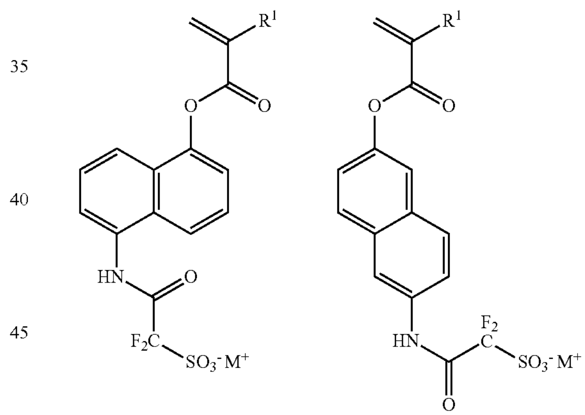
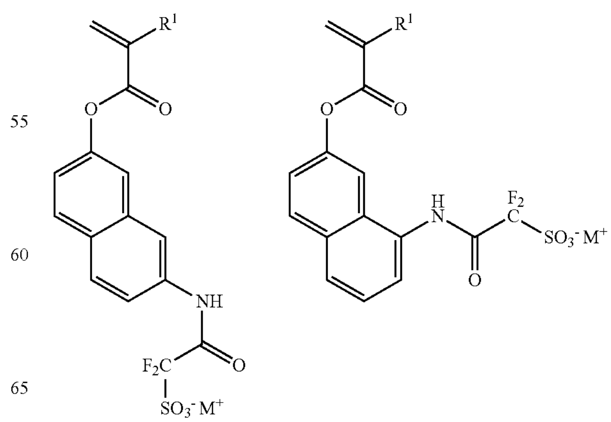

-continued
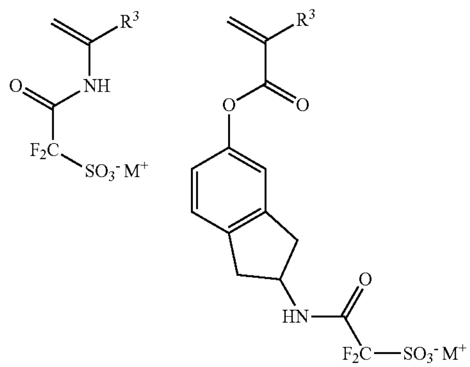
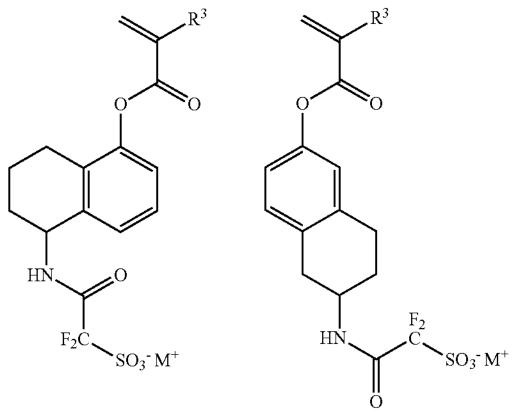
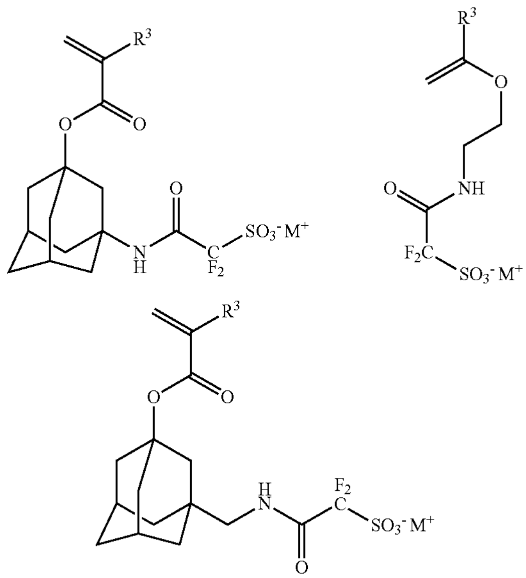
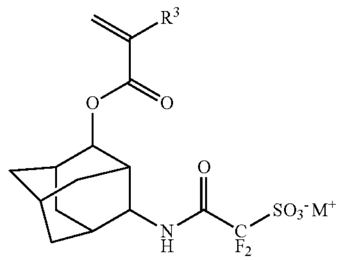
-continued
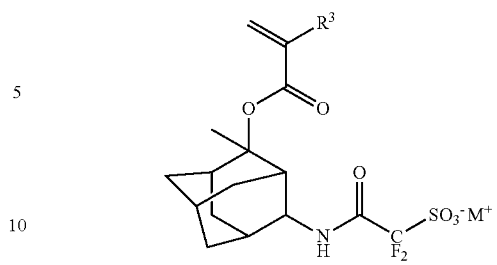
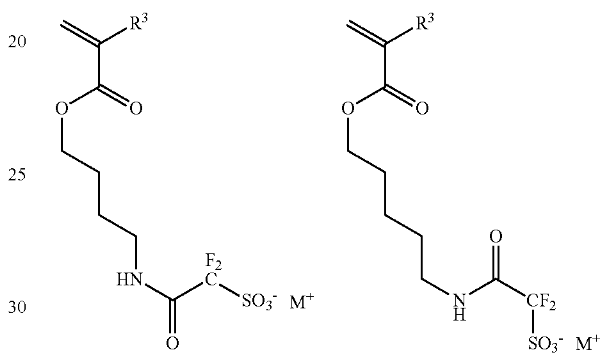
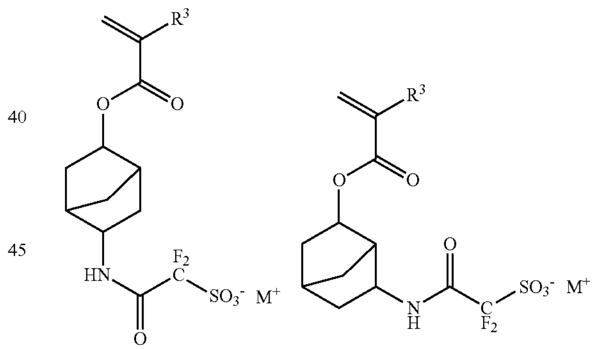
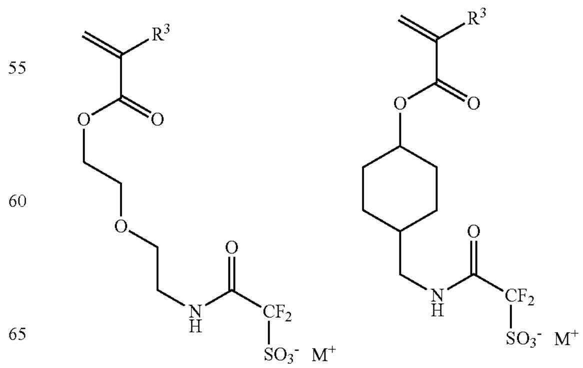

-continued
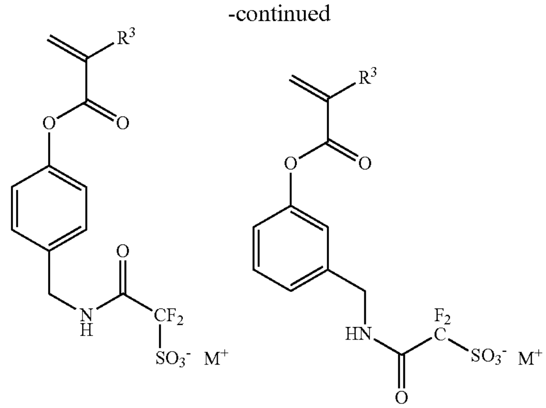
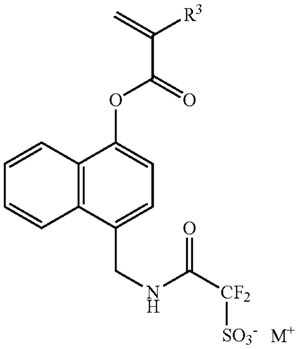
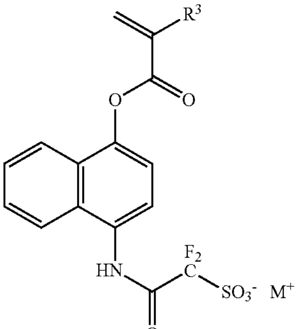
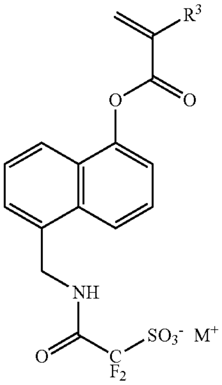
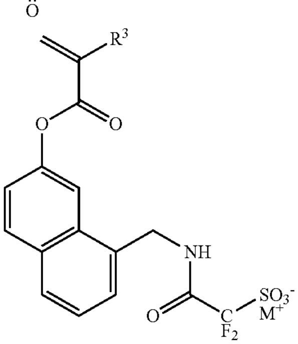
-continued
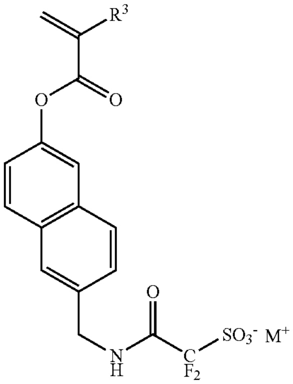
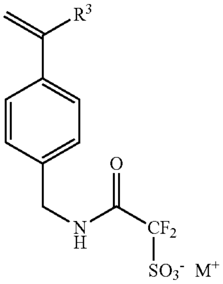
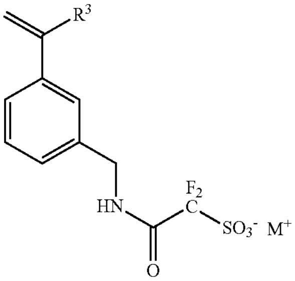
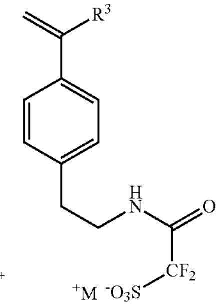
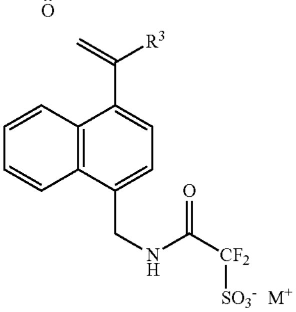
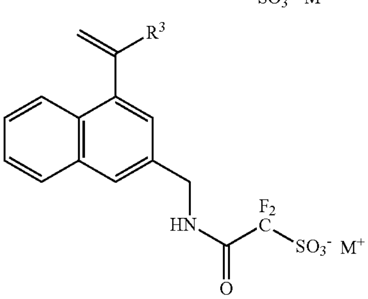
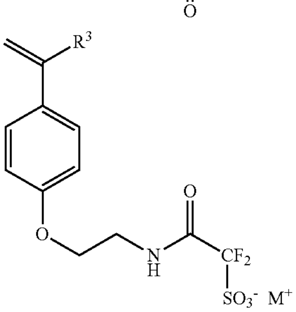

-continued
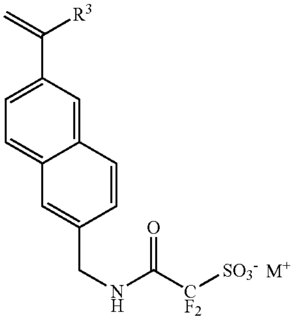
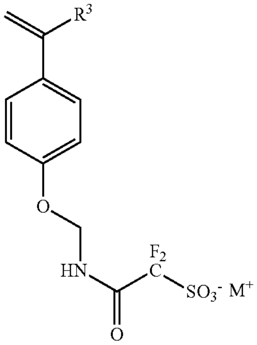
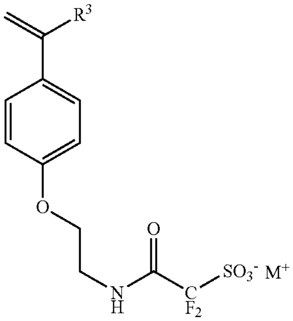
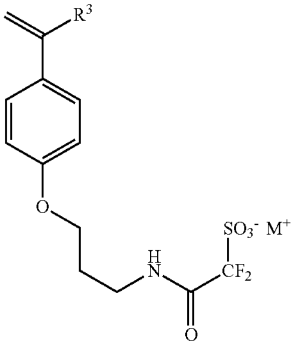
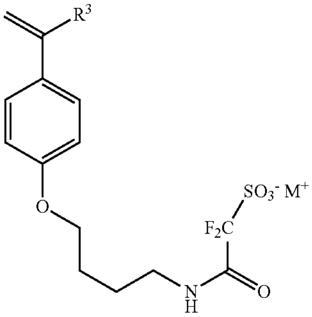
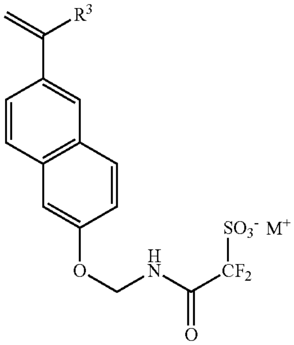
-continued
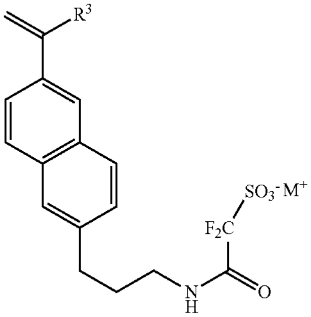
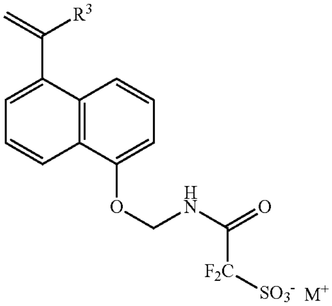
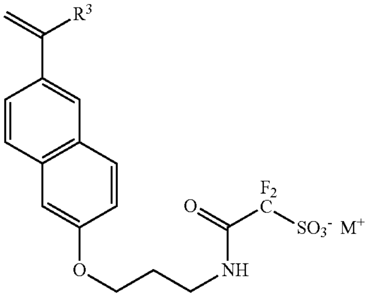
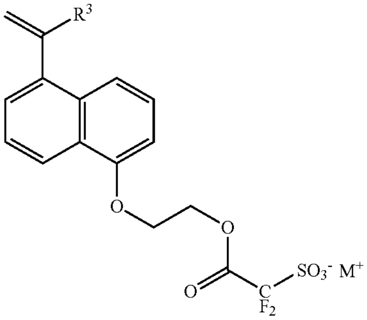
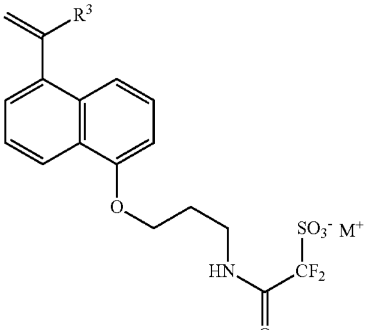

-continued
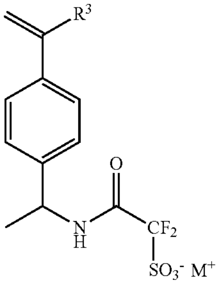
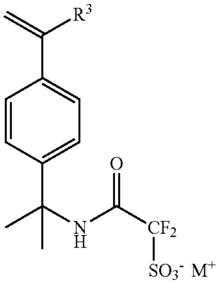
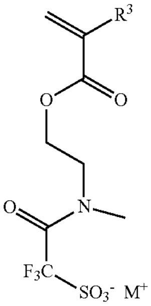
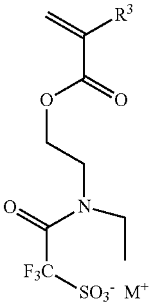
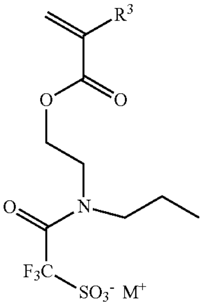
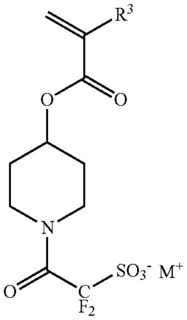
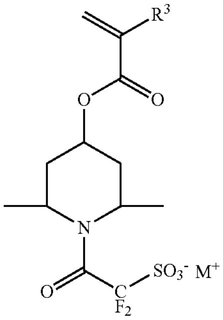
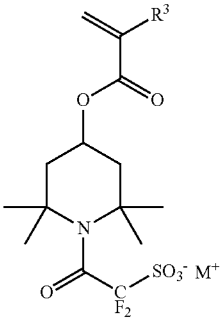
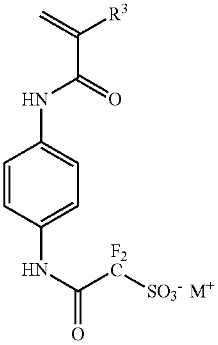
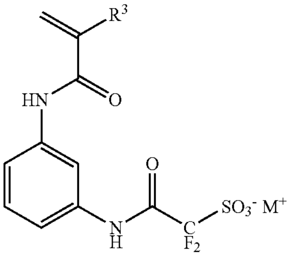
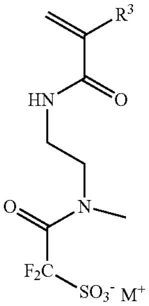
-continued
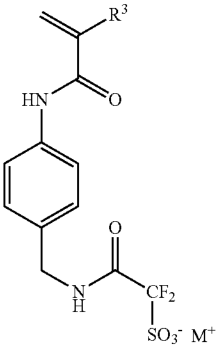
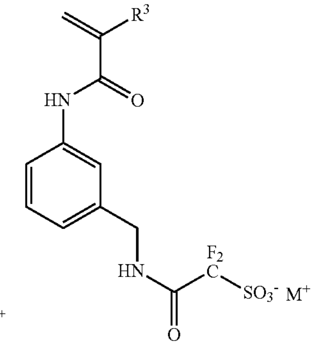
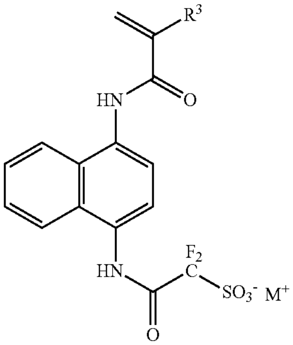
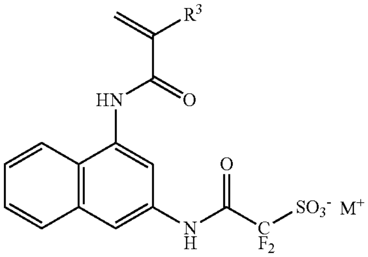
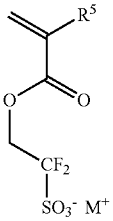
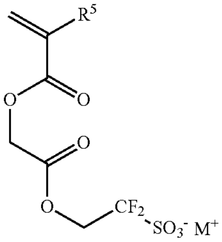
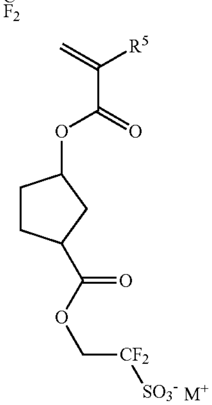
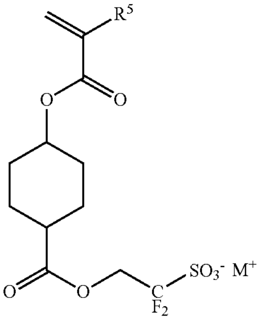

-continued
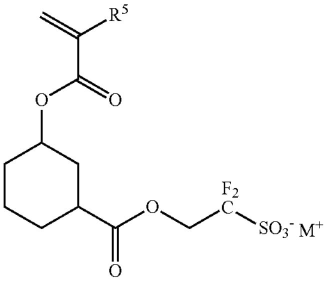
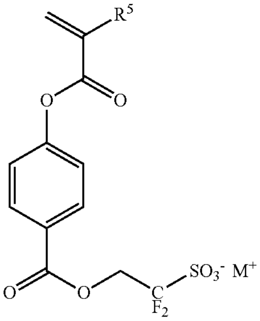
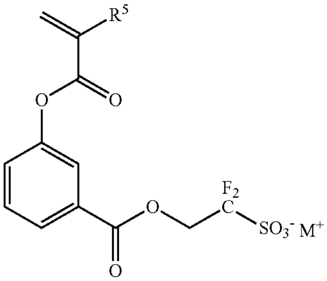
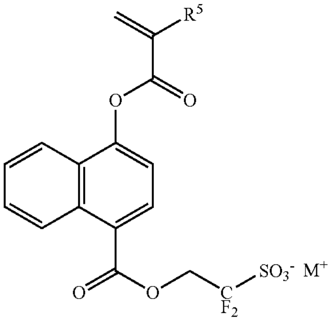
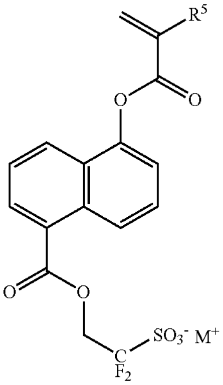
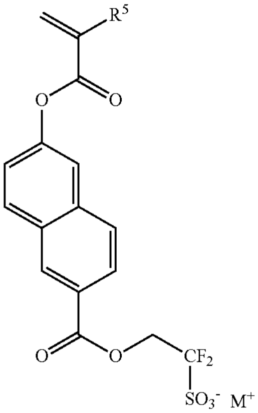
-continued
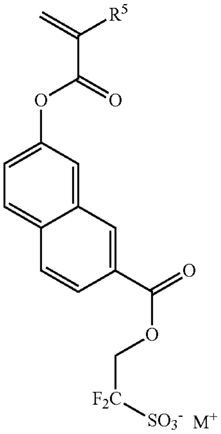
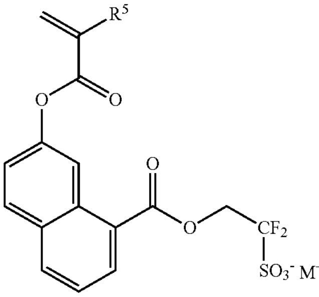
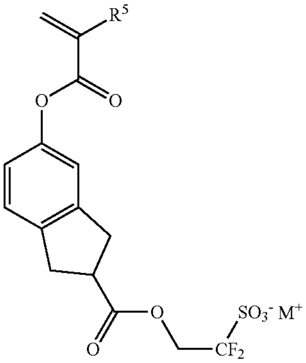
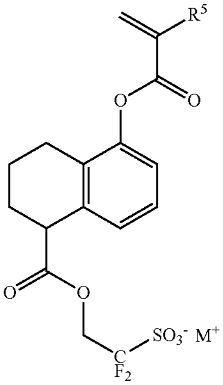
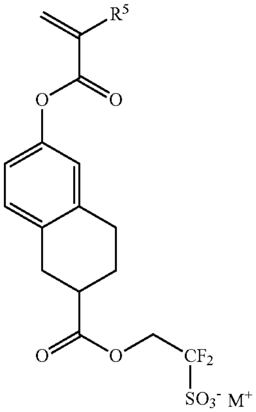
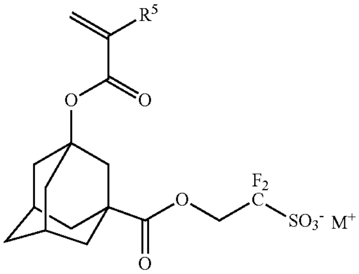

-continued
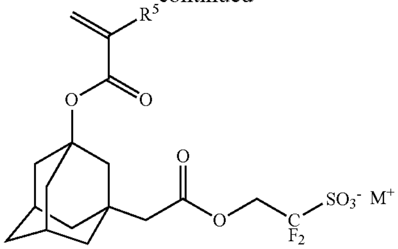
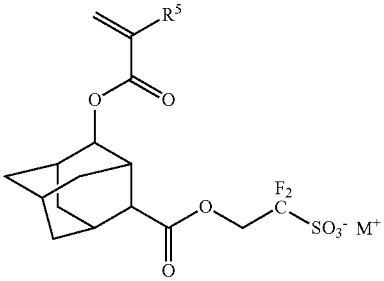
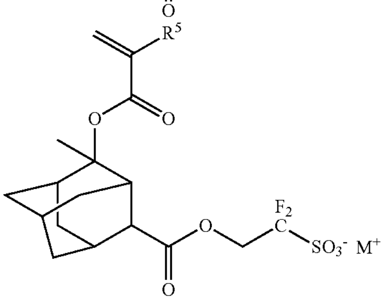
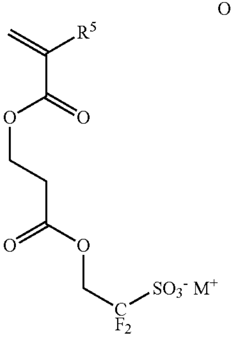
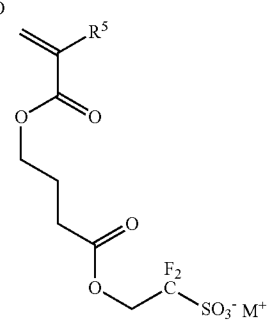
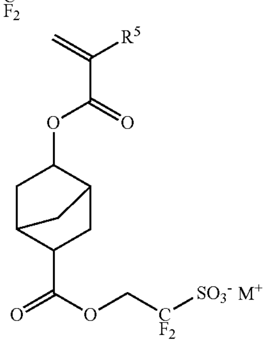
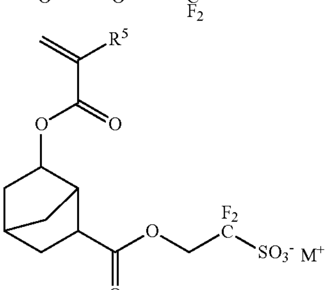
-continued
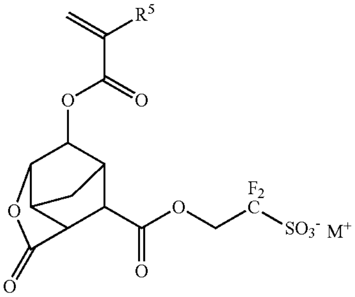
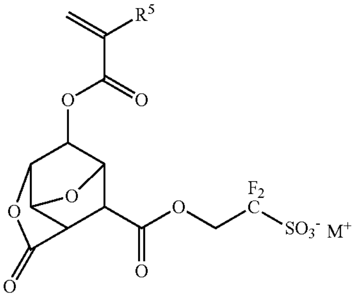
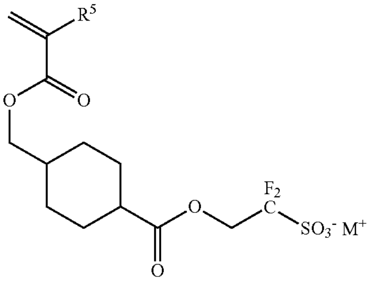
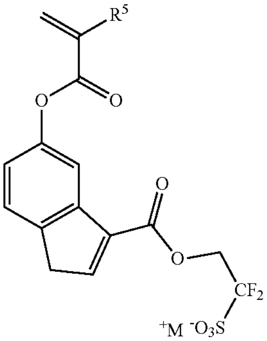
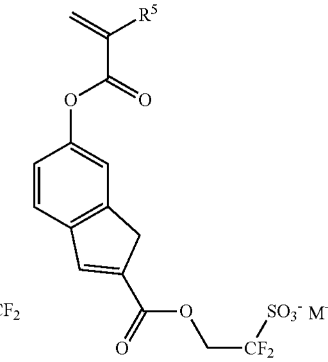
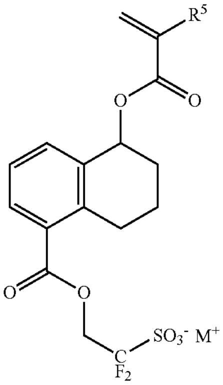
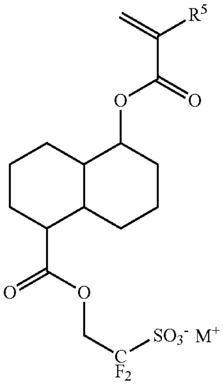

-continued
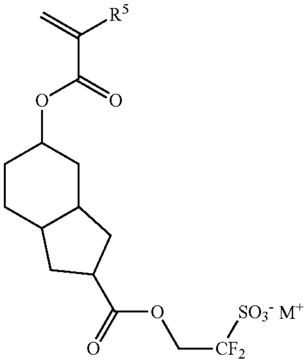
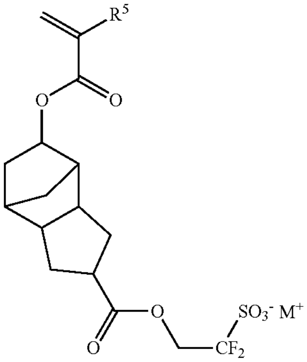
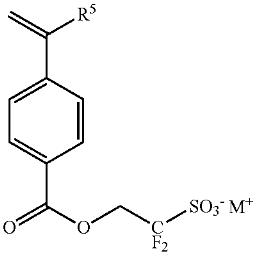
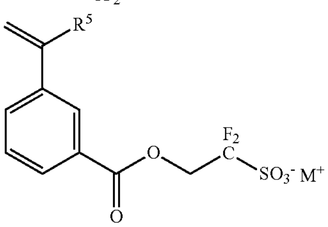
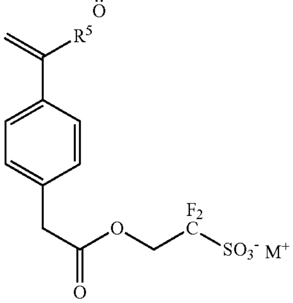
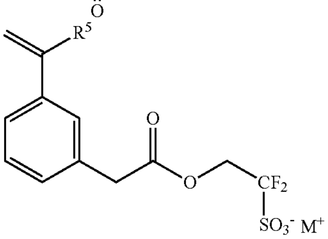
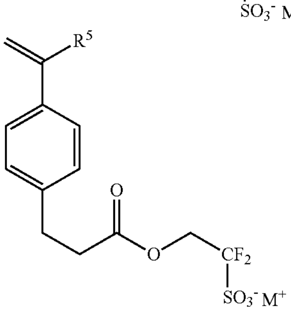
-continued
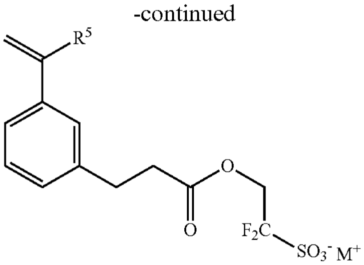
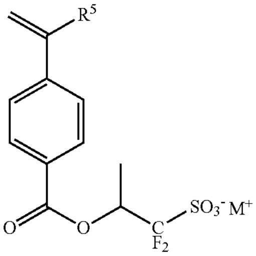
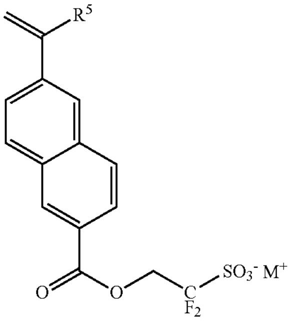
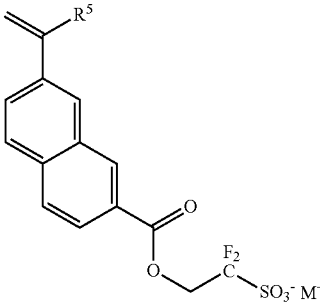
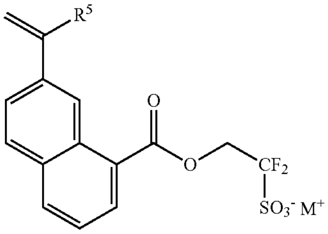
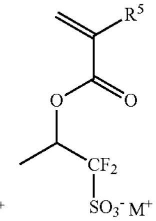
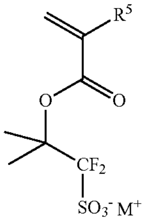
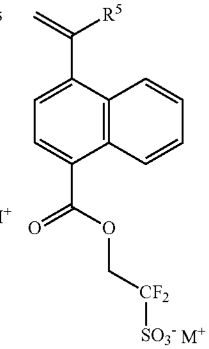

-continued
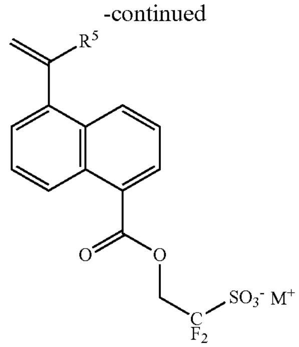
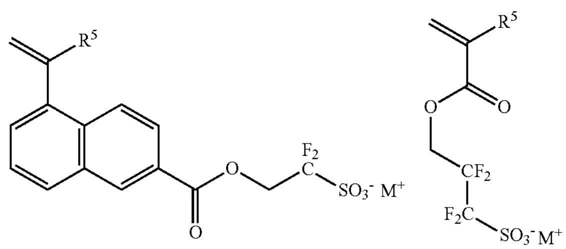
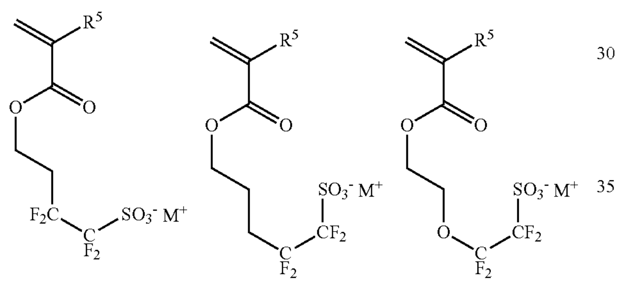
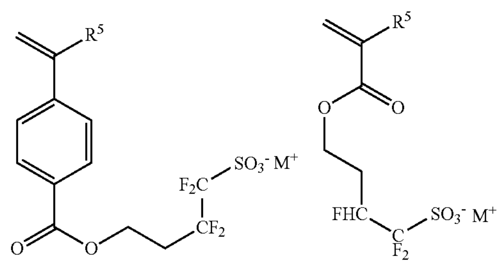
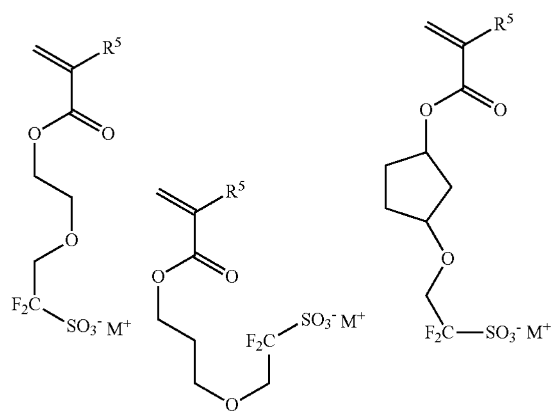
-continued
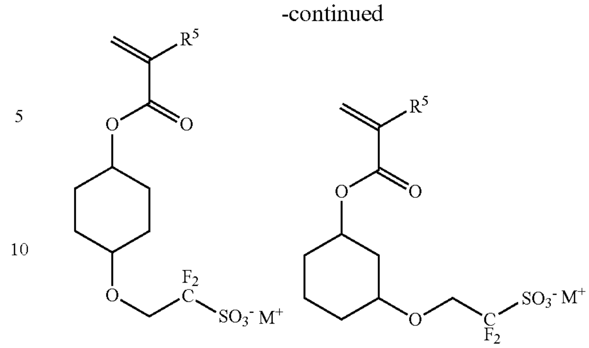
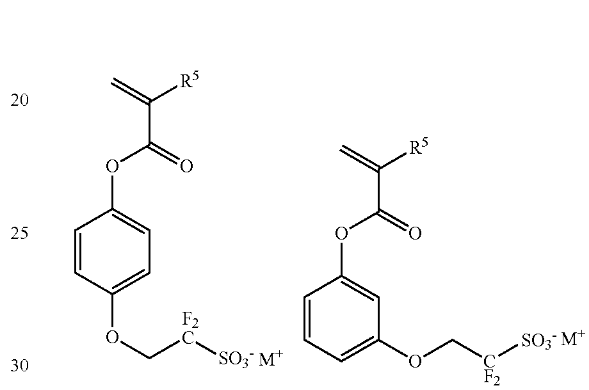
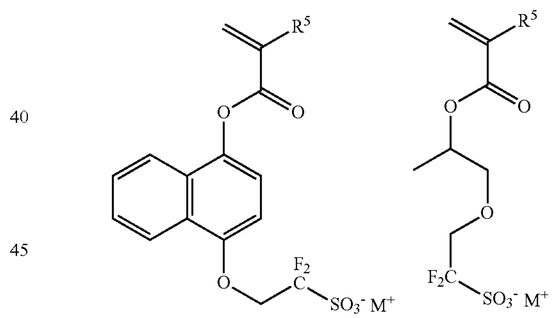
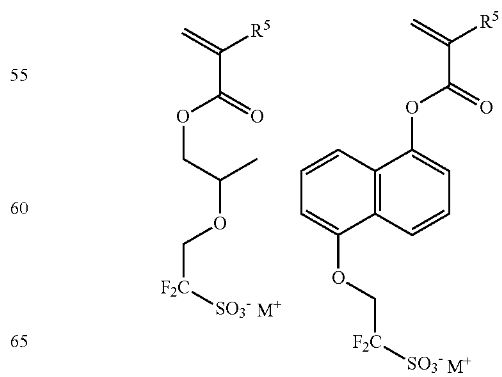

-continued
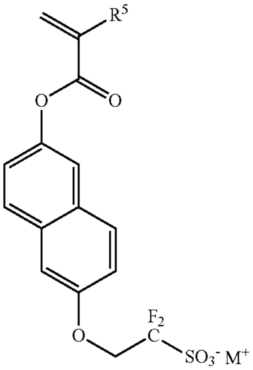
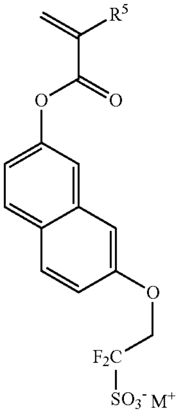
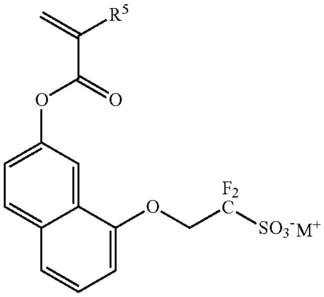
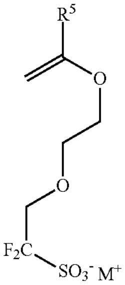
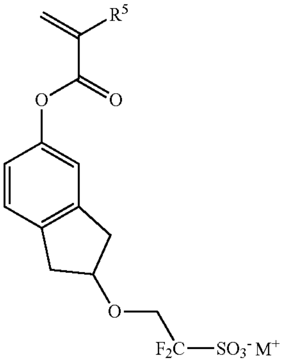
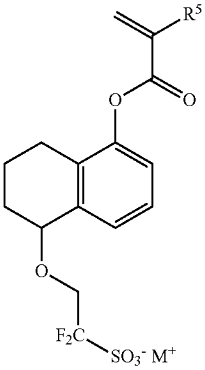
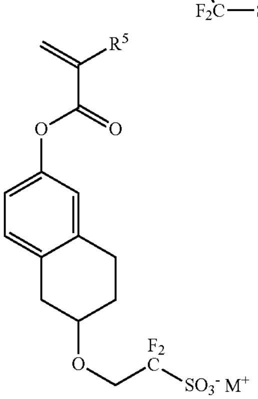
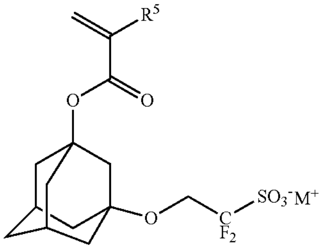
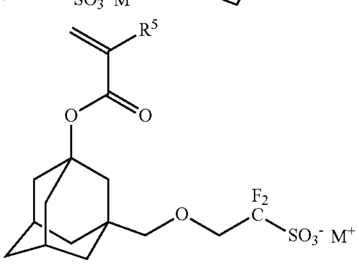
-continued
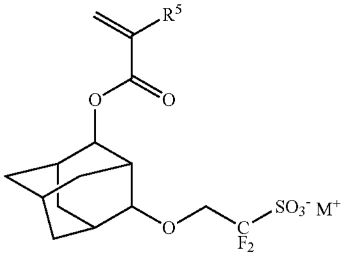
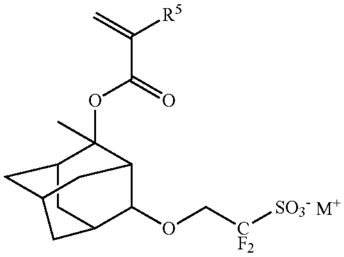
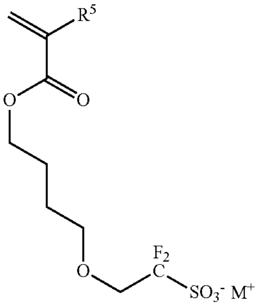
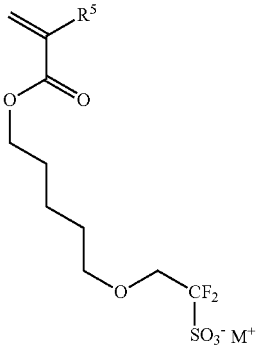
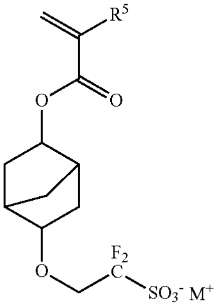
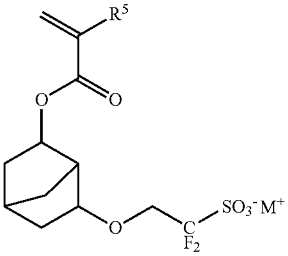
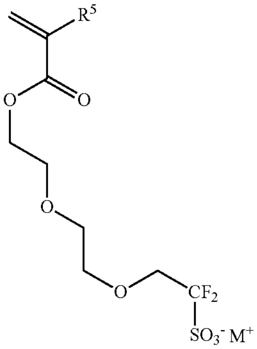
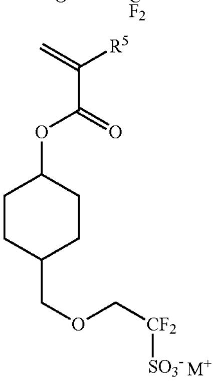

-continued
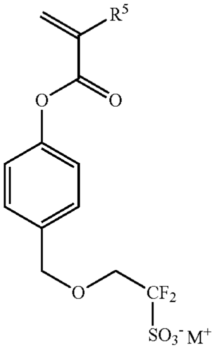
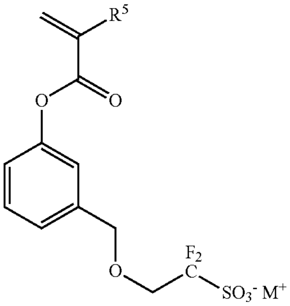
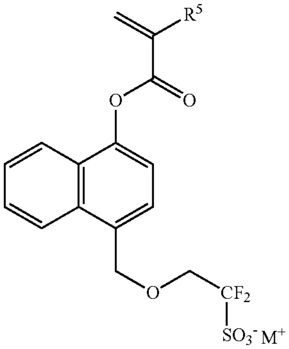
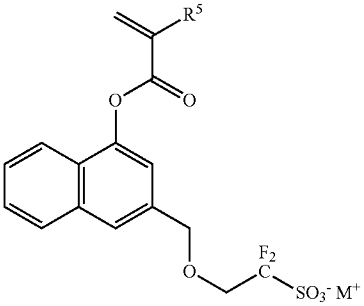
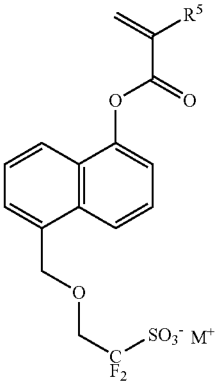
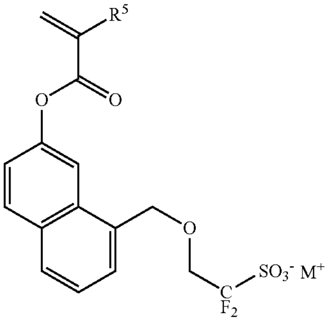
-continued
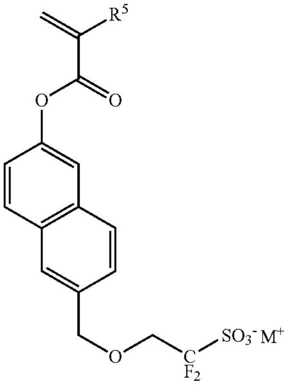
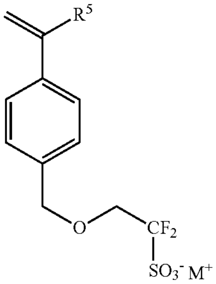
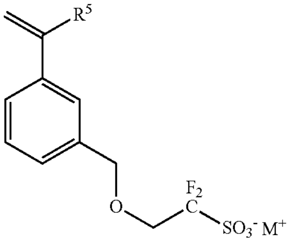
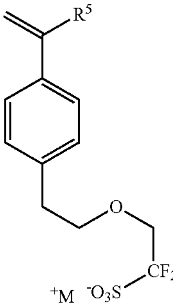
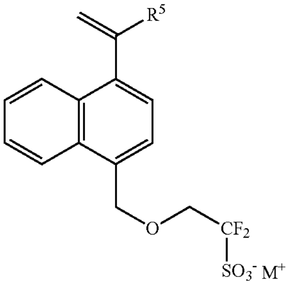
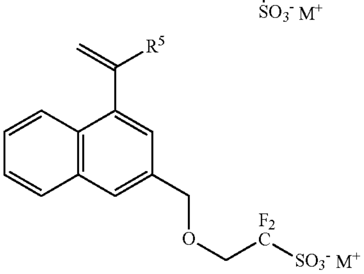
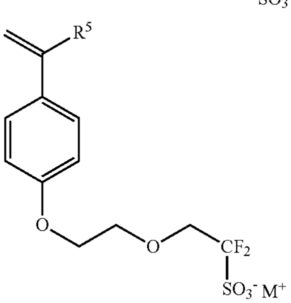

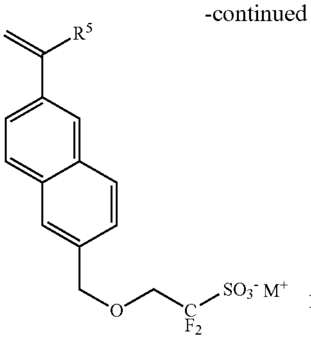
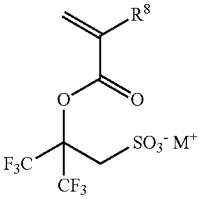
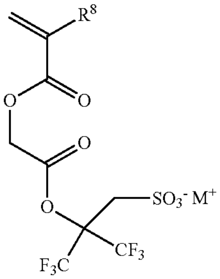
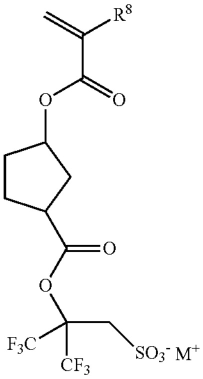
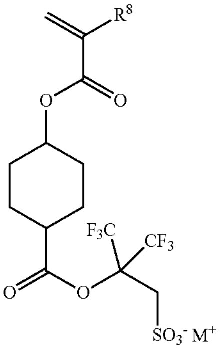
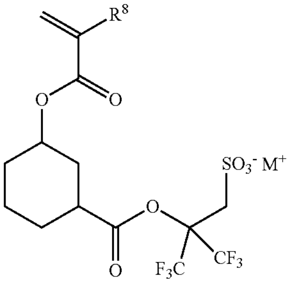
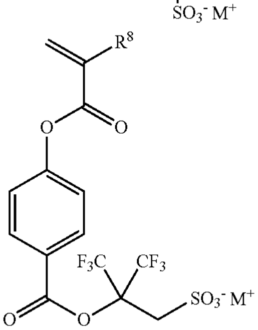
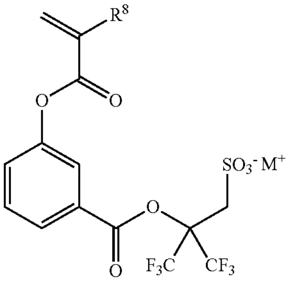
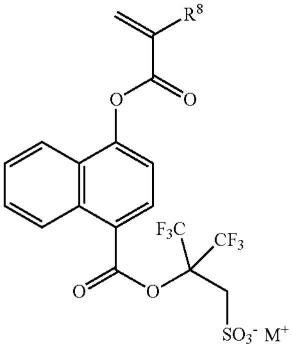
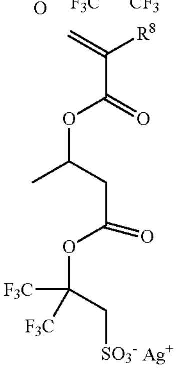
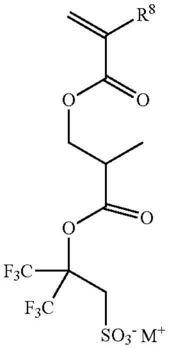
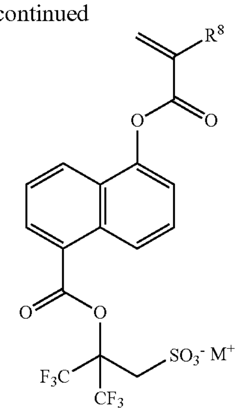
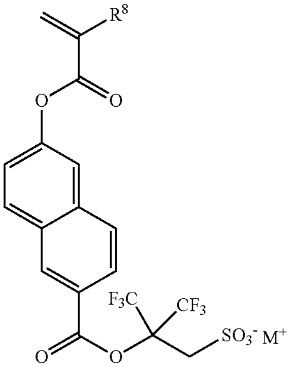
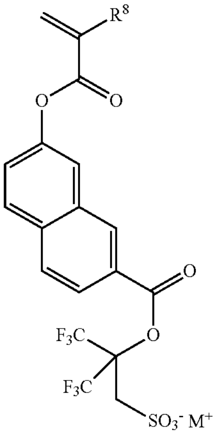
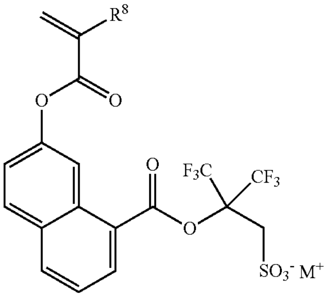
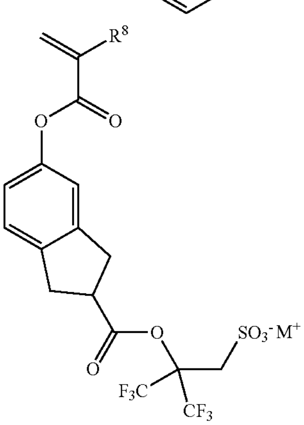
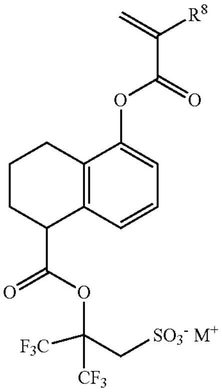

-continued
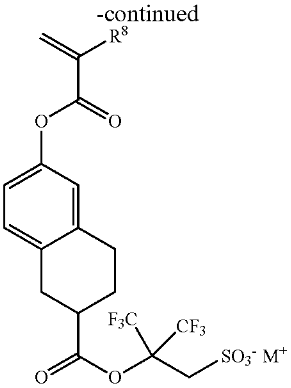
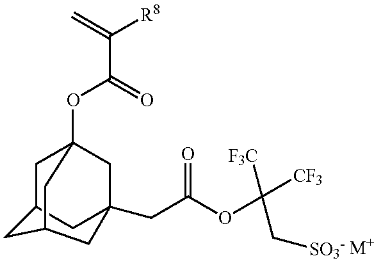
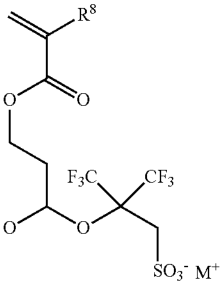
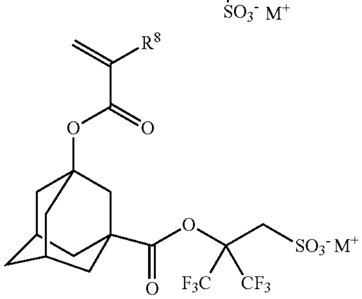
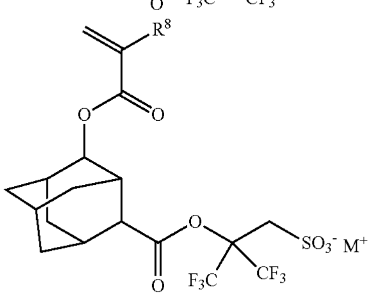
-continued
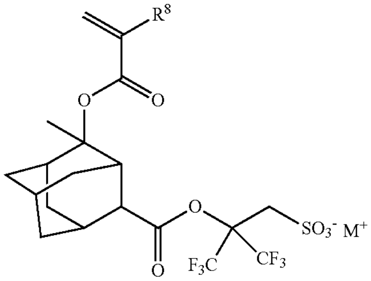
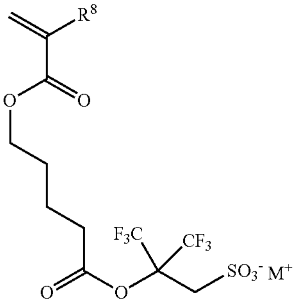
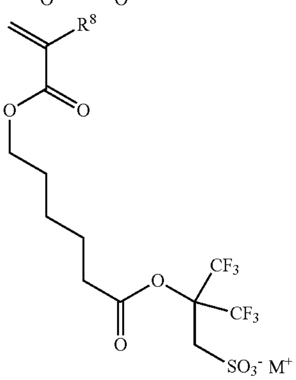
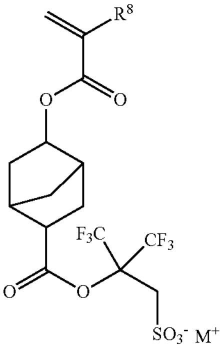
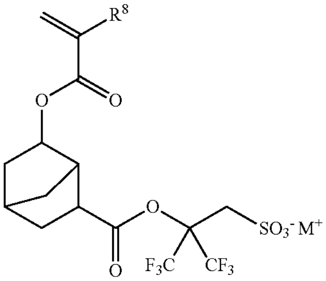
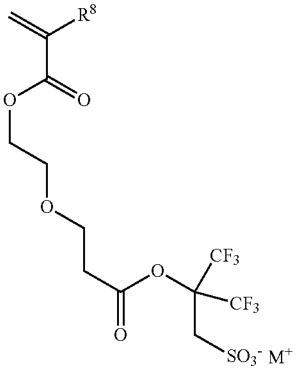
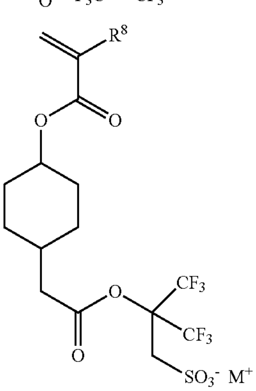

-continued
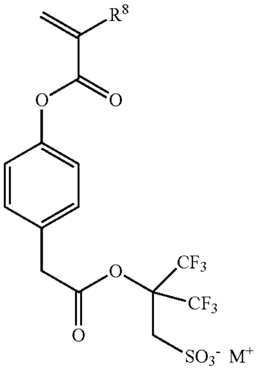
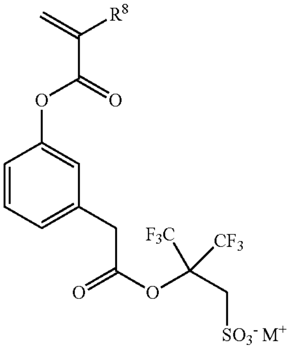
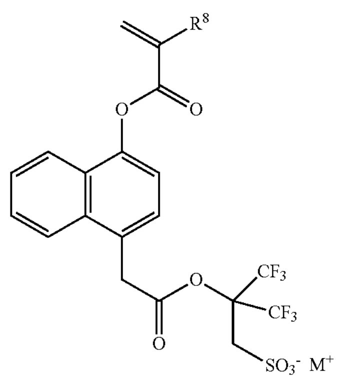
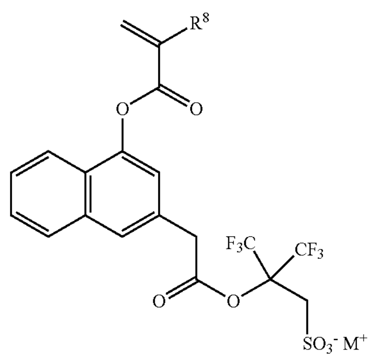
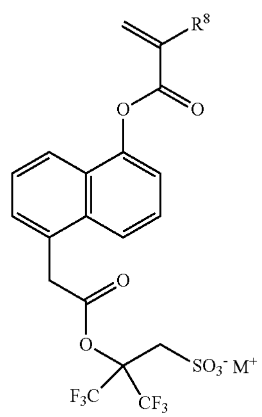
-continued
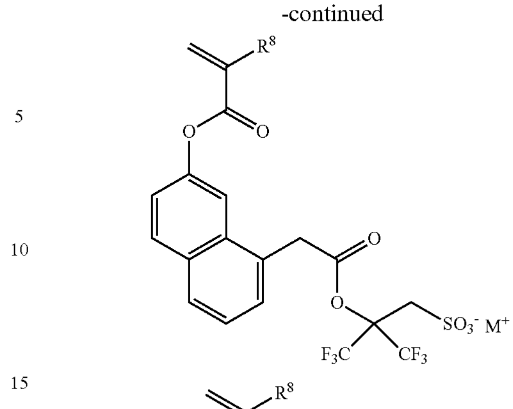
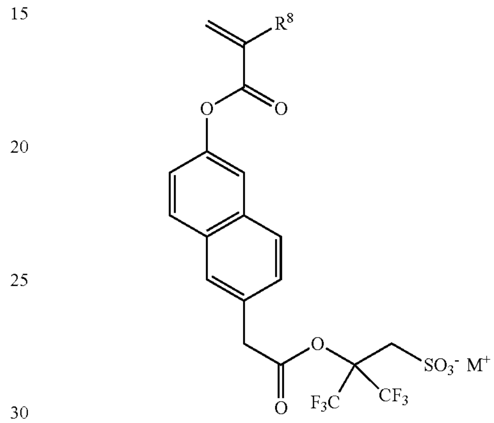
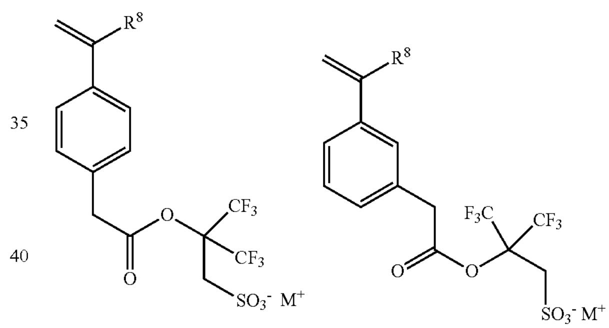
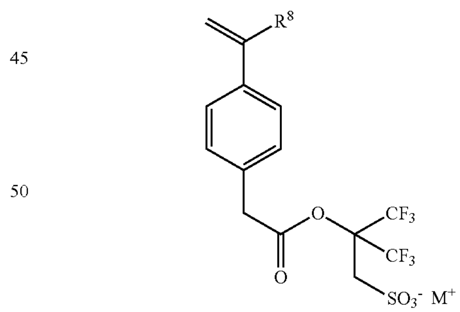
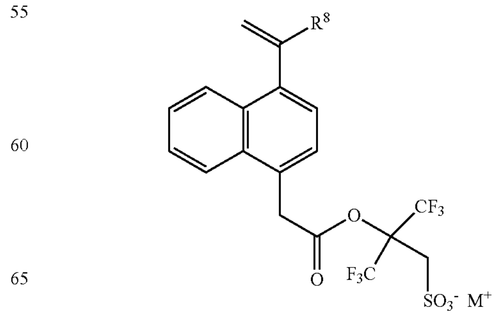

-continued
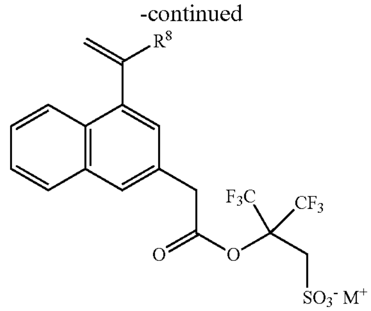
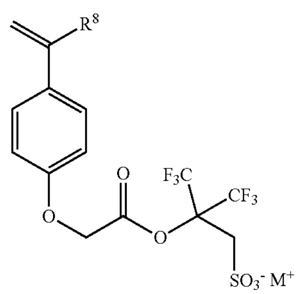
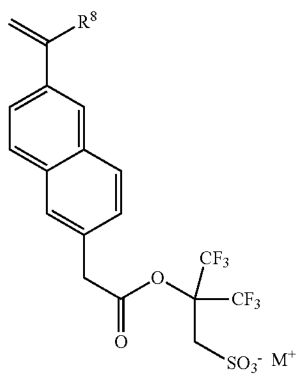
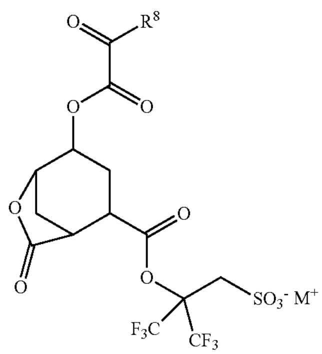
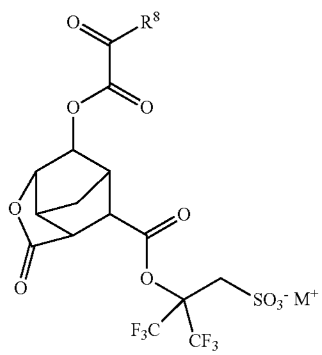
-continued
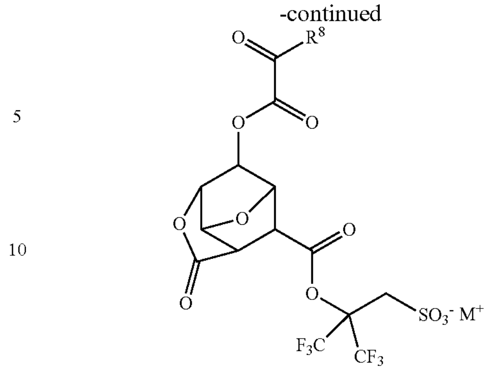
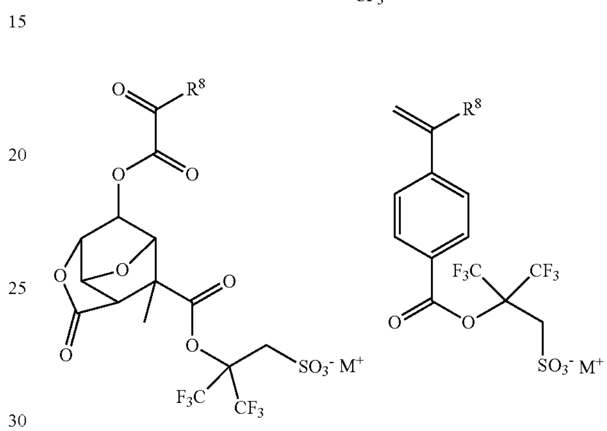
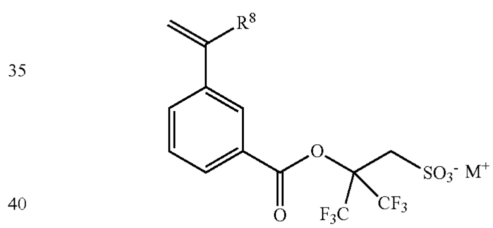
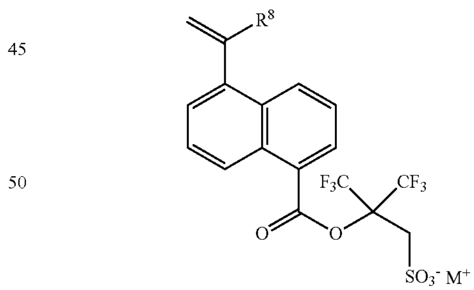
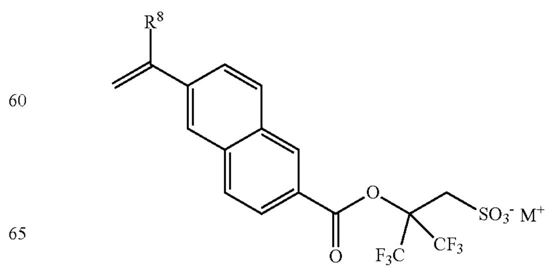

-continued
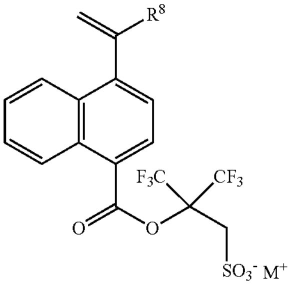
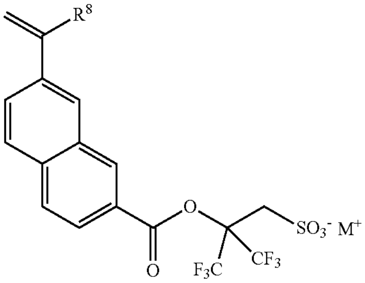
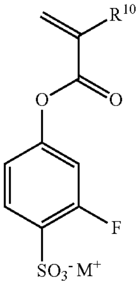
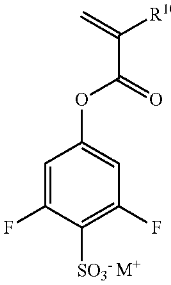
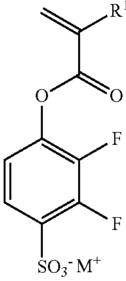
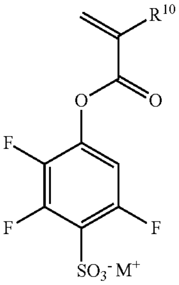
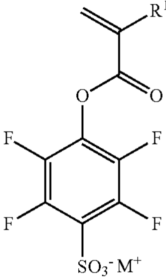
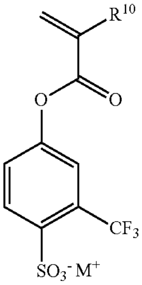
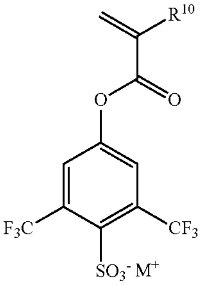
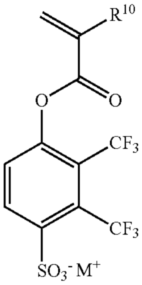
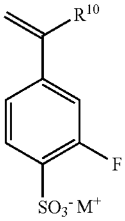
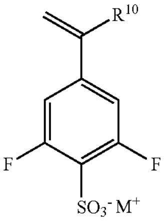
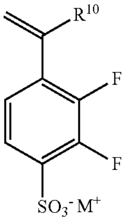
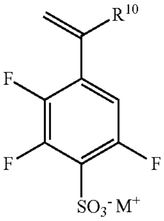
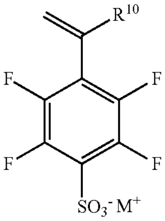
-continued
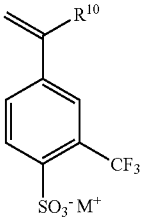
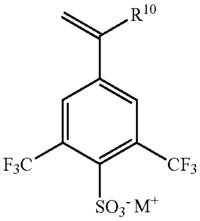
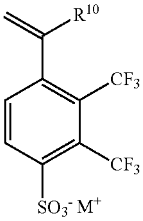
Specific examples of sulfonimide monomers and sulfonimide salt monomers for obtaining the repeating unit-A6 of the above general formula can include the following.
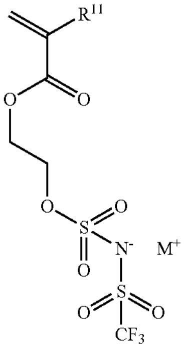
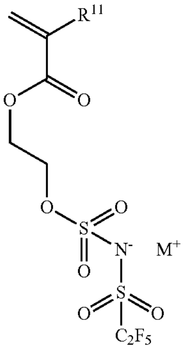
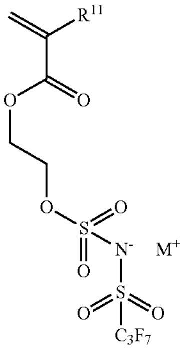
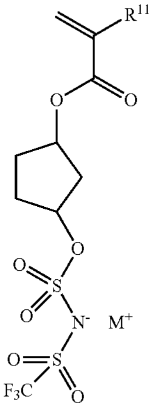
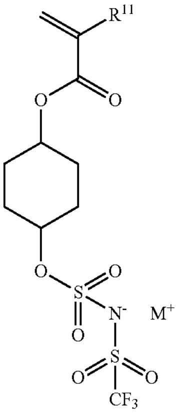
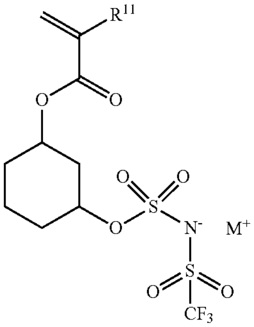
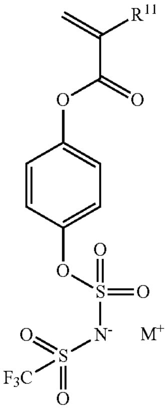

-continued
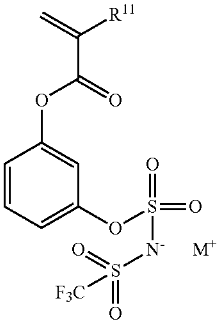
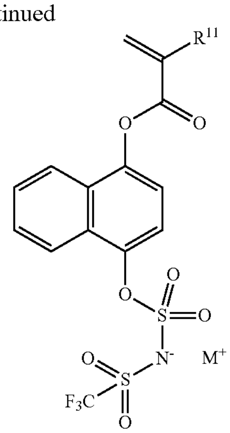
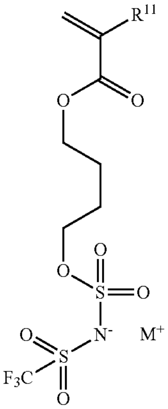
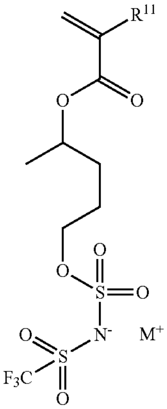
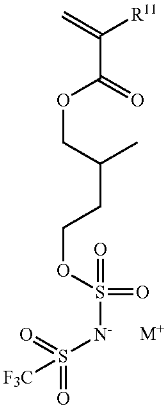
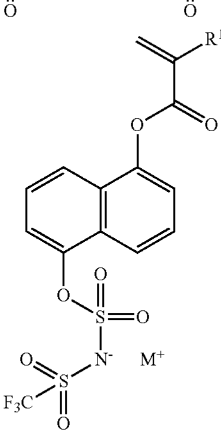
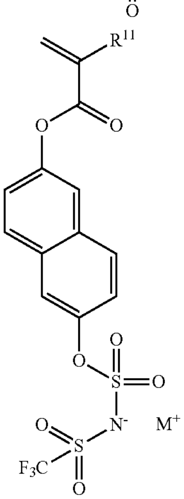
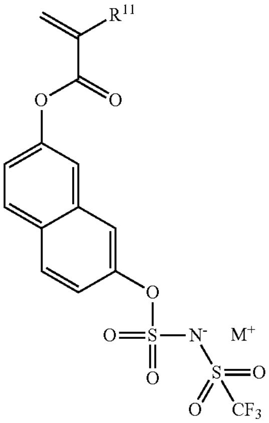
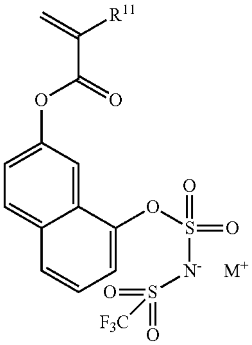
-continued
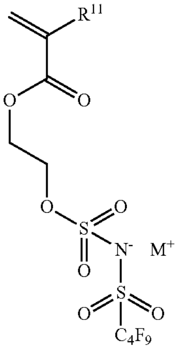
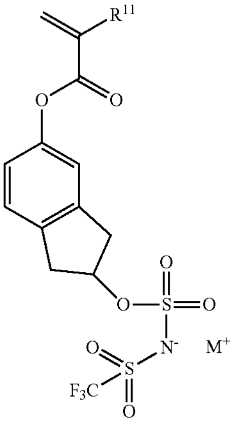
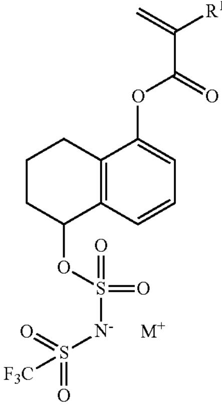
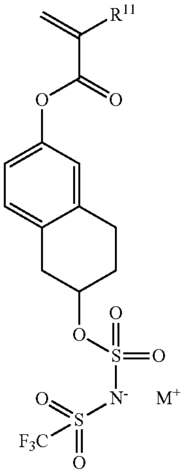
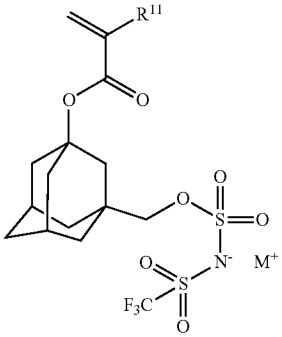
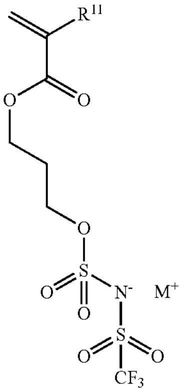
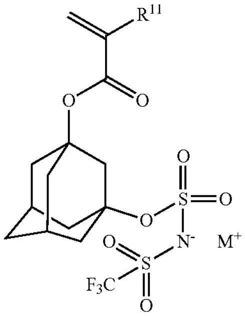
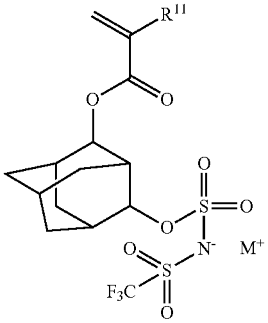

-continued
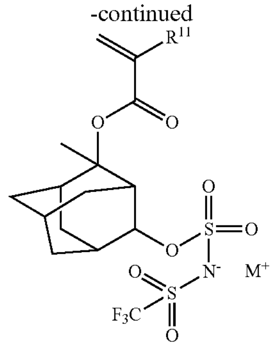
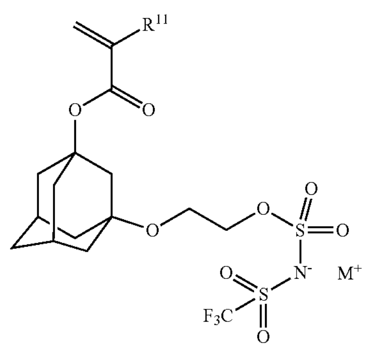
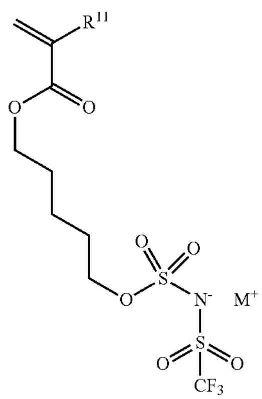
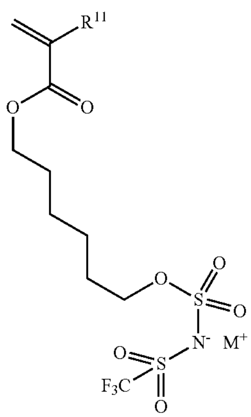
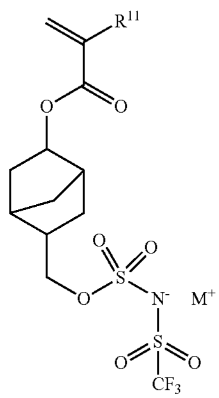
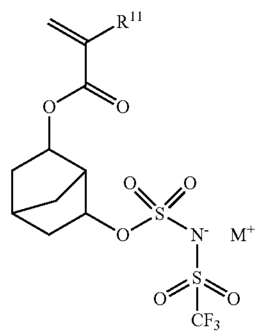
-continued
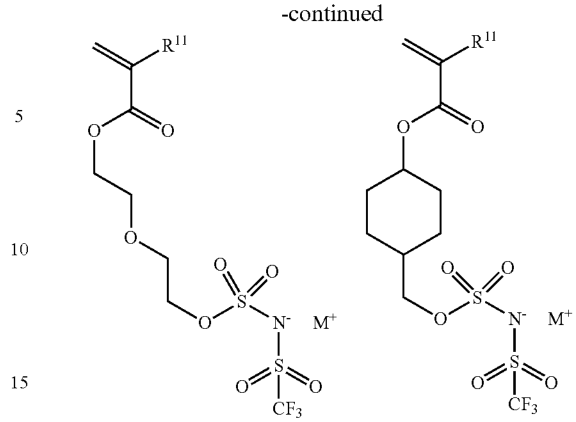
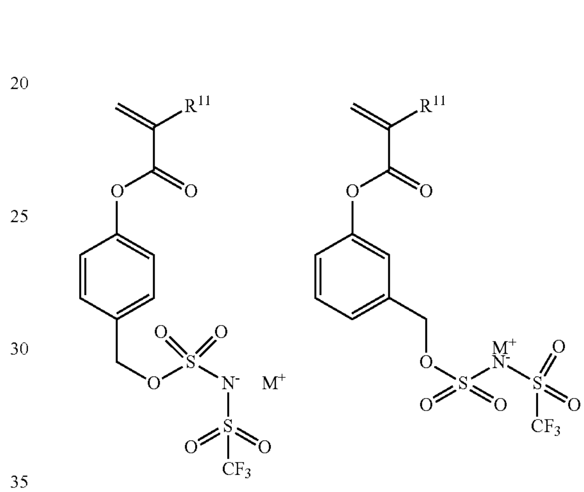
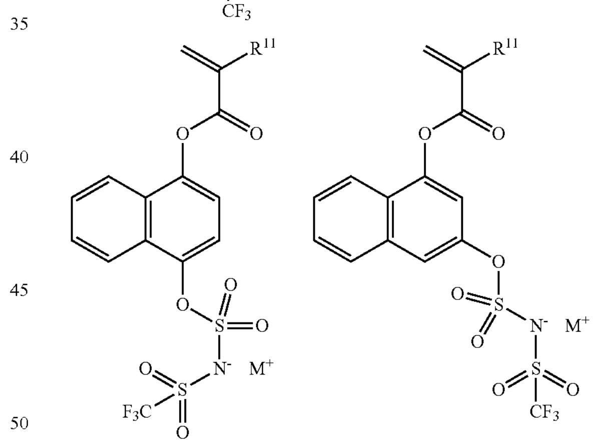
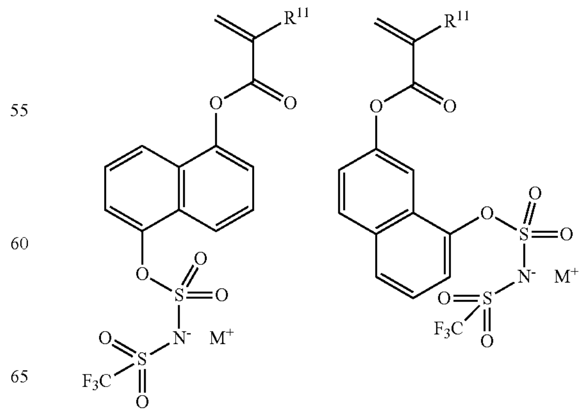

-continued
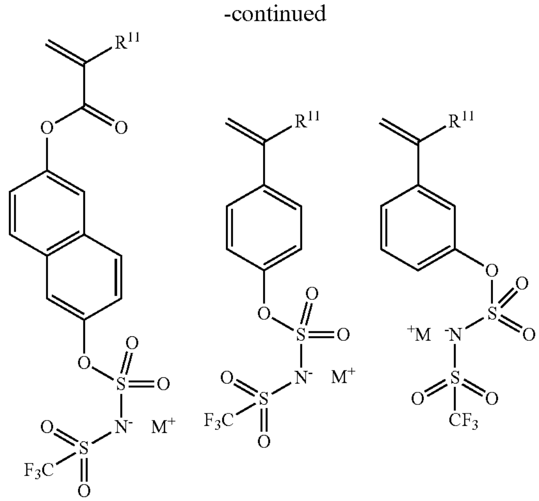
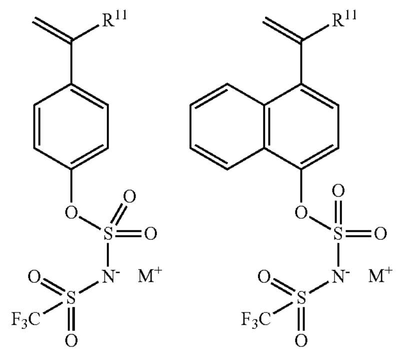
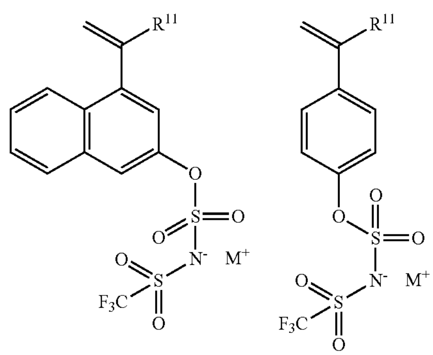
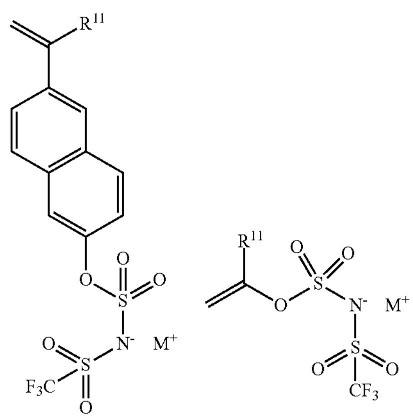
-continued
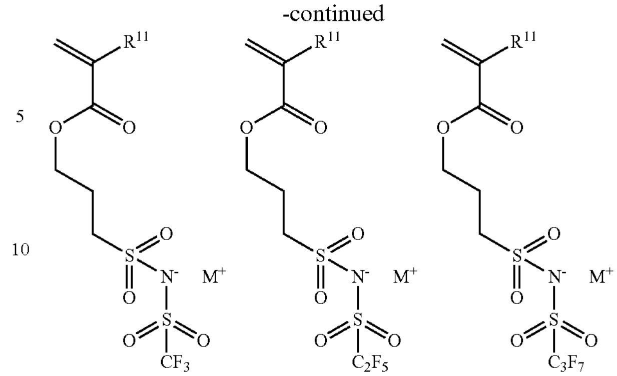
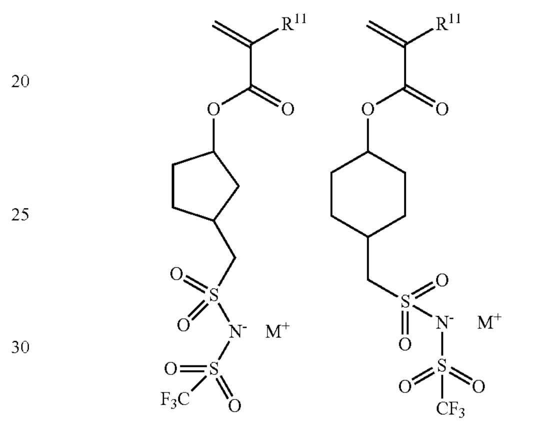
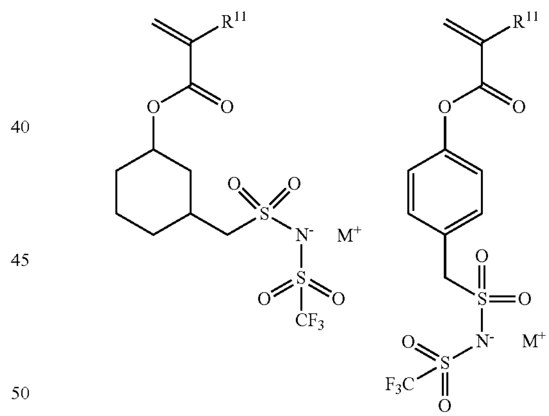
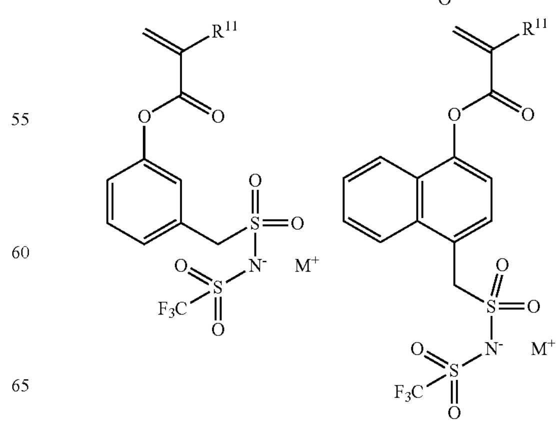

-continued
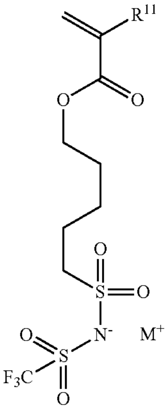
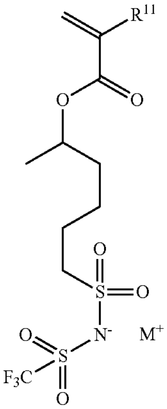
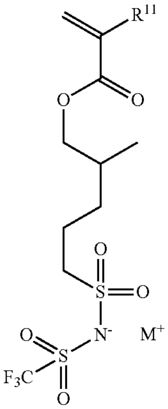
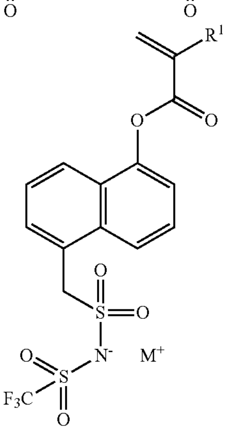
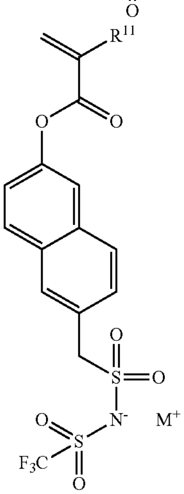
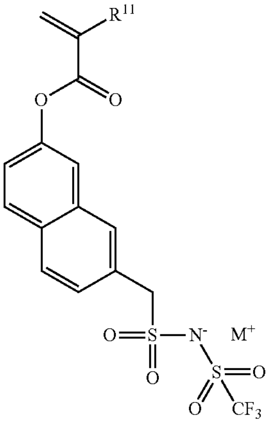
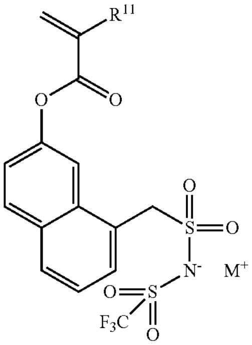
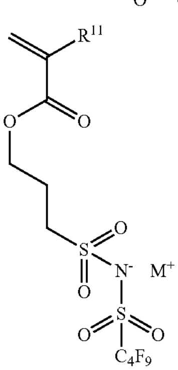
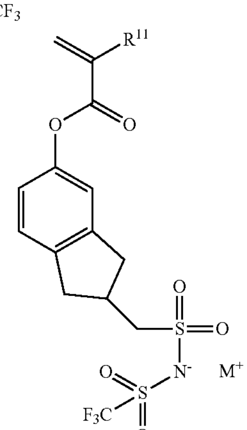
-continued
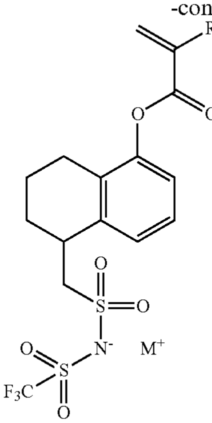
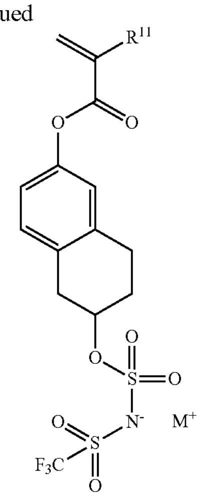
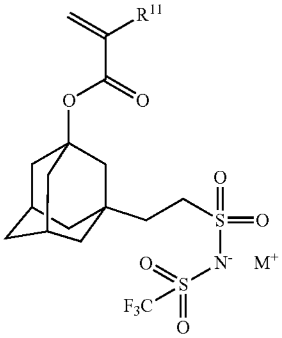
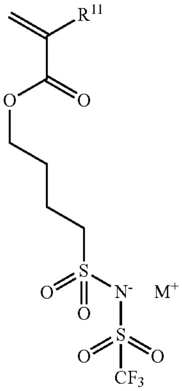
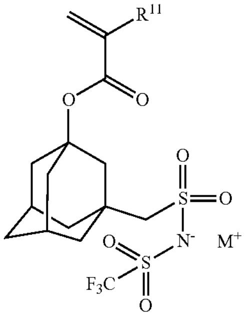
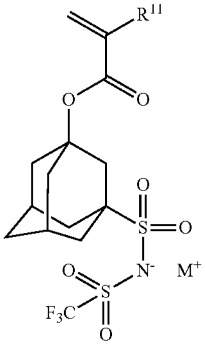
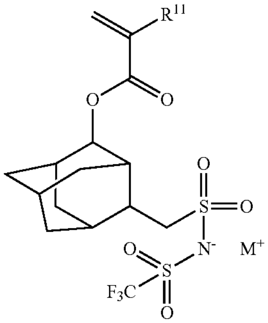
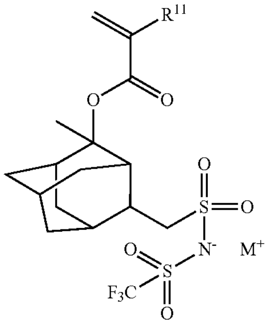

-continued
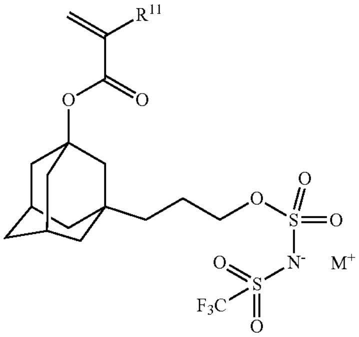
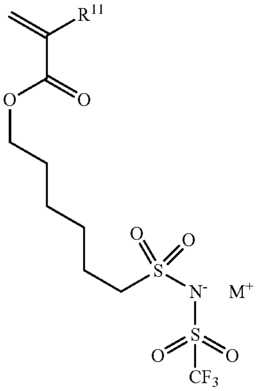
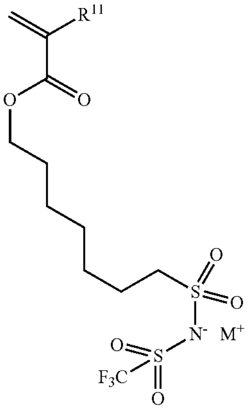
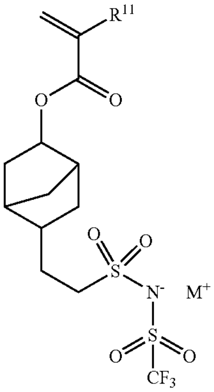
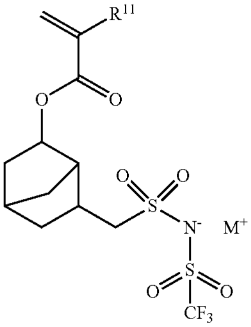
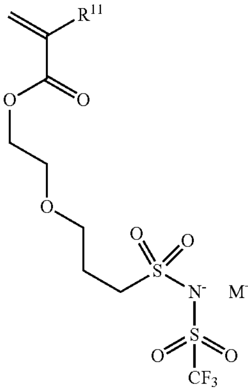
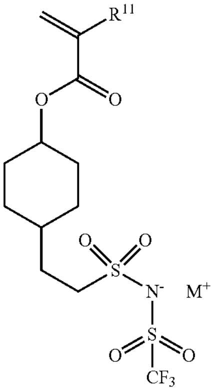
-continued
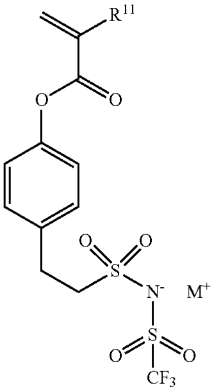
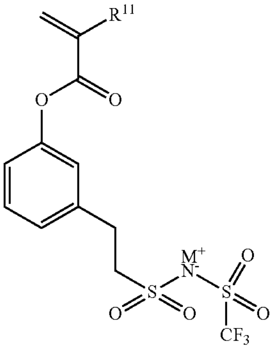
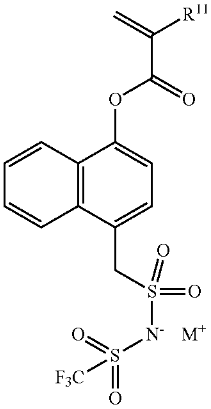
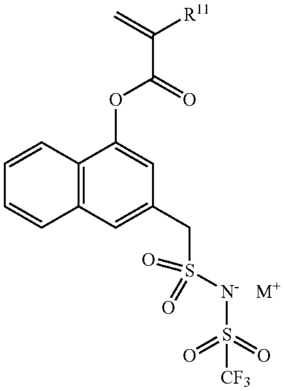
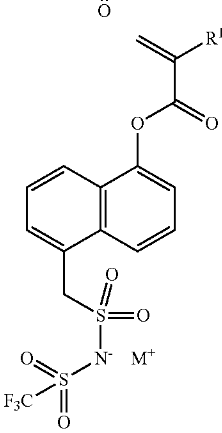
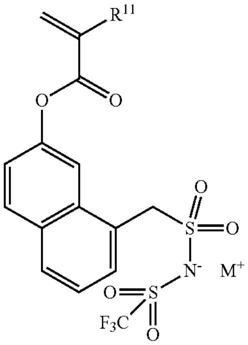
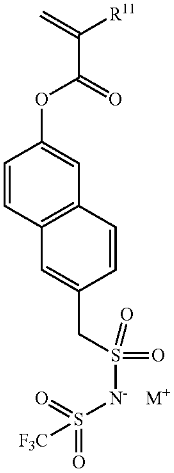
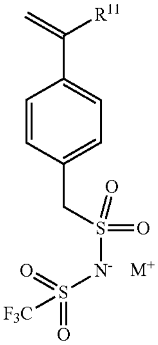
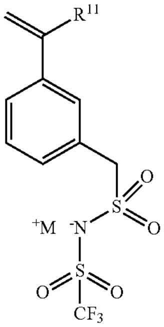

-continued
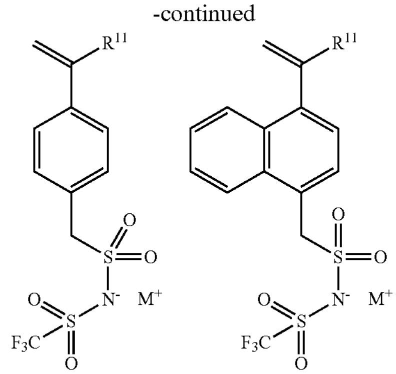
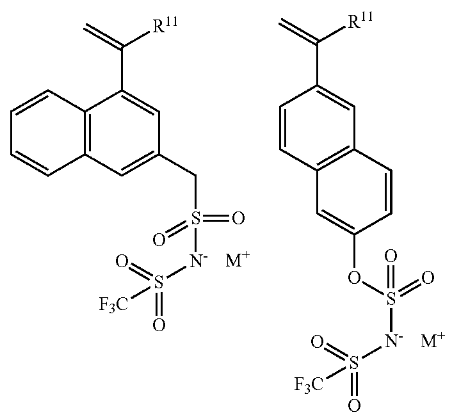
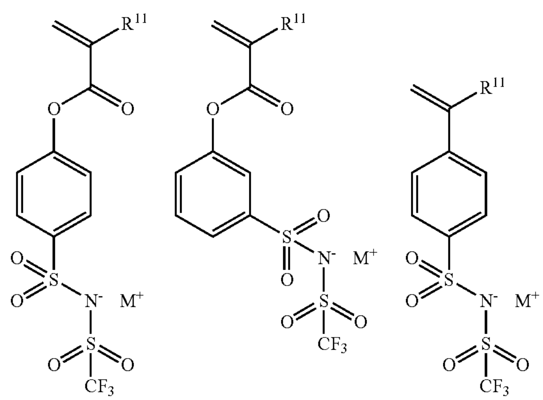
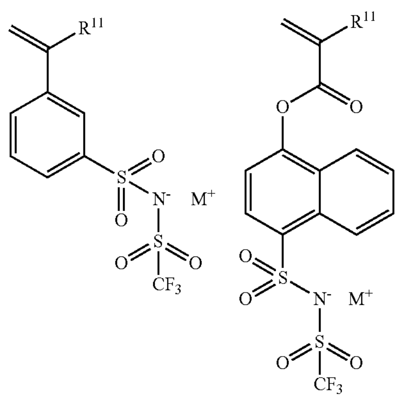
-continued
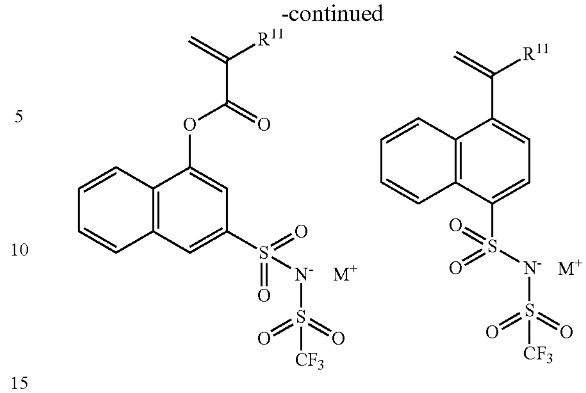
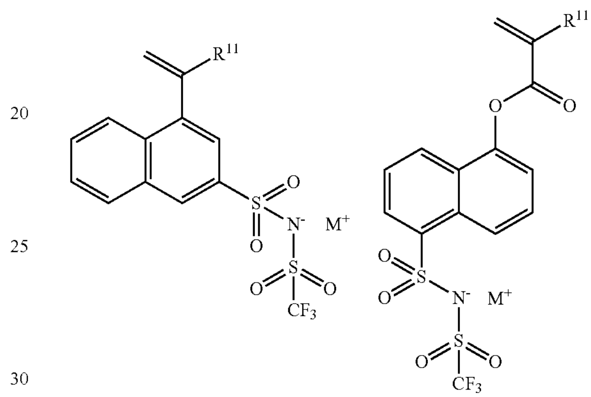
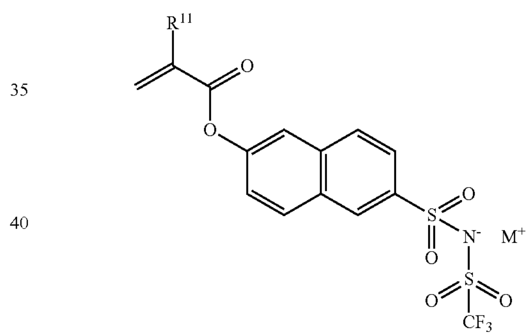
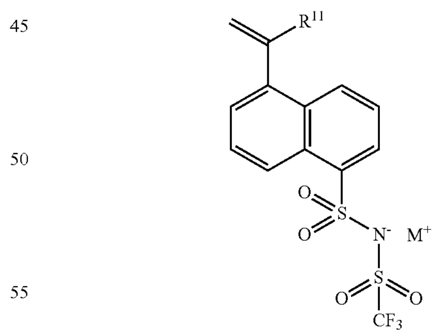
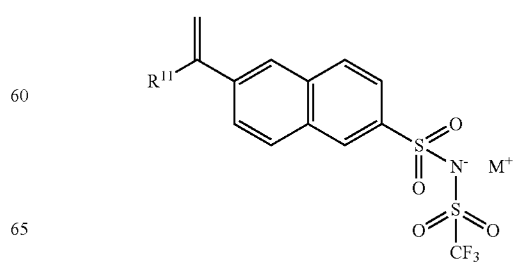

-continued
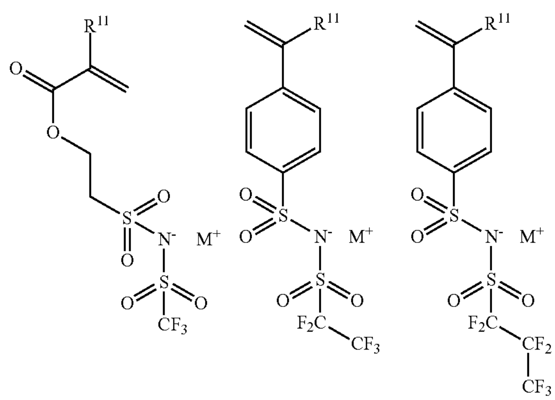
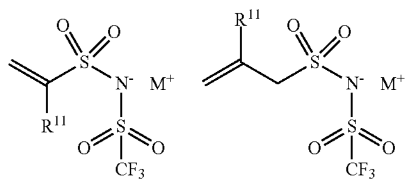
Specific examples of N-carbonyl-sulfonamide monomers and N-carbonyl-sulfonamide salt monomers for obtaining the repeating unit-A7 of the above general formula can include the following.
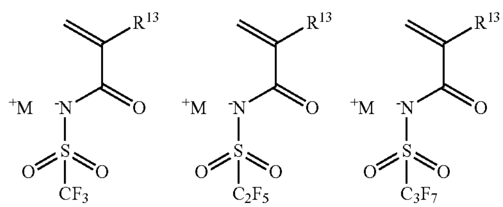
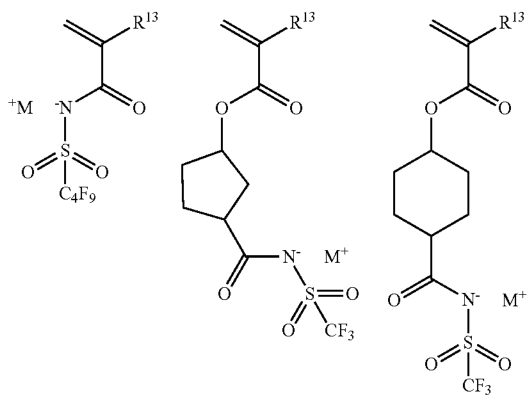
-continued
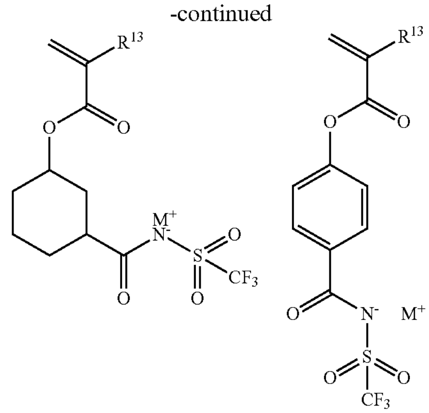
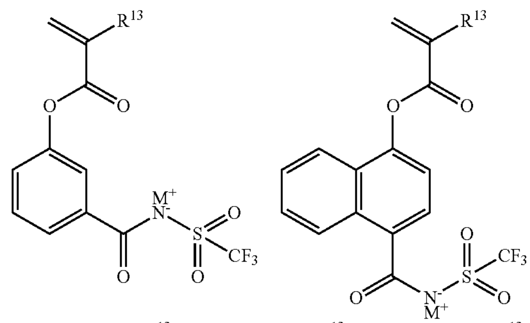
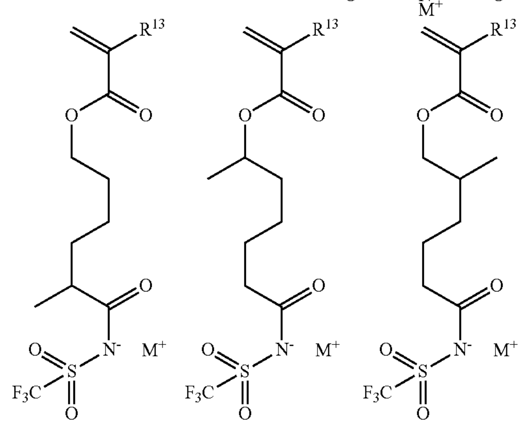
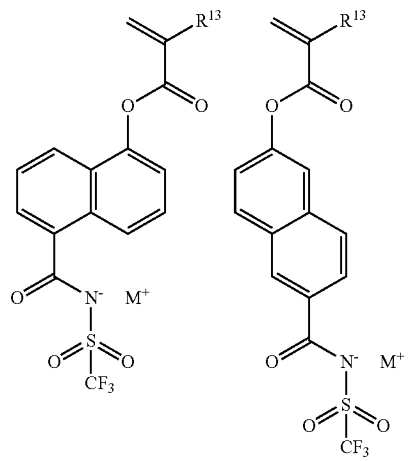

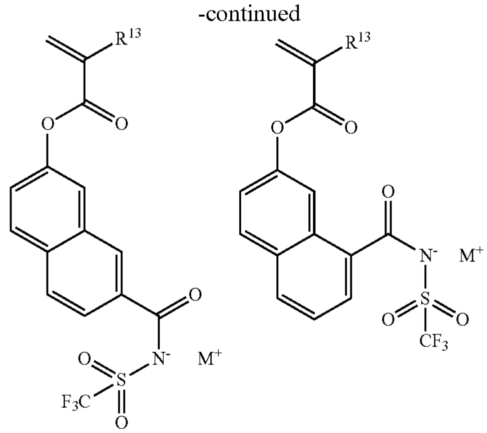
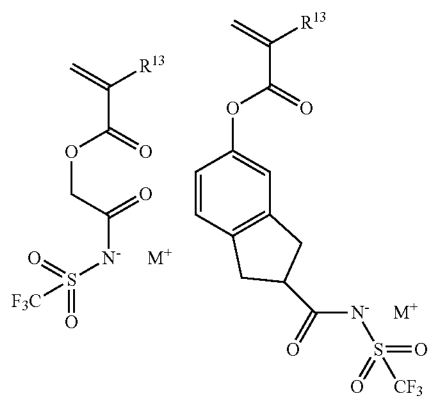
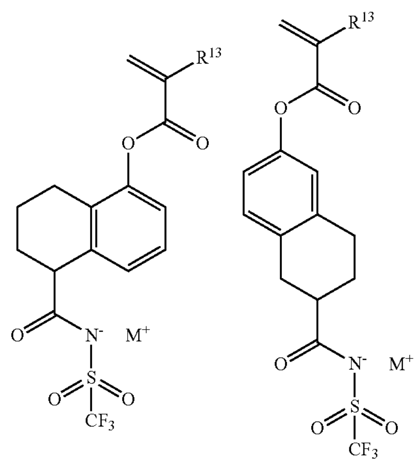
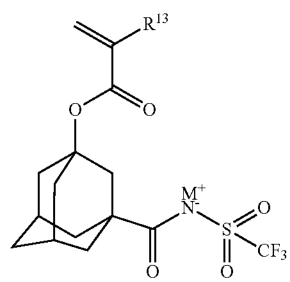
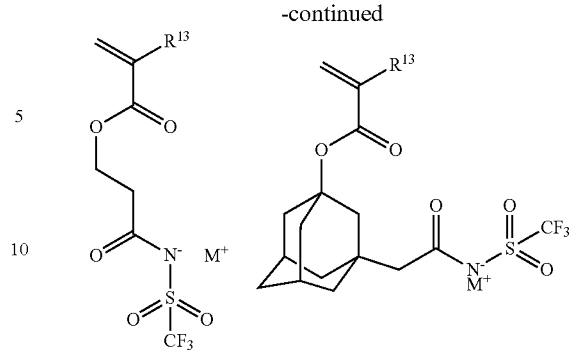
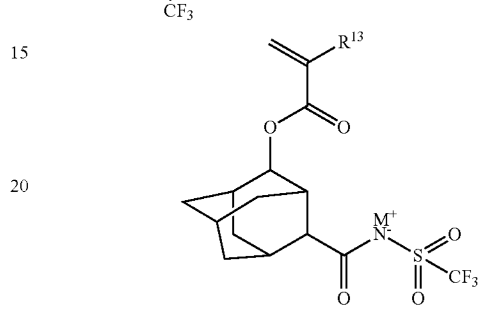
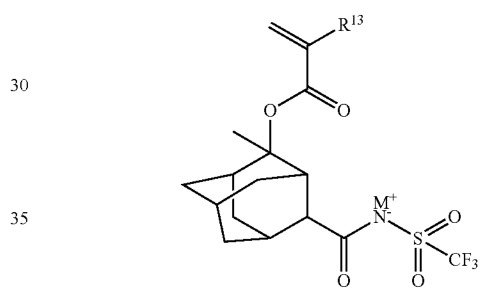
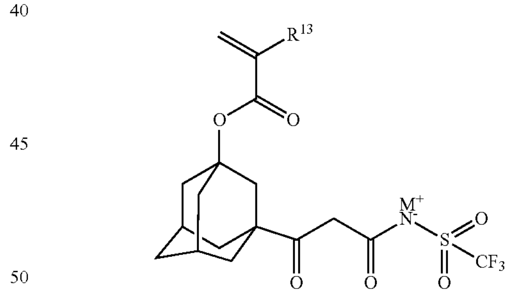
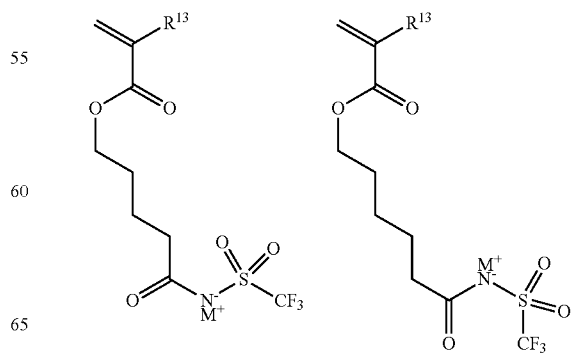

-continued
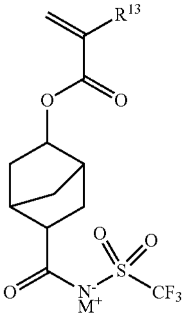
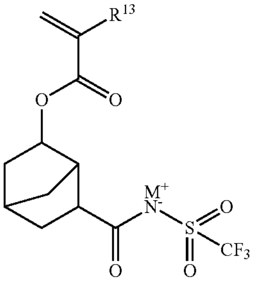
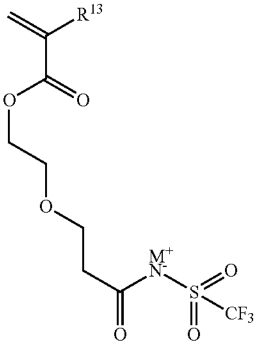
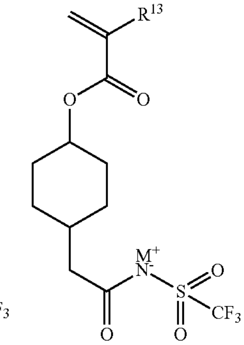
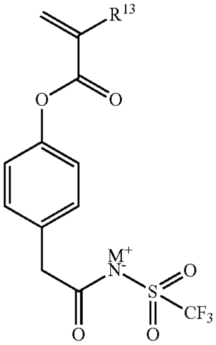
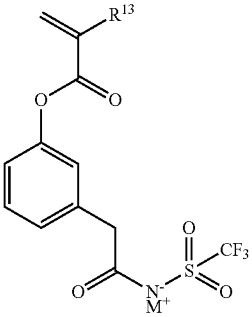
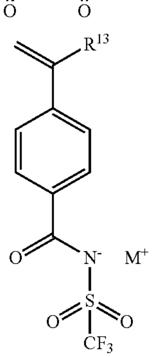
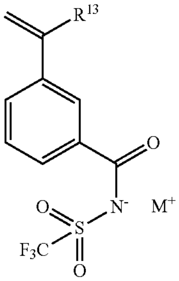
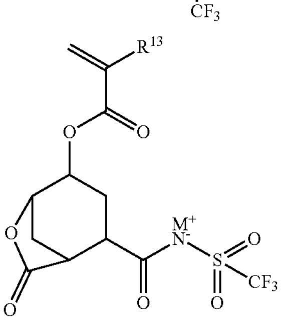
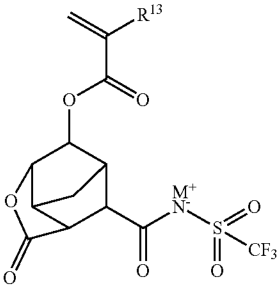
-continued
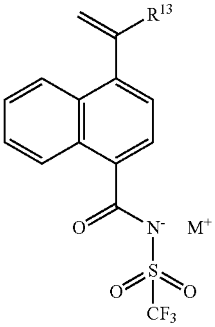
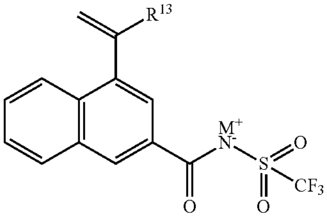
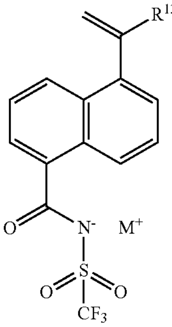
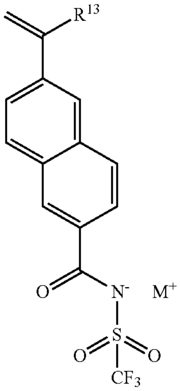
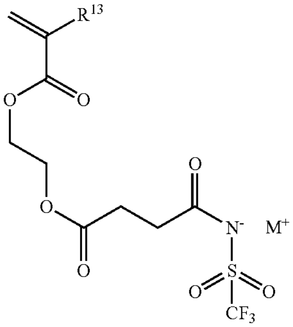
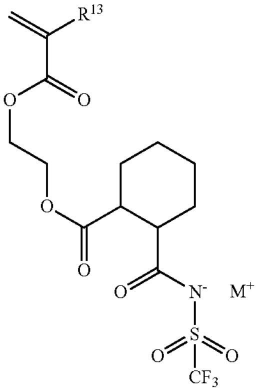
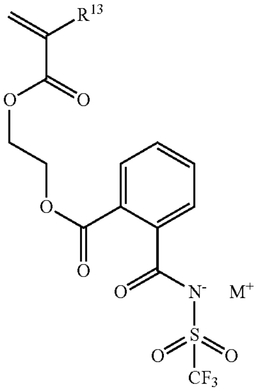
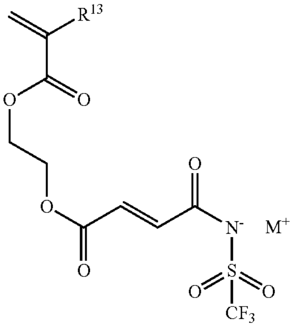

-continued

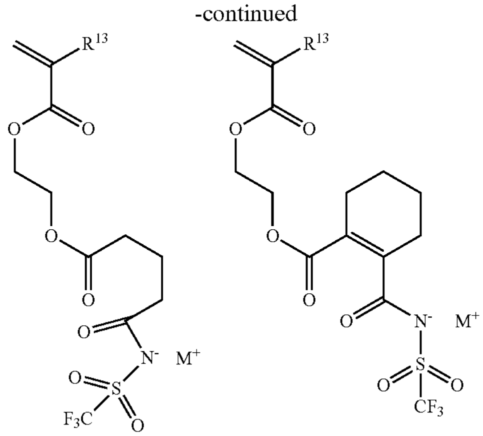

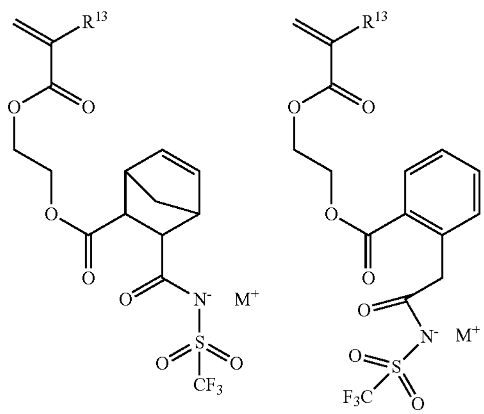

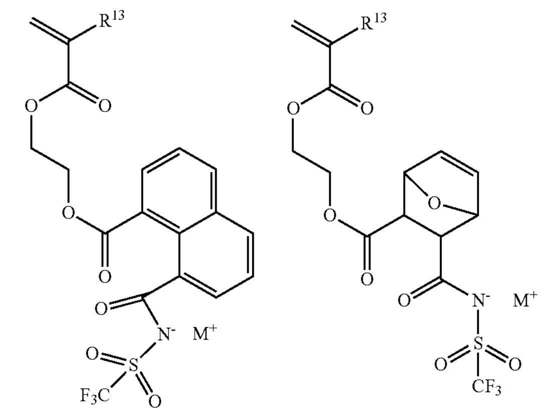

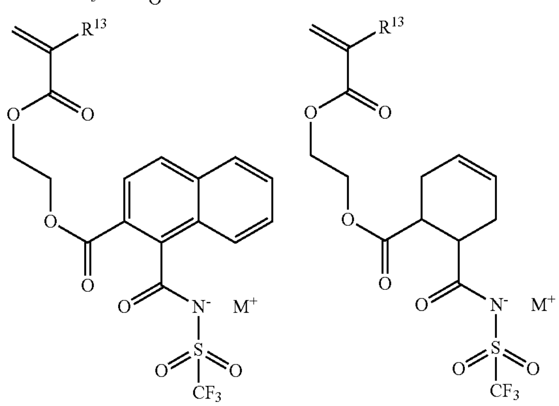

-continued

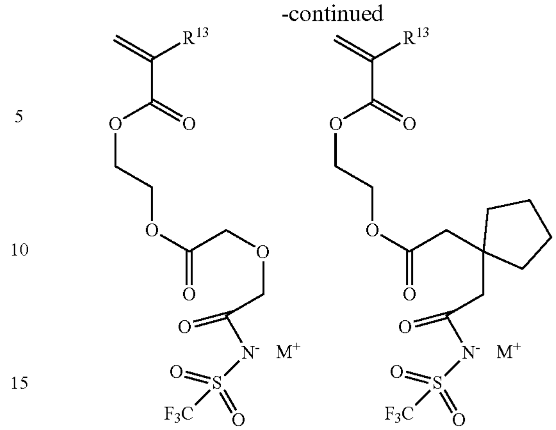

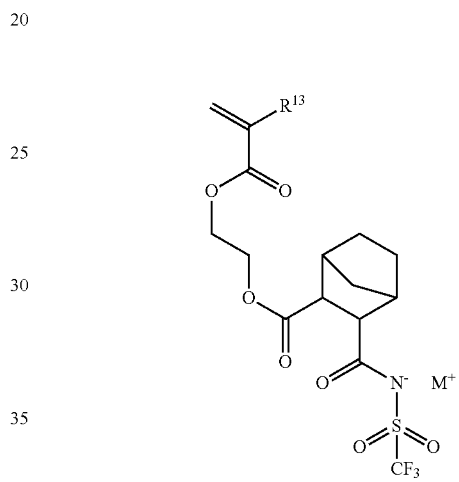

In the formulae, $R^1$, $R^3$, $R^5$, $R^8$, $R^{10}$, $R^{11}$, and $R^{13}$ are as defined above.

(Repeating Unit-b)

Dopant polymer (B), which is contained in the electro-conductive polymer composite to form the electro-conductive polymer composite layer making up the inventive electrode, can also be copolymerized with a repeating unit "b" having a glyme chain in addition to the repeating units-A1 to -A7 in order to enhance ionic conductivity. Specific examples of a monomer for obtaining the repeating unit-b having a glyme chain can include the following. The copolymerization with the repeating unit having a glyme chain facilitates the movement of ions released from the skin in dry electrode film and thus can increase the sensitivity of a dry electrode.

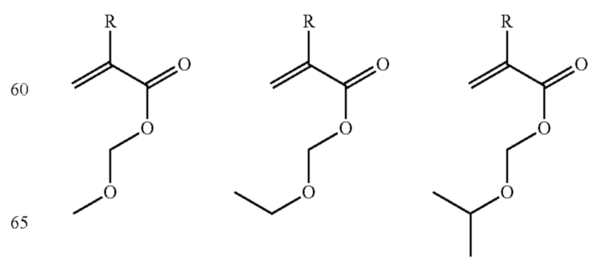

-continued
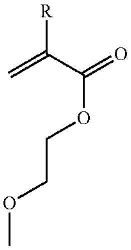
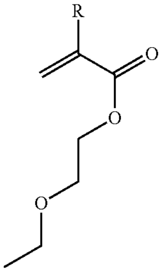
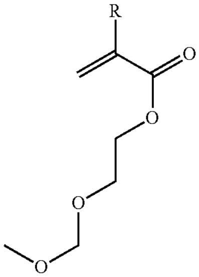
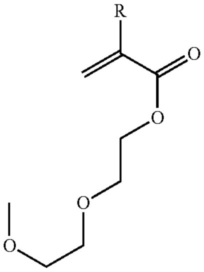
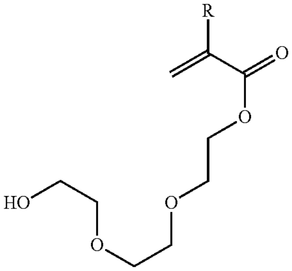
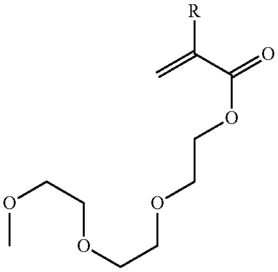
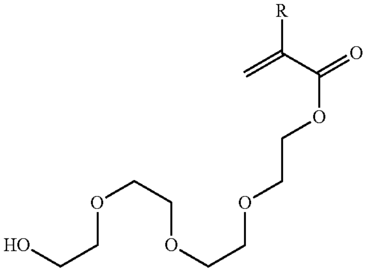
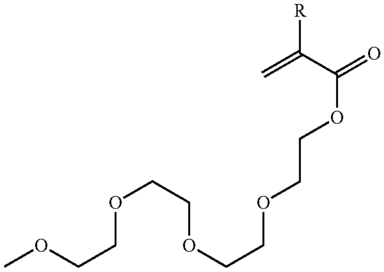
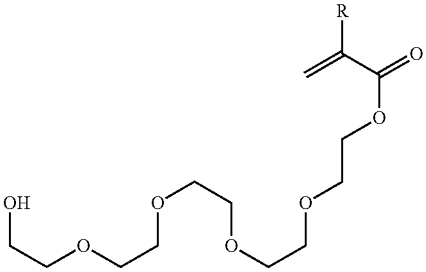
-continued
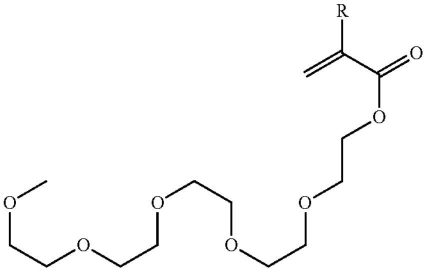
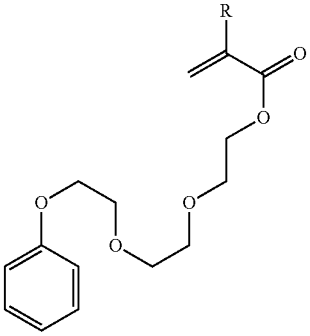
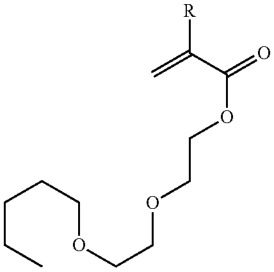
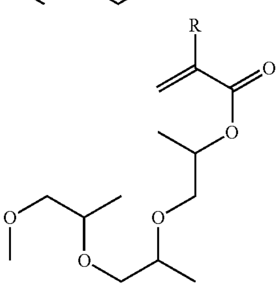
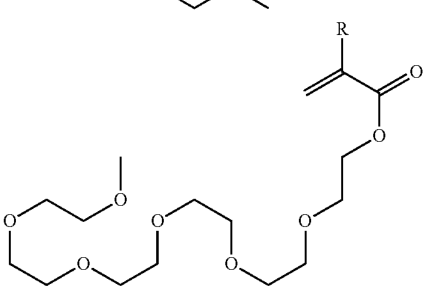
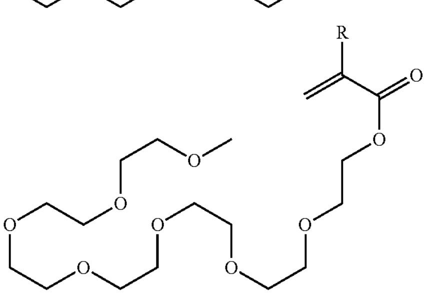

-continued
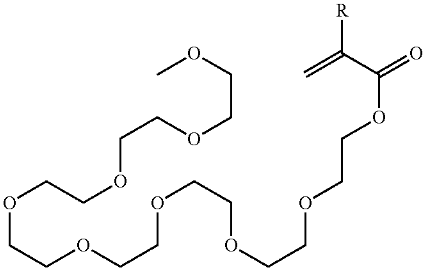
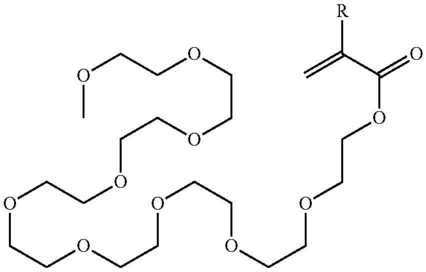
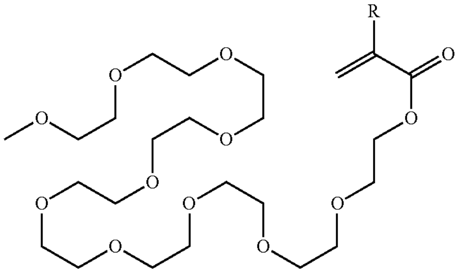
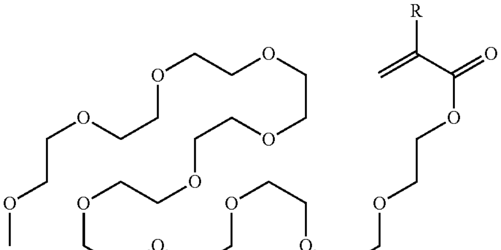
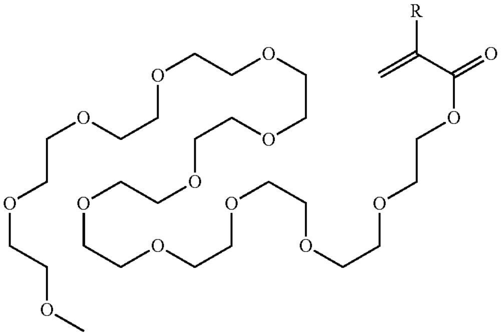
-continued
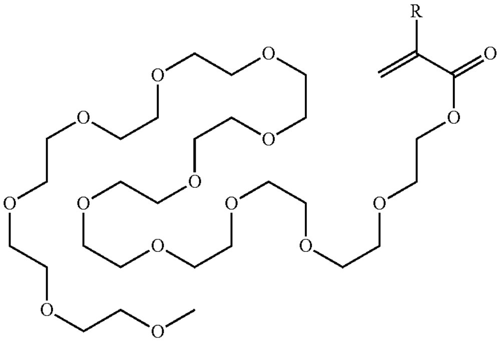
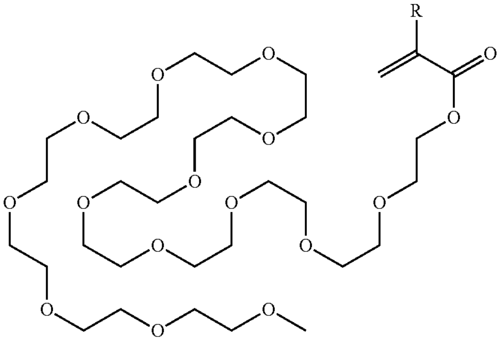
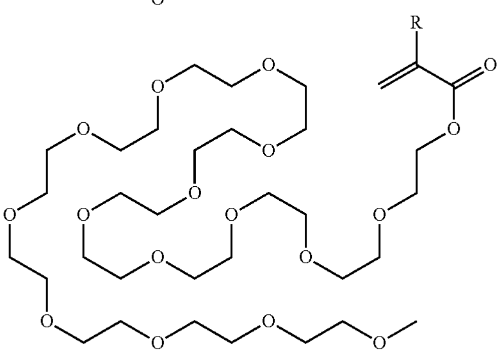
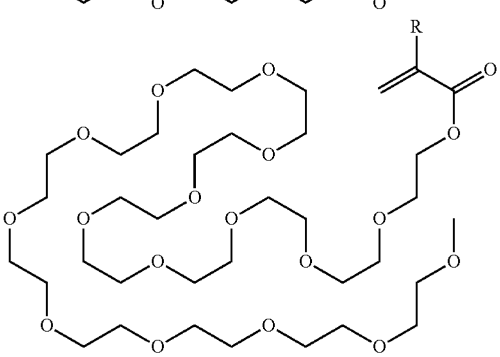
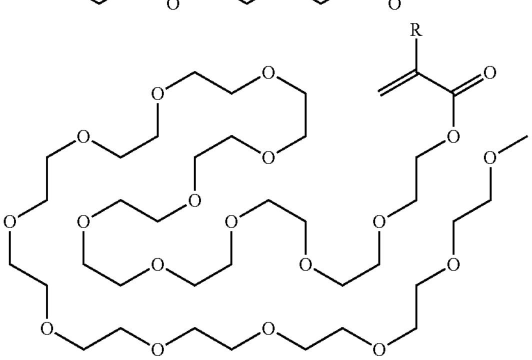

-continued
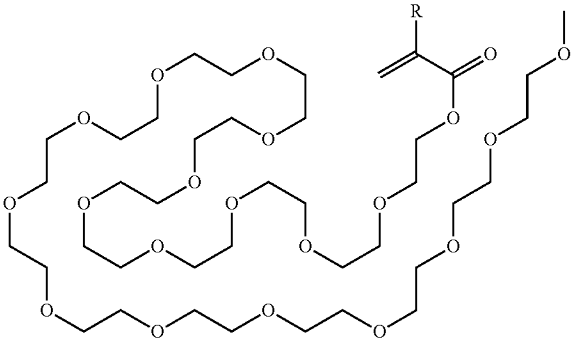
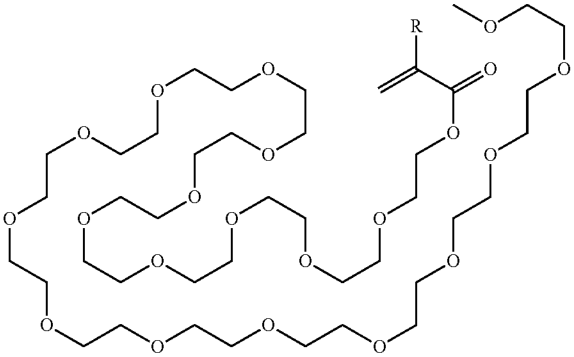
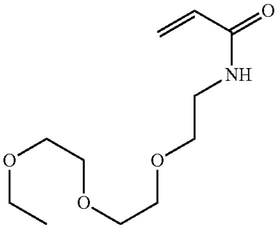
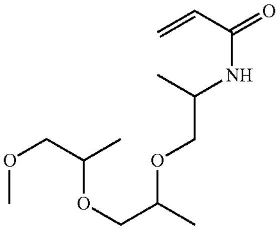
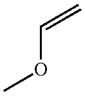
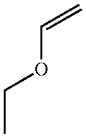
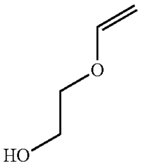
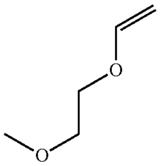
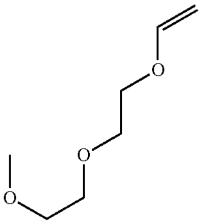
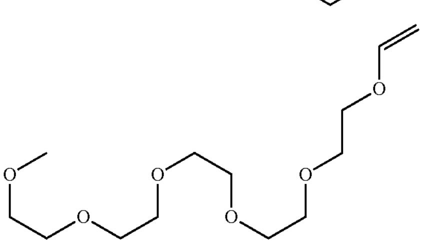
-continued
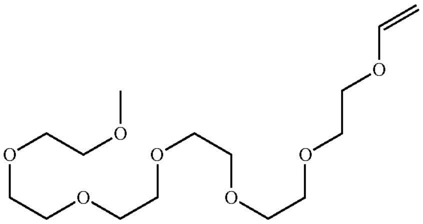
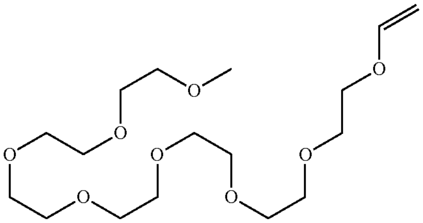
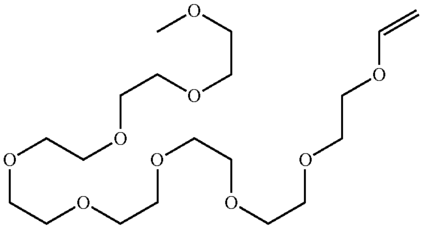
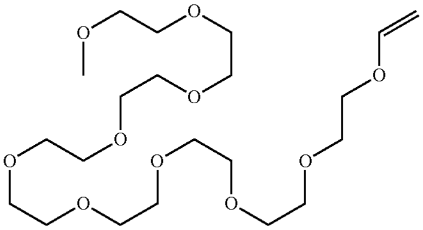
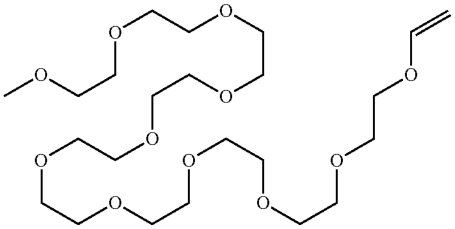
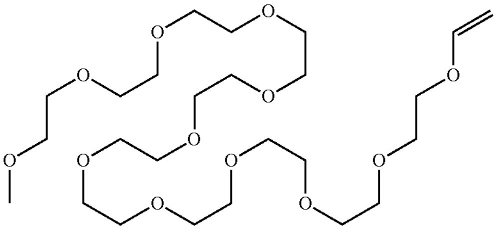
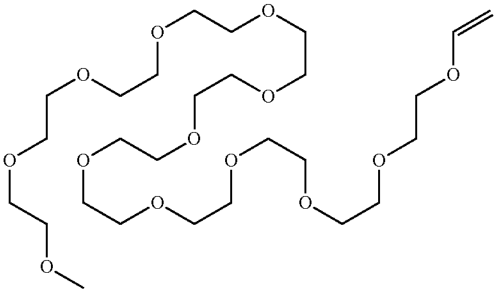

-continued
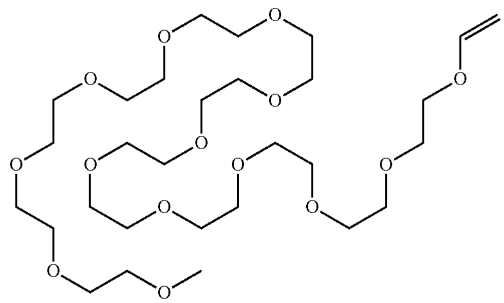
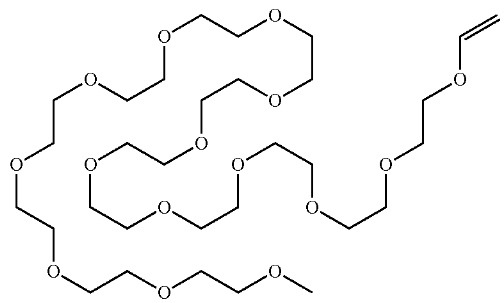
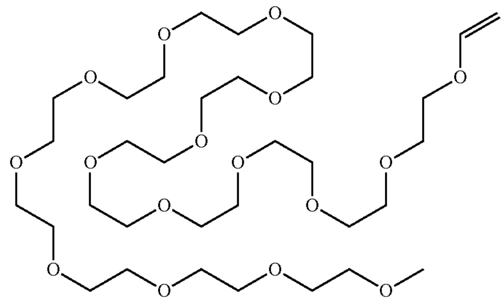
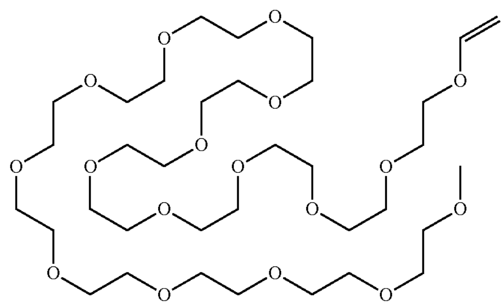
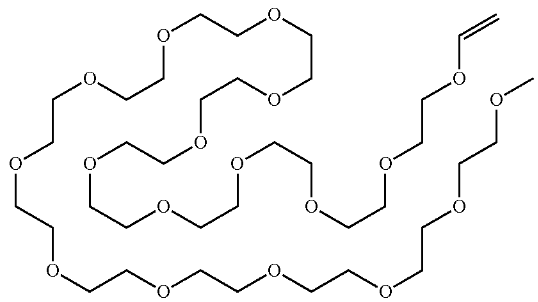
-continued
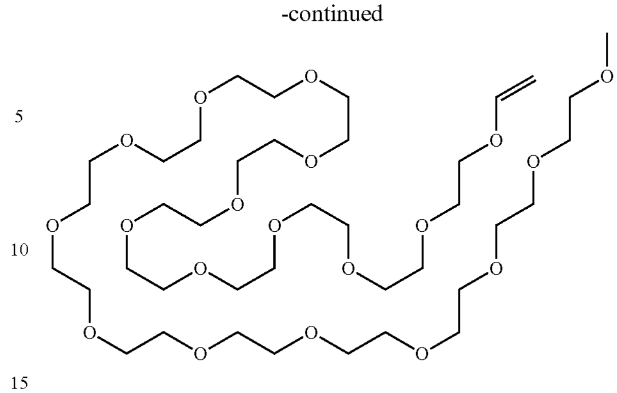
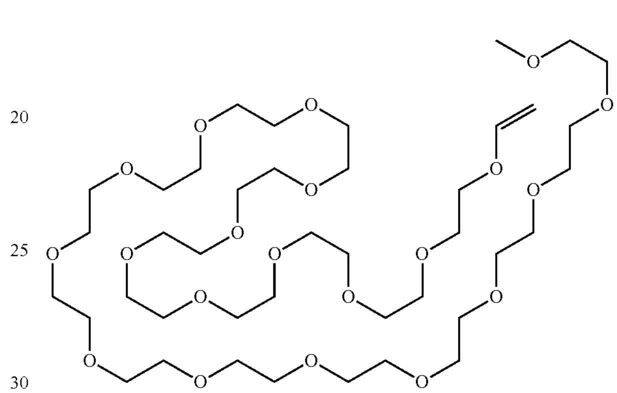
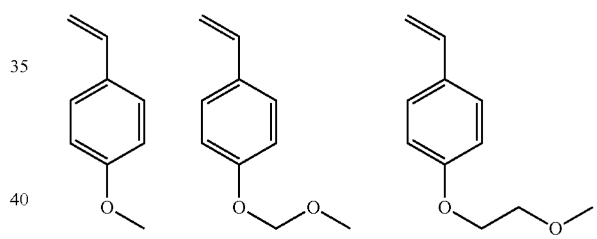
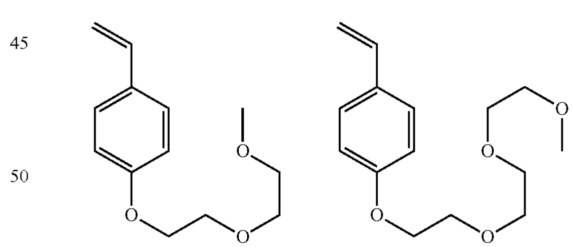
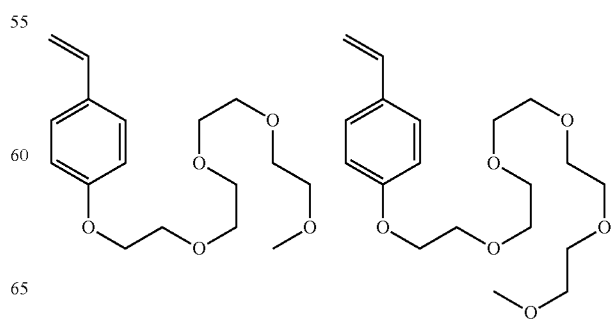

-continued

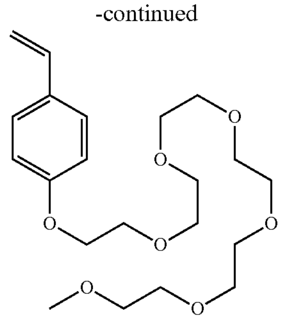

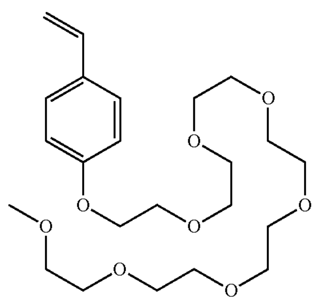

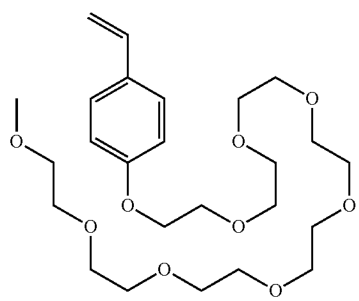

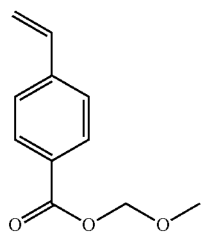

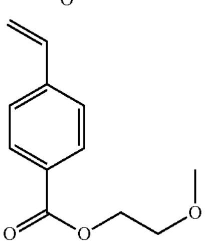

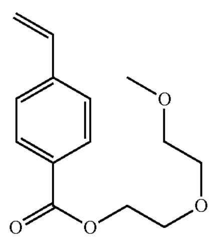

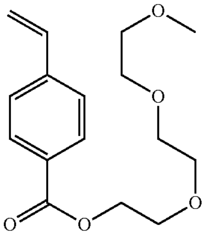

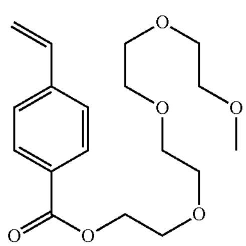

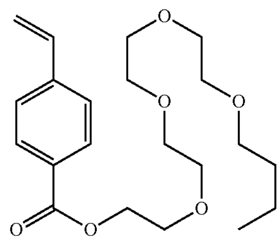

-continued

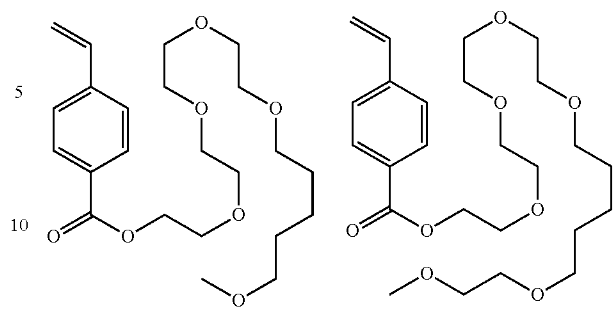

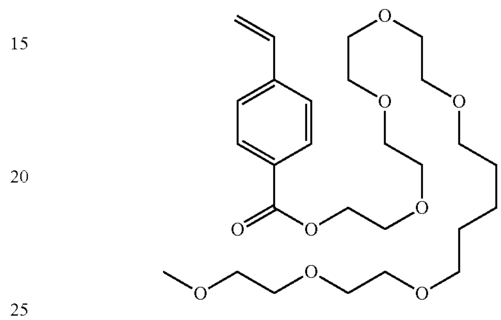

In the formulae, R represents a hydrogen atom or a methyl group.

(Repeating Unit-c)

Dopant polymer (B), which is contained in the electro-conductive polymer composite to form the electro-conductive polymer composite layer making up the inventive electrode, can also be copolymerized with a hydrophilic repeating unit "c" having a hydroxy group, a carboxy group, an ammonium salt, a betaine, an amide group, pyrrolidone, a lactone ring, a lactam ring, a sultone ring, sulfonic acid, a sodium salt of sulfonic acid, or a potassium salt of sulfonic acid, in addition to the repeating units-A1 to -A7 and -b, in order to enhance electro-conductivity. Specific examples of a monomer to obtain the hydrophilic repeating unit-c can include the following. The copolymerization with the repeating unit containing such hydrophilic groups can increase the sensitivity of the dry electrode by increasing the sensitivity to ions released from the skin.

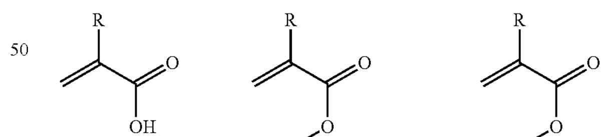

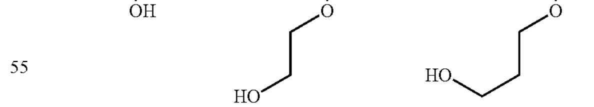

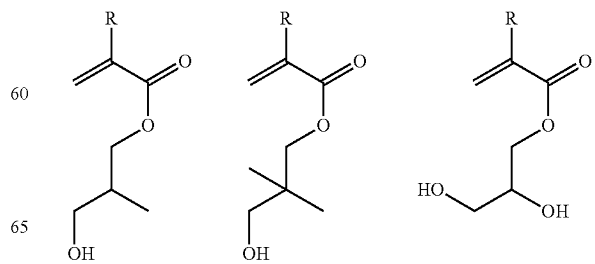

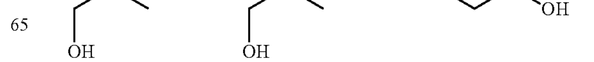

-continued
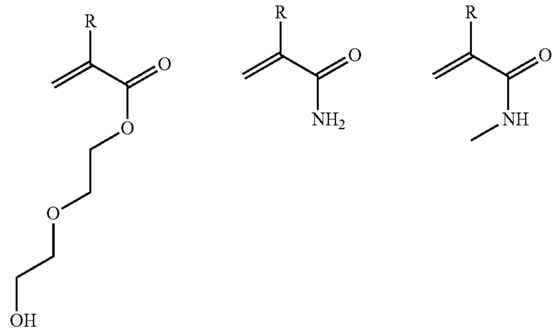
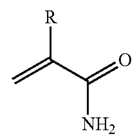
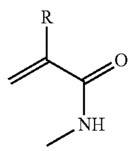
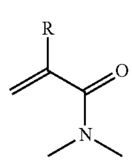
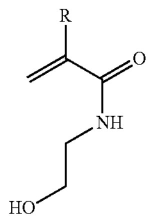
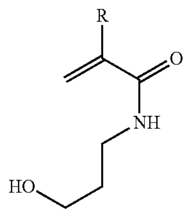
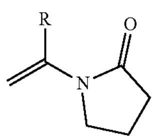
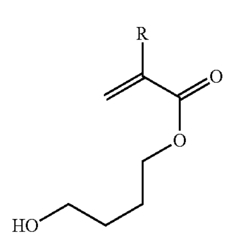
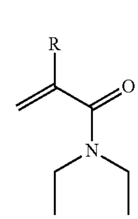
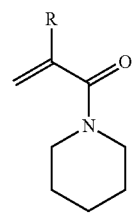
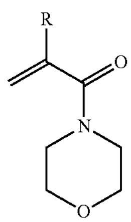
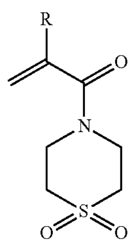
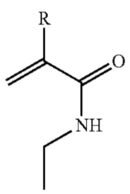
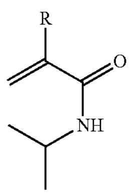
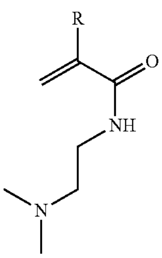
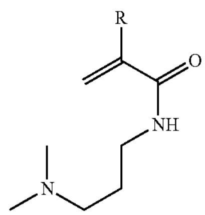
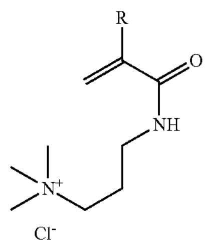
-continued
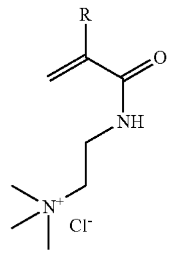
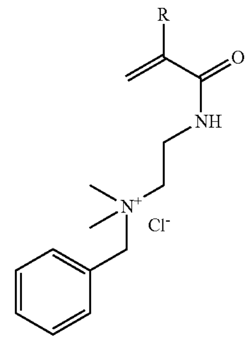
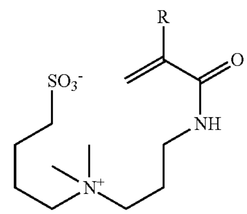
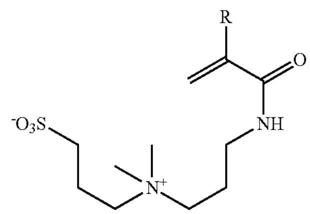
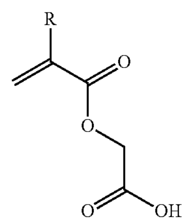
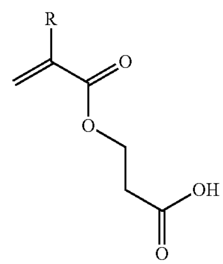
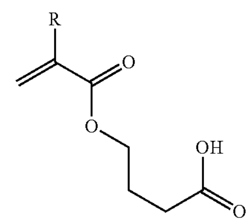
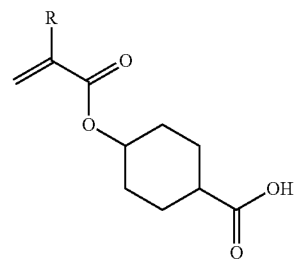
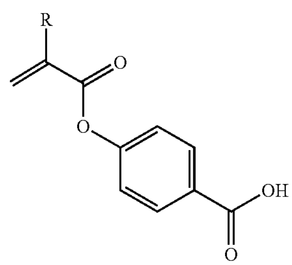
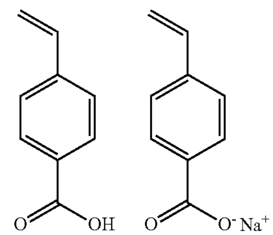
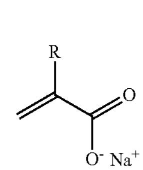
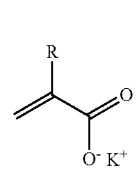
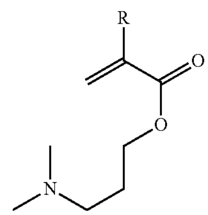

-continued
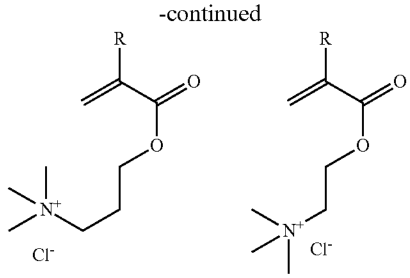
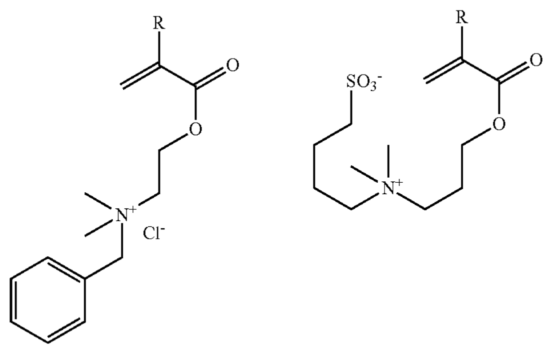
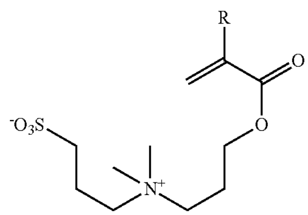
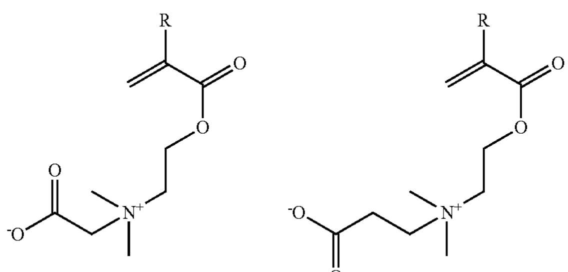
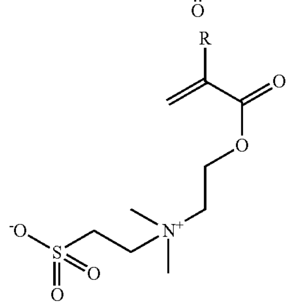
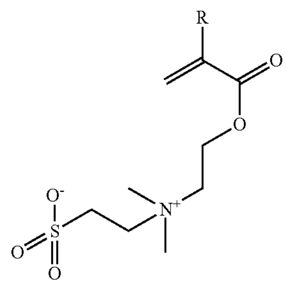
-continued
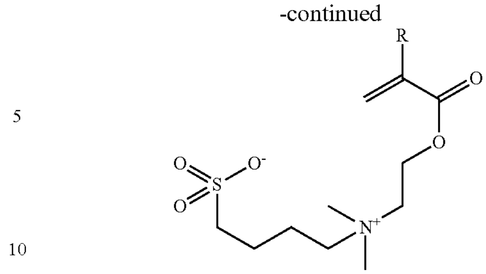
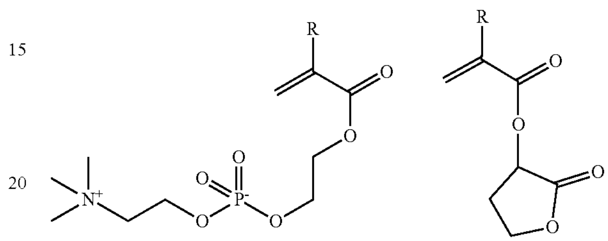
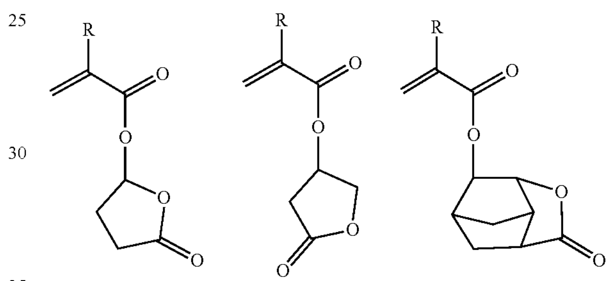
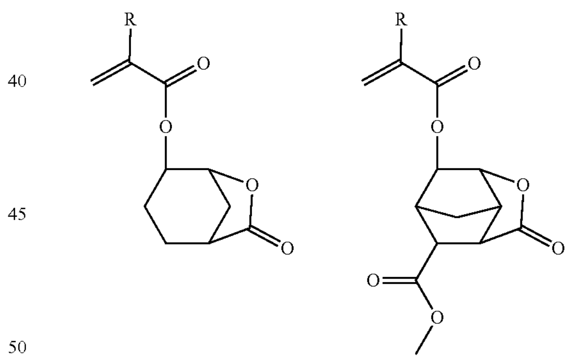
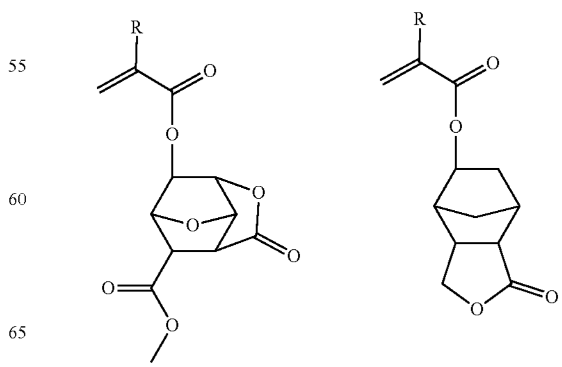

-continued
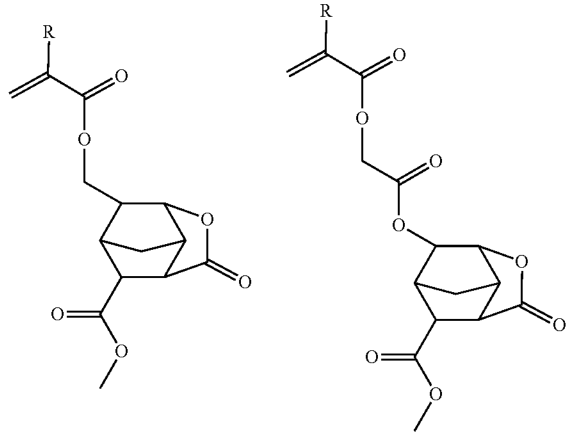
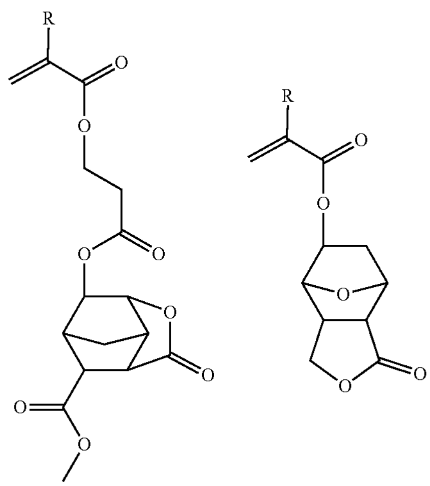
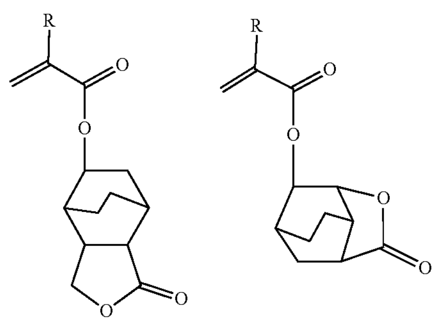
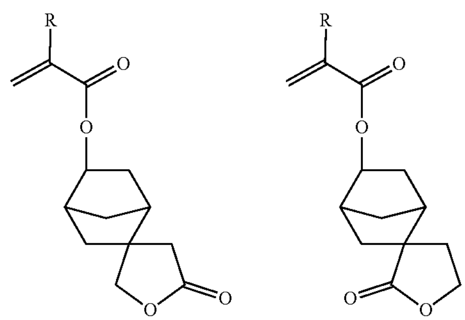
-continued
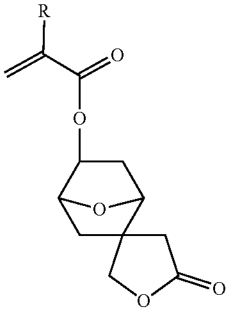
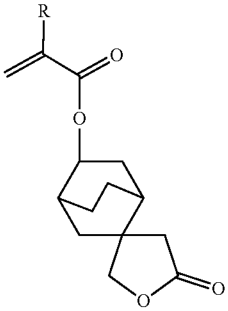
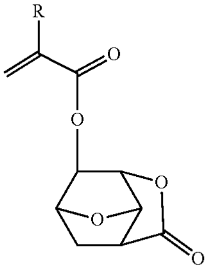
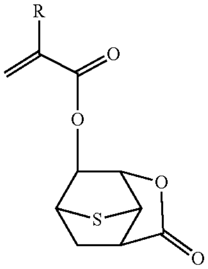
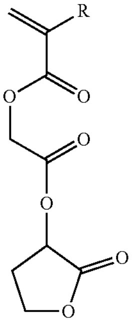
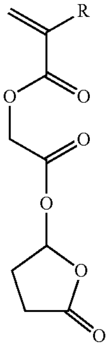
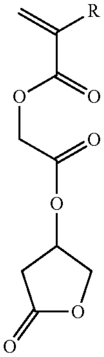
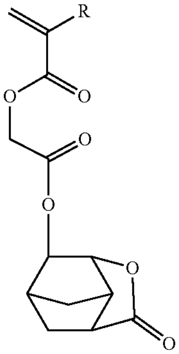
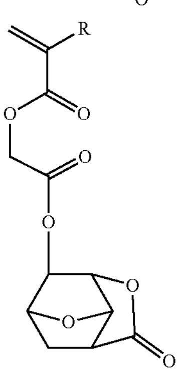
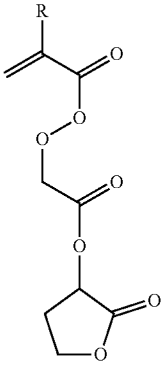
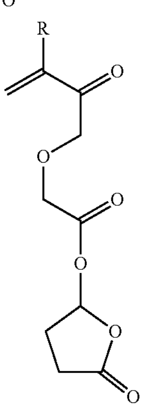
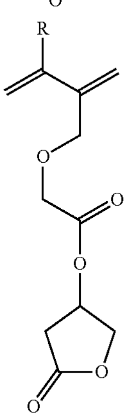

-continued

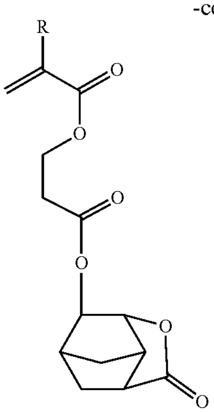

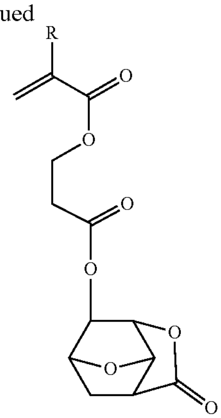

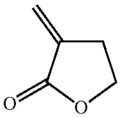

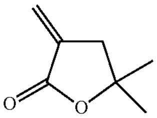

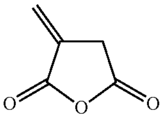

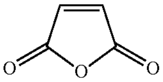

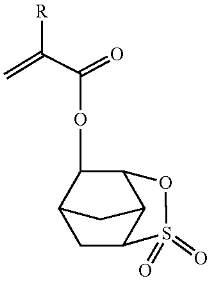

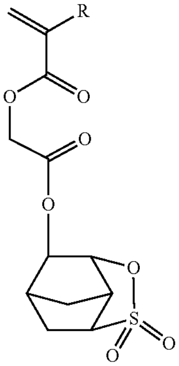

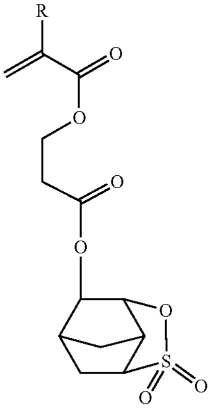

In the formulae, R represents a hydrogen atom or a methyl group.

(Repeating Unit-d)

Dopant polymer (B), which is contained in the electro-conductive polymer composite to form the electro-conductive polymer composite layer making up the inventive electrode, can have a repeating unit-d containing fluorine, in addition to the repeating units selected from the group consisting of the repeating units-A1 to -A7, -b, and -c.

Specific examples of a monomer to obtain the repeating unit-d containing fluorine can include the following.

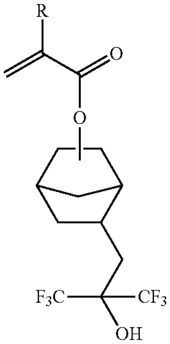

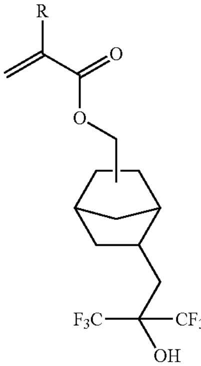

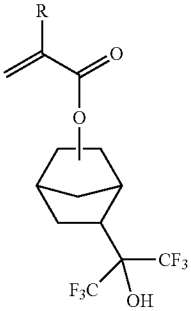

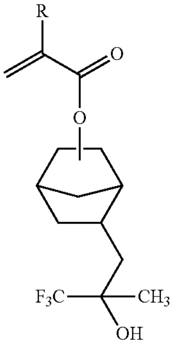

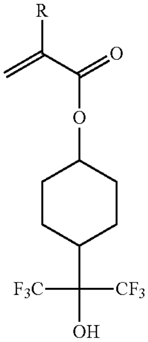

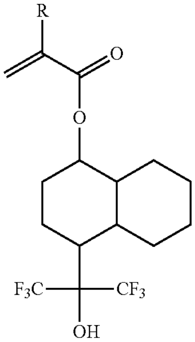

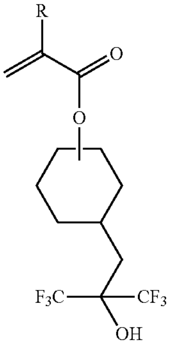

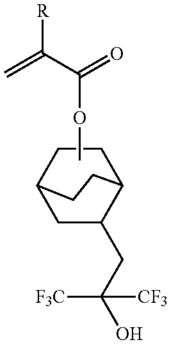

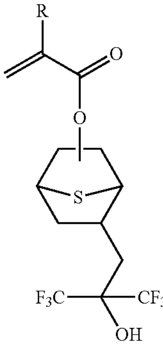

-continued
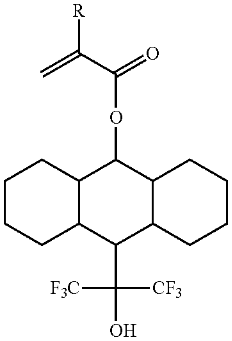
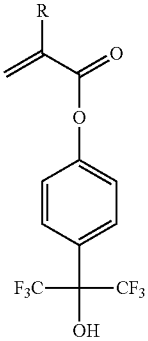
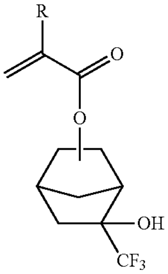
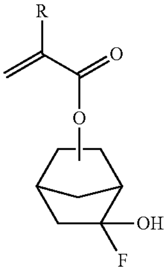
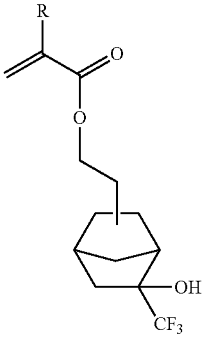
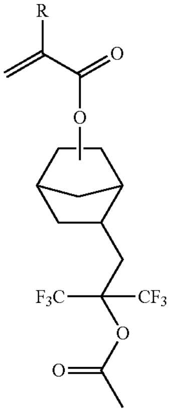
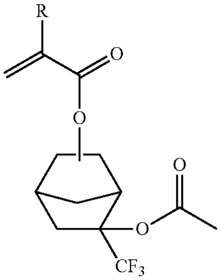
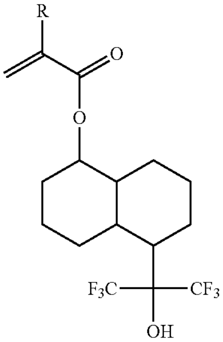
-continued
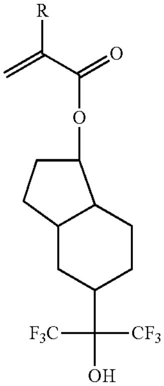
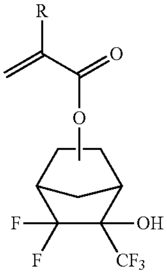
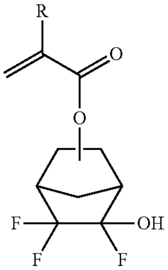
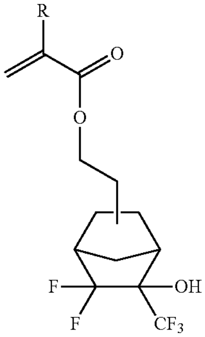
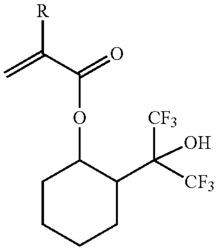
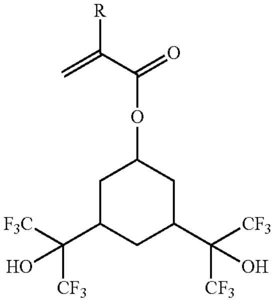
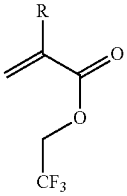
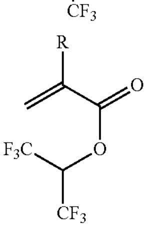
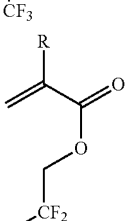
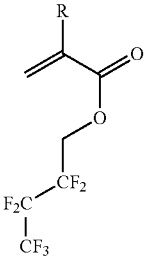
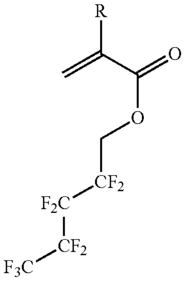
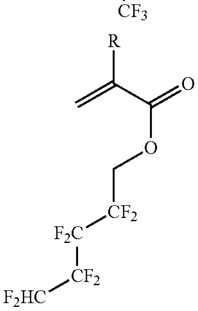

-continued
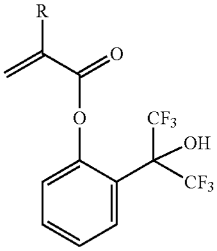
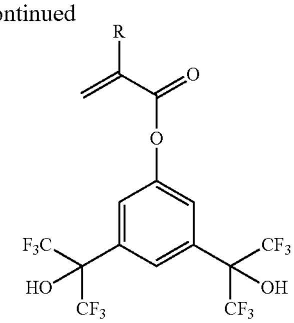
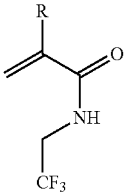
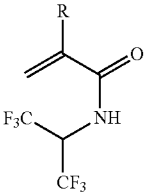
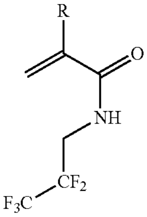
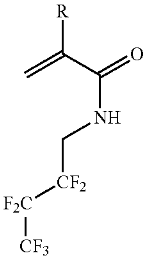
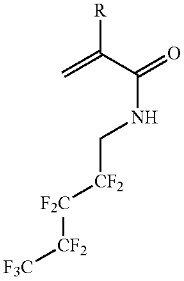
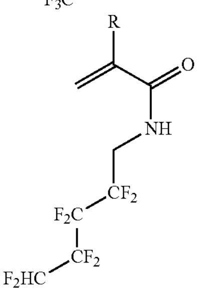
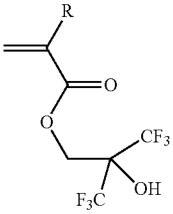
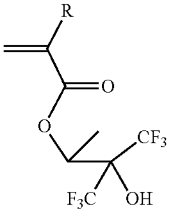
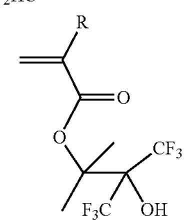
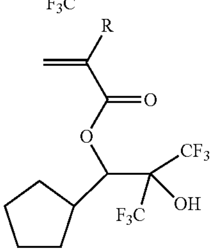
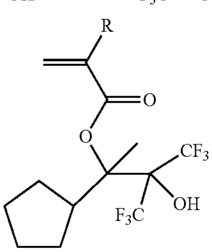
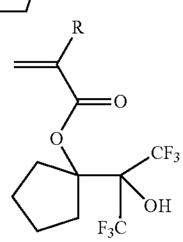
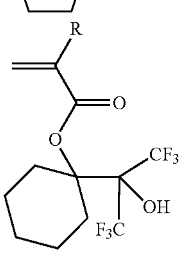
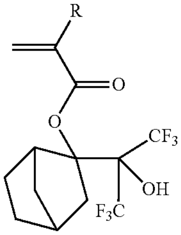
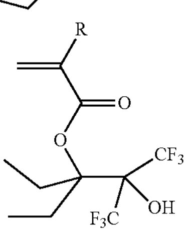
-continued
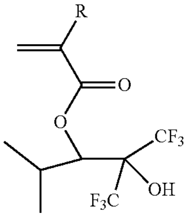
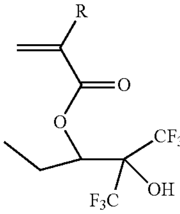
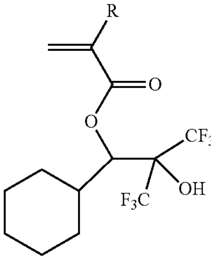
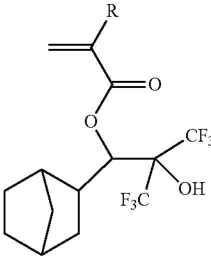
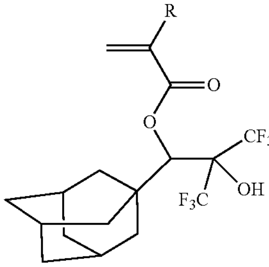
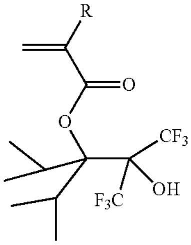
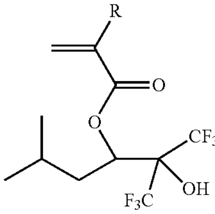
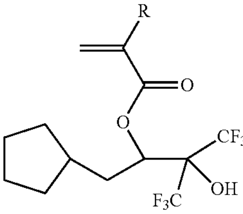
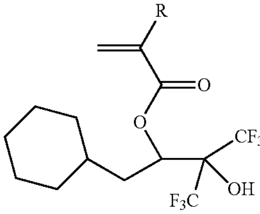
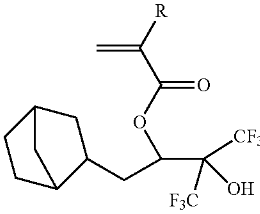
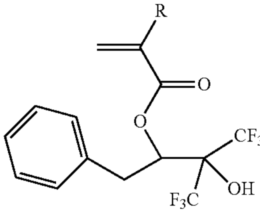
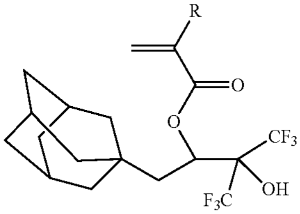

-continued
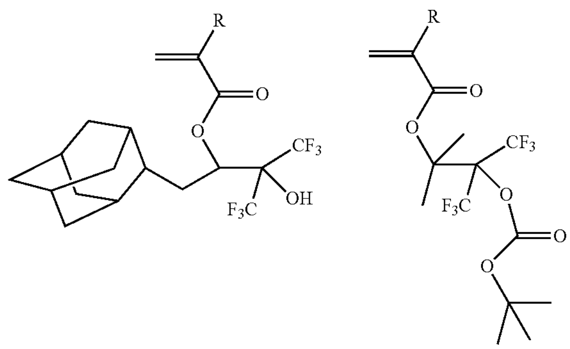
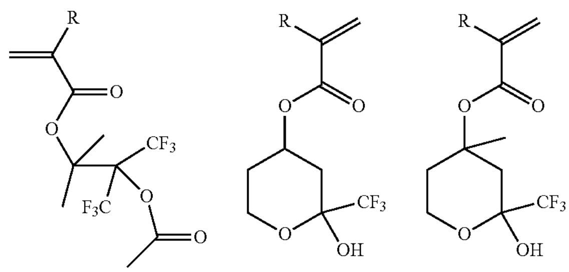
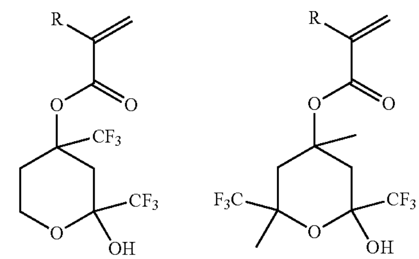
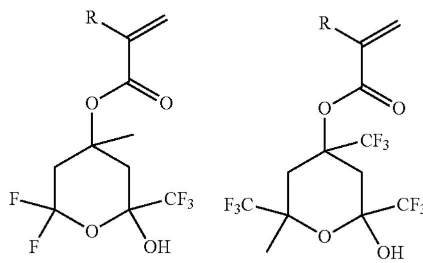
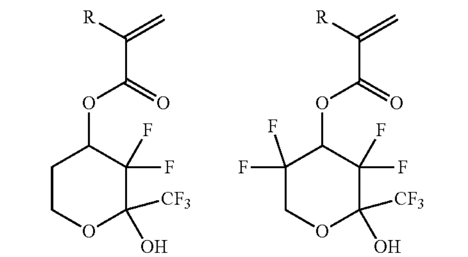
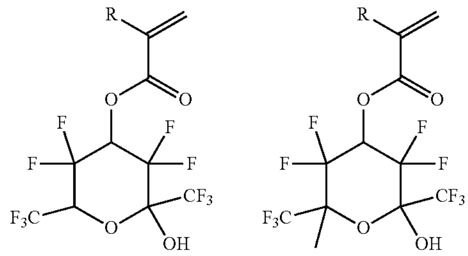
-continued
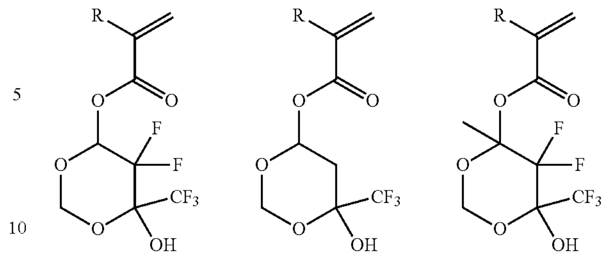
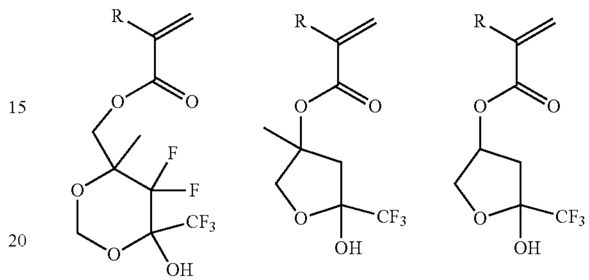
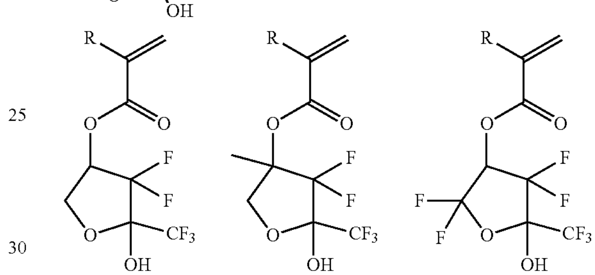
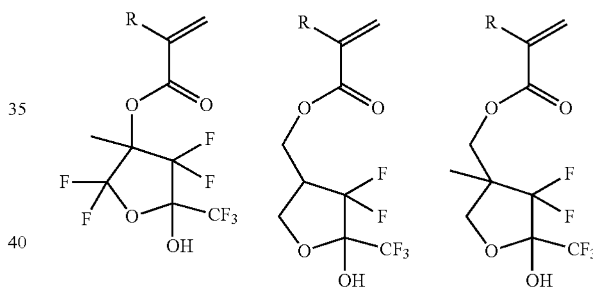
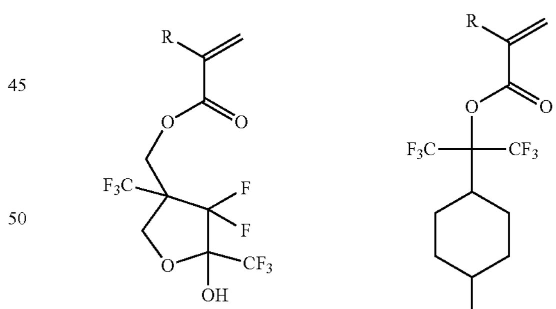
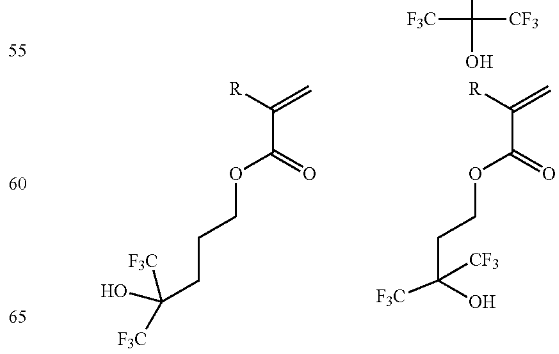

-continued
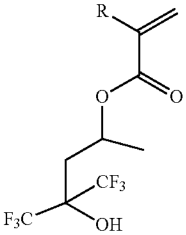
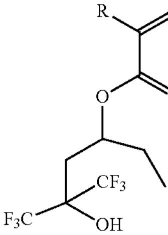
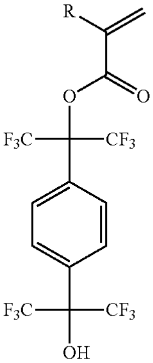
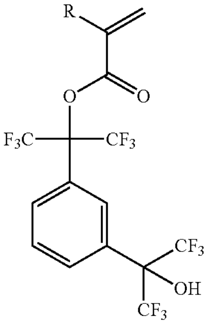
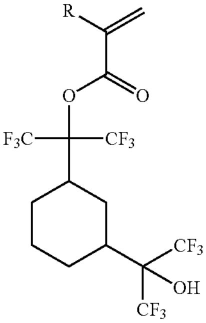
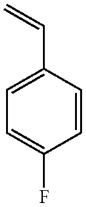
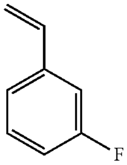
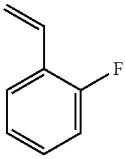
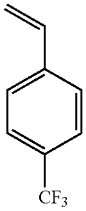
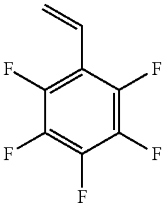
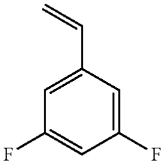
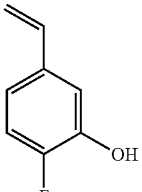
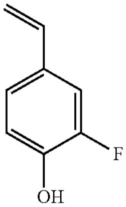
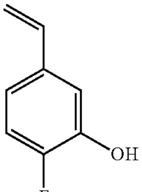
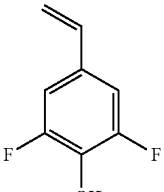
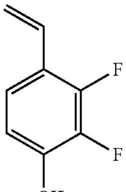
-continued
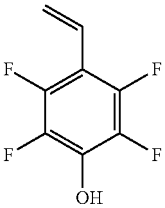
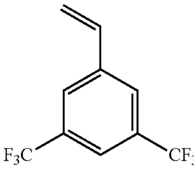
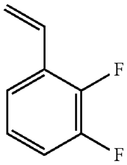
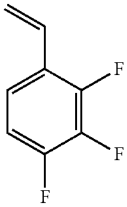
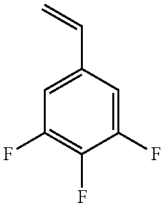
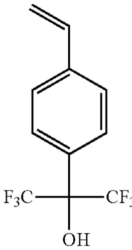
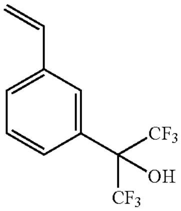
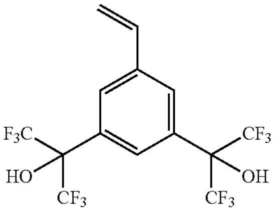
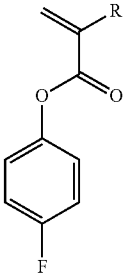
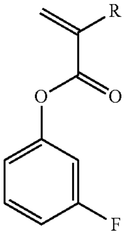
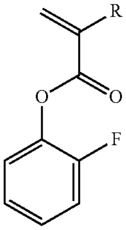
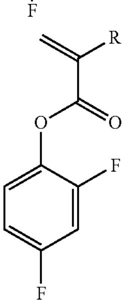
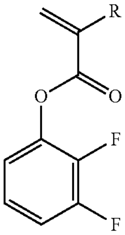
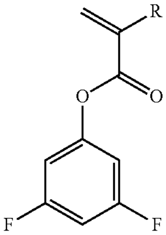
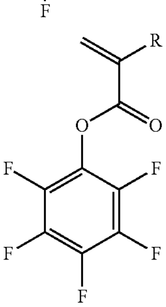
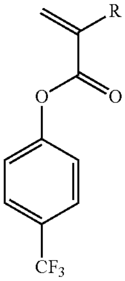
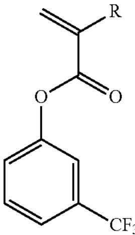

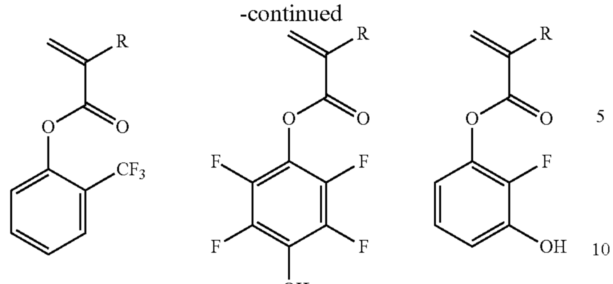

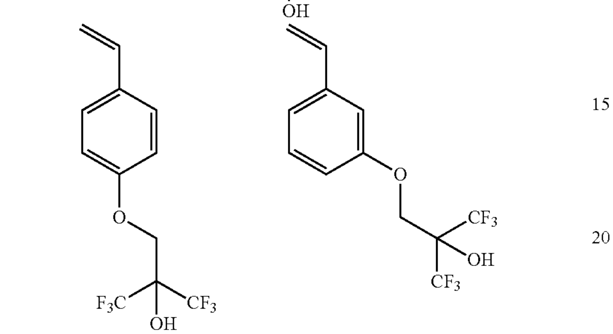

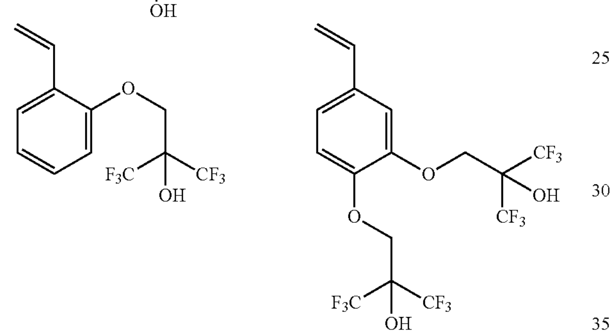

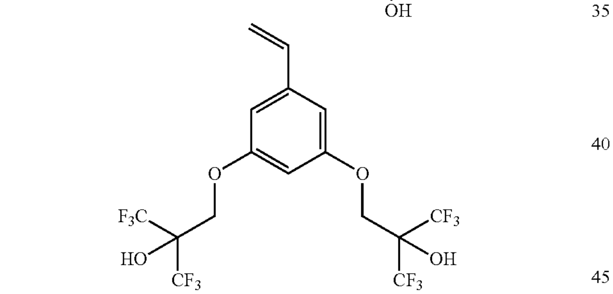

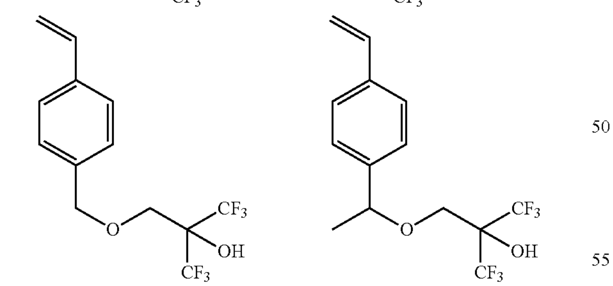

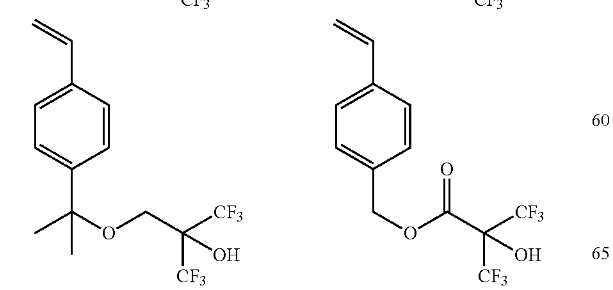

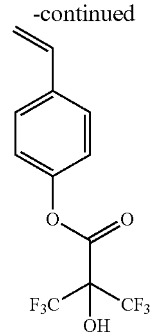

In the formulae, R represents a hydrogen atom or a methyl group.

(Repeating Unit-e)

Dopant polymer (B), which is contained in the electro-conductive polymer composite to form the electro-conductive polymer composite layer making up the inventive electrode, can further have a repeating unit-e having a nitro group, in addition to the repeating units selected from the group consisting of the above repeating units-A1 to -A7, -b, -c, and -d.

Specific examples of a monomer to obtain the repeating unit-e having a nitro group can include the following.

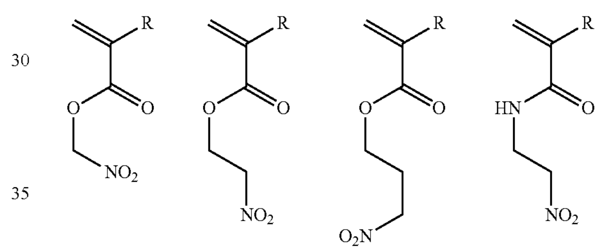

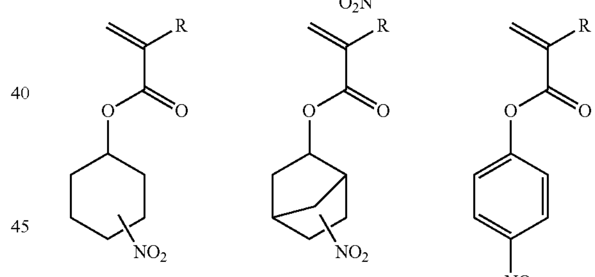

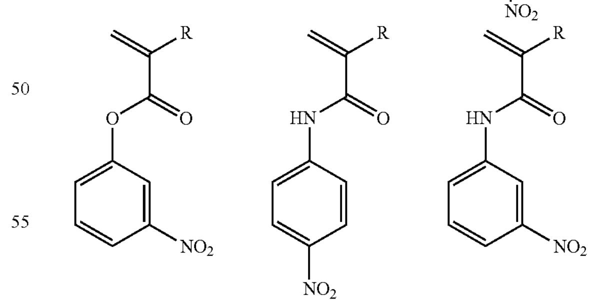

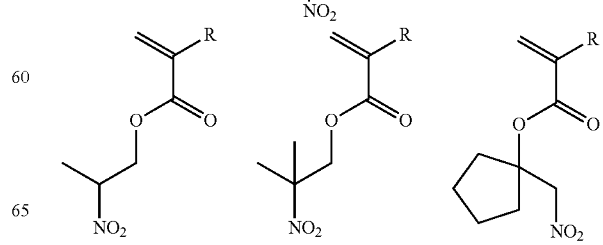

-continued
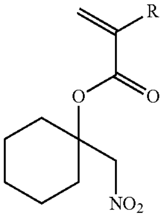
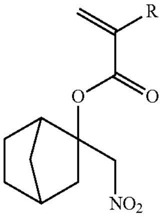
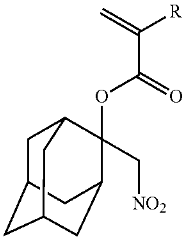
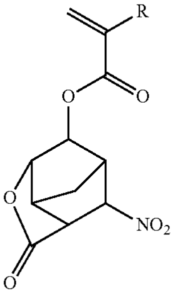
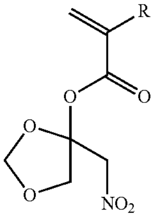
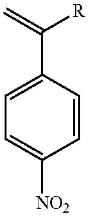
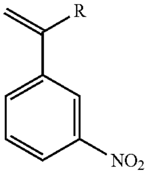
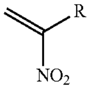
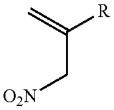
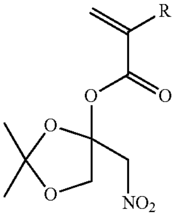
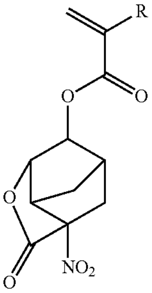
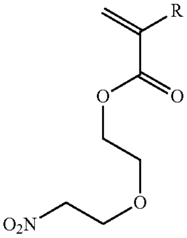
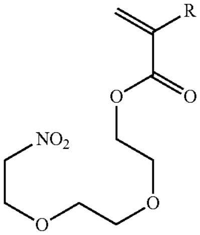
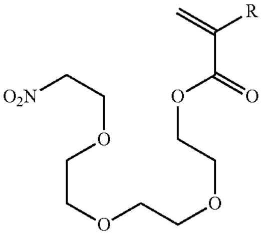
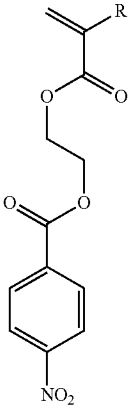
-continued
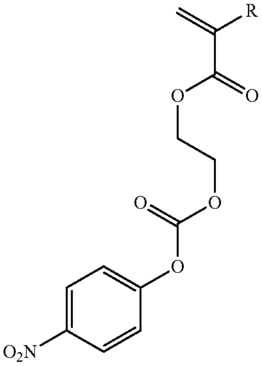
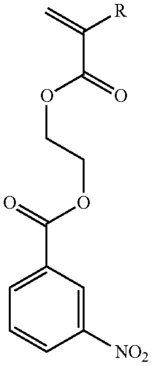
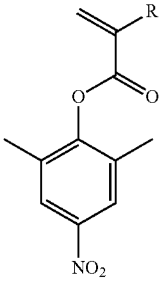
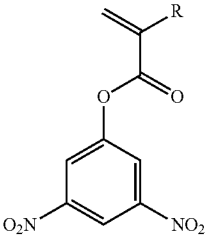
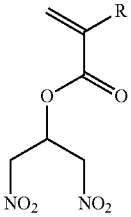
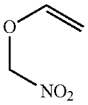
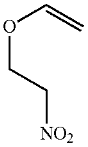
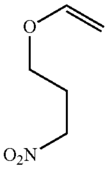
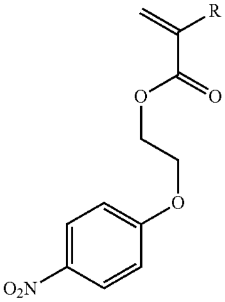
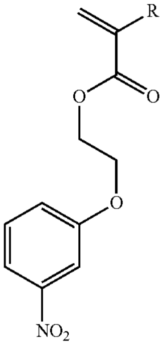
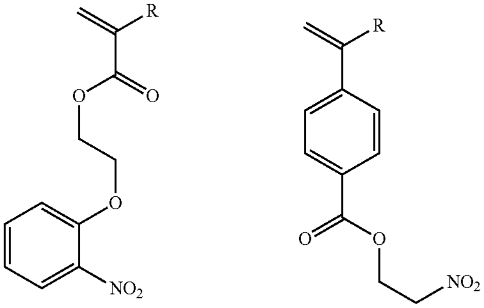

-continued
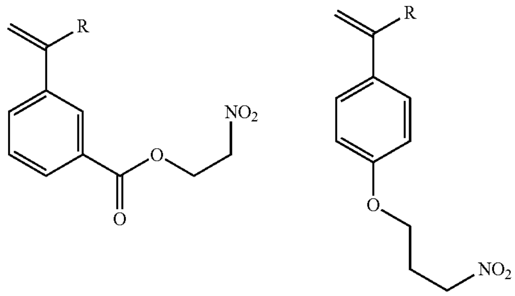
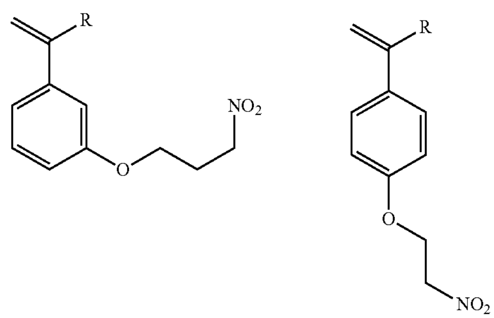
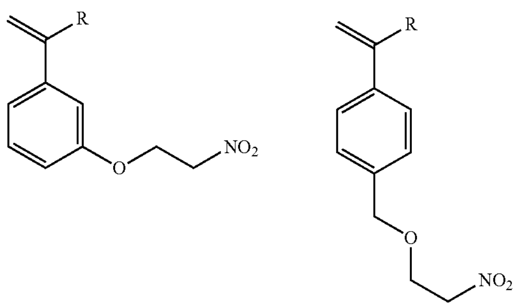
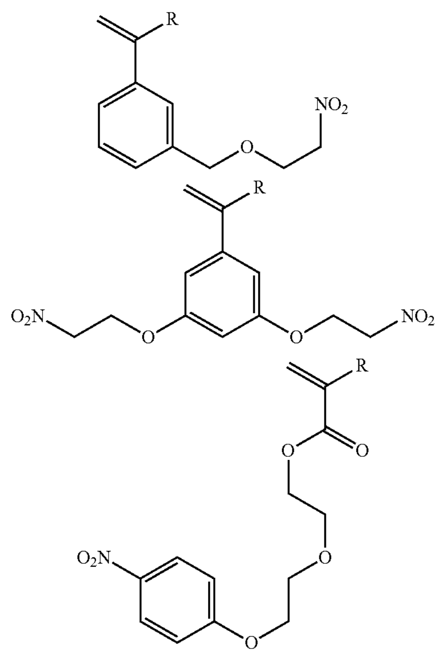
-continued
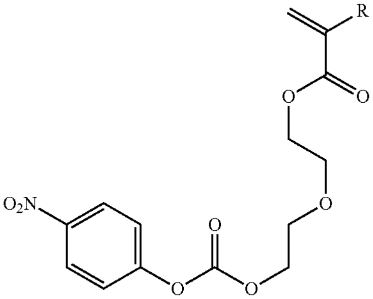
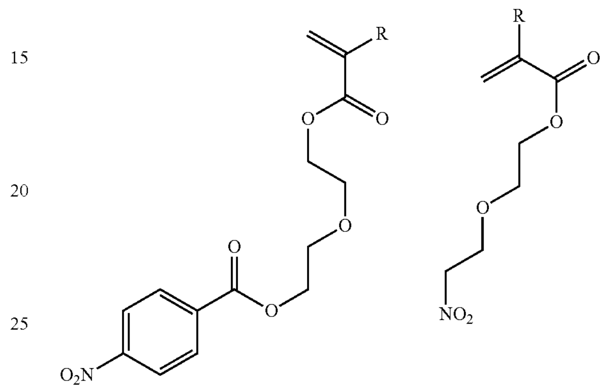
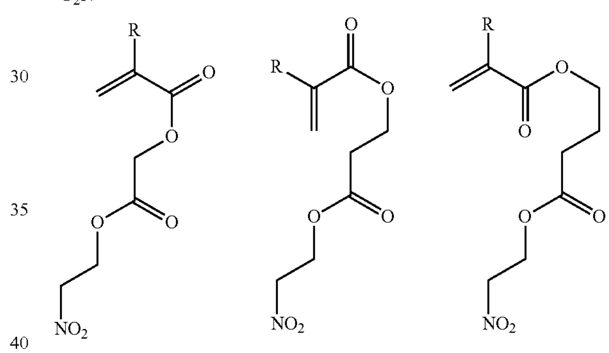
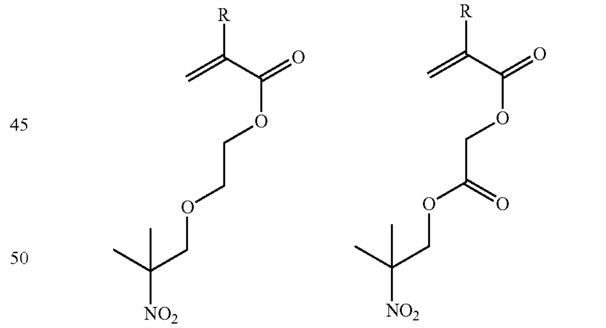
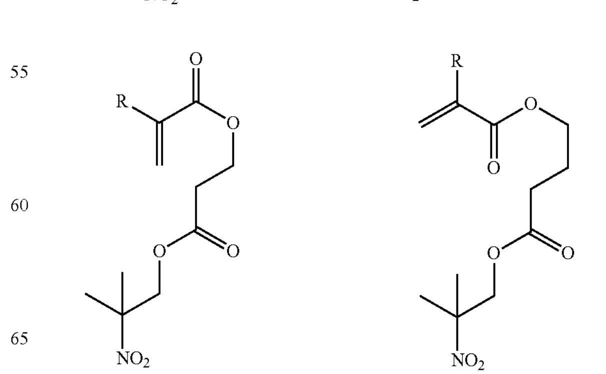

-continued
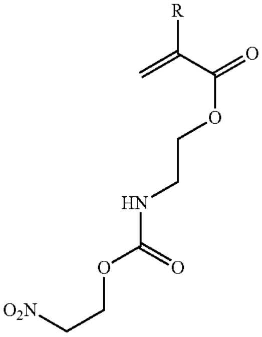
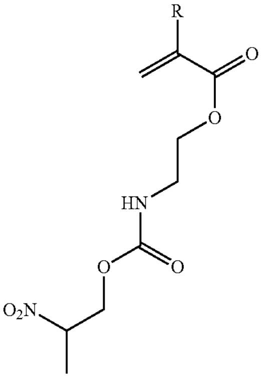
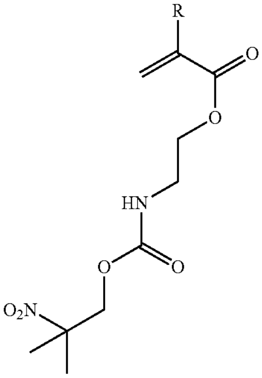
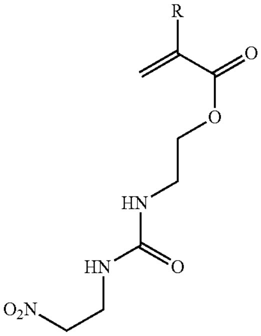
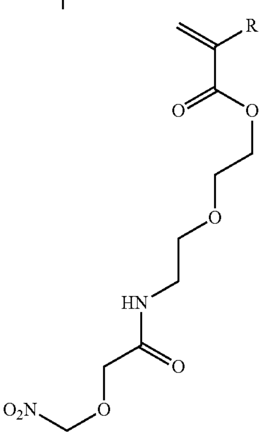
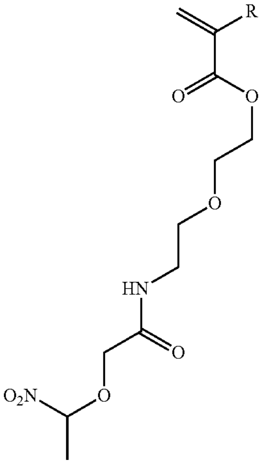
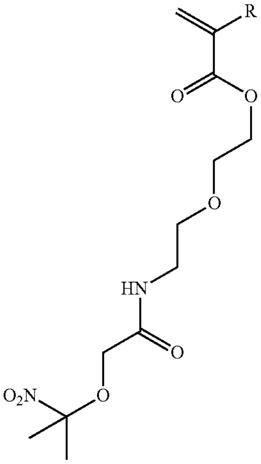
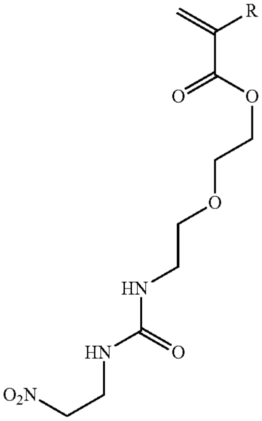
-continued
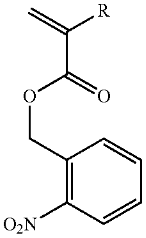
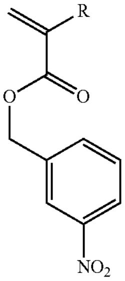
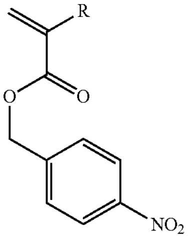
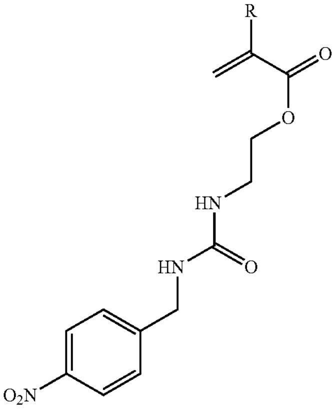
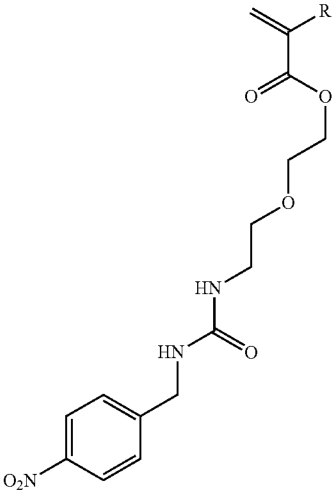
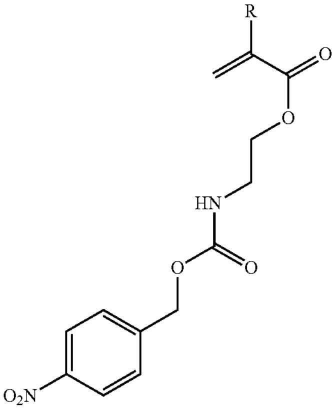

-continued
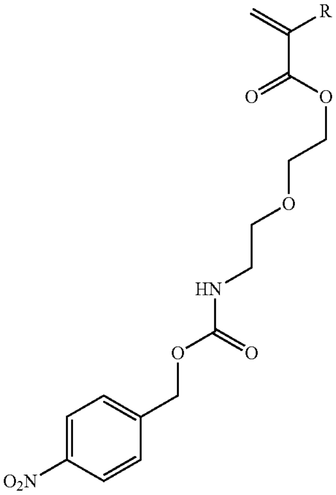
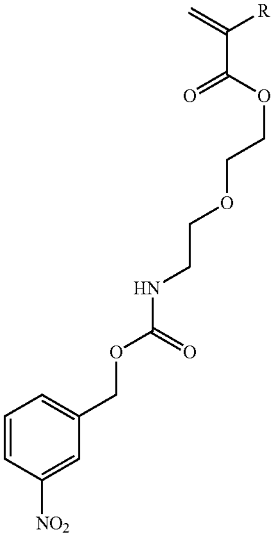
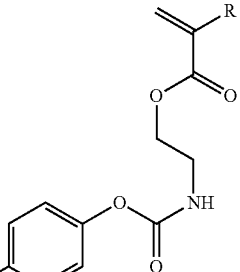
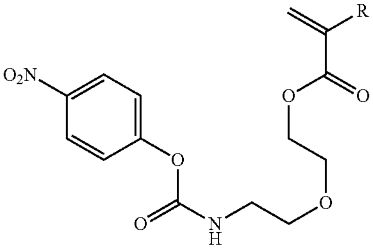
-continued
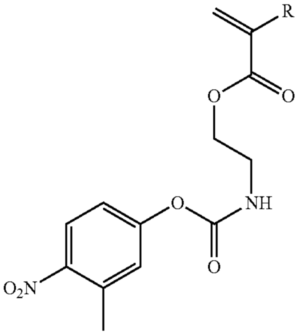
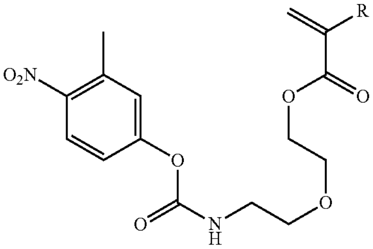
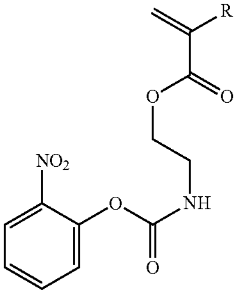
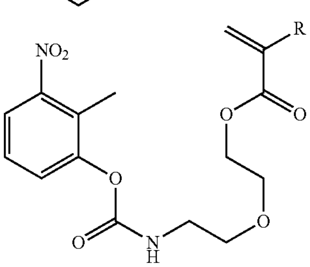
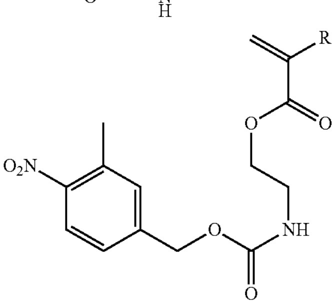
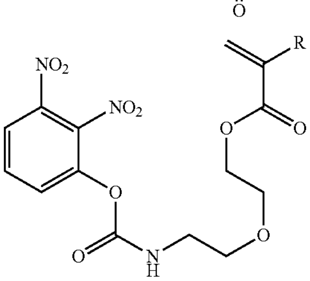

-continued
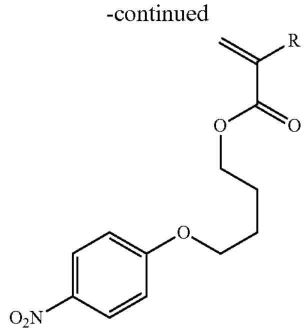
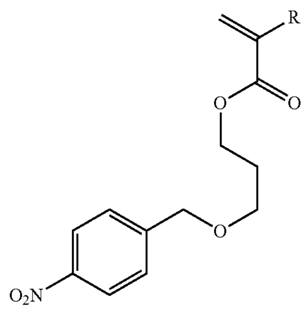
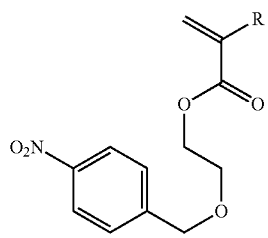
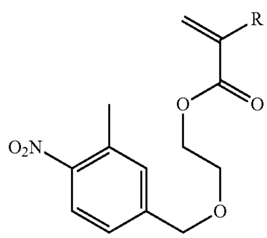
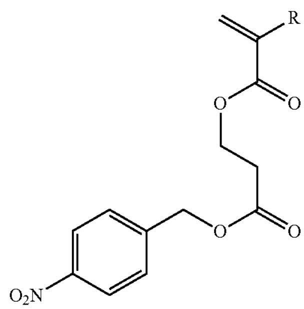
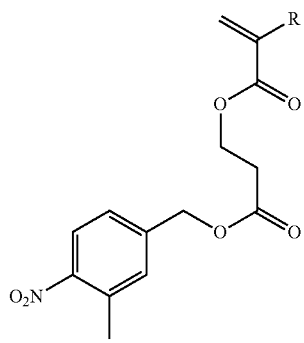
-continued
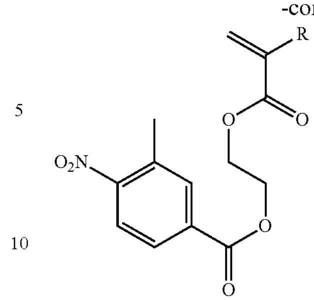
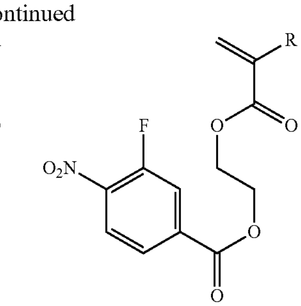
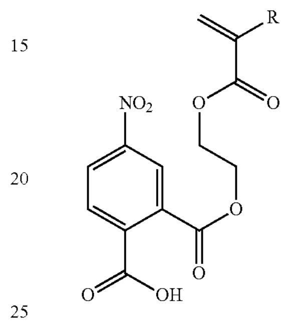
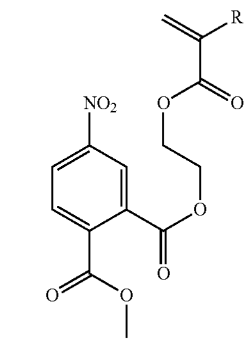
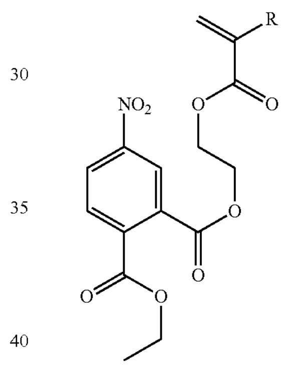
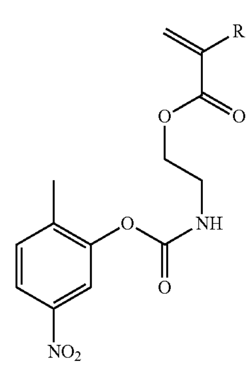
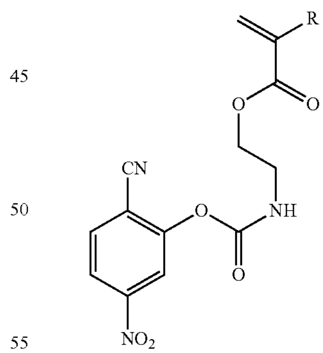
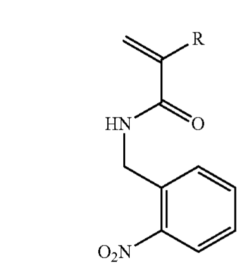
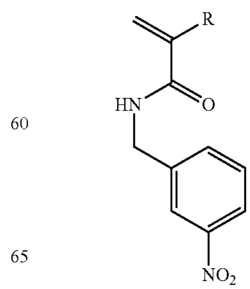
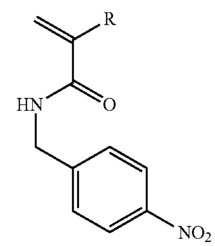

-continued
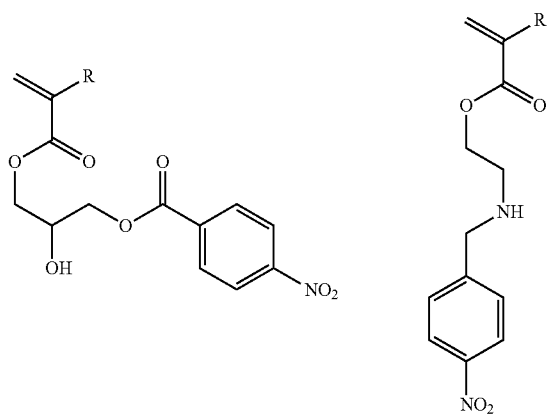
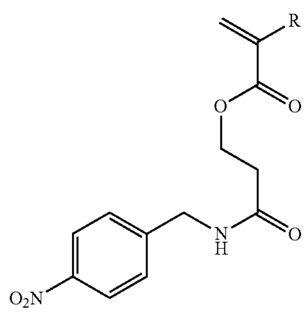
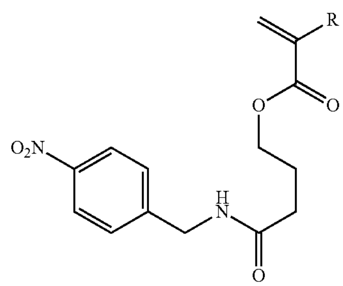
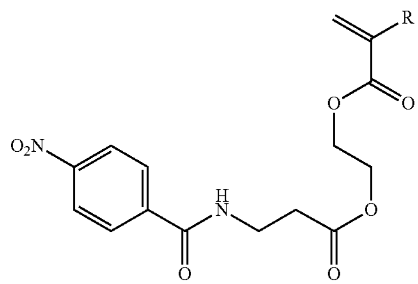
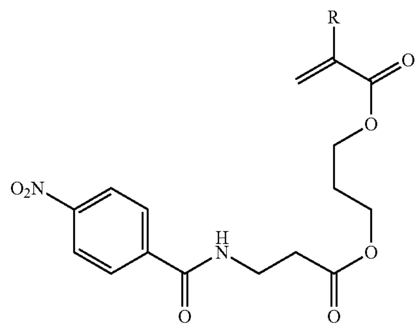
-continued
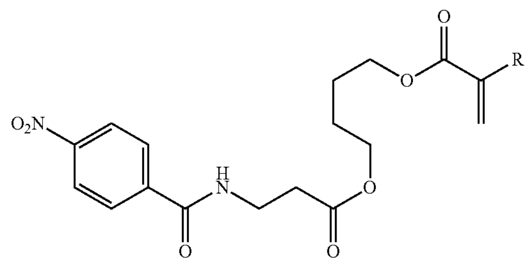
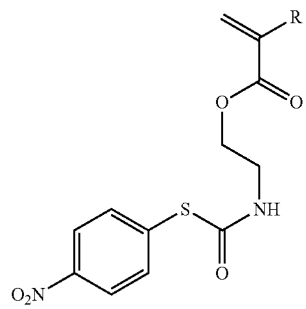
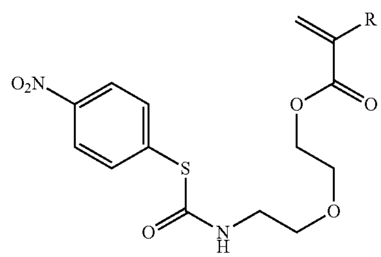
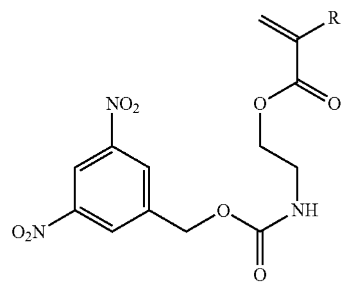
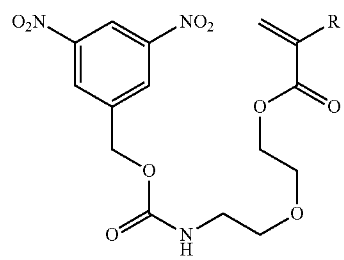
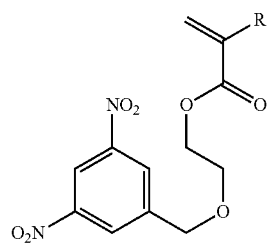

-continued
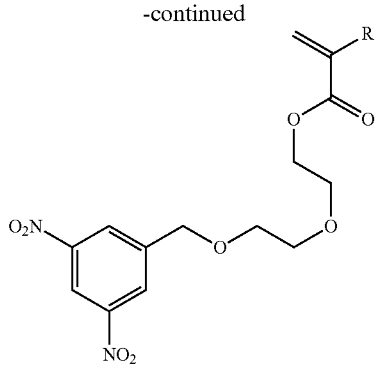
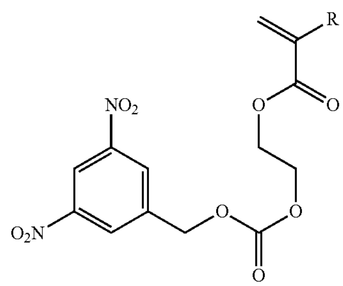
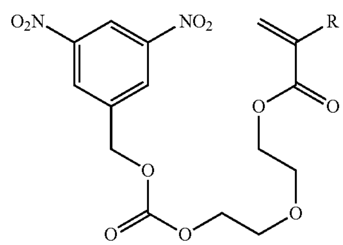
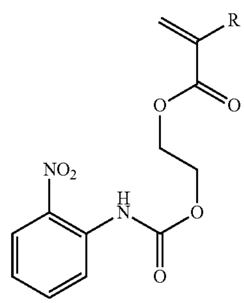
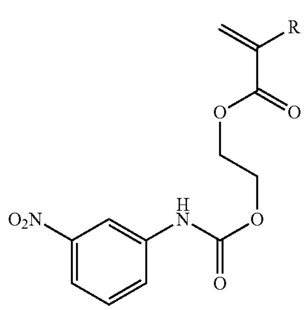
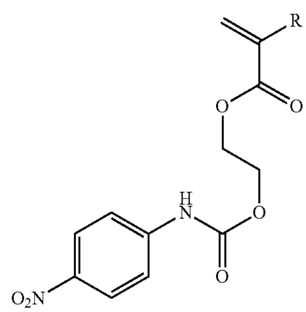
-continued
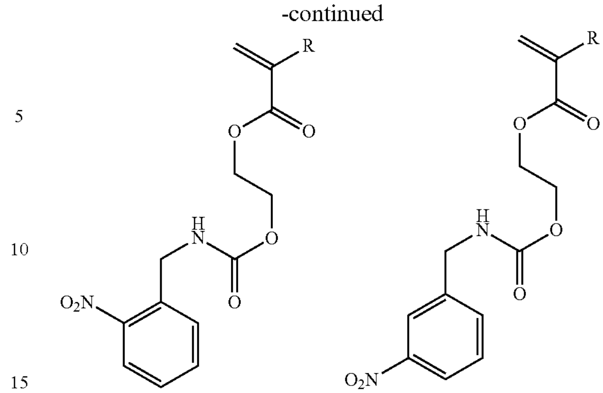
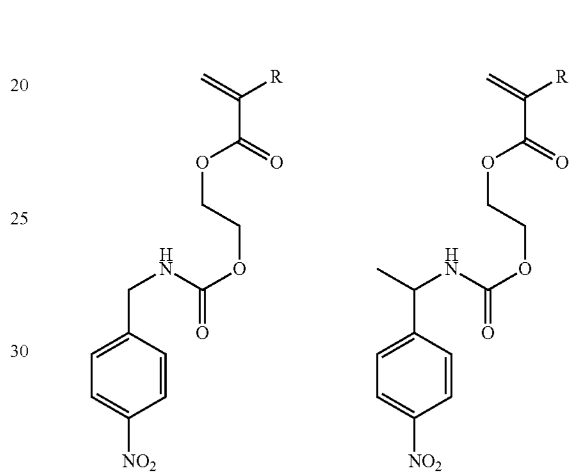
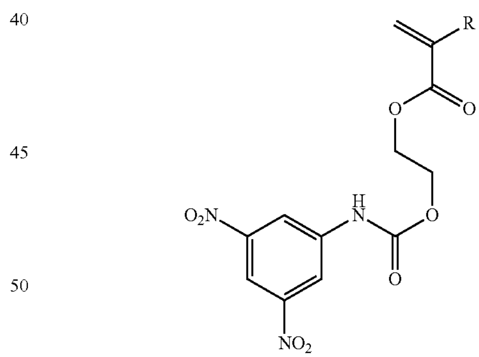
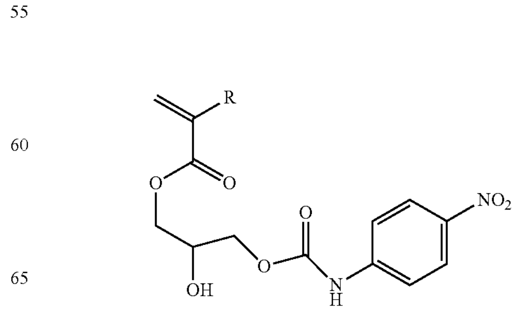

-continued

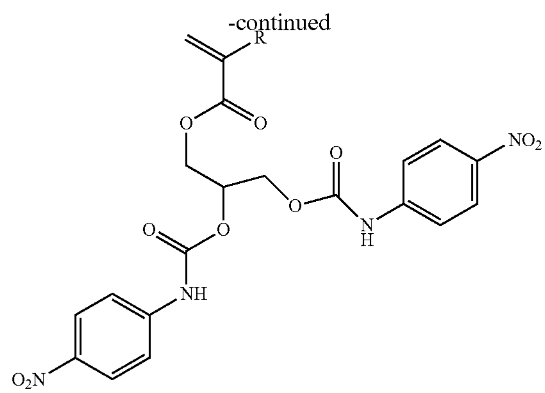

In the formulae, R represents a hydrogen atom or a methyl group.

(Repeating Unit-f)

Dopant polymer (B), which is contained in the electro-conductive polymer composite to form the electro-conductive polymer composite layer making up the inventive electrode, can further have a repeating unit-f having a cyano group, in addition to the repeating units selected from the group consisting of the above repeating units-A1 to -A7, -b, -c, -d, and -e.

Specific examples of a monomer to obtain the repeating unit-f having a cyano group can include the following.

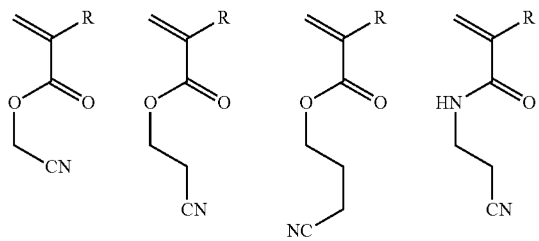

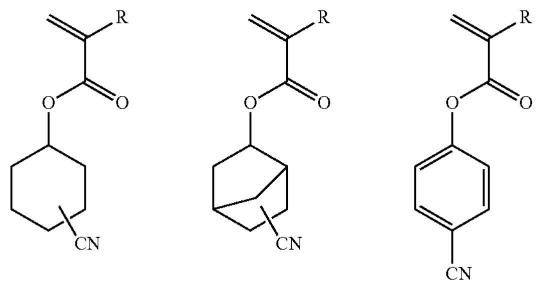

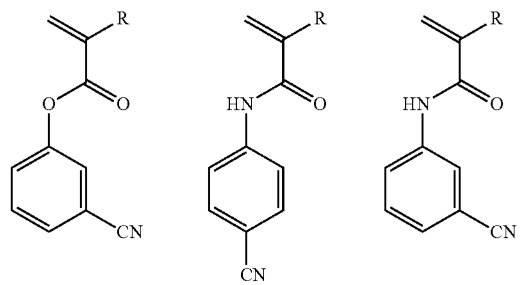

-continued

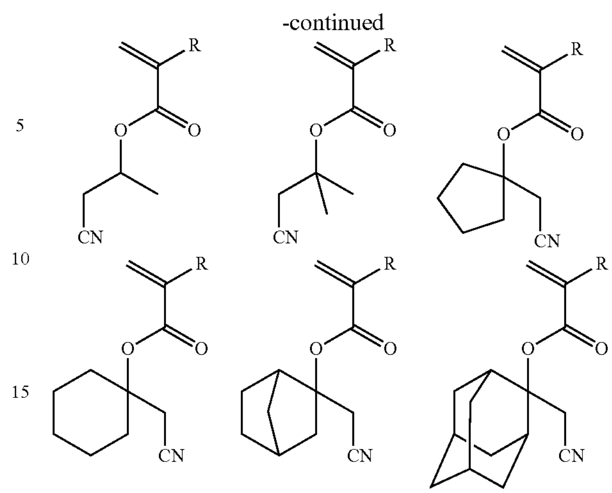

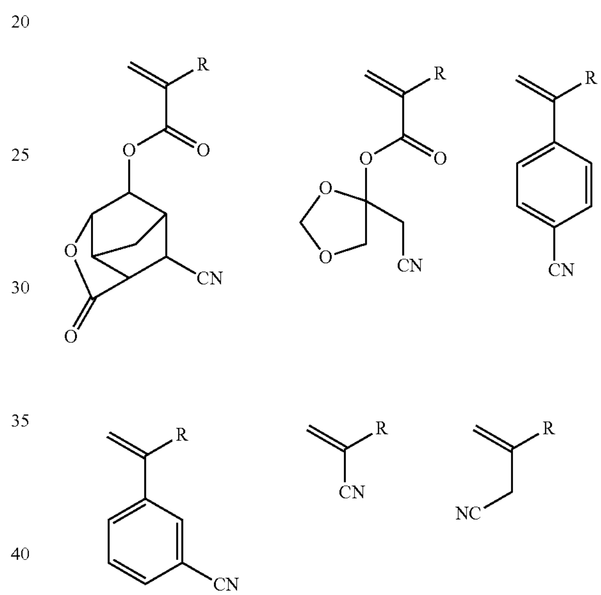

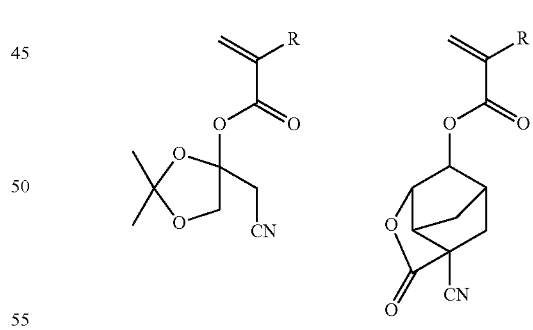

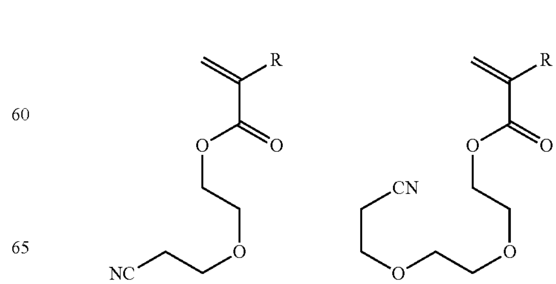

-continued
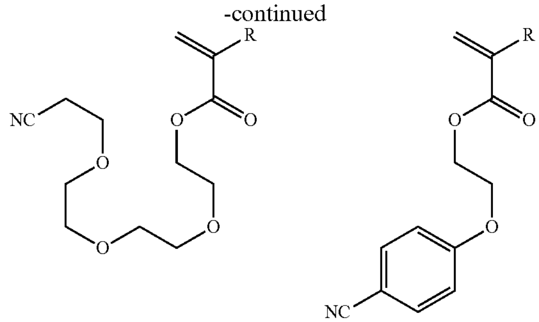
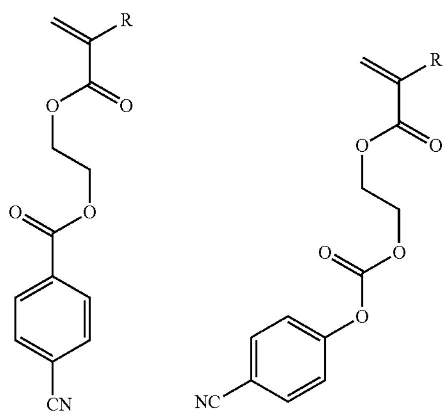
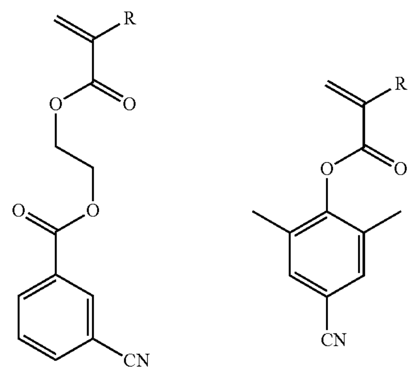
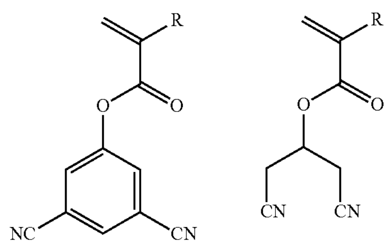
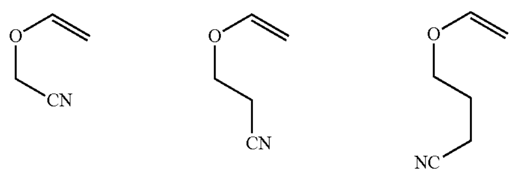
-continued
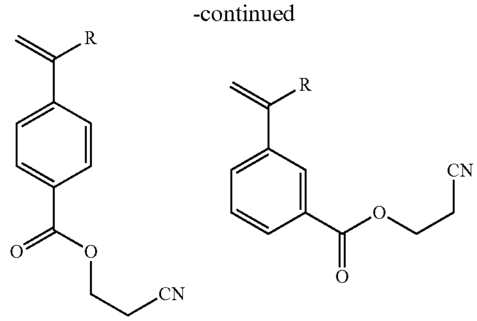
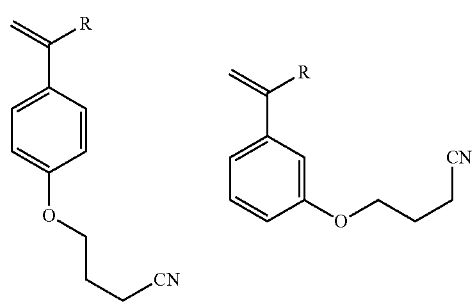
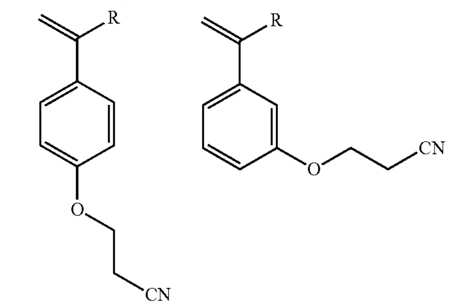
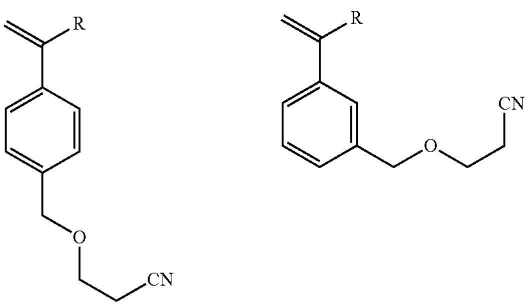
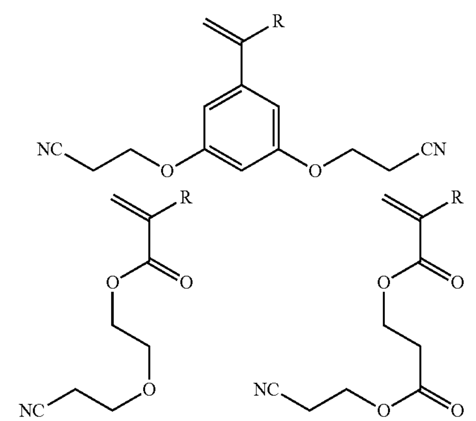

-continued

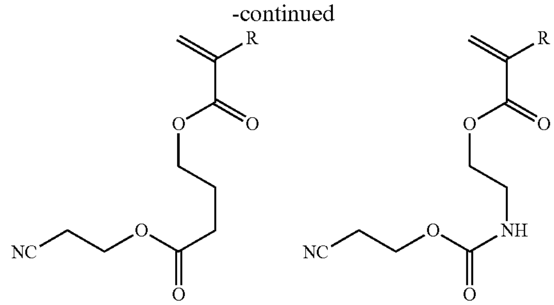

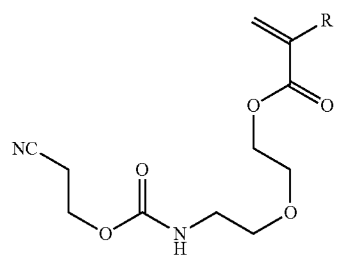

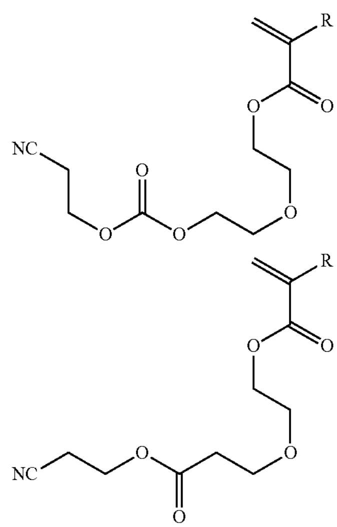

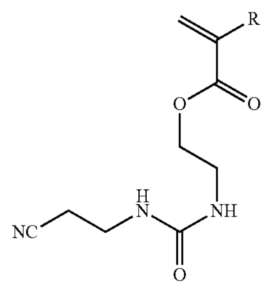

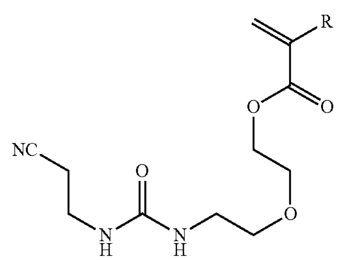

-continued

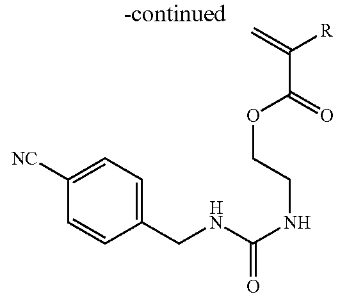

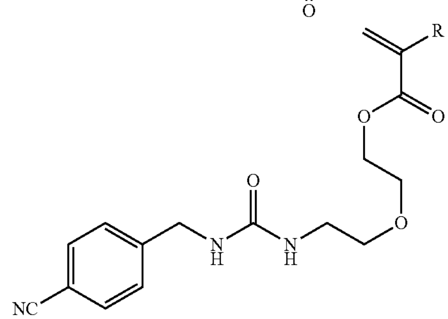

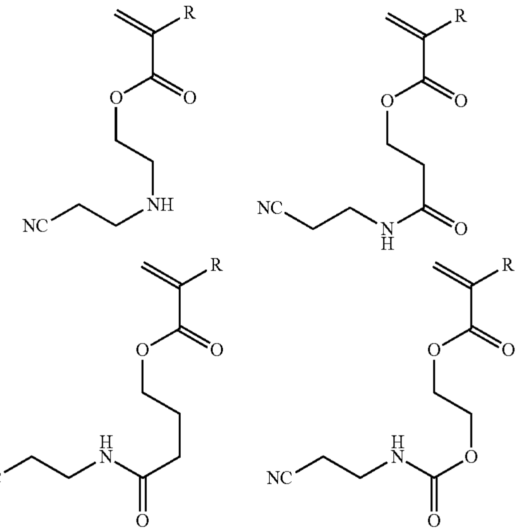

In the formulae, R represents a hydrogen atom or a methyl group.

In addition, the repeating unit "a" preferably contains, as the ammonium ion constituting the ammonium salt, an ammonium ion (ammonium cation) represented by the following general formula (3).

(3)

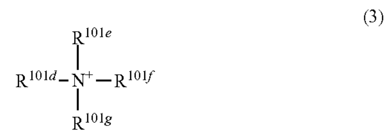

In the general formula (3), $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, and may include one or more kinds selected from the group consisting of an ether group, a carbonyl group, an ester group, a hydroxy group, a carboxy group, an amino group, a nitro group, a sulfonyl group, a sulfinyl group, a halogen atom, and a sulfur atom. $R^{101d}$ and $R^{101e}$, or $R^{101d}$, $R^{101e}$, and $R^{101f}$ may form a ring together with a nitrogen atom bonded to $R^{101d}$ and $R^{101e}$, or $R^{101d}$, $R^{101e}$, and $R^{101f}$. When a ring is formed, $R^{101d}$ and $R^{101e}$, or $R^{101d}$, $R^{101e}$, and $R^{101f}$ form an alkylene group having 3 to 10 carbon atoms or a heteroaromatic ring having, in the ring, the nitrogen atom shown in the general formula (3).

Specific examples of the ammonium ion represented by the general formula (3) can include the following.

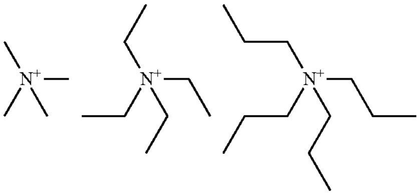

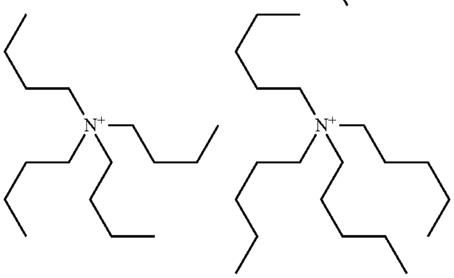

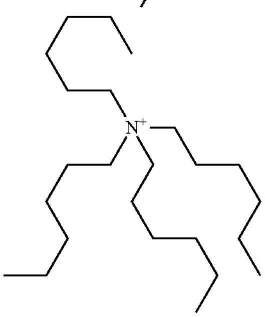

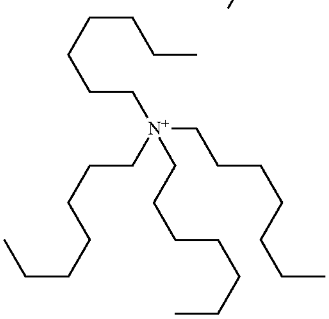

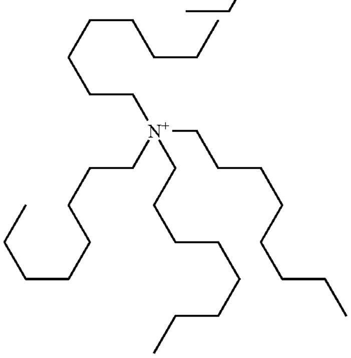

-continued

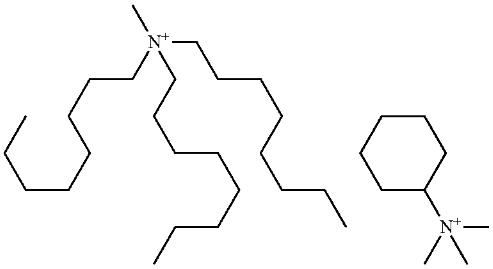

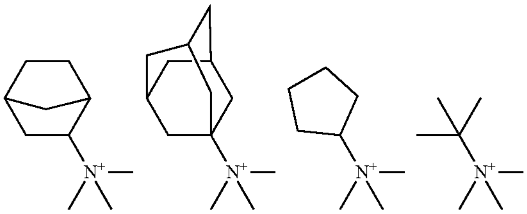

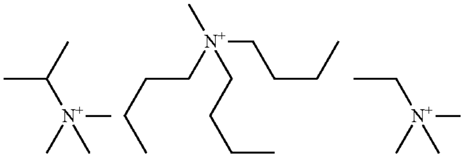

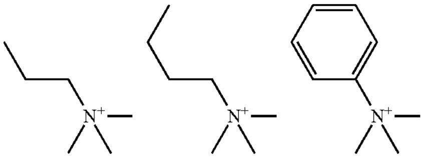

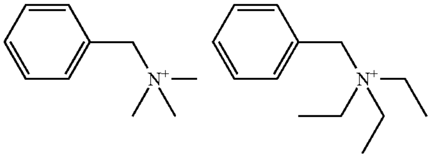

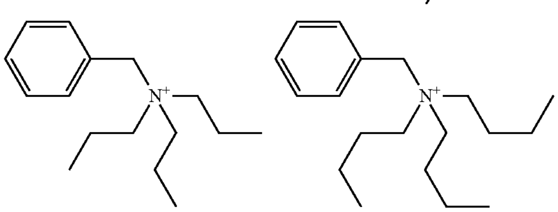

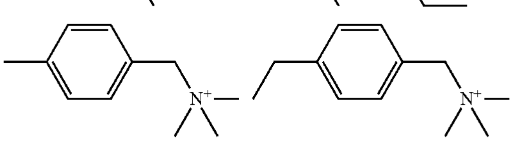

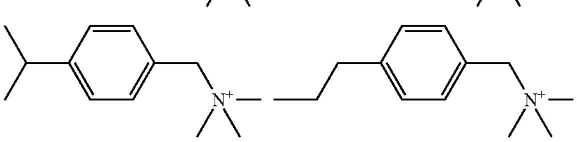

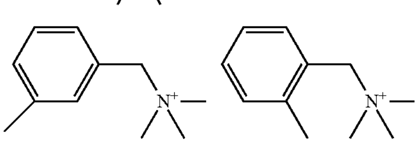

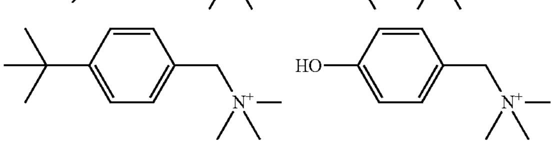

-continued
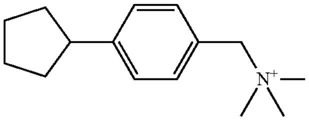
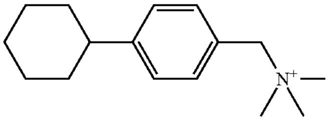
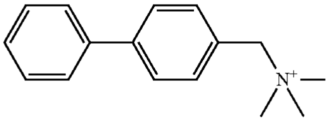
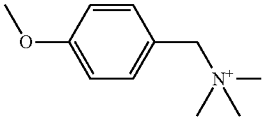
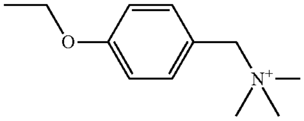
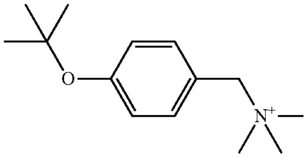
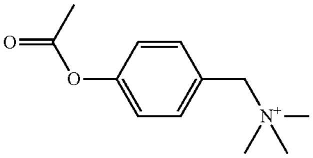
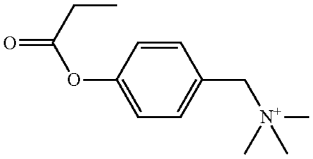
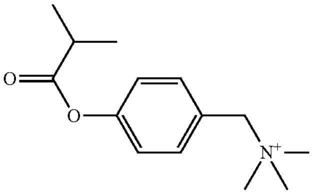
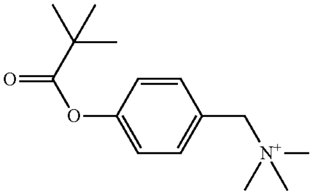
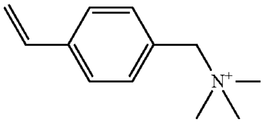
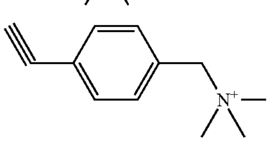
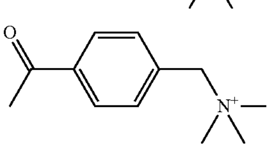
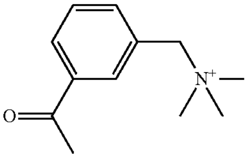
-continued
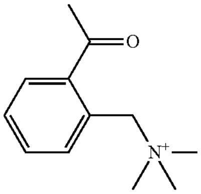
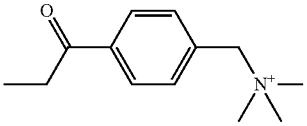
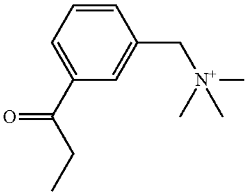
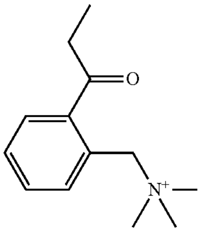
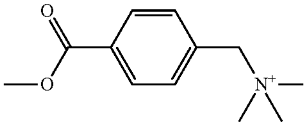
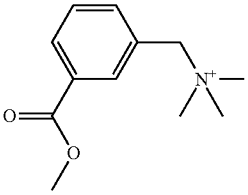
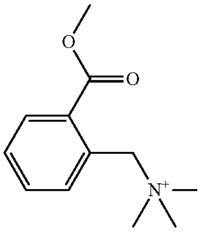
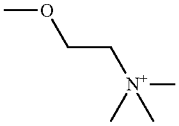
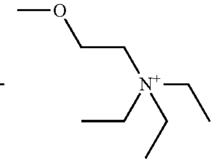
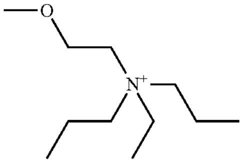
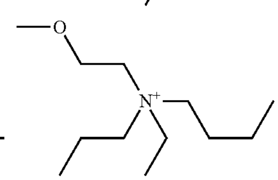
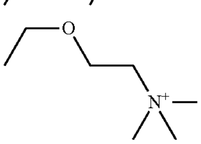
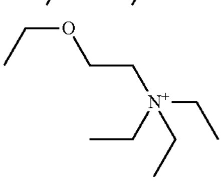
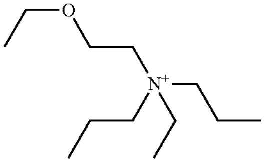
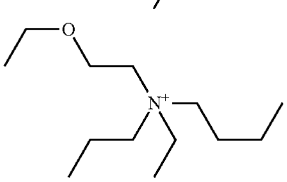
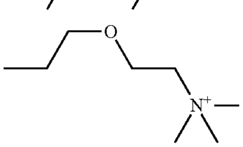
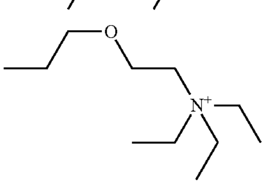

-continued
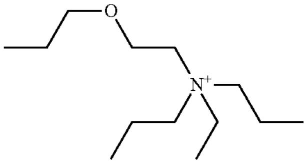
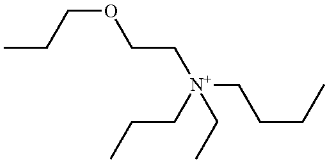
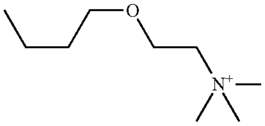
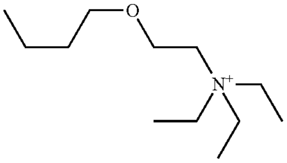
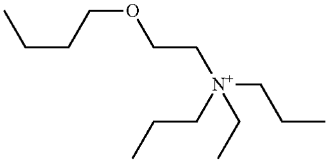
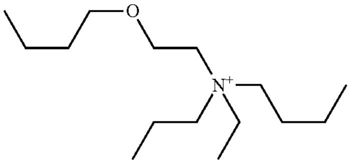
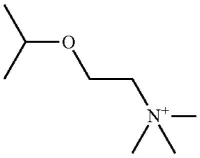
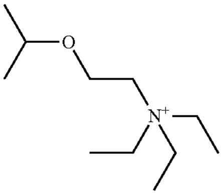
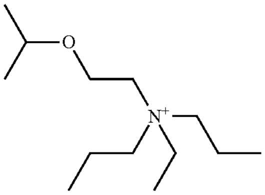
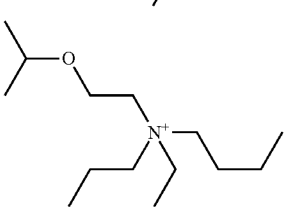
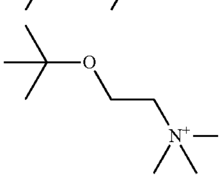
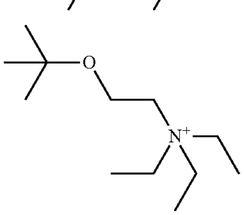
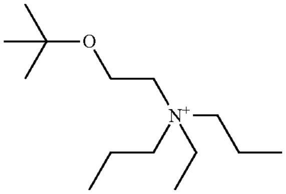
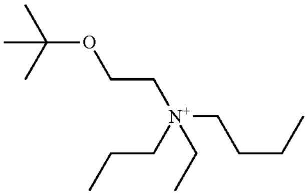
-continued
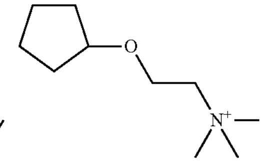
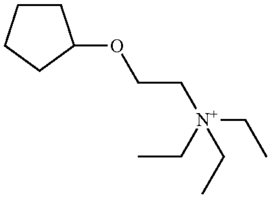
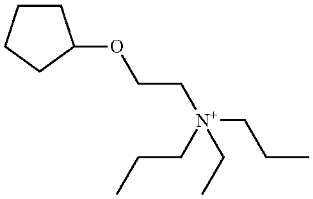
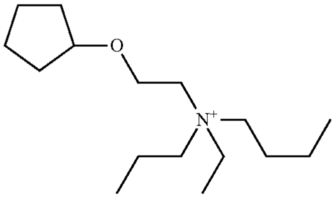
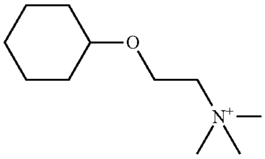
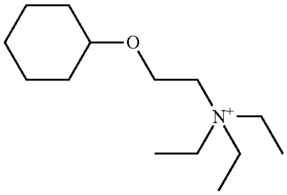
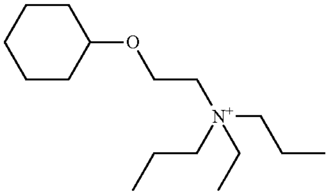
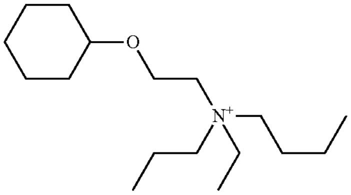
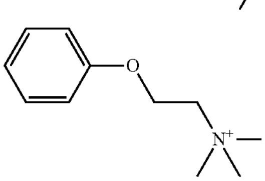
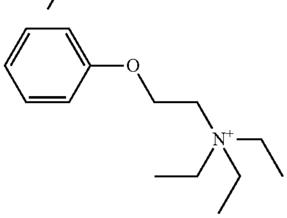

-continued
-continued
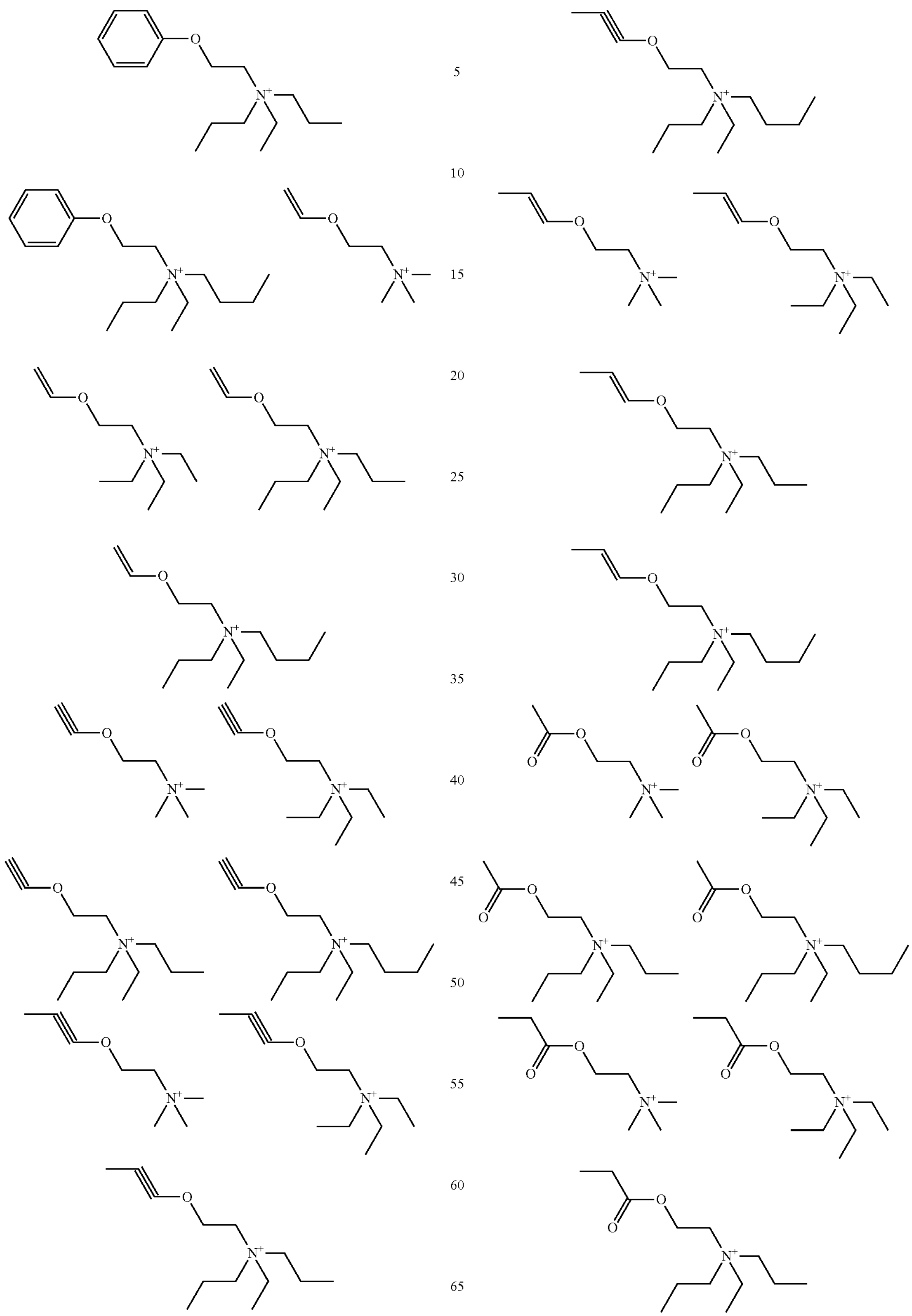

-continued
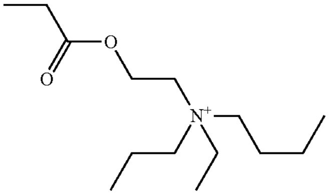
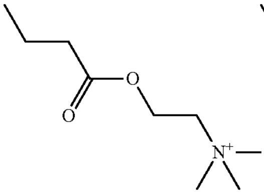
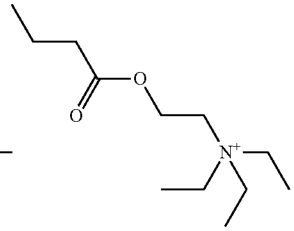
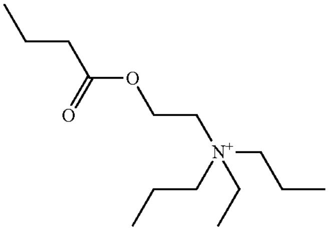
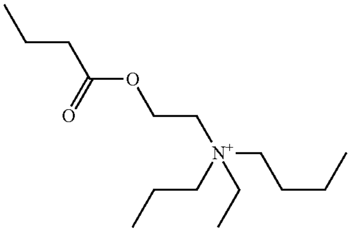
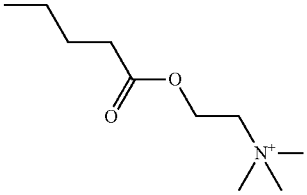
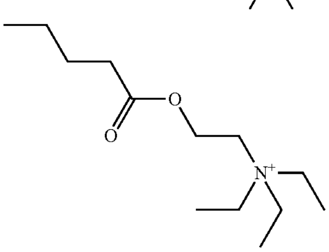
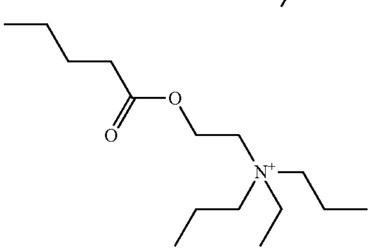
-continued
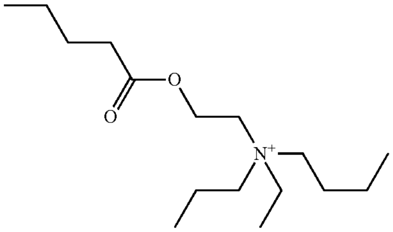
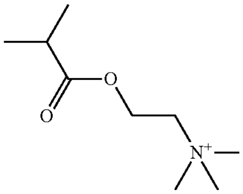
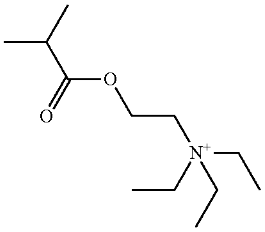
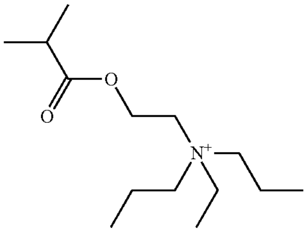
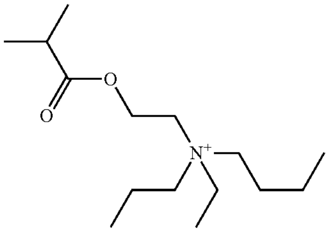
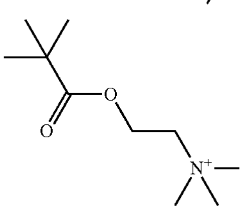
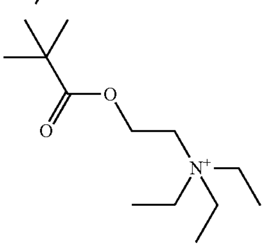
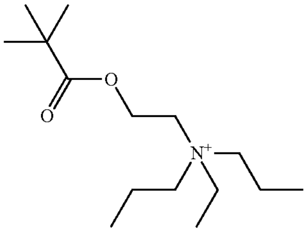
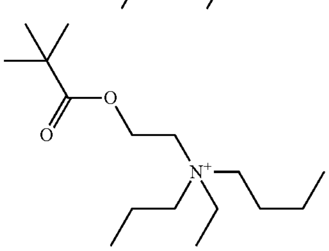

-continued
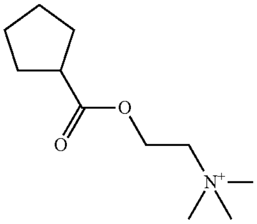
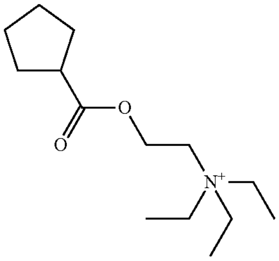
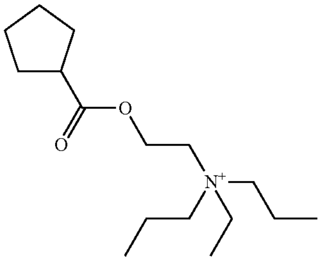
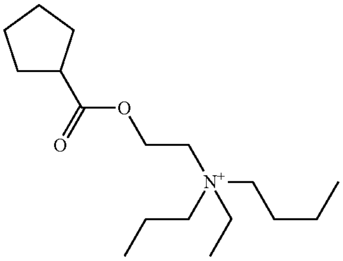
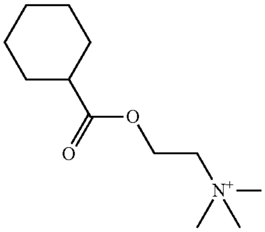
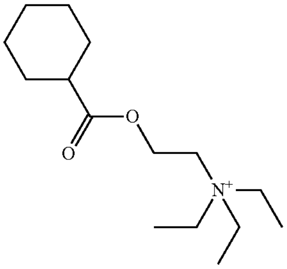
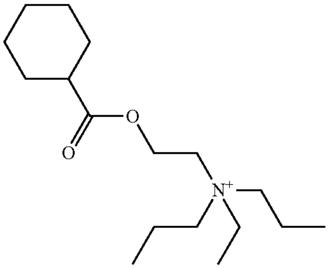
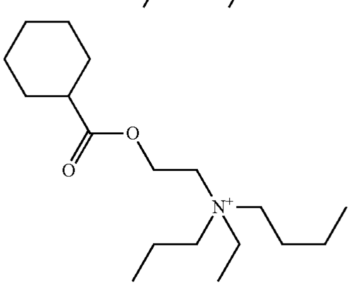
-continued
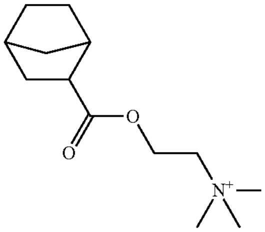
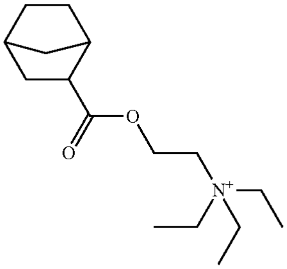
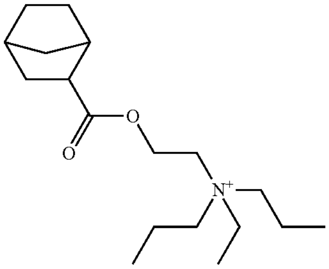
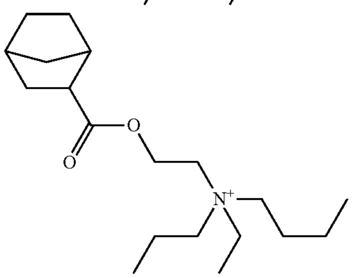
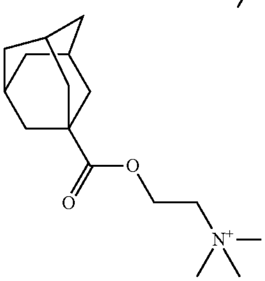
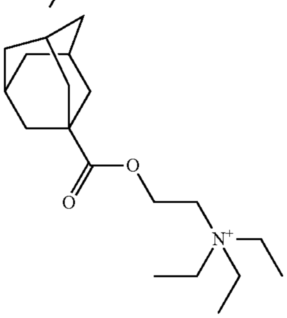
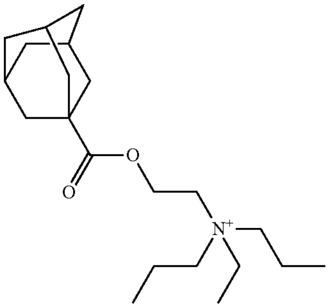
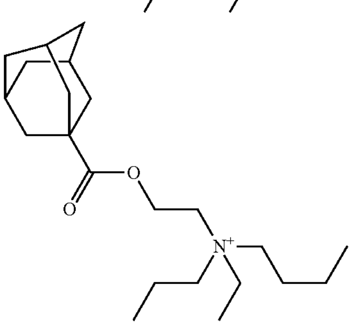

-continued
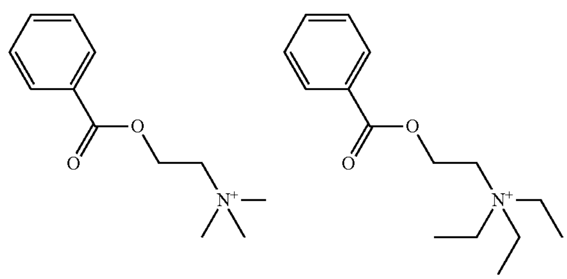
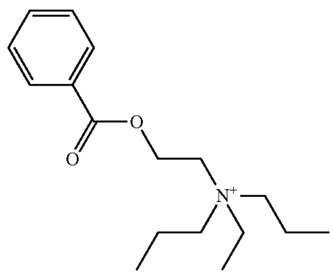
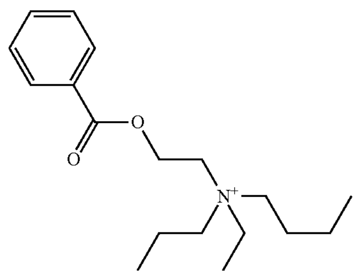
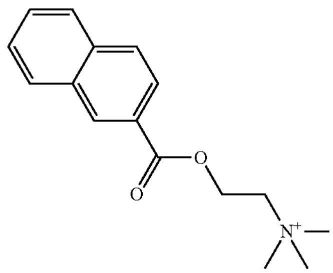
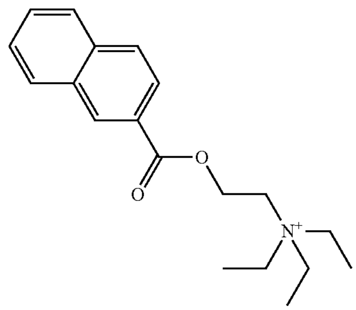
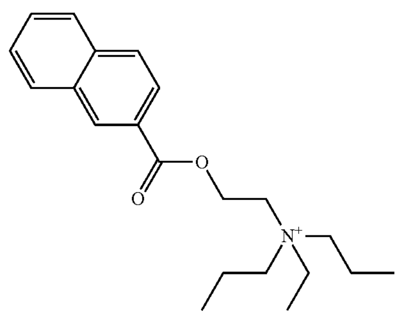
-continued
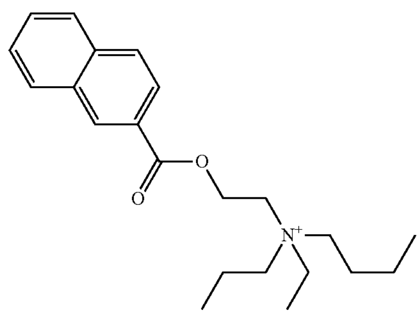
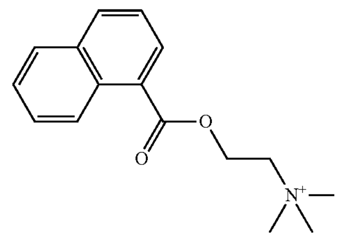
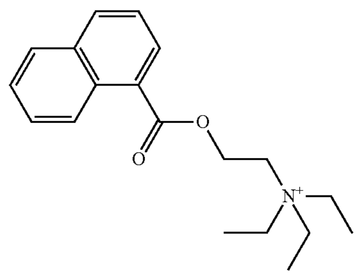
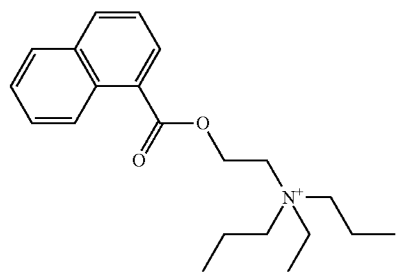
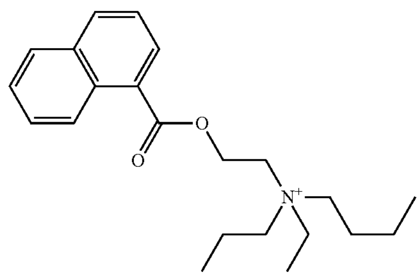
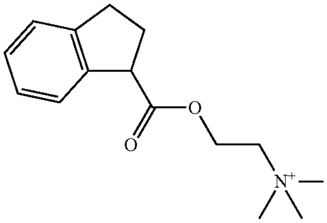

-continued
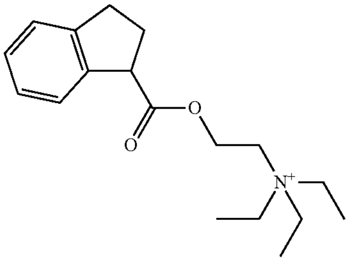
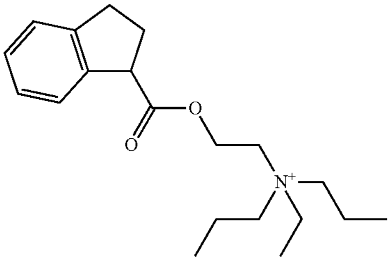
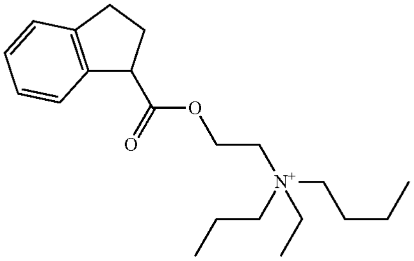
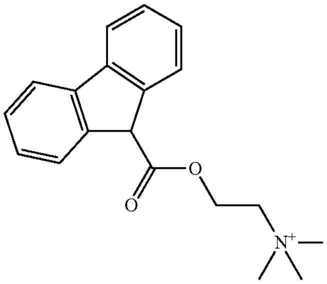
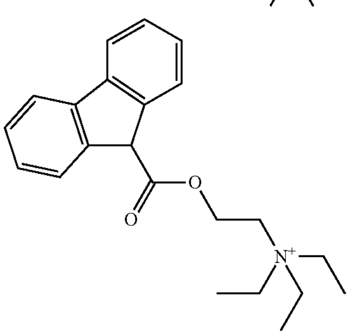
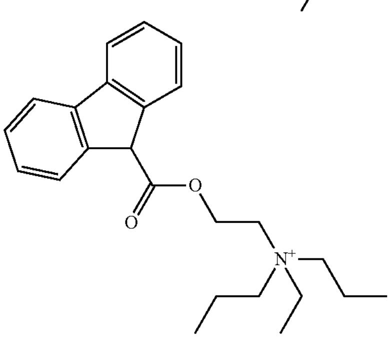
-continued
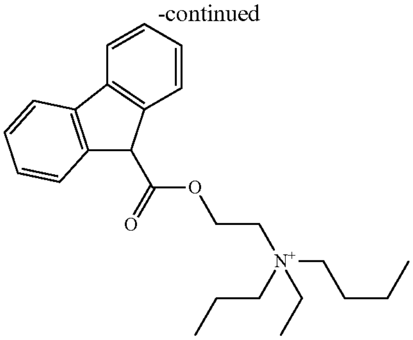
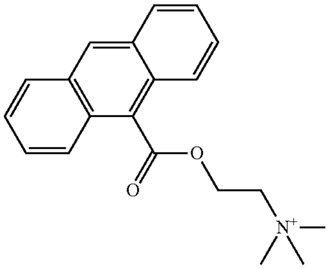
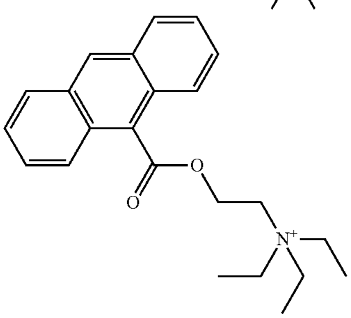
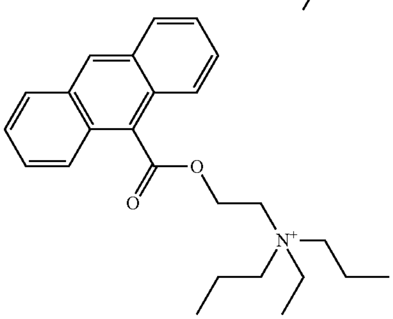
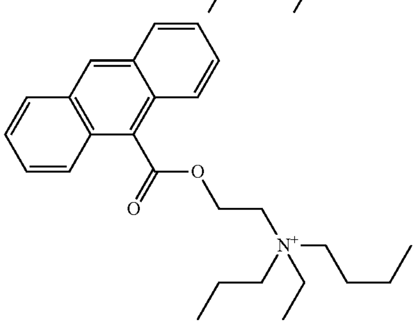
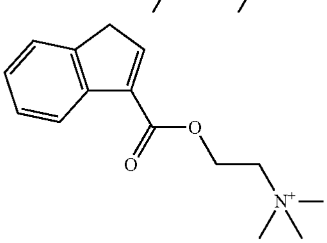

-continued
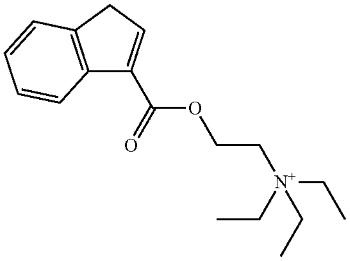
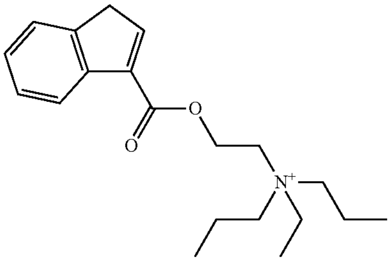
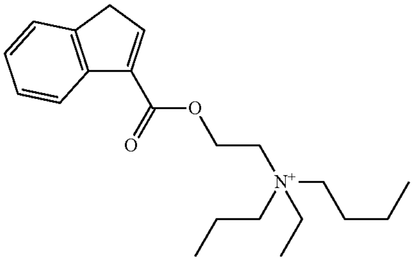
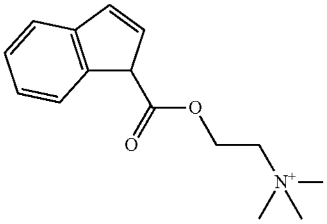
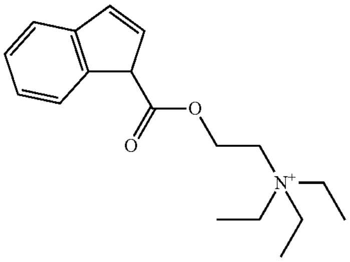
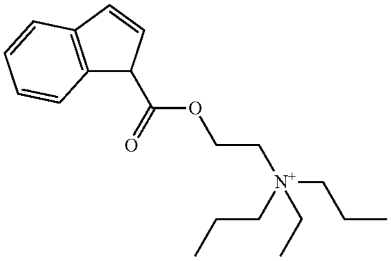
-continued
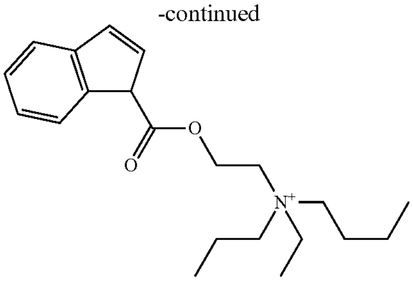
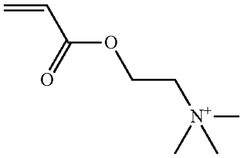
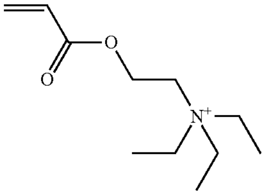
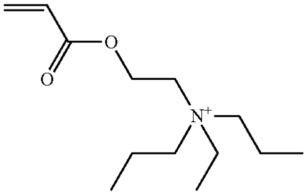
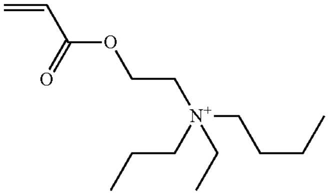
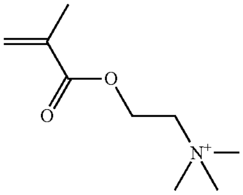
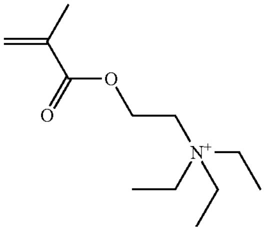
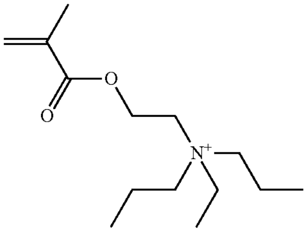
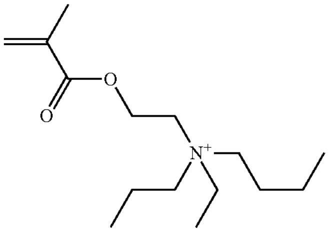

-continued
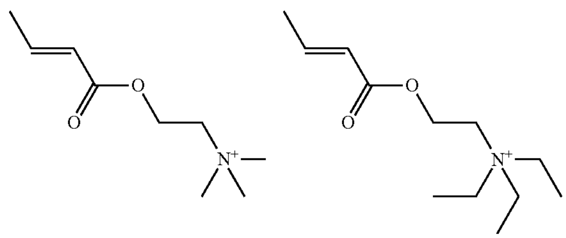
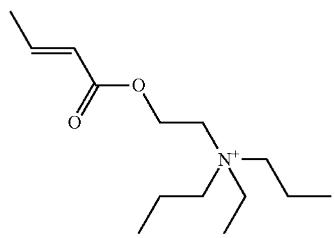
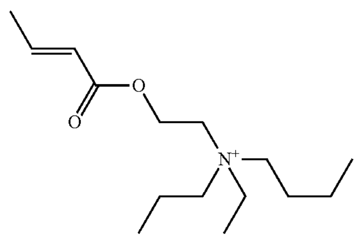
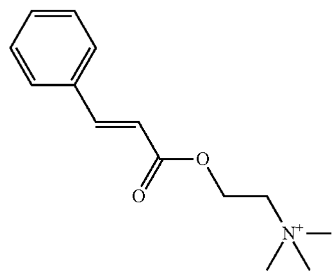
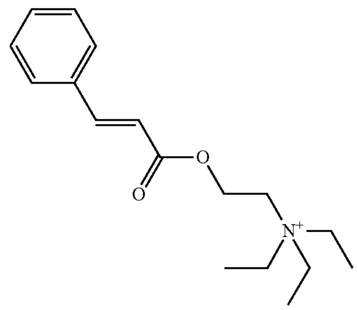
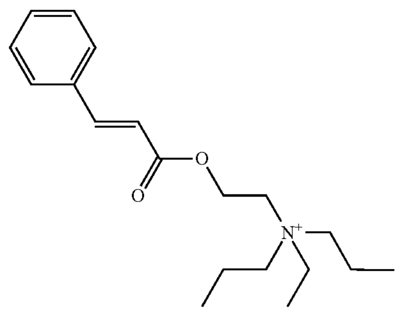
-continued
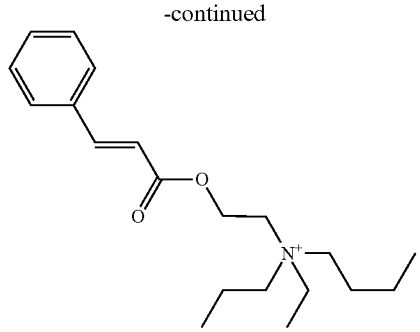
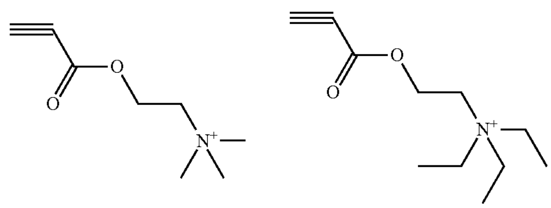
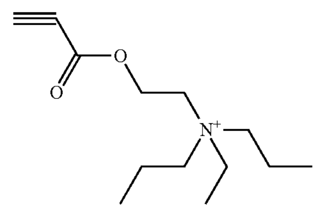
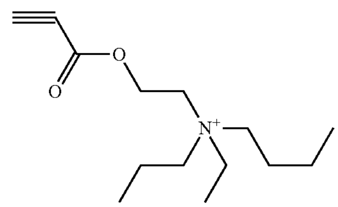
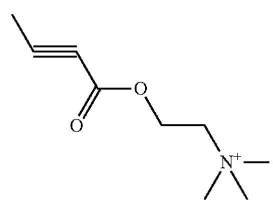
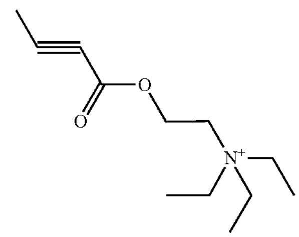
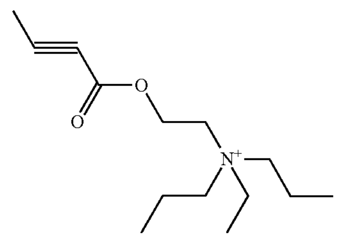

-continued
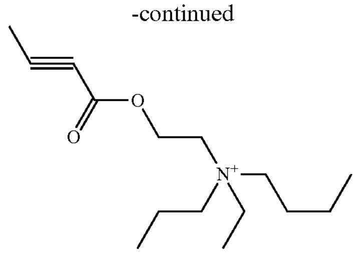
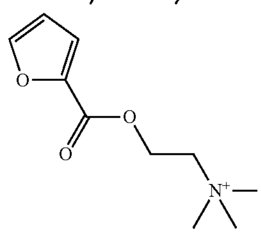
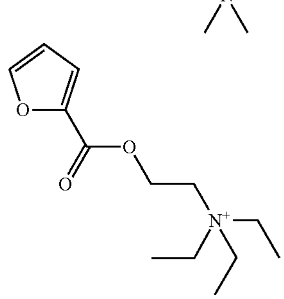
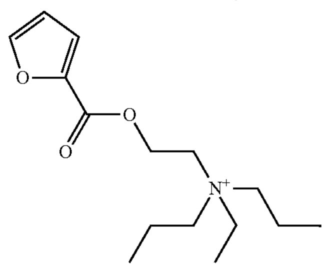
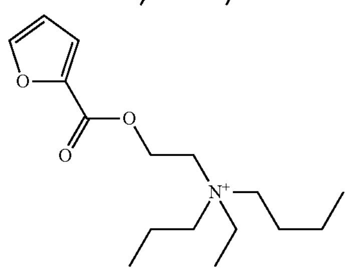
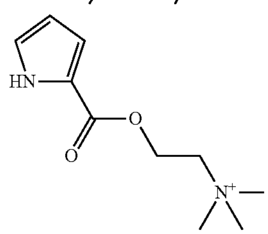
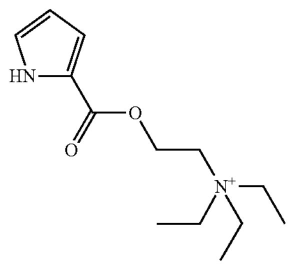
-continued
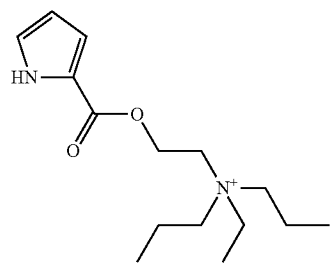
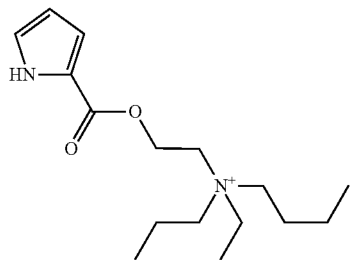
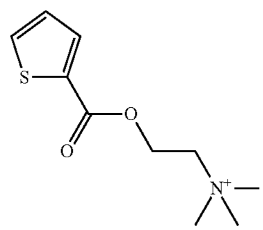
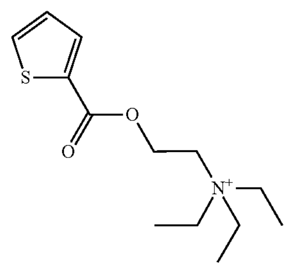
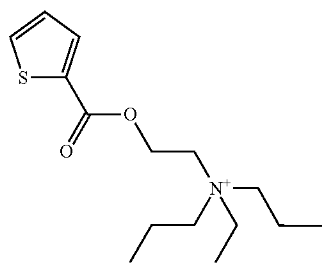
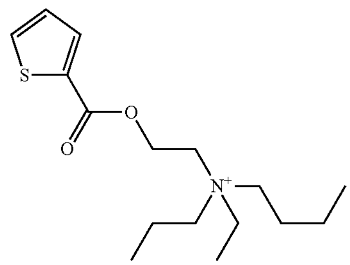

-continued
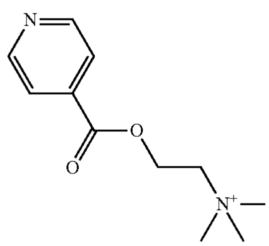
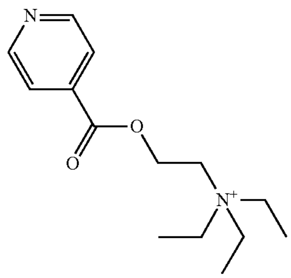
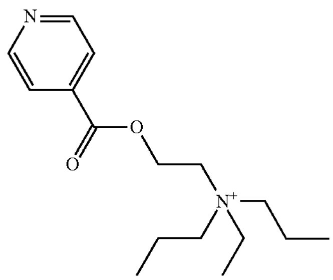
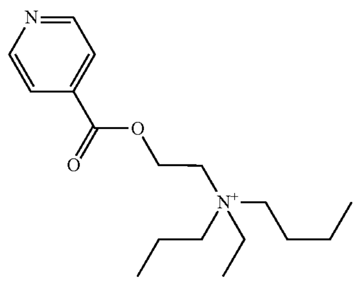
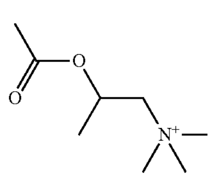
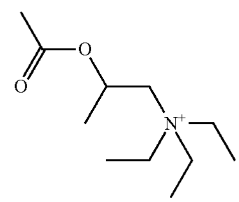
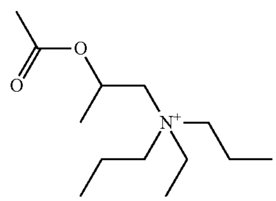
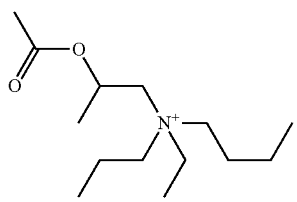
-continued
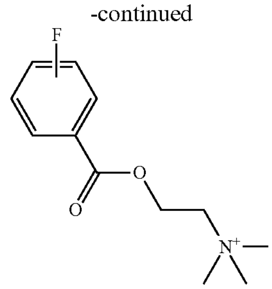
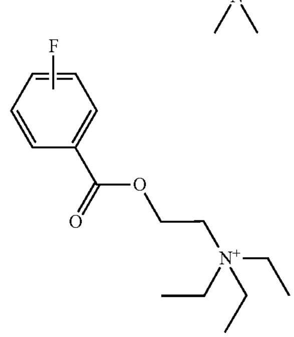
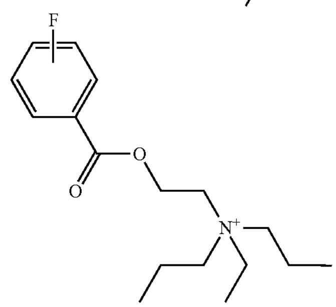
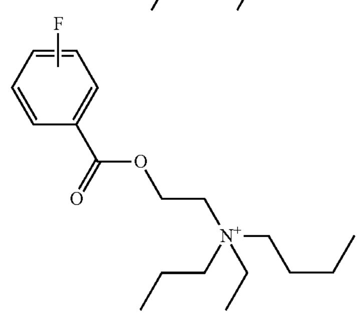
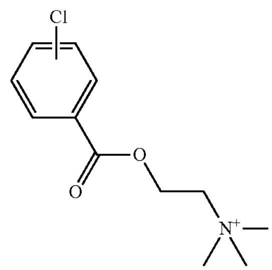
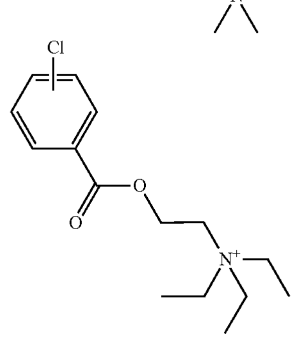

-continued
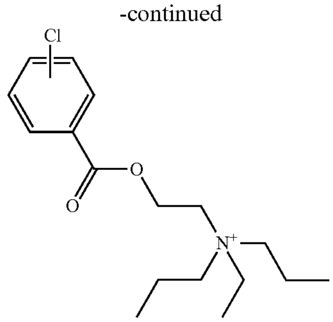
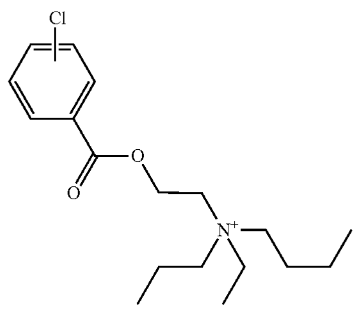
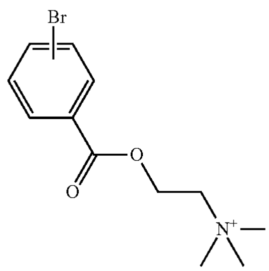
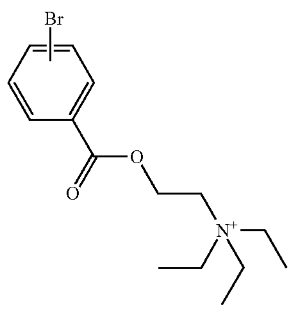
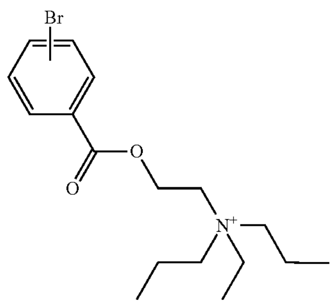
-continued
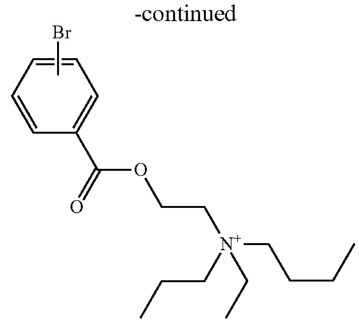
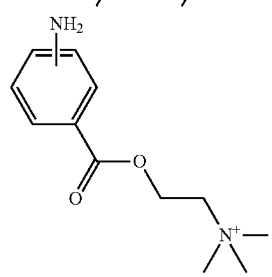
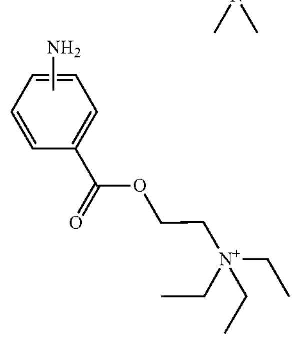
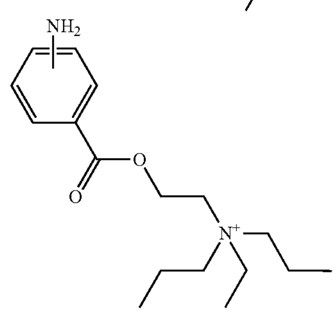
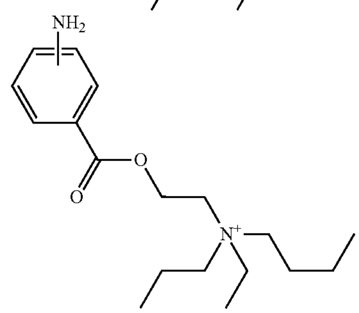
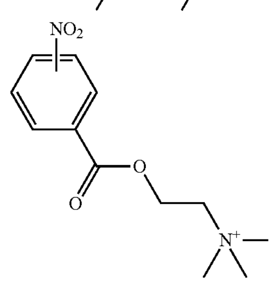

-continued
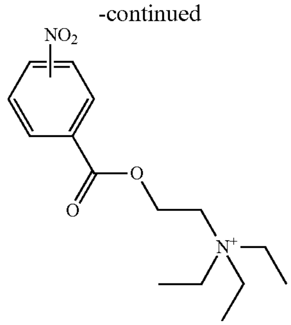
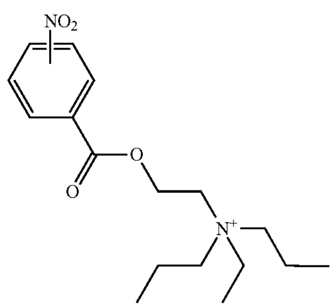
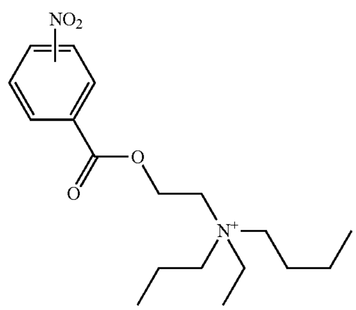
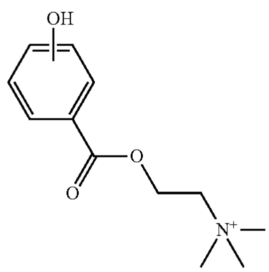
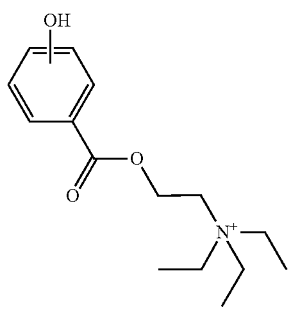
-continued
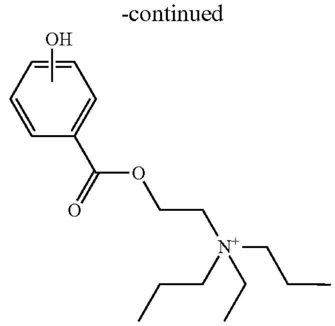
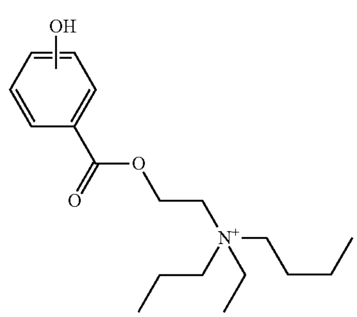
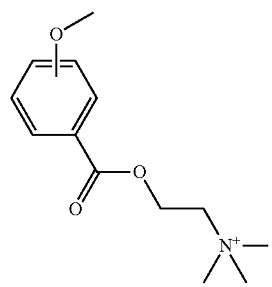
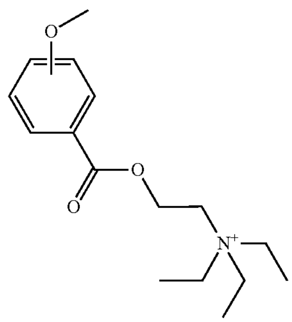
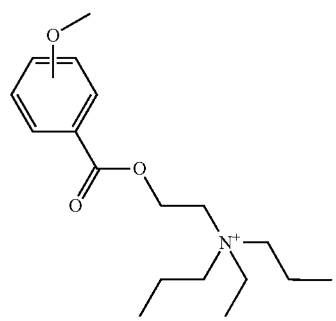

-continued
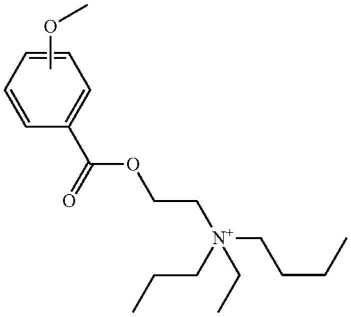
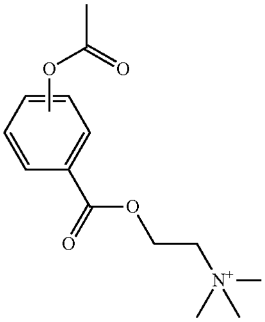
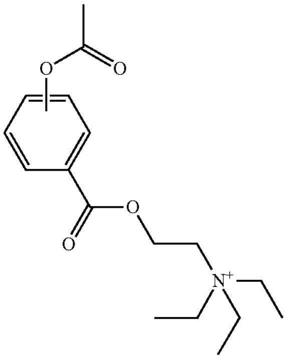
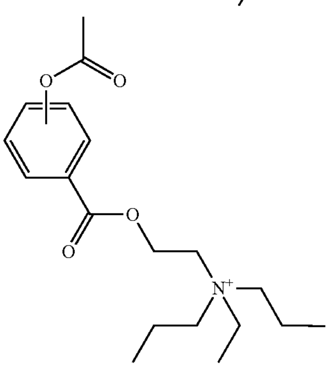
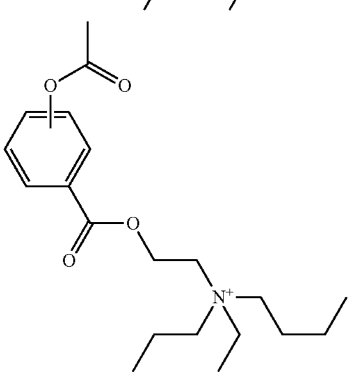
-continued
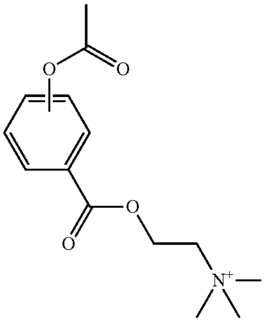
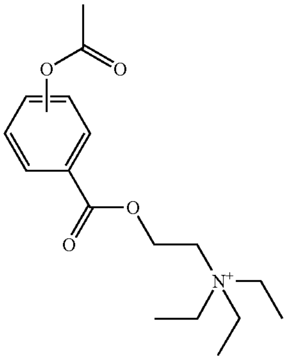
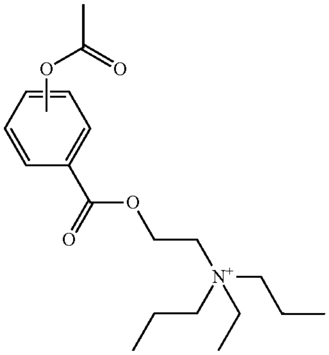
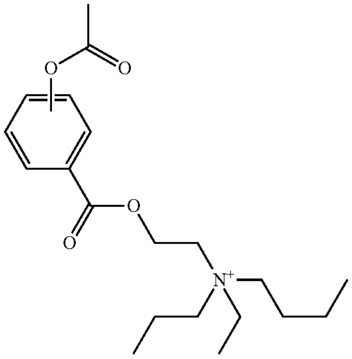
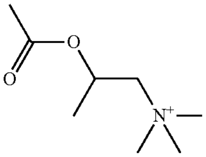
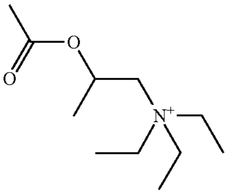

-continued
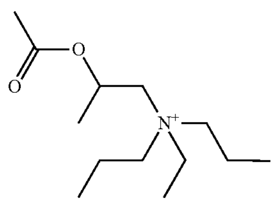
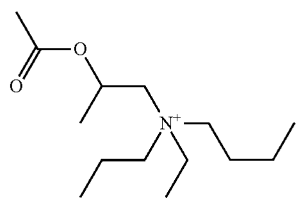
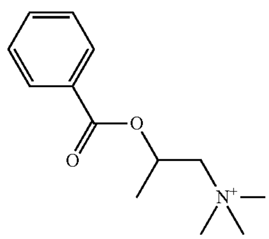
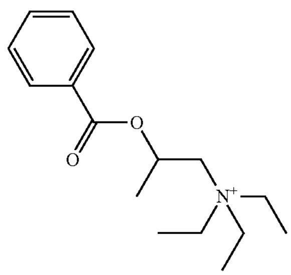
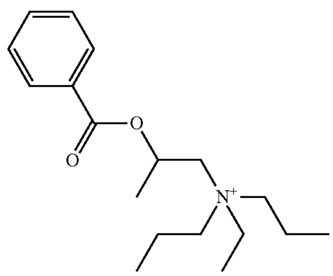
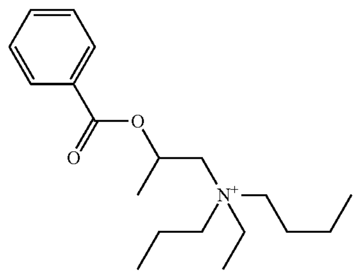
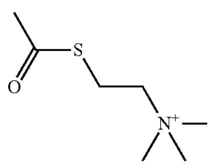
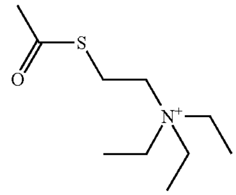
-continued
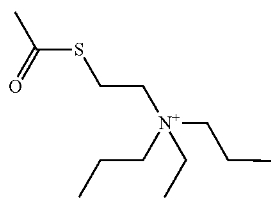
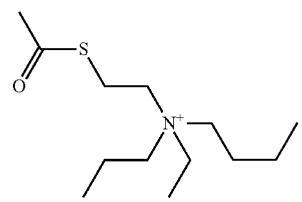
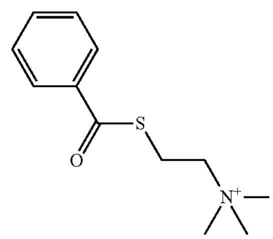
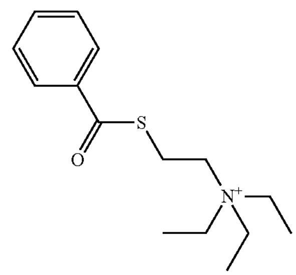
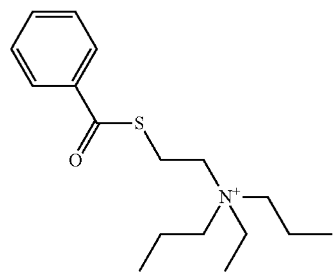
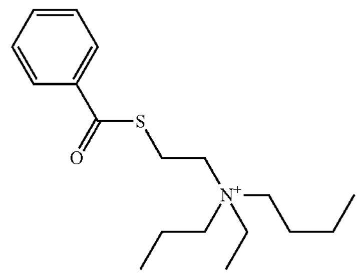
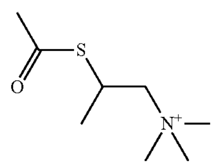
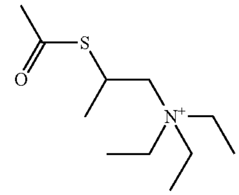

179
-continued
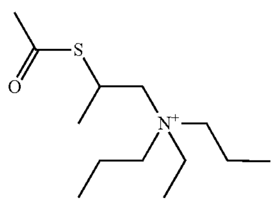
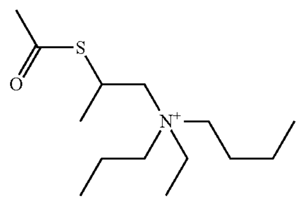
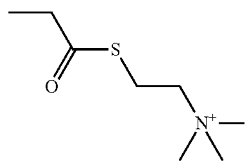
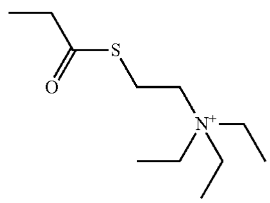
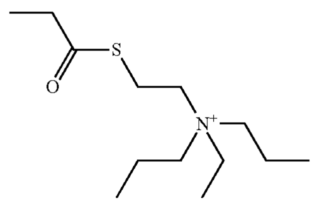
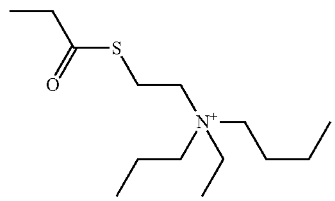
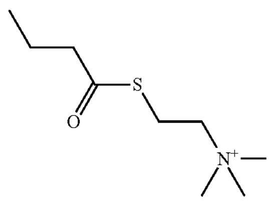
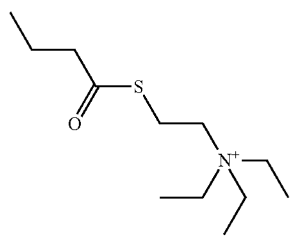
180
-continued
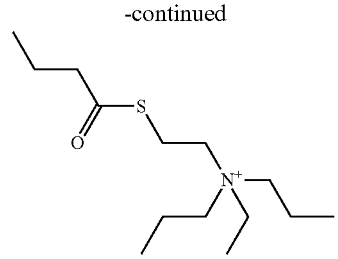
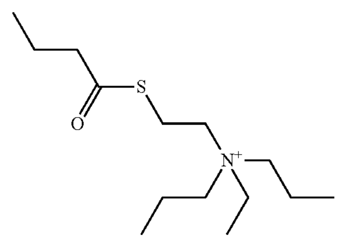
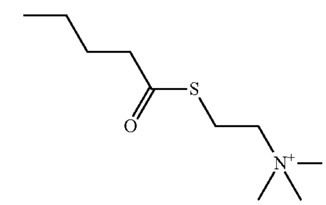
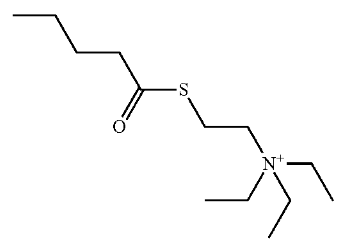
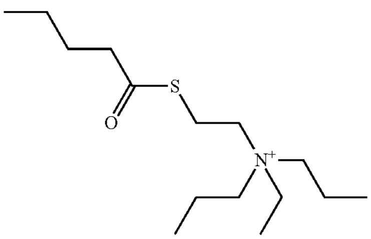
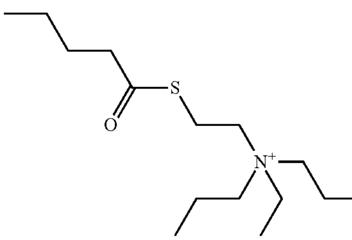
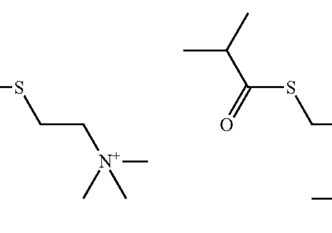

-continued
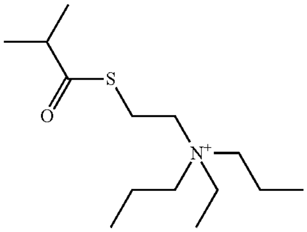
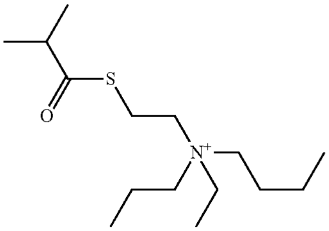
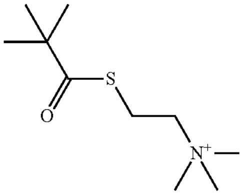
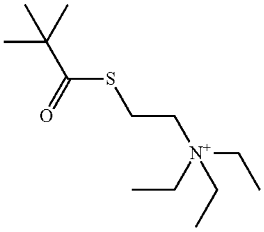
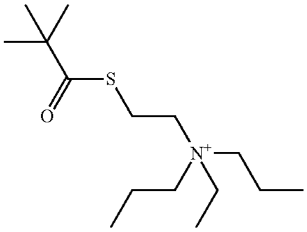
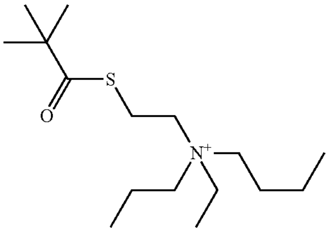
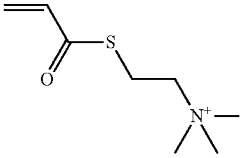
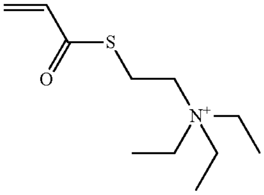
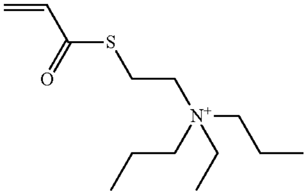
-continued
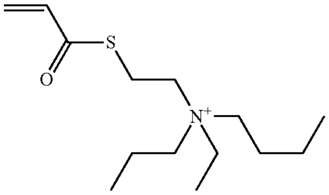
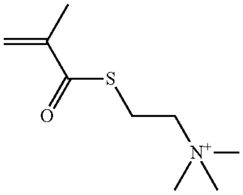
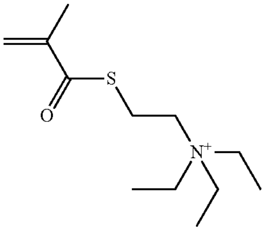
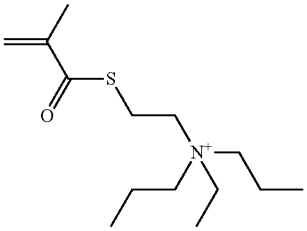
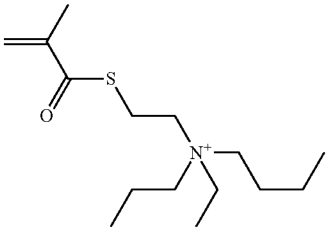
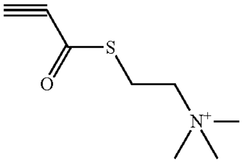
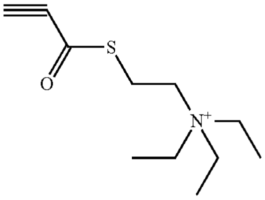
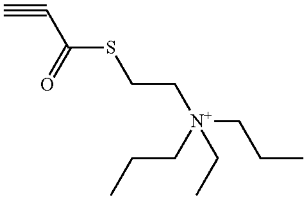
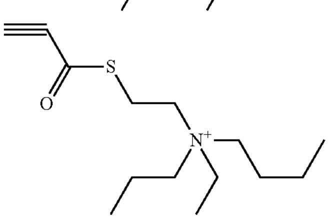
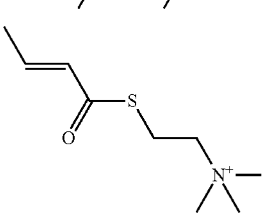

-continued
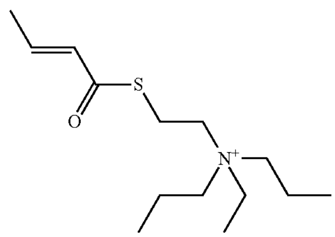
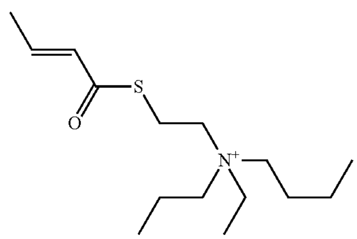
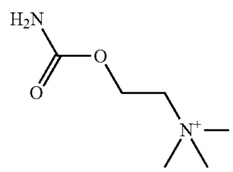
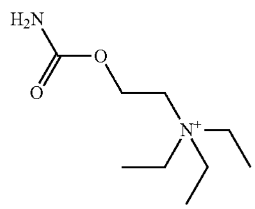
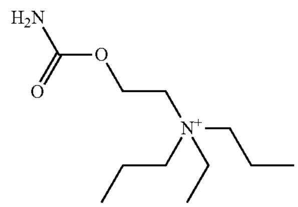
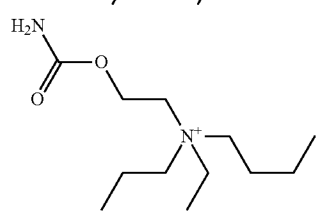
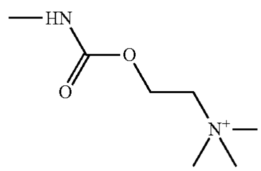
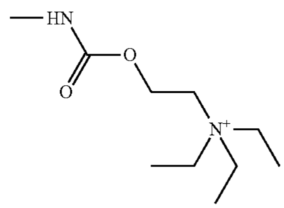
-continued
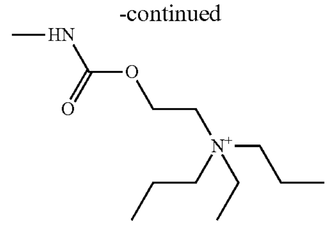
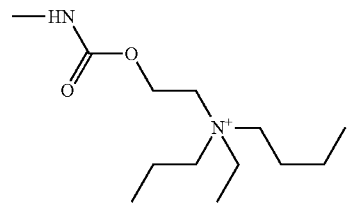
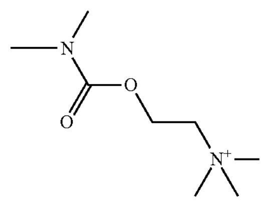
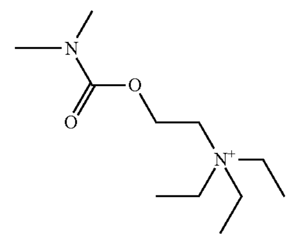
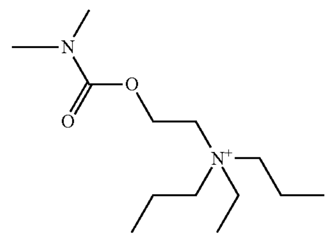
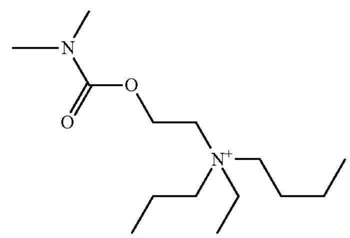
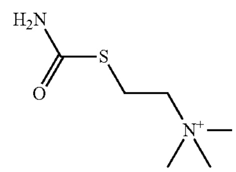
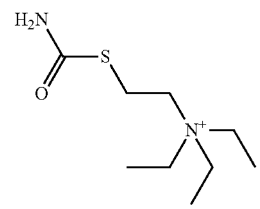
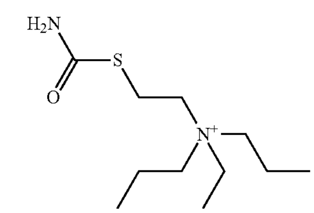
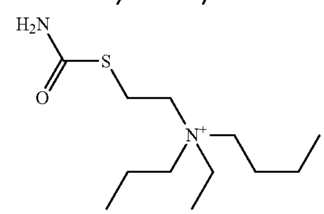

-continued
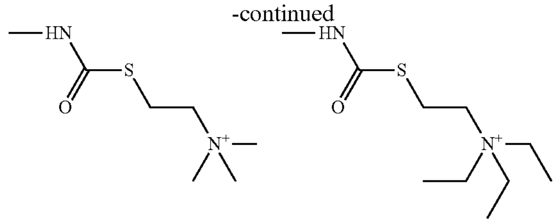
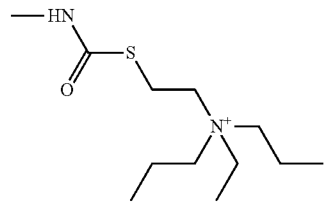
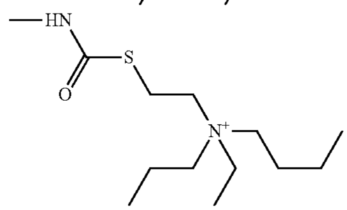
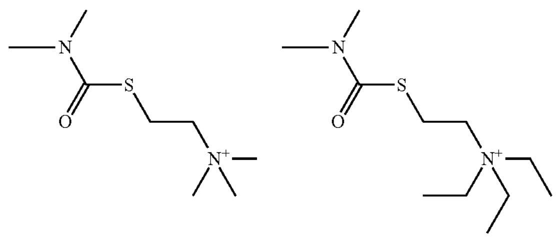
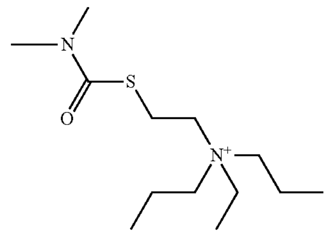
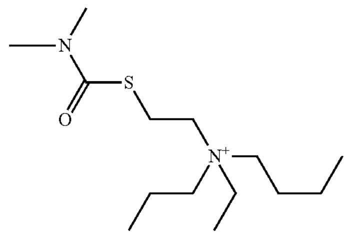
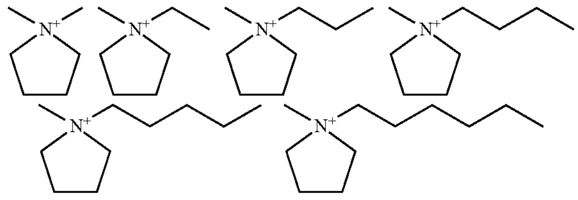
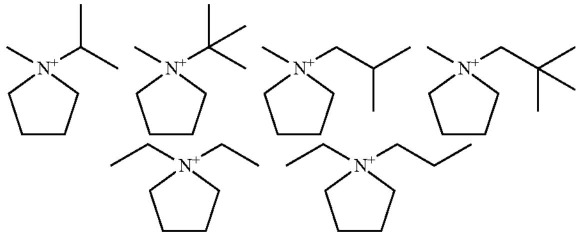
-continued
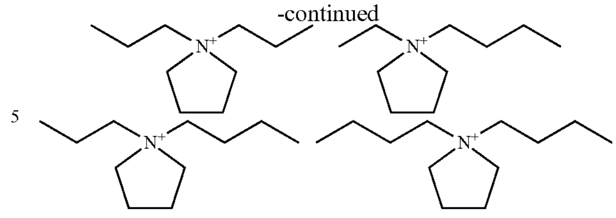
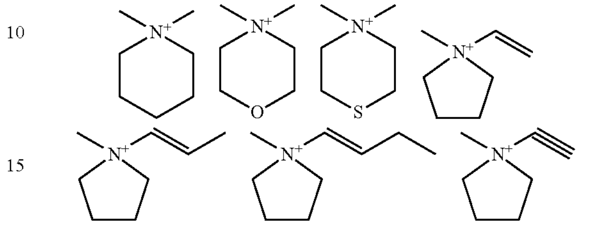
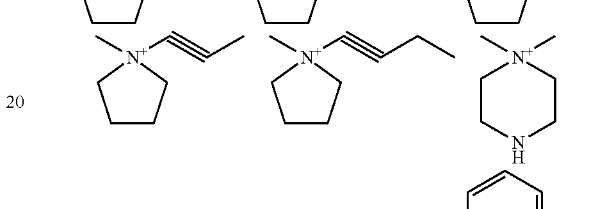
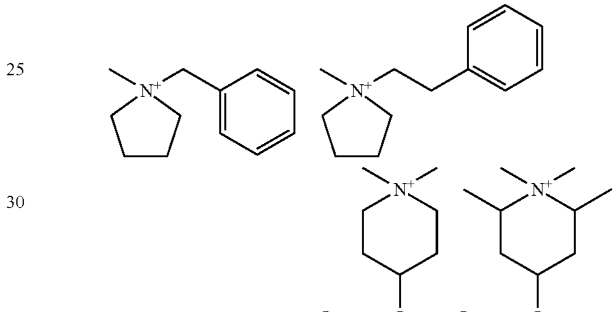
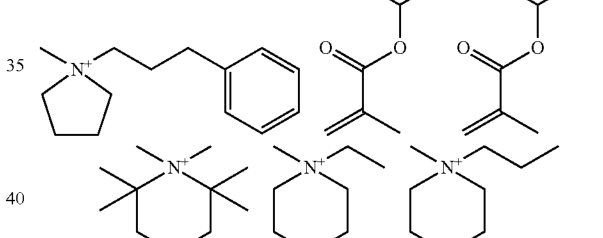
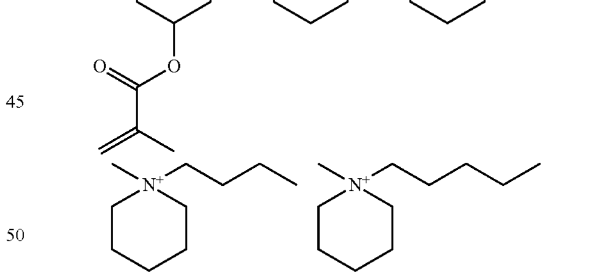
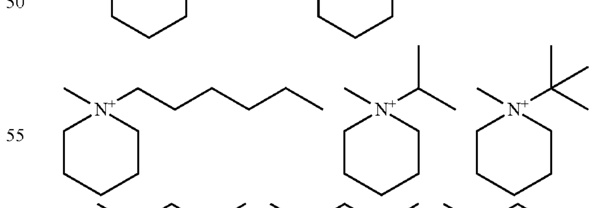
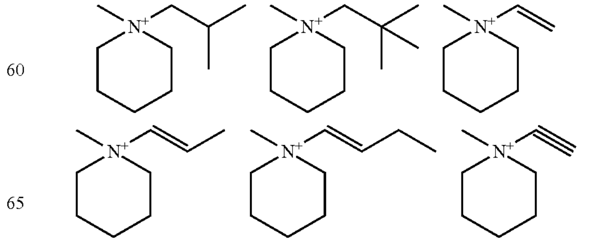

-continued
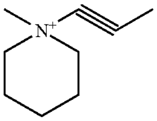
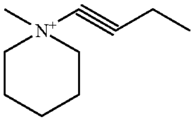
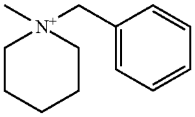
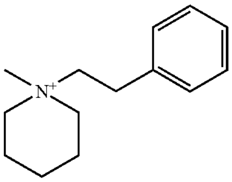
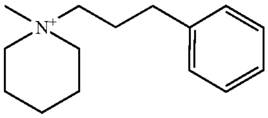
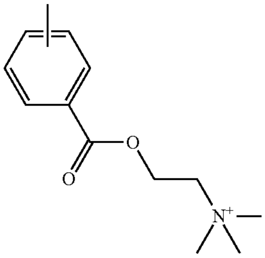
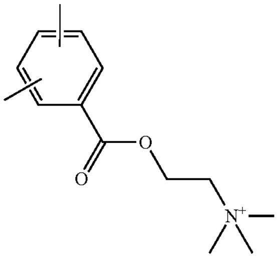
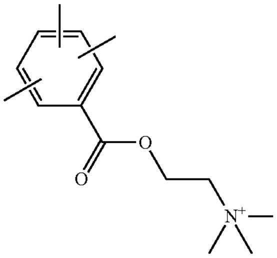
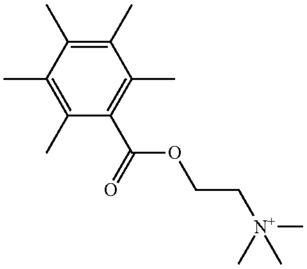
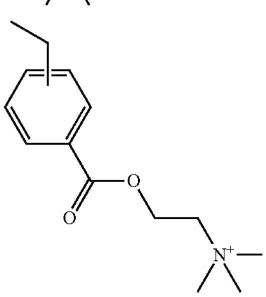
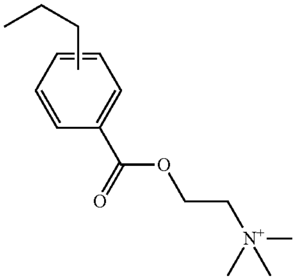
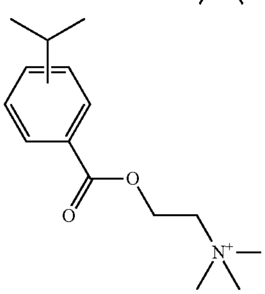
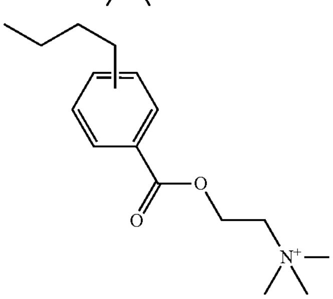
-continued
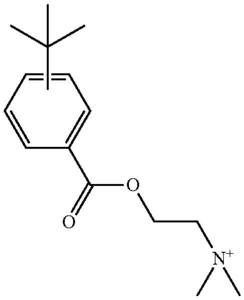
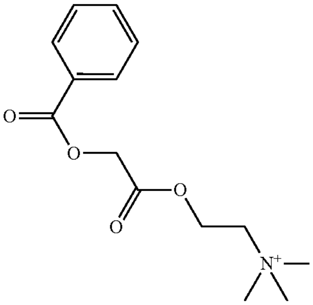
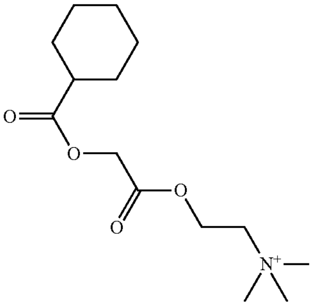
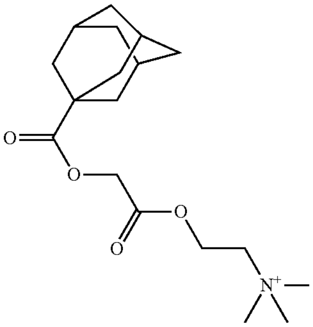
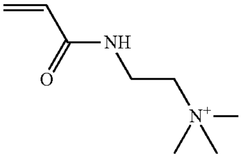
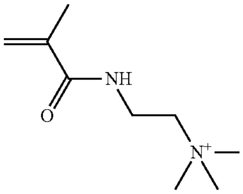
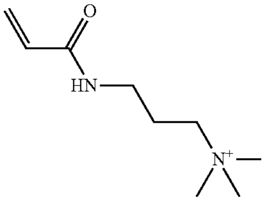
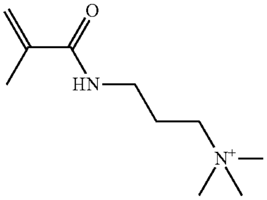
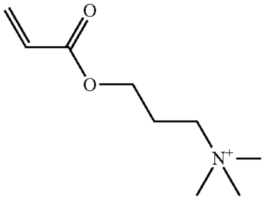
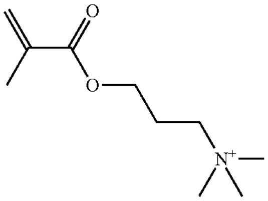
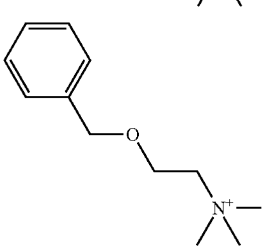

-continued
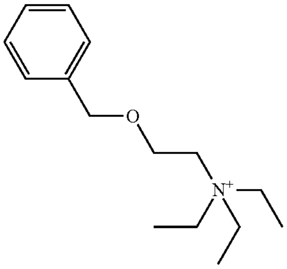
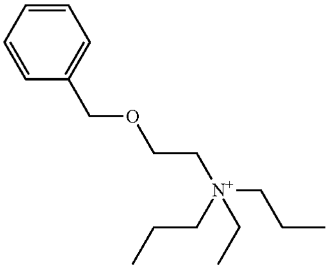
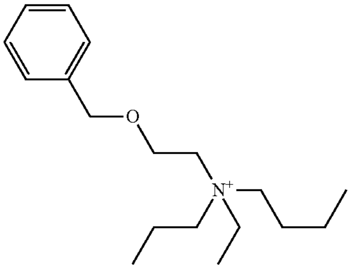
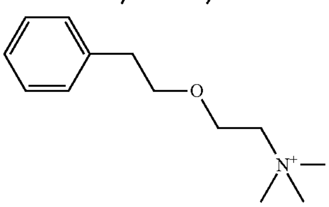
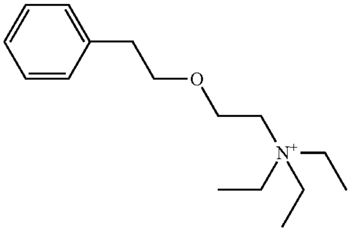
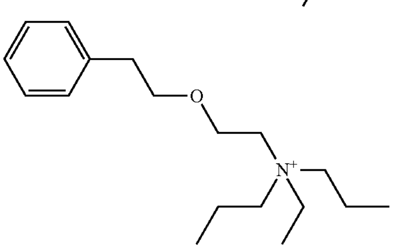
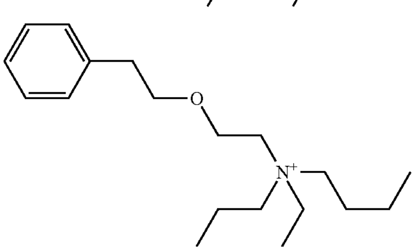
-continued
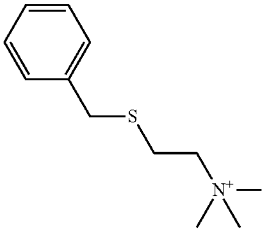
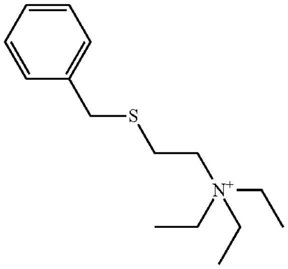
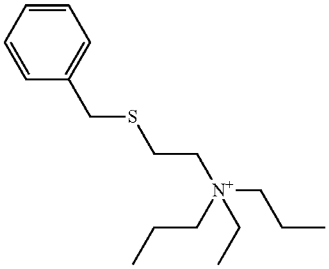
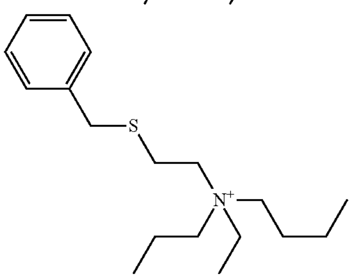
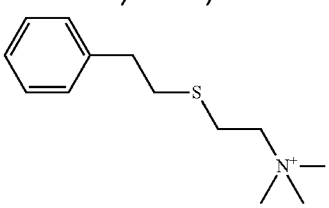
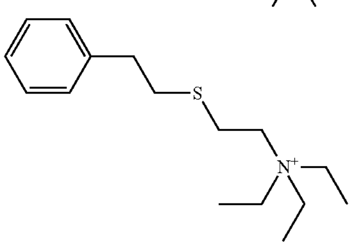
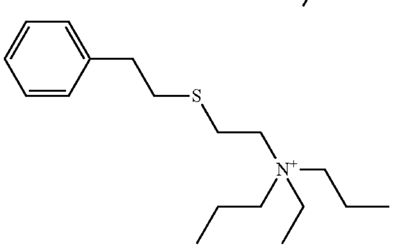
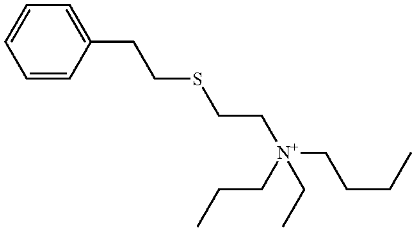

-continued
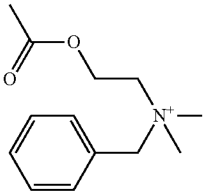
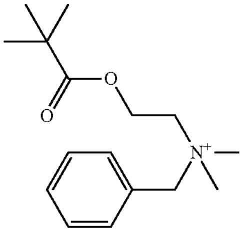
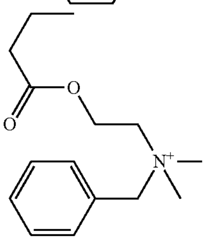
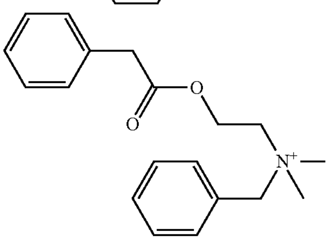
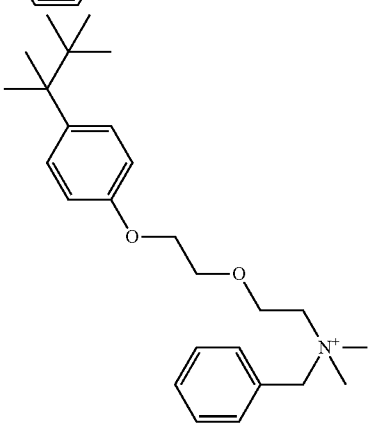
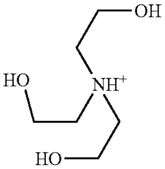
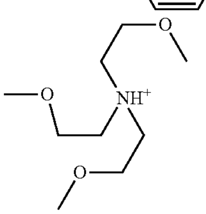
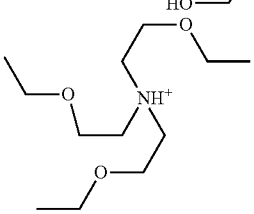
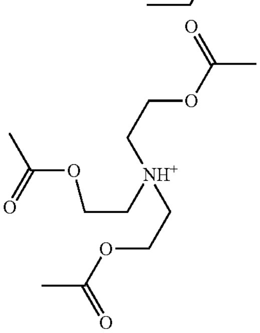
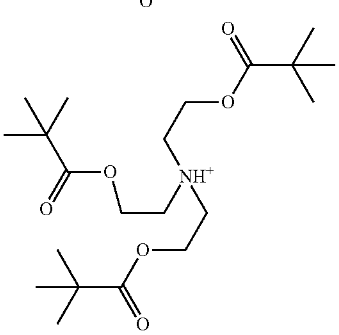
-continued
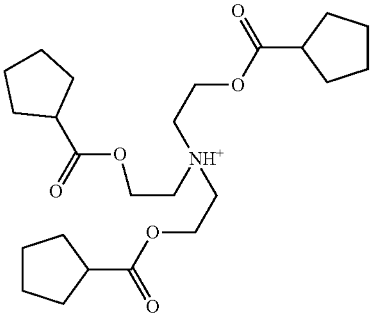
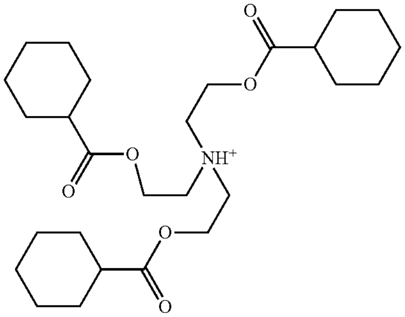
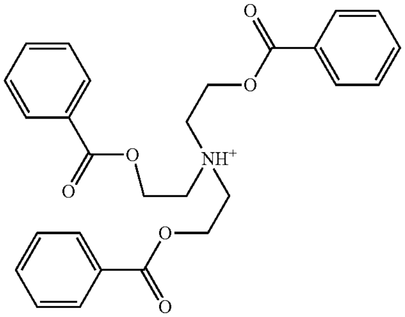
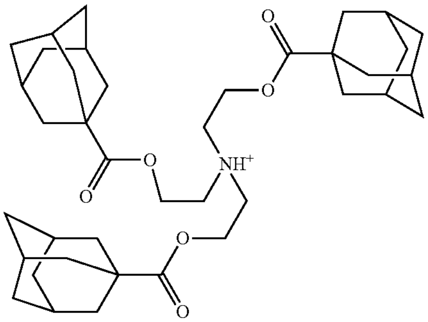
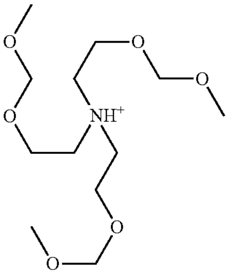
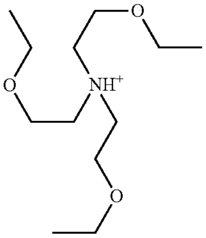

-continued
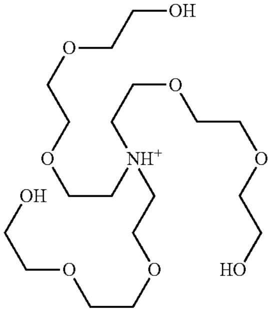
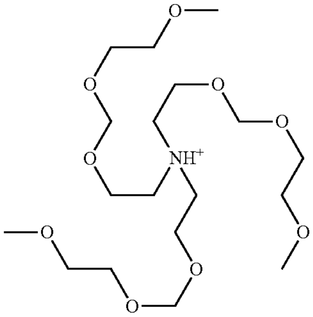
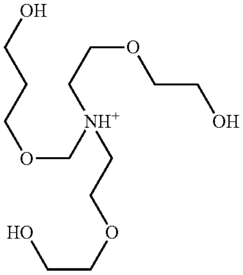
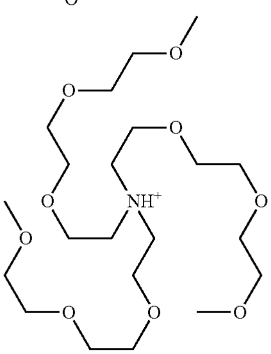
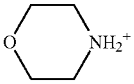
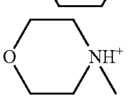
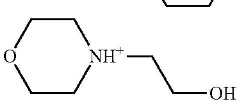
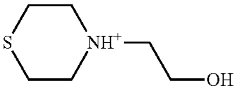
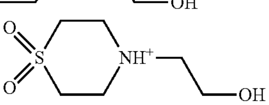
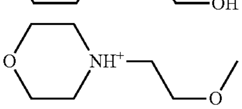
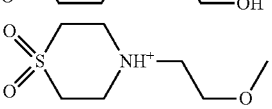
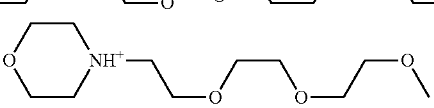
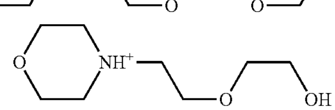
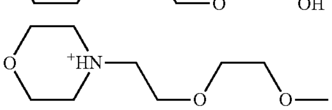
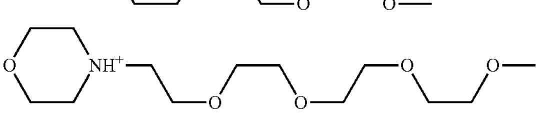
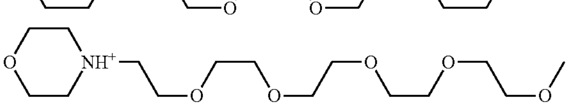
-continued
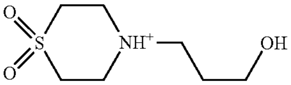
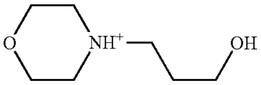
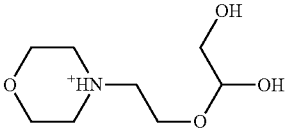
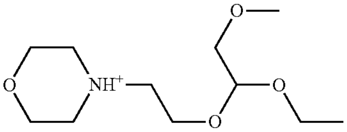
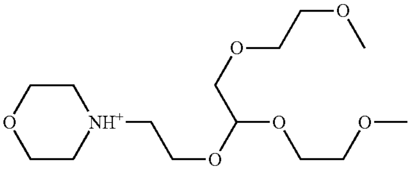
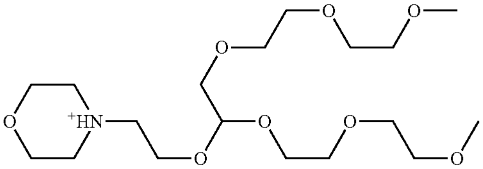
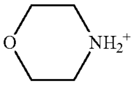
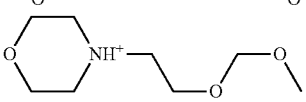
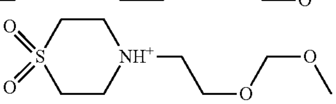
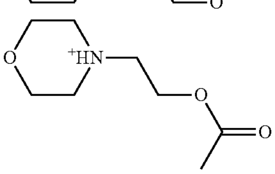
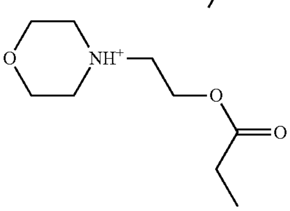
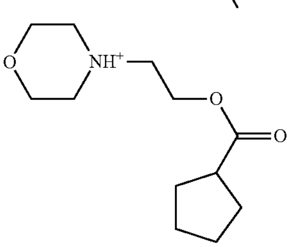
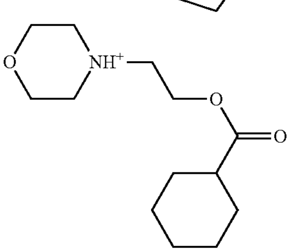

-continued
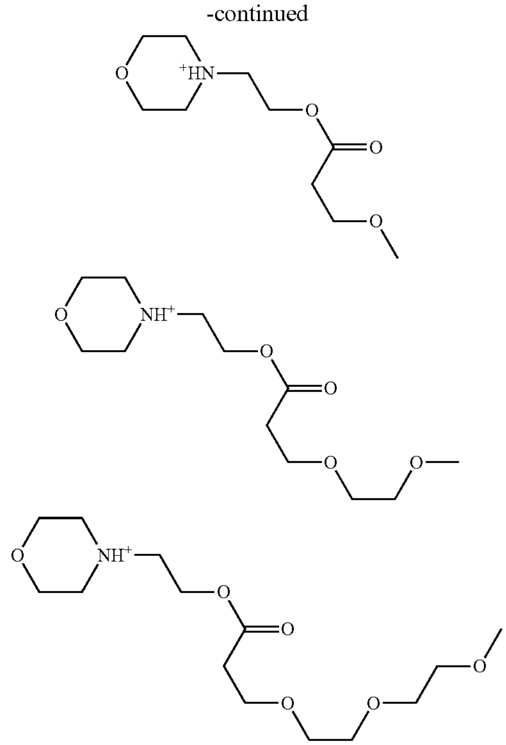
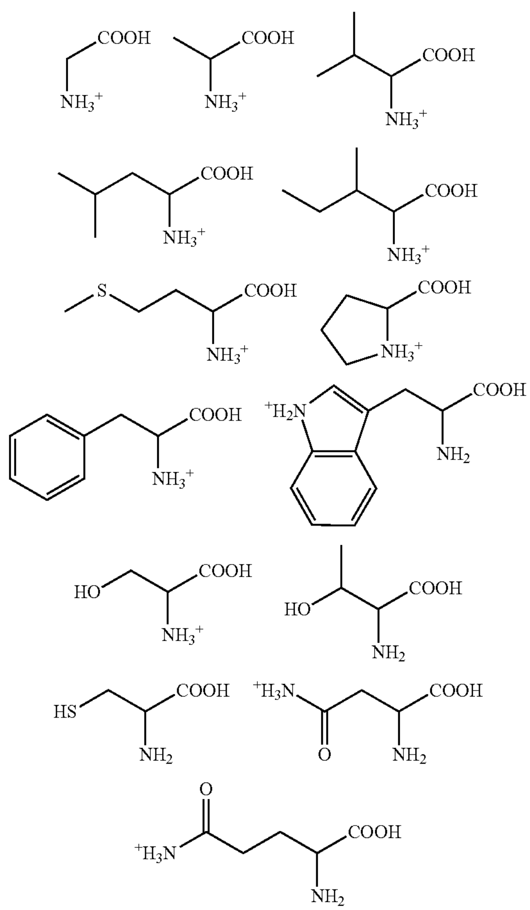
-continued
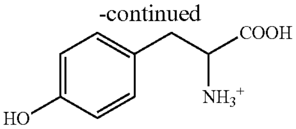
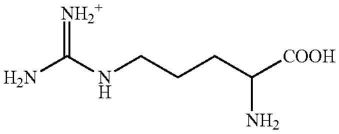
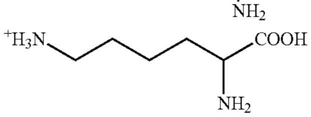
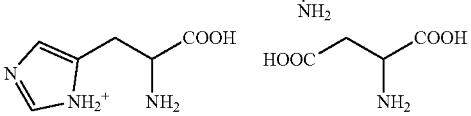
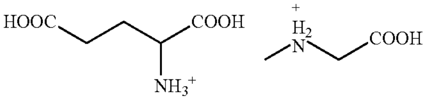
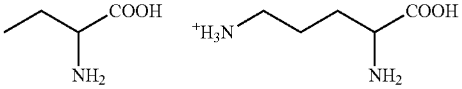
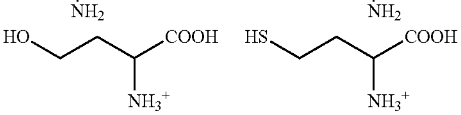
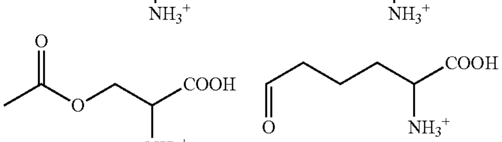
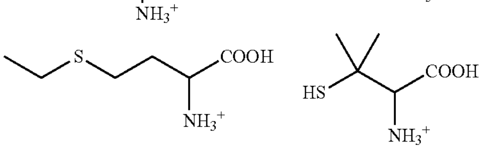
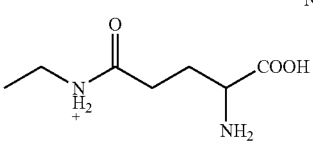
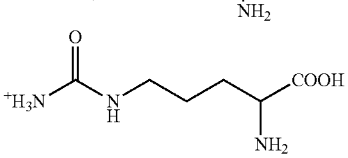
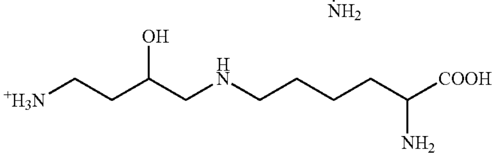
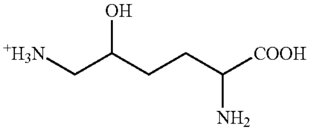
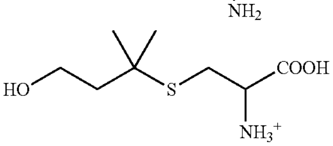
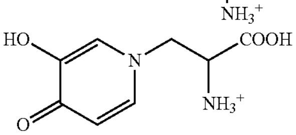

-continued

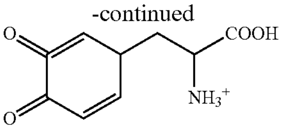

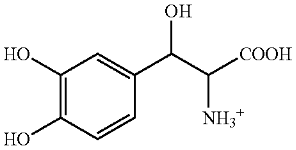

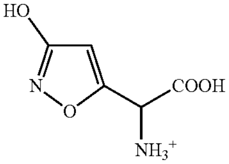

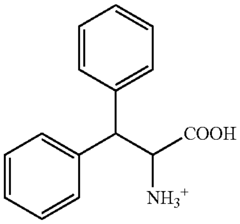

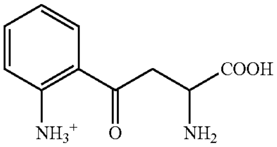

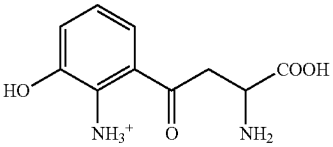

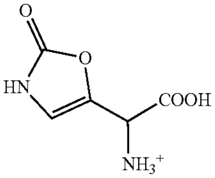

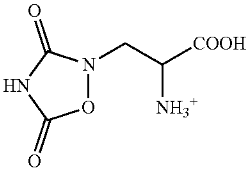

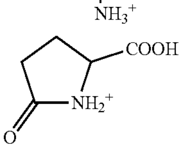

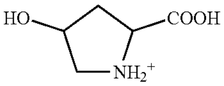

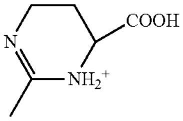

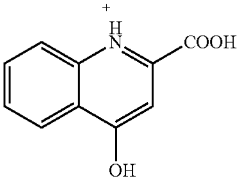

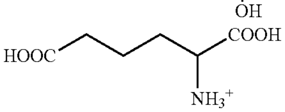

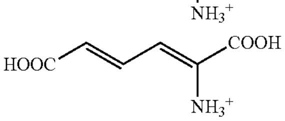

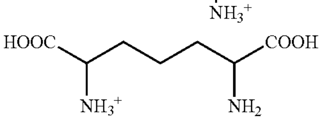

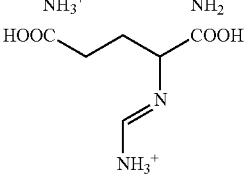

-continued

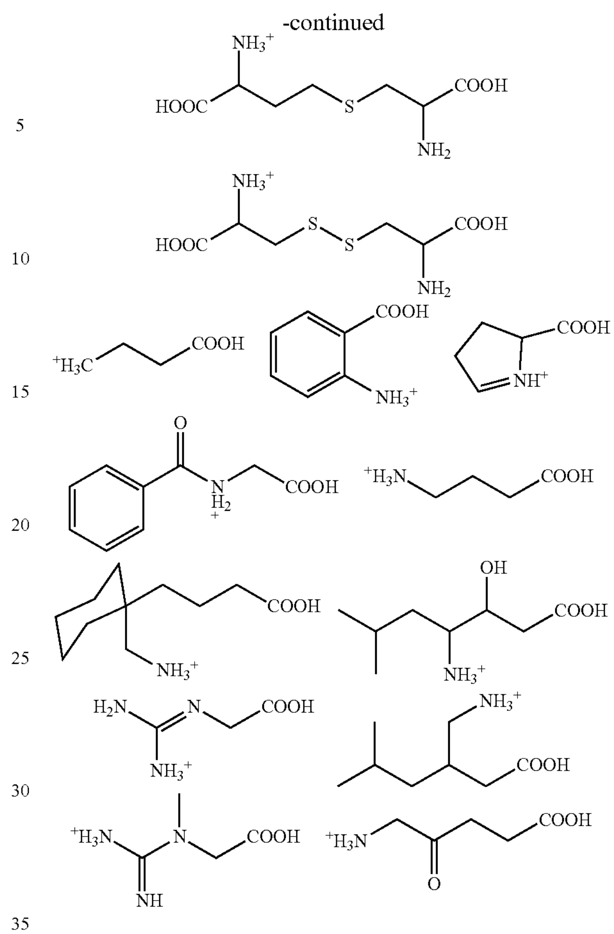

As a method for synthesizing the component (B) dopant polymer, for example, desired monomers among the monomers providing the above repeating units-A1 to -A7, -b, -c, -d, -e, and -f is subjected to polymerization under heating in an organic solvent by adding a radical polymerization initiator, to obtain a dopant polymer which is a (co)polymer.

Examples of the organic solvent to be used for the polymerization can include toluene, benzene, tetrahydrofuran, diethyl ether, dioxane, cyclohexane, cyclopentane, methyl ethyl ketone, γ-butyrolactone, etc.

Examples of the radical polymerization initiator can include 2,2'-azobisisobutyronitrile (AIBN), 2,2'-azobis(2,4-dimethylvaleronitrile), dimethyl 2,2'-azobis(2-methylpropionate), benzoyl peroxide, lauroyl peroxide, etc.

The reaction temperature is preferably 50 to 80° C. The reaction time is preferably 2 to 100 hours, more preferably 5 to 20 hours.

In the component (B) dopant polymer, monomers providing the repeating units-A1 to -A7 may be one kind or two or more kinds.

When two or more kinds of monomers are used for providing the repeating units-A1 to -A7, each monomer may be randomly copolymerized or may be copolymerized in a block.

In addition, the monomers providing the repeating units-A1 to -A7, -b, -c, -d, -e, and -f may be randomly copolymerized, or each may be copolymerized in a block.

When the random copolymerization is carried out by radical polymerization, a common method is to mix monomers to be copolymerized and a radical polymerization initiator and polymerize the mixture under heating. When polymerization is initiated in the presence of a first monomer and a radical polymerization initiator and a second monomer is added later, one side of the polymer molecule has a structure in which the first monomer is polymerized, and the other side has a structure in which the second monomer is polymerized. In this case, however, the repeating units of the first and second monomers are mixed in the intermediate portion, and the form is different from that of the block copolymer. For forming the block copolymer by radical polymerization, living radical polymerization is preferably used.

In the living radical polymerization method called the RAFT polymerization (Reversible Addition Fragmentation chain Transfer polymerization), the radical at the polymer end is always living, so that it is possible to form a di-block copolymer having both a block of the repeating unit of the first monomer and a block of the repeating unit of the second monomer by initiating the polymerization with the first monomer and adding the second monomer when the first monomer is consumed. Further, a tri-block copolymer can also be formed by: initiating the polymerization with the first monomer; adding the second monomer when the first monomer is consumed; and then adding a third monomer.

When the RAFT polymerization is carried out, there is a characteristic that a narrow dispersion polymer whose molecular weight distribution (dispersity) is narrow is formed. In particular, when the RAFT polymerization is carried out by adding the monomers at a time, a polymer having a narrower molecular weight distribution can be formed.

Note that it is preferable the component (B) dopant polymer has a narrow molecular weight distribution (Mw/Mn) such as 1.0 to 2.0, particularly preferably 1.0 to 1.5. When the dispersity is narrow, it is possible to prevent a decrease in the transmittance of the electro-conductive polymer composite layer, which is formed with the electro-conductive polymer composite containing such a dopant.

For carrying out the RAFT polymerization, a chain transfer agent is necessary. Specific examples thereof can include 2-cyano-2-propylbenzothioate, 4-cyano-4-phenylcarbonothioylthiopentanoic acid, 2-cyano-2-propyl dodecyl trithiocarbonate, 4-cyano-4-[(dodecylsulfanylthiocarbonyl) sulfanyl] pentanoic acid, 2-(dodecylthiocarbonothioylthio)-2-methylpropanoic acid, cyanomethyl dodecyl thiocarbonate, cyanomethyl methyl(phenyl) carbamothioate, bis(thiobenzoyl)disulfide, and bis(dodecylsulfanylthiocarbonyl)disulfide. Among these, 2-cyano-2-propylbenzothioate is particularly preferable.

The component (B) dopant polymer has a weight-average molecular weight of 1,000 to 500,000, preferably 2,000 to 200,000. If the weight-average molecular weight is less than 1,000, the heat resistance is poor, and the uniformity of the composite solution with the component (A) is degraded. Meanwhile, if the weight-average molecular weight exceeds 500,000, electro-conductivity is degraded, and viscosity increases to degrade workability. Furthermore, dispersibility in water and an organic solvent is reduced.

Note that, in the present invention, the weight-average molecular weight (Mw) is a value measured in terms of polyethylene oxide, polyethylene glycol, or polystyrene, by gel permeation chromatography (GPC) using water, dimethylformamide (DMF), or tetrahydrofuran (THF) as an eluent.

Note that, as the monomer constituting the component (B) dopant polymer, a monomer having a sulfo group may be used. Alternatively, the polymerization reaction may be carried out using a monomer which is a lithium salt, a sodium salt, a potassium salt, an ammonium salt, or a sulfonium salt of a sulfo group, followed by conversion to a sulfo group using an ion exchange resin.

Here, the proportions of the repeating units-A1 to -A7, -b, -c, -d, -e, and -f in the ionic material (B) are preferably $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, $0 < a1+a2+a3+a4+a5+a6+a7 \leq 1.0$, $0 \leq b < 1.0$, $0 \leq c < 1.0$, $0 \leq d < 1.0$, $0 \leq e < 1.0$, and $0 \leq f < 1.0$; more preferably $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, $0.1 \leq a1+a2+a3+a4+a5+a6+a7 \leq 1.0$, $0 \leq b \leq 0.8$, $0 \leq c \leq 0.8$, $0 \leq d \leq 0.8$, $0 \leq e \leq 0.8$, and $0 \leq f \leq 0.8$; further preferably $0 \leq a1 \leq 1.0$, $0 \leq a2 \leq 1.0$, $0 \leq a3 \leq 1.0$, $0a4 \leq 1.0$, $0 \leq a5 \leq 1.0$, $0 \leq a6 \leq 1.0$, $0 \leq a7 \leq 1.0$, $0.25a1+a2+a3+a4+a5+a6+a7 \leq 1.0$, $0 < b \geq 0.7$, $0 \leq c \leq 0.7$, $0 \leq d \leq 0.7$, $0 \leq e \leq 0.7$, and $0 \leq f \leq 0.7$. "a1" to "a7", "b", "c", "d", "e", and "f" each represent the proportions of the repeating units-A1 to -A7, and -b to -f.

The electro-conductive polymer composite, which forms the electro-conductive polymer composite layer of the inventive bio-electrode, includes the above component (A) π-conjugated polymer and the above component (B) dopant polymer, and the component (B) dopant polymer forms a composite by coordinating with the component (A) π-conjugated polymer.

It is preferable that the electro-conductive polymer composite has dispersibility in water or an organic solvent and can improve film-formability by spin-coating and flatness of film against an inorganic or organic base (a base having inorganic film or organic film on its surface).

(Method for Manufacturing Electro-Conductive Polymer Composite)

The electro-conductive polymer composite can be obtained, for example, by adding a raw-material monomer of the component (A) (thiophene, or its derivative monomer) into an aqueous solution of the component (B) or a mixed solution of the component (B) in water and an organic solvent, and then adding an oxidizing agent and, if necessary, an oxidizing catalyst to the mixed solution, to carry out oxidative polymerization.

The oxidizing agent and the oxidizing catalyst which can be used include: a peroxodisulfate (persulfate) such as ammonium peroxodisulfate (ammonium persulfate), sodium peroxodisulfate (sodium persulfate), and potassium peroxodisulfate (potassium persulfate), etc.; a transition metal compound such as ferric chloride, ferric sulfate, cupric chloride, etc.; a metal oxide such as silver oxide, cesium oxide, etc.; a peroxide such as hydrogen peroxide, ozone, etc.; an organic peroxide such as benzoyl peroxide, etc.; oxygen, etc.

As the reaction solvent for carrying out the oxidative polymerization, water or a mixed solvent of water and a solvent may be used. It is preferable that the solvent to be used here is miscible with water and can dissolve or disperse the components (A) and (B). Examples of the solvent include polar solvents such as N-methyl-2-pyrrolidone, N, N'-dimethylformamide, N, N'-dimethylacetamide, dimethylsulfoxide, and hexamethylene phosphotriamide, etc.; alcohols such as methanol, ethanol, propanol, butanol, etc.; polyhydric aliphatic alcohols such as ethylene glycol, propylene glycol, dipropylene glycol, 1, 3-butylene glycol, 1, 4-butylene glycol, D-glucose, D-glucitol, isoprene glycol, butanediol, 1,5-pentanediol, 1, 6-hexanediol, 1, 9-nonanediol, neopentyl glycol, etc.; carbonate compounds such as ethylene carbonate, propylene carbonate, etc.; cyclic ether compounds such as dioxane, tetrahydrofuran, etc.; linear ethers such as dialkyl ether, ethylene glycol monoalkyl ether, ethylene glycol dialkyl ether, propylene glycol monoalkyl ether, propylene glycol dialkyl ether, polyethylene glycol dialkyl ether, and polypropylene glycol dialkyl ether, etc.; heterocyclic compounds such as 3-methyl-2-oxazolidinone, etc.; nitrile compounds such as acetonitrile, glutaronitrile, methoxyacetonitrile, propionitrile, benzonitrile, etc. These solvents may be used alone, or a mixture of two or more kinds thereof may be used. It is preferable the blended amount of these solvents miscible with water is 50 mass % or less based on the whole reaction solvent.

After the synthesis of the electro-conductive polymer composite, a neutralization reaction may be performed to obtain a sodium salt, a potassium salt, an ammonium salt, or a sulfonium salt.

The electro-conductive polymer composite obtained in the above manner can be used, if necessary, after being subjected to fine pulverization using a homogenizer, a ball mill, or the like.

For fine pulverization, it is preferable to use a mixing-dispersing machine which can provide high shearing force. Examples of the mixing-dispersing machine can include a homogenizer, a high-pressure homogenizer, a bead mill, etc. In particular, a high-pressure homogenizer is preferable.

Specific examples of the high-pressure homogenizer can include Nanovater manufactured by Yoshida Kikai Co., Ltd., Microfluidizer manufactured by Powrex Corp., Artimizer manufactured by Sugino Machine Limited, etc.

Examples of a dispersing treatment using the high-pressure homogenizer include a treatment in which the composite solution before subjecting to the dispersing treatment is subjected to counter-collision with high pressure; a treatment in which the solution is passed through an orifice or slit with high pressure; etc.

Before or after the fine pulverization, impurities may be removed by a method such as filtration, ultrafiltration, and dialysis, and purification may be carried out using a cation-exchange resin, an anion-exchange resin, a chelate resin, or the like.

Note that a total contained amount of the components (A) and (B) is preferably 0.05 to 5.0 mass % in the electro-conductive polymer composite solution. When the total contained amount of the components (A) and (B) is 0.05 mass % or more, sufficient conductivity is obtained. When the total contained amount is 5.0 mass % or less, a uniform electro-conductive coating film is easily obtained.

The contained amount of the component (B) is preferably such that the amount of sulfo groups, sulfonamide groups, and sulfonimide groups in the component (B) is 0.1 to 10 mol, more preferably 1 to 7 mol, based on 1 mol of the component (A). When the sulfo groups in the component (B) is 0.1 mol or more, the doping effect to the component (A) is high, and sufficient electro-conductivity can be ensured. Meanwhile, when the sulfo groups in the component (B) is 10 mol or less, the contained amount of the component (A) is also suitable, and sufficient electro-conductivity can be achieved.

Examples of the organic solvent, which can be contained in the aqueous solution for the polymerization reaction or can dilute the monomer, can include methanol, ethyl acetate, cyclohexanone, methyl amyl ketone, butanediol monomethyl ether, propylene glycol monomethyl ether, ethylene glycol monomethyl ether, butanediol monoethyl ether, propylene glycol monoethyl ether, ethylene glycol monoethyl ether, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxypropionate, ethyl 3-ethoxypropionate, tert-butyl acetate, t-butyl propionate, propylene glycol mono-t-butyl ether acetate, γ-butyrolactone, mixtures thereof, etc.

Note that, the amount of the organic solvent to be used is preferably 0 to 1,000 mL, particularly preferably 0 to 500 mL, based on 1 mol of the monomer. When the amount of the organic solvent is 1,000 mL or less, the reaction vessel does not become too large so that it is economical.

In the presence of the component (B) dopant polymer, after polymerizing the component (A) to obtain a composite, a neutralizer can also be added. By adding a neutralizer, a sodium salt, a potassium salt, an ammonium salt, or a sulfonium salt is obtained.

Other Components (Surfactant)

In the present invention, a surfactant may be contained to increase wettability of the electro-conductive polymer composite solution to a material to be processed such as a substrate, etc. Examples of such a surfactant include various surfactants such as nonionic, cationic, and anionic surfactants. Specific examples thereof can include nonionic surfactants such as polyoxyethylene alkyl ether, polyoxyethylene alkylphenyl ether, polyoxyethylene carboxylic acid ester, sorbitan ester, polyoxyethylene sorbitan ester, etc.; cationic surfactants such as alkyltrimethyl ammonium chloride, alkylbenzyl ammonium chloride, etc.; anionic surfactants such as alkyl or alkylallyl sulfates, alkyl or alkylallyl sulfonate, dialkyl sulfosuccinate, etc.; amphoteric ionic surfactants such as amino acid type, betaine type, etc. It is preferable that the surfactant is contained in the range of 0.01 to 100 parts by mass based on 100 parts by mass of the electro-conductive polymer composite.

(Conductivity Enhancer)

In the present invention, an organic solvent may be contained as a conductivity enhancer besides the main agent for the purpose of improving the electro-conductivity of the electro-conductive polymer composite. Examples of such a conductivity enhancer can include polar solvents, and its specific examples can include ethylene glycol, diethylene glycol, polyethylene glycol, glycerin, dimethylsulfoxide (DMSO), dimethylformamide (DMF), N-methyl-2-pyrrolidone (NMP), sulfolane, and mixtures thereof. The amount of the conductivity enhancer to be added is preferably 1.0 to 40.0 mass %, particularly preferably 3.0 to 30.0 mass % of the main solvent.

The electro-conductive polymer composite as described above makes it possible to form the electro-conductive polymer composite layer having excellent filterability, excellent film formability by spin-coating, high transparency, and low surface roughness.

The electro-conductive polymer composite (solution) obtained in the above manner can form a bio-electrode by being applied on the electro-conductive layer (C) on the substrate (D). It is preferable that electro-conductive layer contains at least one substance selected from the group consisting of gold, silver, silver chloride, platinum, aluminum, magnesium, tin, tungsten, iron, copper, nickel, stainless steel, chromium, titanium, and carbon. Examples of methods for applying the electro-conductive polymer composite (solution) include coating with a spin coater, etc., bar coating, dipping, comma coating, spray coating, roll coating, screen printing, flexographic printing, gravure printing, inkjet printing, etc. After the application, a bio-electrode can be formed by a heat treatment using a hot air circulation furnace, a hot plate, etc.

[(E) Resin]

The component (E) resin blended in the electro-conductive polymer composite to form the electro-conductive polymer composite layer of the inventive bio-electrode is a component to prevent elution of the composite by being compatible with the above component (B) dopant polymer (salt) and to hold an electric conductivity improver such as a metal powder, a carbon powder, a silicon powder, and a lithium titanate powder, etc., which will be described later. The resin (E) is preferably one or more kinds selected from the group consisting of a (meth)acrylate resin, a (meth) acrylamide resin, a urethane resin, polyvinyl alcohol, polyvinylpyrrolidone, polyoxazoline, polyglycerin, polyglycerin-modified silicone, cellulose, polyethylene glycol, and polypropylene glycol. The added amount is preferably in the range of 1 to 100 parts by mass based on 100 parts by mass of the electro-conductive polymer composite.

[Component (F)]

The electro-conductive polymer composite to form the electro-conductive polymer composite layer of the inventive bio-electrode can further contain, as the component (F), one or more selected from the group consisting of a carbon powder, a metal powder, a silicon powder, and a lithium titanate powder. Among the component (F), the carbon powder and the metal powder are added in order to enhance electron conductivity, and the silicon powder and the lithium titanate powder are added in order to enhance ion reception sensitivity. The added amount is preferably in the range of 5 to 30 parts by mass based on 100 parts by mass of the electro-conductive polymer composite.

[Metal Powder]

The electro-conductive polymer composite to form the electro-conductive polymer composite layer of the inventive bio-electrode can contain a metal powder selected from the group consisting of gold, silver, platinum, copper, tin, titanium, nickel, aluminum, tungsten, molybdenum, ruthenium, chromium, and indium, in order to enhance electron conductivity. The added amount of the metal powder is preferably in the range of 1 to 50 parts by mass based on 100 parts by mass of the electro-conductive polymer composite.

As the kind of the metal powder, gold, silver, and platinum are preferable from the viewpoint of electric conductivity, and silver, copper, tin, titanium, nickel, aluminum, tungsten, molybdenum, ruthenium, and chromium are preferable from the viewpoint of cost. From the viewpoint of biocompatibility, noble metals are preferable. From a comprehensive viewpoint including the above, silver is the most preferable.

Shapes of the metal powder include a spherical shape, a disk shape, a flaky shape, and a needle shape. Flaky powder or needle-shaped powder is preferable because the highest electric conductivity is obtained when they are added. In the case of a flaky powder, the metal powder is preferably a flake having relatively low density and large specific surface area with a size of 100 μm or less, a tapped density of not more than 5 $g/cm^3$, and a specific surface area of not less than 0.5 $m^2/g$. In the case of a needle-shaped powder, the diameter is preferably 1 to 200 nm, and the length is preferably 1 to 500 μm.

[Carbon Material]

A carbon material can be contained as an electric conductivity improver. Examples of the carbon material can include carbon black, graphite, carbon nanotube, carbon fiber, etc. The carbon nanotube may be a single layer or multilayer, and the surface may be modified with an organic group (s). In particular, the carbon material is preferably either or both of carbon black and a carbon nanotube. The added amount of carbon material is preferably in the range of 1 to 50 parts by mass based on 100 parts by mass of the electro-conductive polymer composite.

[Silicon Powder]

The electro-conductive polymer composite to form the electro-conductive polymer composite layer of the inventive bio-electrode can contain a silicon powder to enhance ion reception sensitivity. Examples of the silicon powder can include powders of silicon, silicon monoxide, or silicon carbide. The particle size of the powder is preferably smaller than 100 μm, more preferably 1 μm or less. Finer particles have a larger surface area and can receive a larger number of ions, and thus such a bio-electrode has higher sensitivity. The amount of silicon powder is preferably in the range of 1 to 50 parts by mass based on 100 parts by mass of the electro-conductive polymer composite.

[Lithium Titanate Powder]

The electro-conductive polymer composite to form the electro-conductive polymer composite layer of the inventive bio-electrode can contain a lithium titanate powder to enhance ion reception sensitivity. Examples of the lithium titanate powder can include powders containing a compound shown by molecular formulae $Li_2TiO_3$, $LiTiO_2$, or $Li_4Ti_5O_{12}$ with a spinel structure. The lithium titanate powder preferably has a spinel structure. It is also possible to use carbon-incorporated lithium titanate particles. The particle size of the powder is preferably smaller than 100 μm, more preferably 1 μm or less. Finer particles have a larger surface area and can receive a larger number of ions, and thus such a bio-electrode has higher sensitivity. The aforementioned powders may be composite powders with carbon. The added amount of the lithium titanate powder is preferably in the range of an amount of 1 to 50 parts by mass based on 100 parts by mass of the electro-conductive polymer composite.

When a silver nanowire or a carbon nanotube, which is a needle-shaped or fibrous electro-conductive additive, is contained in the electro-conductive polymer composite solution, sufficient electric conductivity as a bio-electrode can be ensured even without providing an underlying electro-conductive layer.

[Optional Components]

The electro-conductive polymer composite to form the electro-conductive polymer composite layer of the inventive bio-electrode can contain optional components such as an ionic additive, a silicone compound having a polyglycerin structure, an organic solvent, etc.

[Ionic Additive]

The electro-conductive polymer composite to form the electro-conductive polymer composite layer of the inventive bio-electrode can contain an ionic additive to enhance ionic conductivity. In consideration of bio-compatibility, examples of the ionic additive can include sodium chloride, potassium chloride, calcium chloride, saccharin, acesulfame potassium, and salts disclosed in JP 2018-044147 A, JP 2018-059050 A, JP 2018-059052 A, and JP 2018-130534 A.

Ammonium salts of a sulfonic acid, a fluorosulfonic acid, a fluoroimidic acid, and a fluoromethide acid are known as ionic liquids. Specifically, it is also possible to add such ionic liquids described in "Trulove C, Mantz R. 2003. Ionic Liquids in Synthesis, Chapter 3.6: Electrochemical Properties of Ionic Liquids." The blended amount of the ionic liquids is preferably an amount of 1 to 50 parts by mass, more preferably 2 to 30 parts by mass, based on 100 parts by mass of the total of the components (A) and (B).

[Silicone Compound Having Polyglycerin Structure]

The electro-conductive polymer composite to form the electro-conductive polymer composite layer of the inventive bio-electrode can contain also a silicone compound having a polyglycerin structure in order to improve moisture-holding property of the electro-conductive polymer composite layer and thus to enhance the ionic conductivity and the sensitivity to ions released from the skin. The blended amount of silicone compound having a polyglycerin structure is preferably 0.01 to 100 parts by mass, more preferably 0.5 to 60 parts by mass, based on 100 parts by mass of the total of components (A) and (B). the silicone compound having a polyglycerin structure may be used alone, or two or more kinds may be used in mixture.

The silicone compound having a polyglycerin structure is preferably represented by the following general formulae (4)' or (5)'.

(4)'

(4)'-1

(4)'-2

(5)'

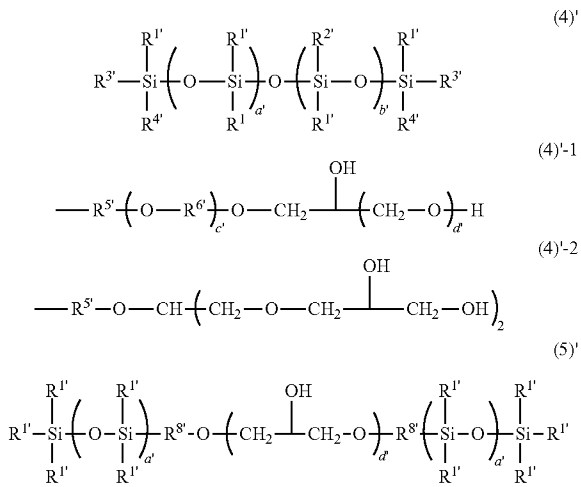

-continued (6)'

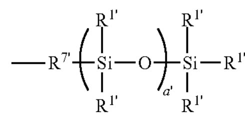

In the formulae (4)' and (5)', each $R^{1'}$ may be identical to or different from one another, and each independently represents a hydrogen atom, a linear or branched alkyl group having 1 to 50 carbon atoms, a phenyl group, may contain an ether group, and may be silicone chain represented by general formula (6)'. $R^{2'}$ represents a group having a polyglycerin group structure shown by the formula (4)'-1 or (4)'-2. Each $R^{3'}$ is identical to or different from the other, and independently represents the $R^{1'}$ group or the $R^{2'}$ group. Each $R^{4'}$ may be identical to or different from the other, and independently represents the $R^{1'}$ group, the $R^{2'}$ group, or an oxygen atom. When $R^{4'}$ represents an oxygen atom, the $R^{4'}$ may bond to each other and constitute an ether group to form a ring together with silicon atoms. Each a' may identical to or different from the other and represents 0 to 100. b' represents 0 to 100, and a'+b' is 0 to 200. Nevertheless, when b' is 0, at least one of $R^{3'}$ is the $R^{2'}$ group. In the formulae (4)'-1 and (4)'-2, $R^{5'}$ represents an alkylene group having 2 to 10 carbon atoms or an aralkylene group having 7 to 10 carbon atoms. $R^{6'}$, $R^{7'}$, and $R^{8'}$ represent an alkylene group having 2 to 6 carbon atoms. $R^{7'}$ may represent an ether bond. c' represents 0 to 20. d' represents 1 to 20.

Examples of such a silicone compound having a polyglycerin structure can include the following.

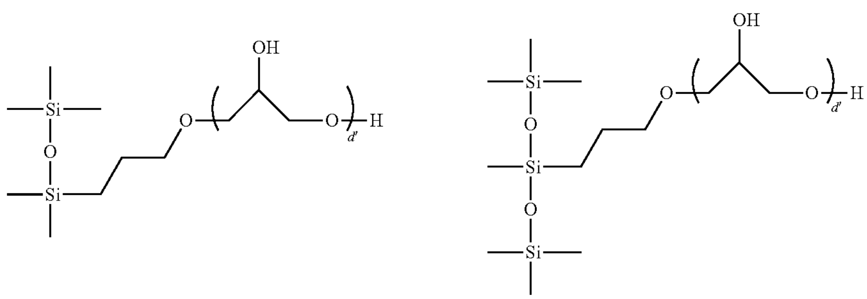

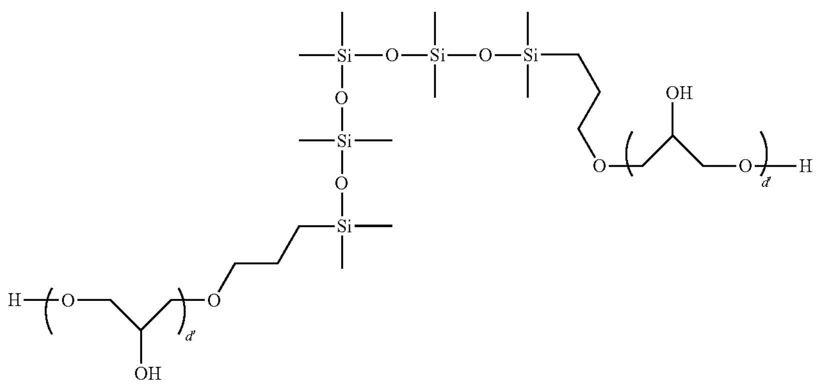

-continued
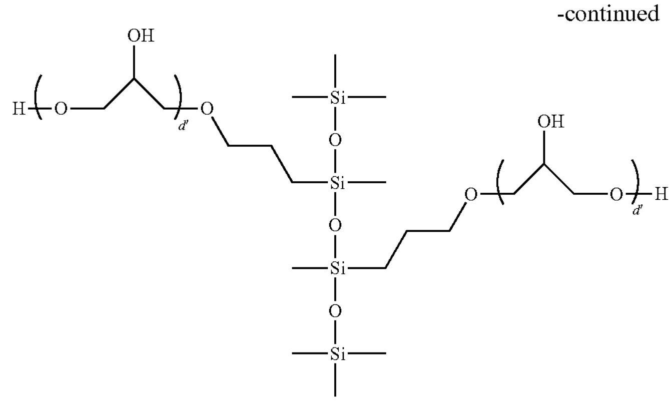
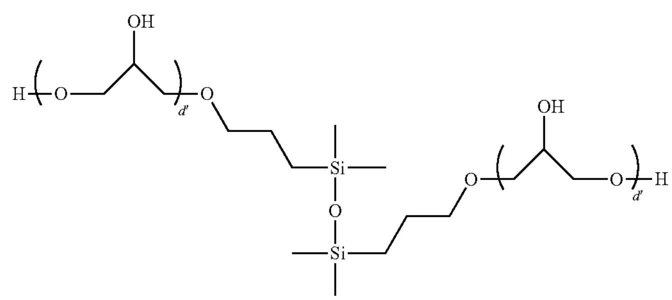
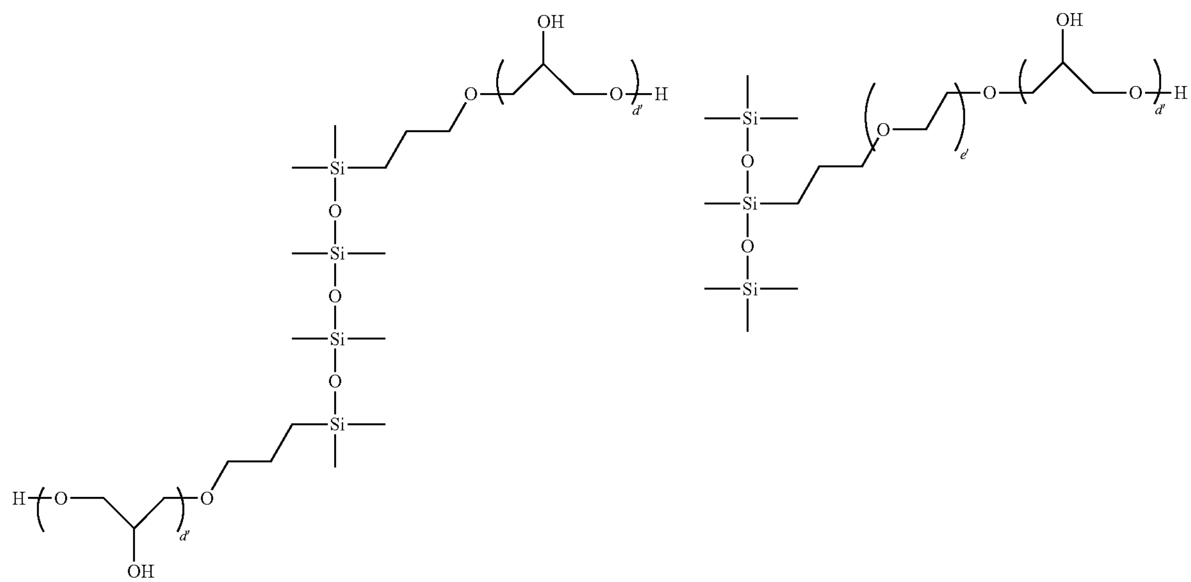
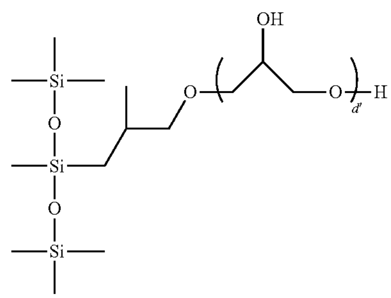
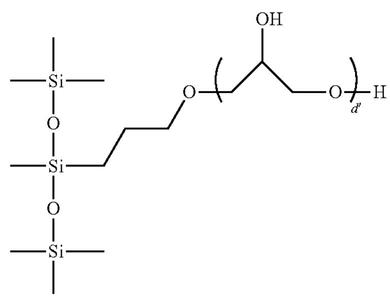

-continued
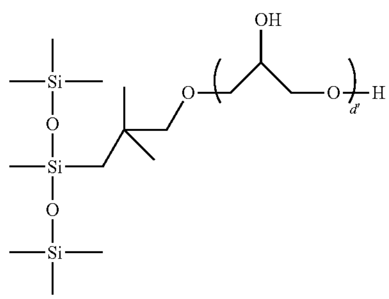
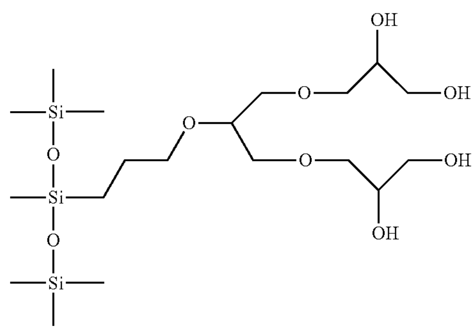
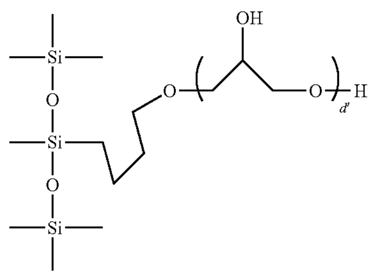
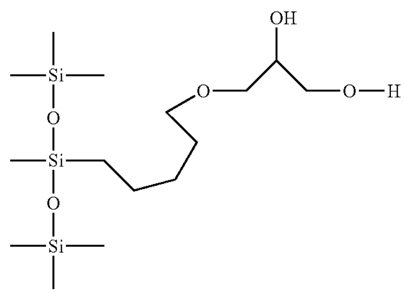
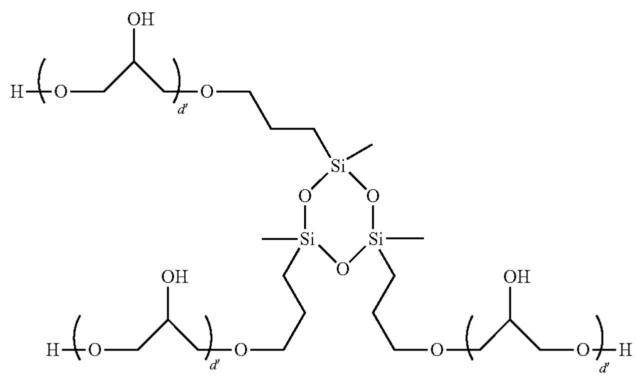
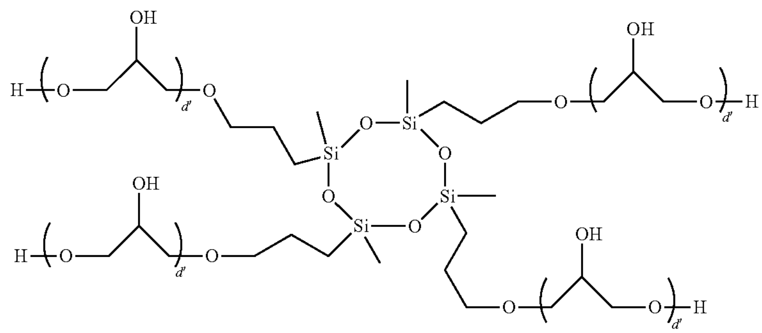
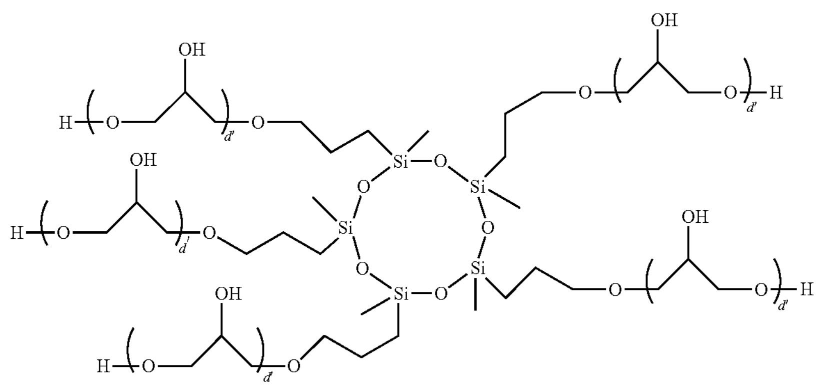

-continued
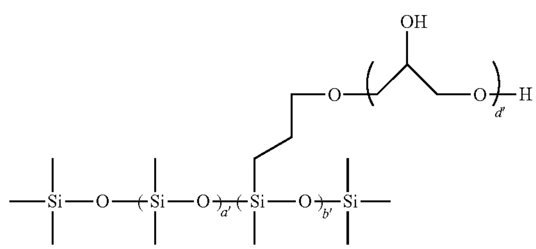
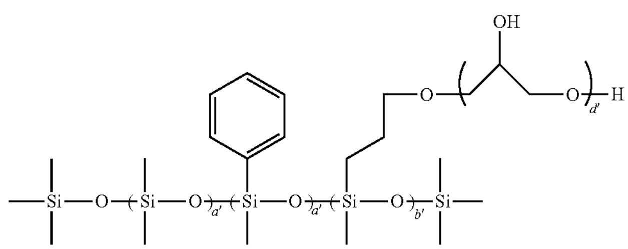
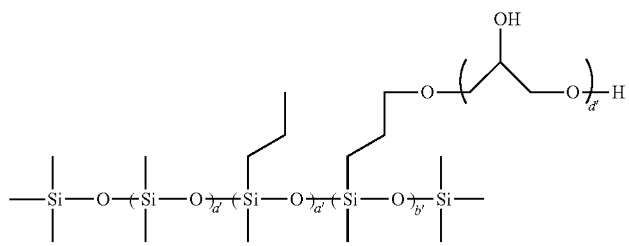
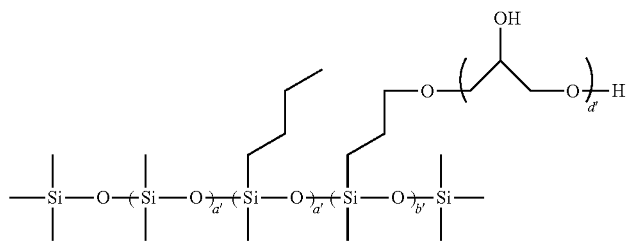
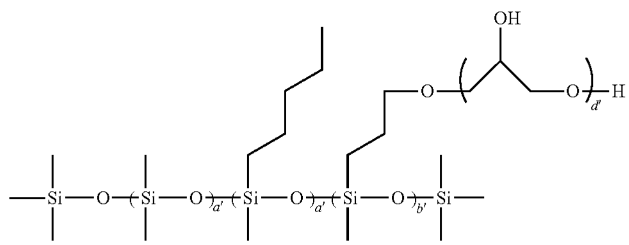
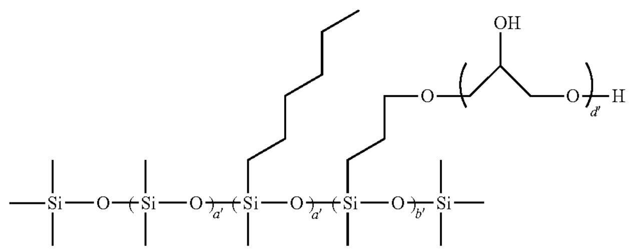
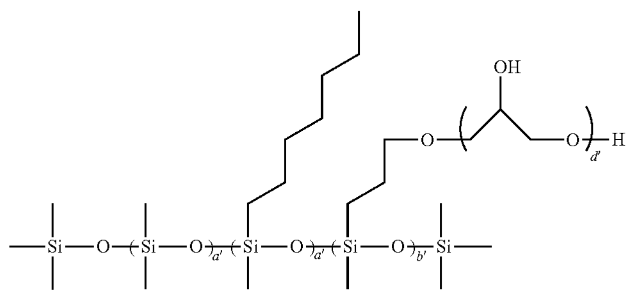

-continued
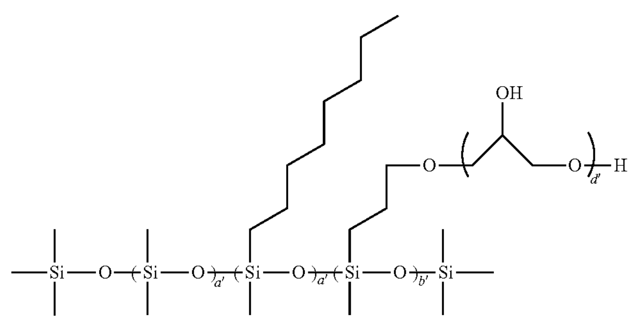
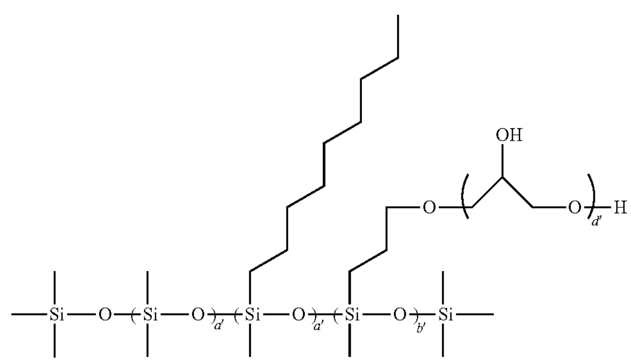
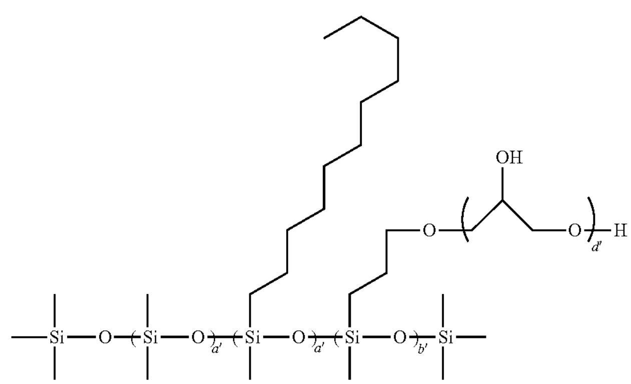
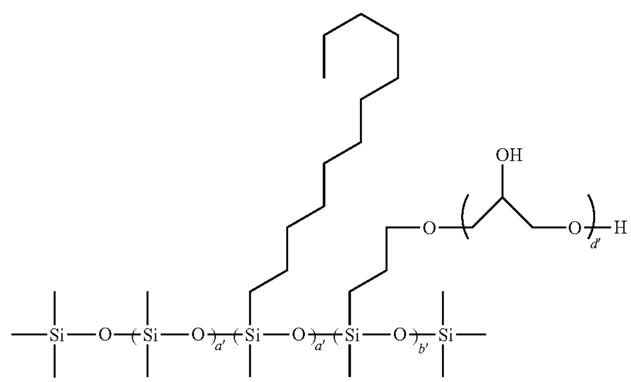

-continued
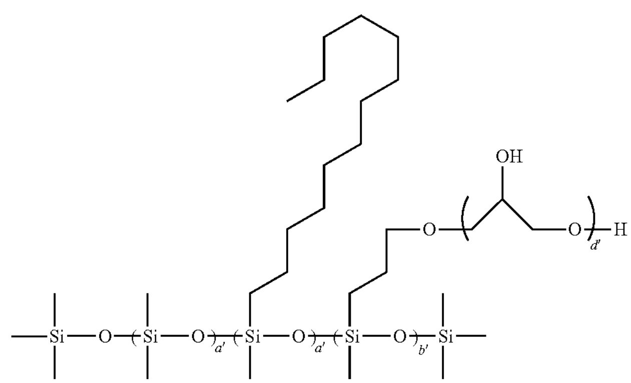
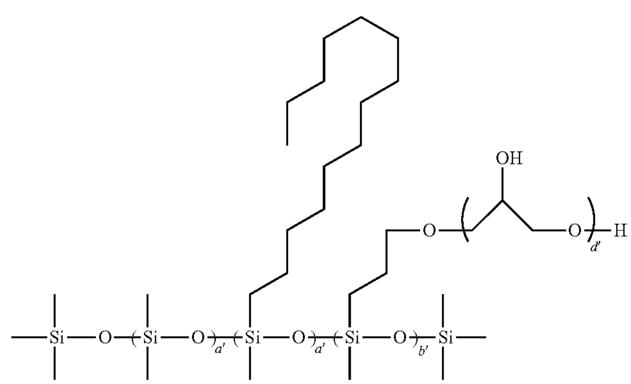
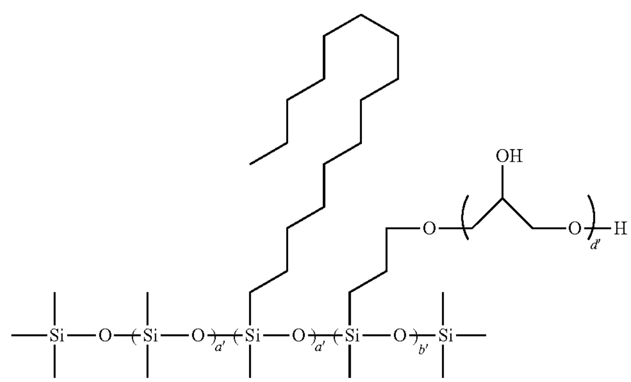
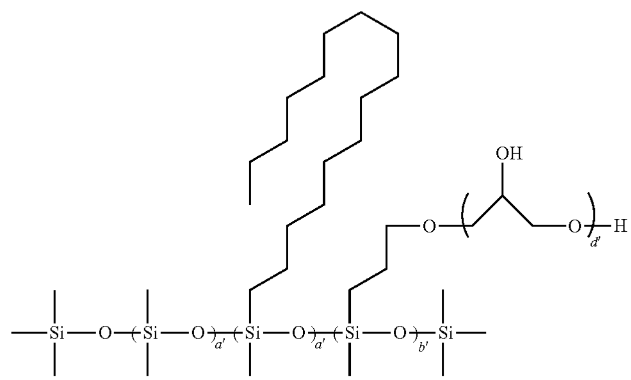

-continued
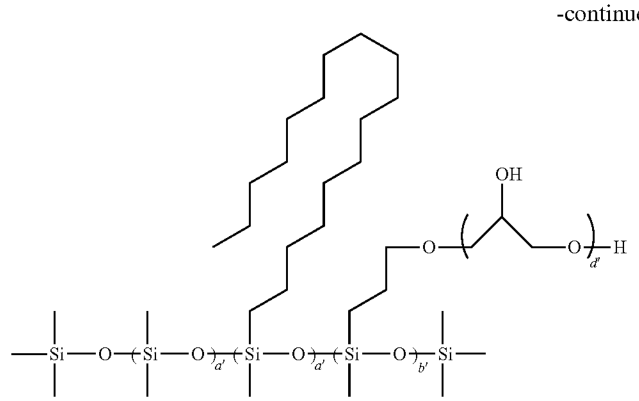
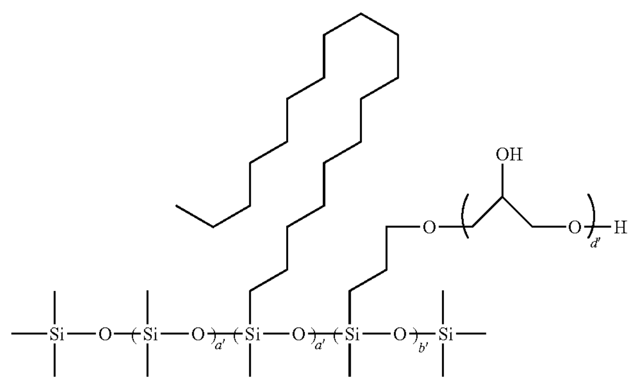
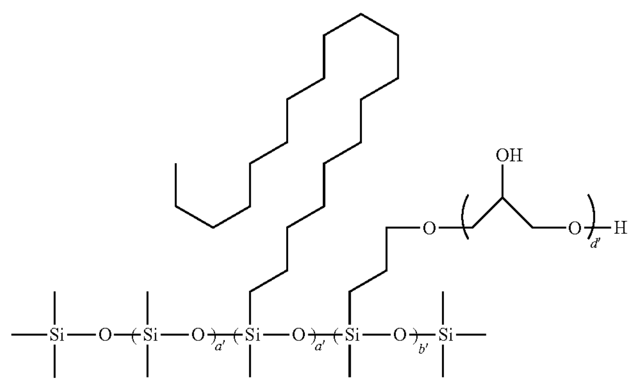
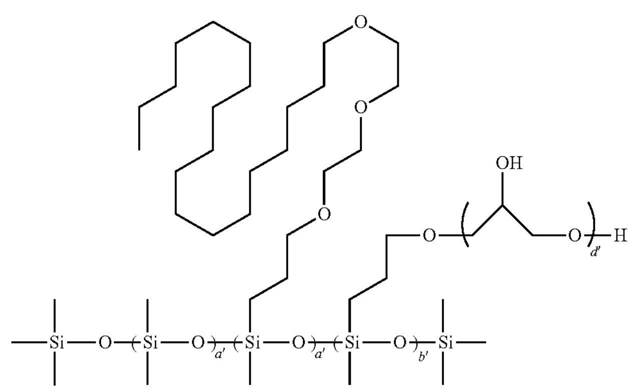

-continued
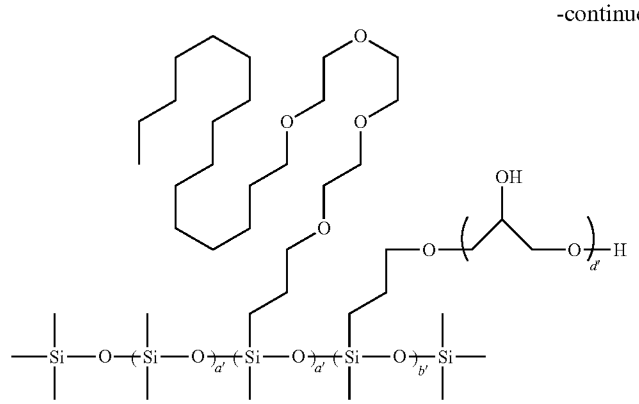
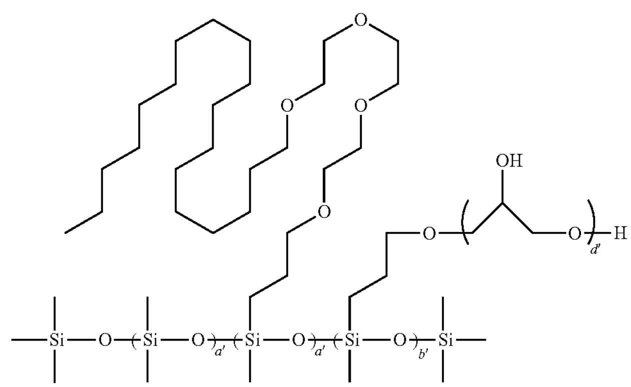
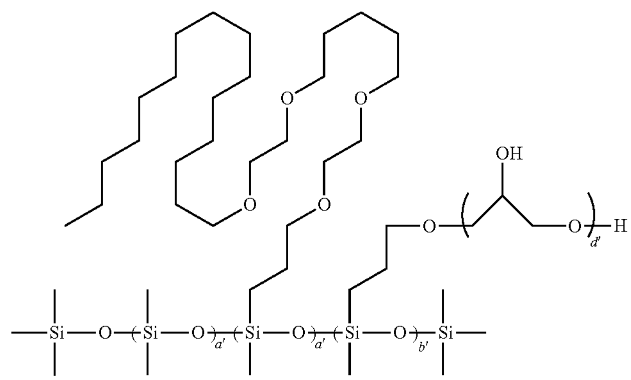
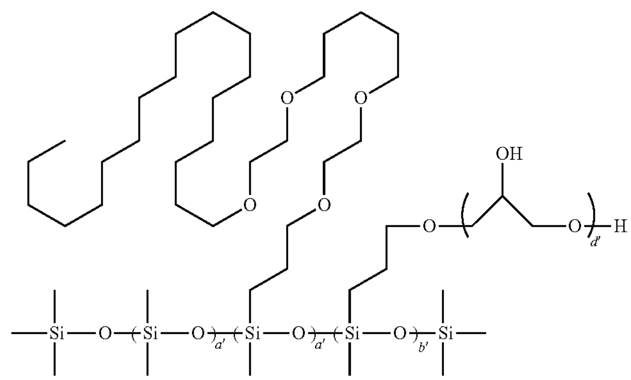

-continued
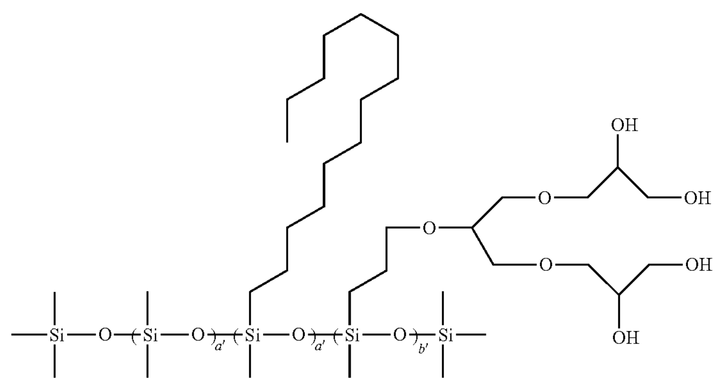
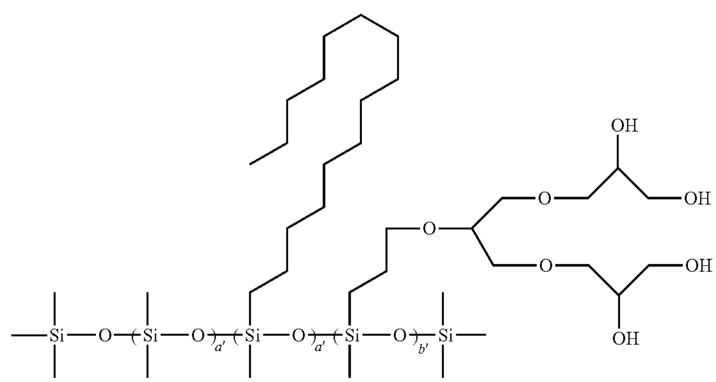
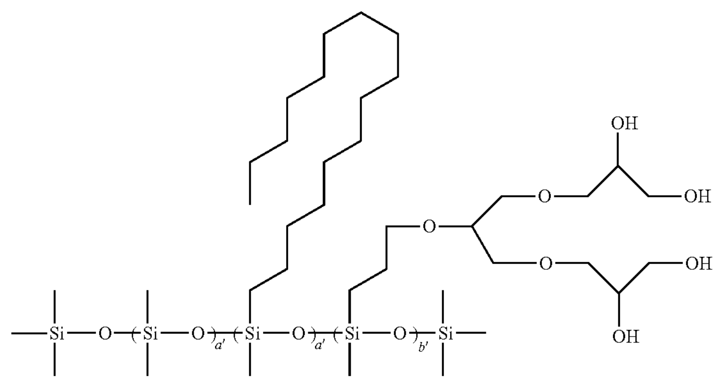
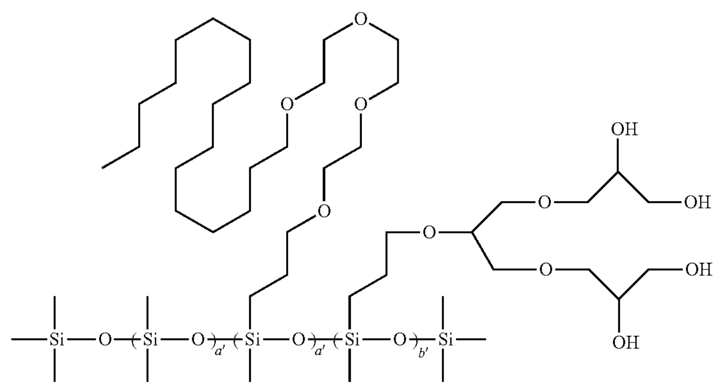

-continued
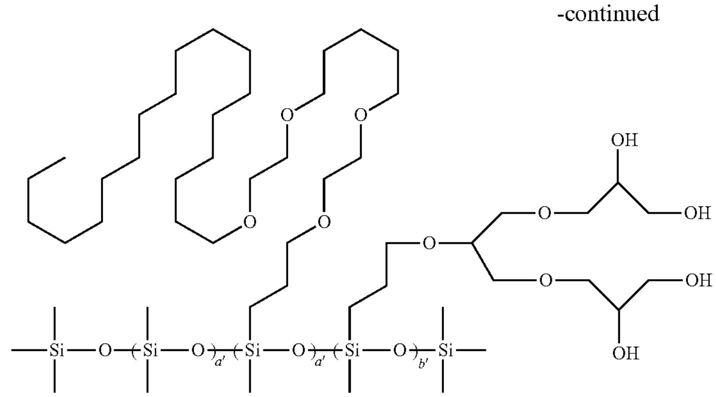
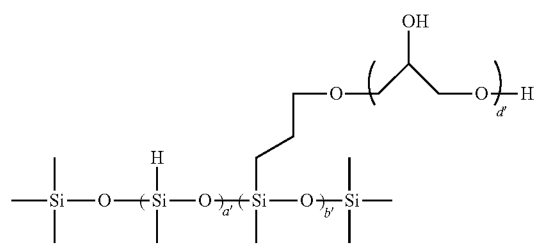
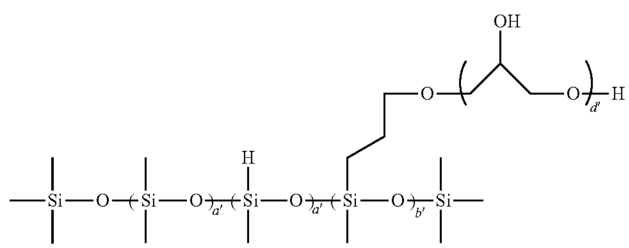
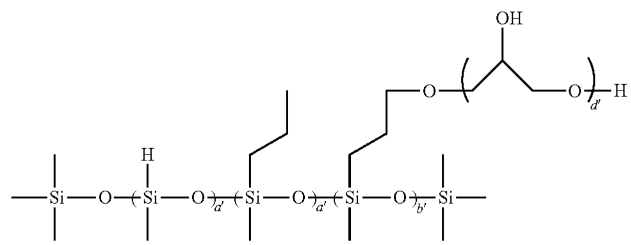
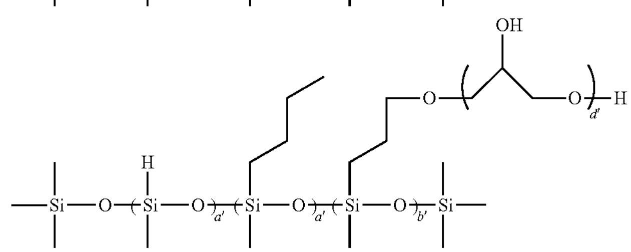
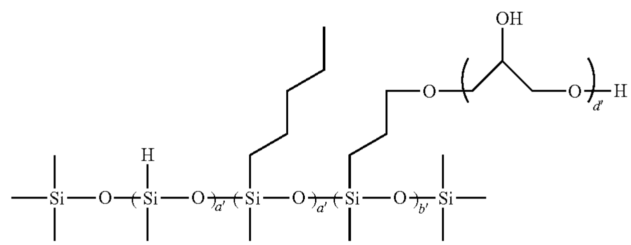
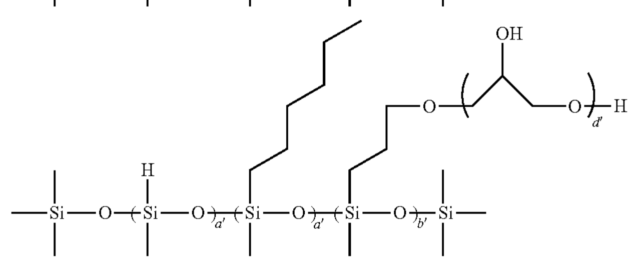

-continued
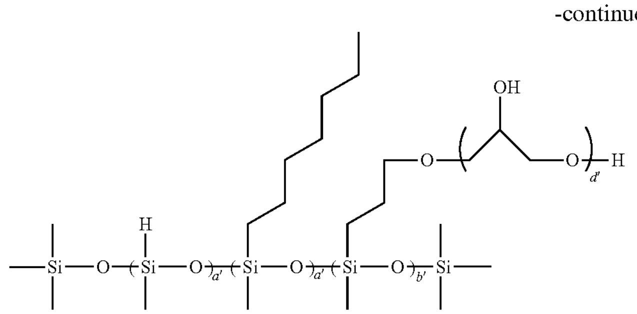
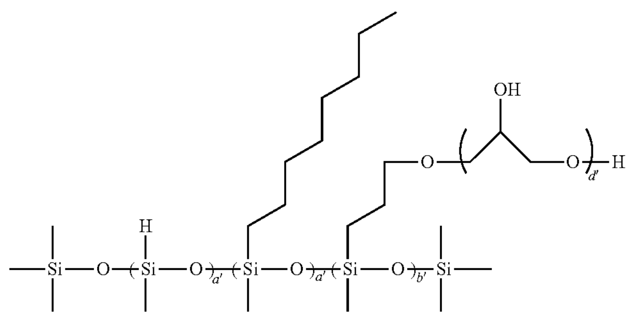
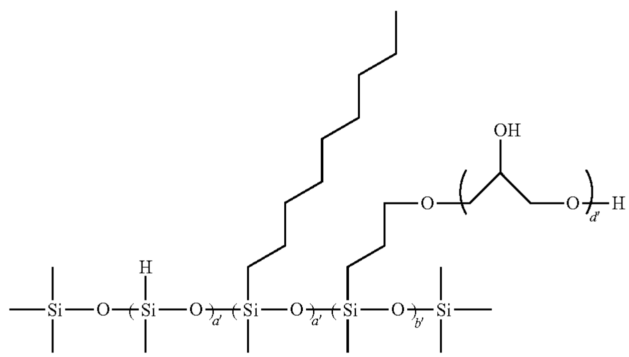
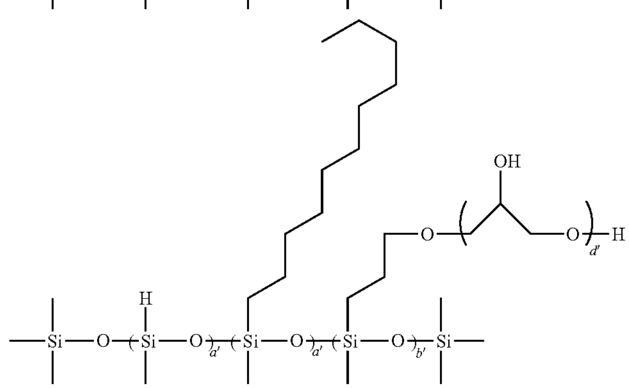
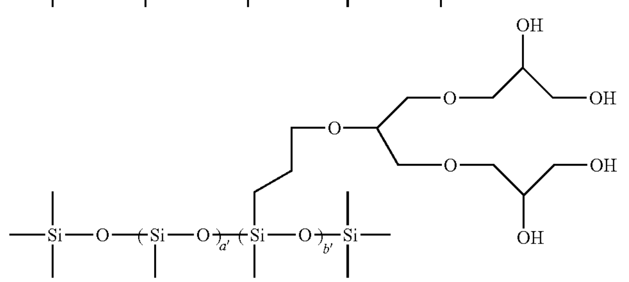

-continued
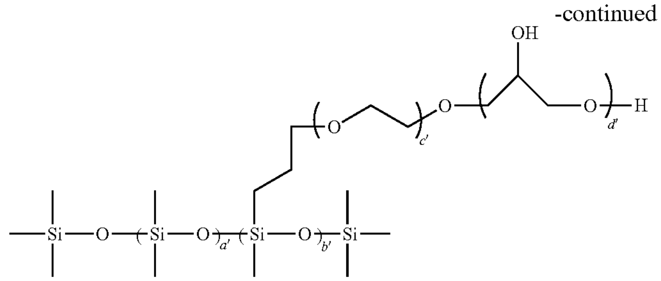
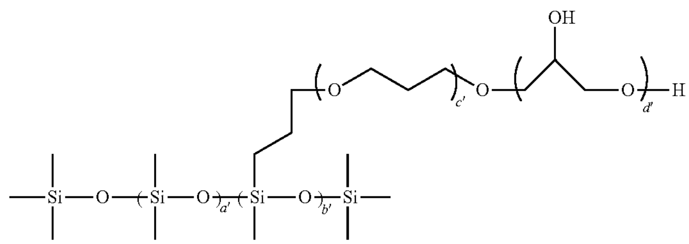
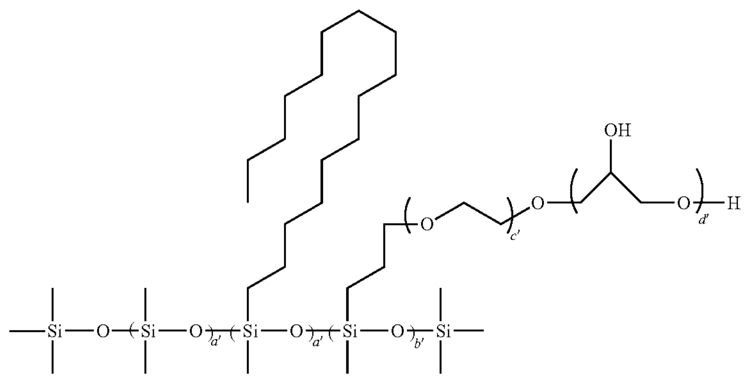
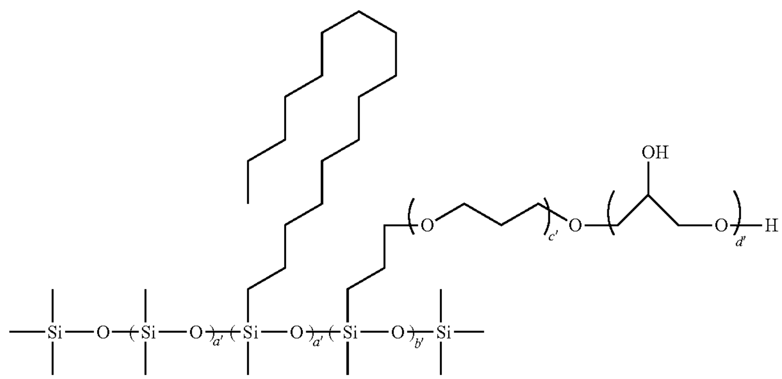
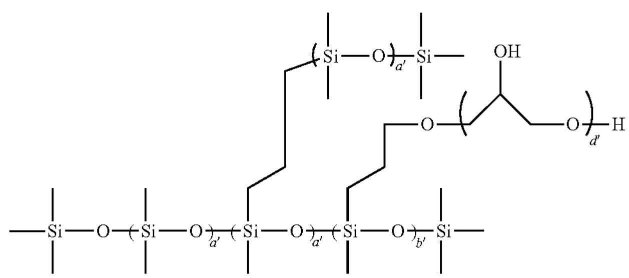

-continued
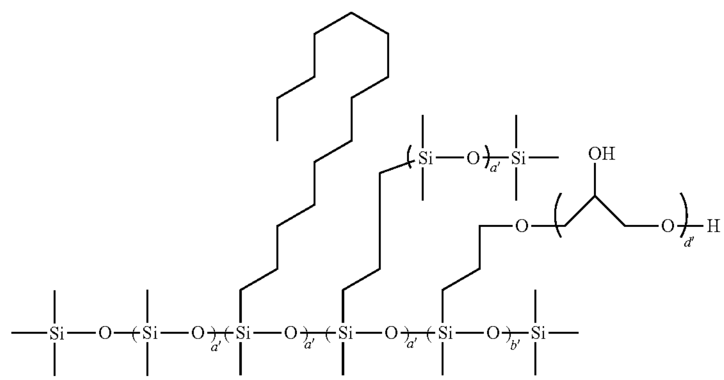
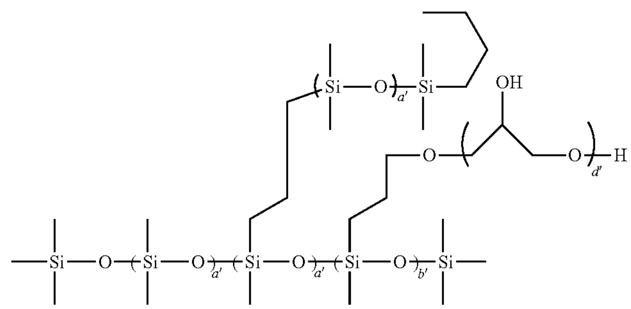
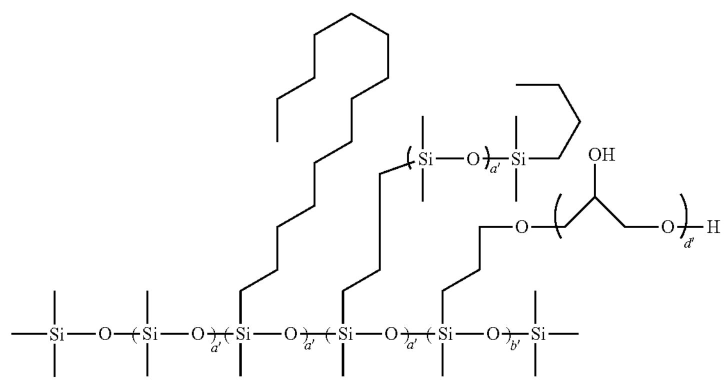
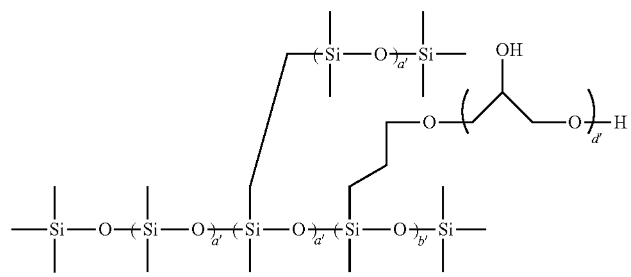
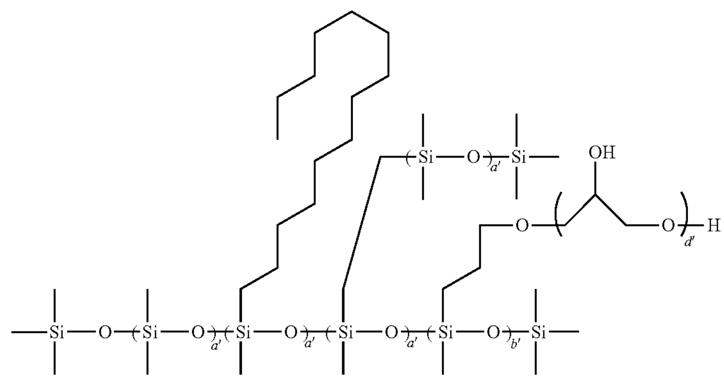

-continued
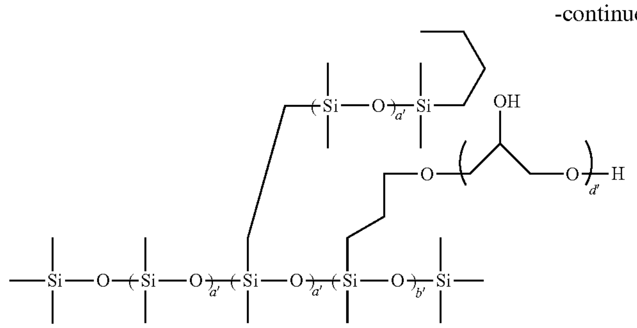
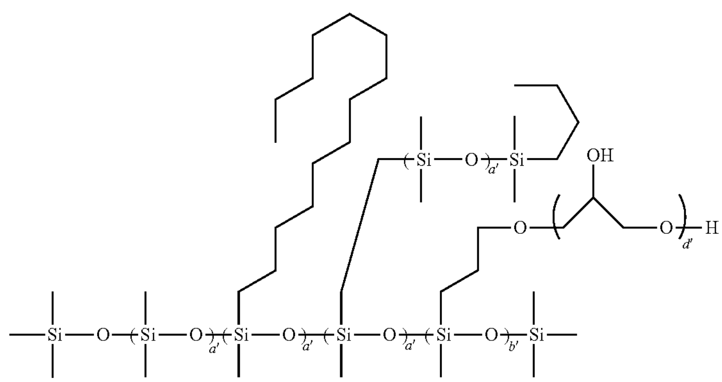
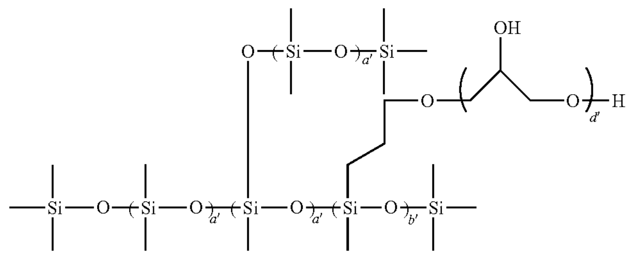
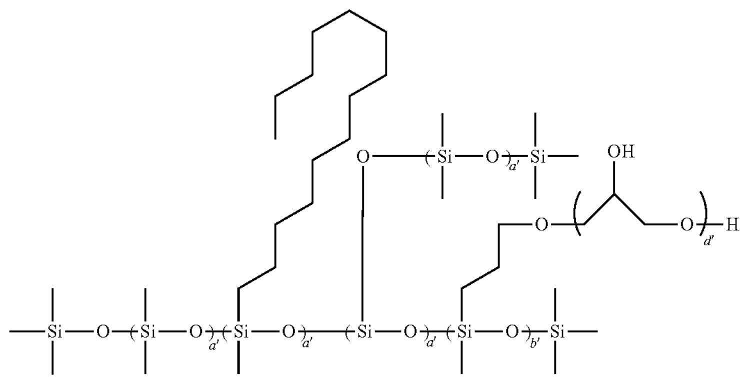
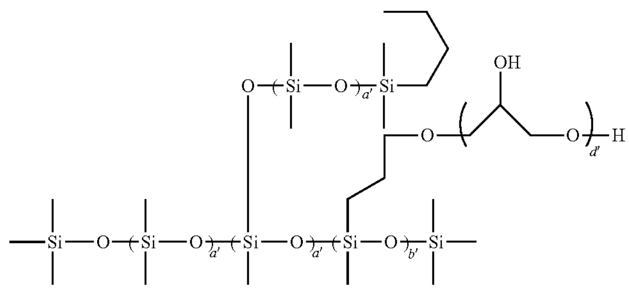

-continued

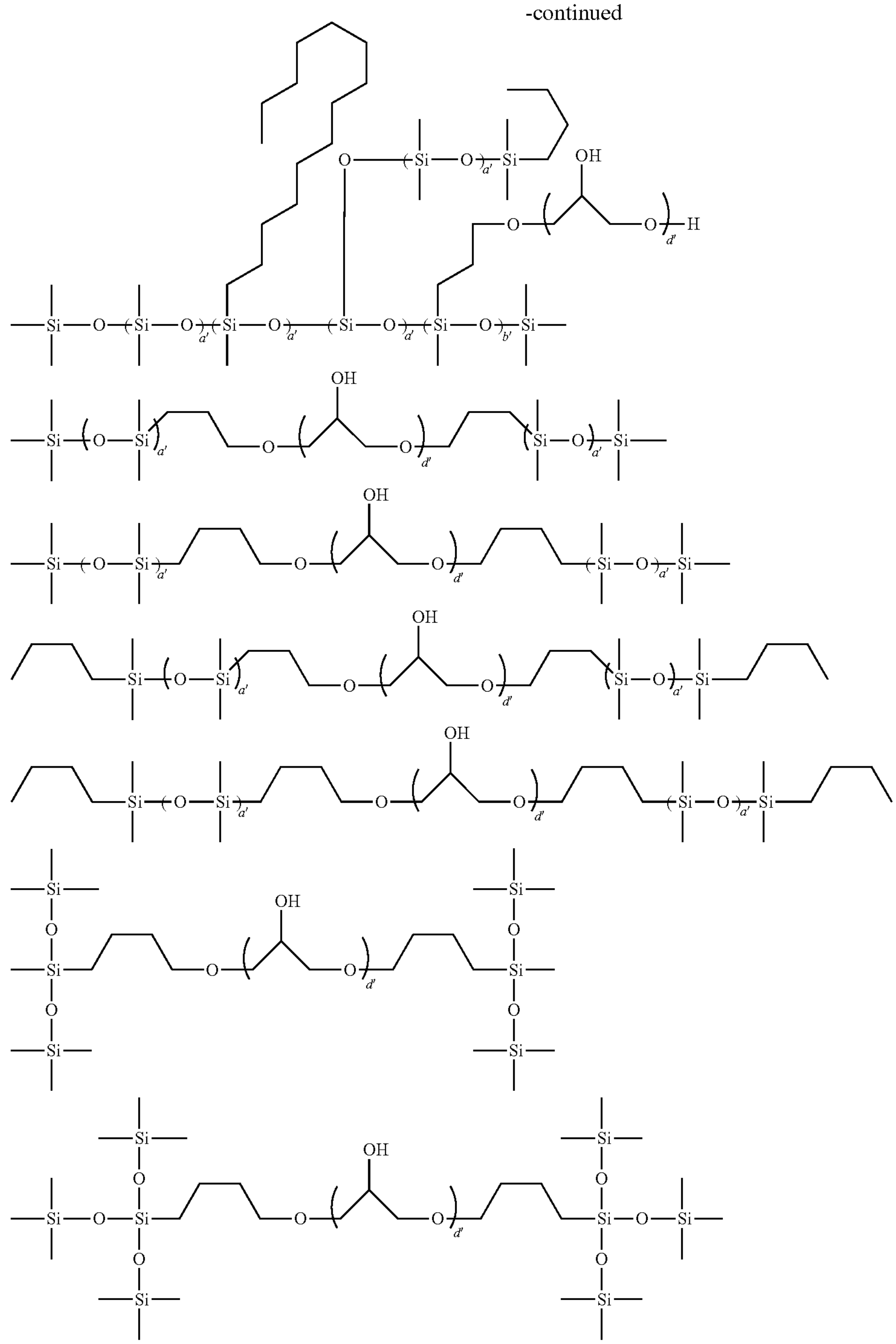

In the formulae, a', b', c', and d' are as defined above.

When such a silicone compound having a polyglycerin structure is contained, the resulting electro-conductive polymer composite can form an electro-conductive polymer composite layer that can exhibit a better moisture-holding property and consequently exhibit better sensitivity to ions released from the skin.

[Organic Solvent]

The electro-conductive polymer composite to form the electro-conductive polymer composite layer of the inventive bio-electrode can contain an organic solvent. Specific examples of the organic solvent can include water, heavy water, alcohols such as methanol, ethanol, propanol, butanol, etc.; polyvalent aliphatic alcohols such as ethylene glycol, propylene glycol, 1, 3-propanediol, dipropylene glycol, 1, 3-butylene glycol, 1,4-butylene glycol, D-glucose, D-glucitol, isoprene glycol, 1, 2-butanediol, 1, 3-butanediol, 1, 4-butanediol, 2, 3-butanediol, 1,2-pentanediol, 1, 5-pentanediol, 1,2-hexanediol, 1, 6-hexanediol, 1, 9-nonanediol, neopentyl glycol, etc.; linear ethers such as dialkyl ether, ethylene glycol monoalkyl ether, ethylene glycol dialkyl ether, propylene glycol monoalkyl ether, propylene glycol dialkyl ether, polyethylene glycol dialkyl ether, polypropylene glycol dialkyl ether, etc.; cyclic ether compounds such as dioxane, tetrahydrofuran, etc.; polar solvents such as cyclohexanone, methyl amyl ketone, ethyl acetate, butanediol monomethyl ether, propylene glycol monomethyl ether, ethylene glycol monomethyl ether, butanediol monoethyl ether, propylene glycol monoethyl ether, ethylene glycol monoethyl ether, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxypropionate, ethyl 3-ethoxypropionate, tert-butyl acetate, t-butyl propionate, propylene glycol mono-t-butyl ether acetate, Y-butyrolactone, N-methyl-2-pyrrolidone, N, N'-dimethylformamide, N, N'-dimethylacetamide, dimethyl sulfoxide, hexamethylene phosphoric triamide, etc.; carbonate compounds such as ethylene carbonate, propylene carbonate, etc.; heterocyclic compounds such as 3-methyl-2-oxazolidinone, etc.; nitrile compounds such as acetonitrile, glutaronitrile, methoxyacetonitrile, propionitrile, benzonitrile, etc.; and mixtures thereof.

The added amount of the organic solvent is preferably in the range of 10 to 50,000 parts by mass based on 100 parts by mass of the total of the components (A) and (B).

Hereinafter, the inventive bio-electrode will be described in detail with reference to the drawings, but the present invention is not limited thereto.

FIG. 1 is a schematic sectional view when an electro-conductive layer 1-1 is formed on a substrate 1 in YR color. In this drawing, the electro-conductive layer 1-1 consists of metal nanowires.

FIG. 2 is a schematic sectional view showing the inventive bio-electrode in which an electro-conductive polymer composite layer 1-2 is formed on the electro-conductive layer 1-1 on the substrate 1 in YR color. The electro-conductive layer 1-1 may be covered by the electro-conductive polymer composite layer 1-2 entirely or may be exposed partially to the surface.

The substrate 1 in YR color may be a single layer as shown in FIG. 2, or may be a laminate having a transparent base material 3 and a film 4 in YR color as shown in FIGS. 3 and 4.

FIG. 5 is a schematic sectional view when the inventive bio-electrode 2 is attached on the skin 6. One side of the electro-conductive polymer composite layer 1-2 gets contact with the skin 6 and the other side gets contact with the electro-conductive layer 1-1.

FIG. 6 is a schematic sectional view of a substrate 1 having an anti-reflective structure 7. Here, the anti-reflective structure 7 may be in YR color.

Schematic sectional views of substrates having a moth-eye typed anti-reflective structure are shown in FIGS. 7 to 9. The moth-eye typed anti-reflective structure is thicker on the substrate surface and thinner toward the top. The cross-section may be triangular, trapezoidal, cylindrical, etc., regardless of the shape.

The moth-eye typed anti-reflective structure may also be in YR color as well as the substrate, as shown in FIG. 10. Further, as shown in FIG. 11, the substrate may be transparent, and the moth-eye typed anti-reflective structure may be in YR color.

FIGS. 12 and 13 are schematic top views of the moth-eye typed anti-reflective structure. The shape of the top view may be circular, polygonal, quadrilateral, triangular, irregular, or any shape. Shape, pitch, and height thereof may be uniform or irregular.

FIG. 14 shows a schematic top view of electro-conductive wiring formed in the shape of straight lines having a width of 200 μm or less by printing. Transparency is improved by the gaps between lines of the wiring, and conductivity is improved by having multiple lines of wiring.

A schematic top view of electro-conductive wiring formed in the shape of zigzag lines having a width of 200 μm or less by printing is shown in FIG. 15. When the electro-conductive wiring is extended or contracted in a horizontal direction, the wiring in a zigzag pattern has less change in electro-conductivity when extended or contracted.

FIG. 16 shows a schematic top view of electro-conductive wiring formed in the shape of zigzag lines having corners rounded (wave lines) and a width of 200 μm or less by printing. The wiring of this shape has less change in electro-conductivity when extended or contracted than those of zigzag shape including straight lines and acute angles.

FIG. 17 shows a schematic top view of electro-conductive wiring formed by printing, in which two zigzag patterns using lines having a width of 200 μm or less are combined. This pattern has less change in electro-conductivity when extended or contracted than those of one zigzag wiring pattern including straight lines and acute angles as shown in FIG. 15.

The zigzag pattern of the electro-conductive wiring may be not only horizontal to a substrate as shown in FIGS. 15 to 17, but also vertical to a substrate as disclosed in JP 2020-107875 A.

The printed pattern of the electro-conductive wiring may be a single independent line as shown in FIGS. 15 to 17, or may have a connection wiring to connect neighboring wirings. For example, the patterns include a reticular pattern (aslant lattice pattern) shown in FIG. 18, a Kikkou pattern shown in FIG. 19, a pattern of connected-circles shown in FIGS. 20 and 21, and a mesh pattern shown in FIG. 12. In addition to these, the patterns can include a Higaki pattern with repeated diagonal rectangles, a Mutsude no Manji pattern that combines hexagons, a Kagome pattern that combines equilateral triangles and straight lines, and a Bishamon tortoiseshell pattern, a Fundo Tsunagi pattern with curved lines crossing diagonally, a Tokkuri Ajiro pattern, and a Hoshishippo pattern with overlapping circles (see http://www.natubunko.net/wagara/kotoba09g.html).

FIG. 23 shows a schematic top view of an electro-conductive layer formed by applying a solution containing a metal nanowire. Gaps between metal nanowires improve transparency. Contact of metal nanowires ensures electro-conductivity when the electro-conductive wiring is extended or contracted.

The moth-eye typed anti-reflective structure can be equipped not only on the front side but also on the backside of the substrate. FIG. 24 shows a case using a substrate 1 having a moth-eye typed anti-reflective structure 8 also on its backside of electro-conductive layer 1-1. When electro-conductive wiring is formed on a non-planar moth-eye typed substrate, a zigzag pattern is formed vertically as disclosed in JP 2020-107875 A, and produces an advantage of excellence in being extended or contracted.

Hereinafter, constituent materials of the inventive bio-electrode each will be described in more detail.

[Adhesive Layer]

The inventive bio-electrode has an electro-conductive polymer composite layer formed on an electro-conductive layer. The electro-conductive polymer composite layer is the part that actually contacts the living body when the bioelectrode is used. To increase adhesive strength, an adhesive layer can be provided around the electro-conductive polymer composite layer.

The adhesive layer preferably has an adhesive strength in the range of 0.5 N/25 mm or more and 20 N/25 mm or less. The adhesive strength is commonly measured by the method described in JIS Z 0237, in which a metal material such as stainless steel (SUS) or polyethylene terephthalate (PET) can be used as a base material. Alternatively, human skin can also be used for measuring. Surface energy of human skin is lower than metals and various plastics and as low as that of Teflon (registered trademark), and thus human skin is hard to be adhered.

The bio-electrode preferably has a thickness of 1 nm or more and 1 mm or less, more preferably 2 nm or more and 0.5 mm or less.

<Method for Manufacturing Bio-Electrode>

The present invention provides a method for manufacturing the bio-electrode, the method including: forming an electro-conductive layer on a substrate; and forming an electro-conductive polymer composite layer on the side, which is attached to the skin, of the electro-conductive layer. That is, the present invention provides a method for forming the bio-electrode described in the above, the method including: forming the electro-conductive layer (C) by applying a solution containing a metal nanowire or by printing electro-conductive paste containing an electro-conductive particle on the substrate (D) having a transmittance of 20% or more at a wavelength of 600 nm and being in a yellow-red (YR) color with a value in the range of 1 to 9 and a chroma in the range of 1 to 12 in the Munsell color system; and forming the electro-conductive polymer composite layer by applying the electro-conductive polymer composite on the electro-conductive layer (C).

A method to form the electro-conductive layer (C) on a substrate (D) can include: printing an electro-conductive paste containing an electro-conductive particle; and coating ink (solution) containing a metal nanowire.

A Method to form the electro-conductive polymer composite layer on the electro-conductive layer (C) can include coating the electro-conductive polymer composite.

A method for coating the electro-conductive polymer composite on the electro-conductive layer (C) is not specifically limited, but includes direct coating and transferring what is coated on another substrate. In either method, the preferable methods are, for example, dip coating, spray coating, spin coating, roll coating, flow coating, doctor coating, screen printing, flexo printing, gravure printing, inkjet printing, etc.

For printing the electro-conductive paste containing an electro-conductive particle and applying a solution containing a metal nanowire, it is possible to use the same method as those for coating the electro-conductive polymer composite.

To evaporate a solvent and cure the film, heating is carried out after printing the electro-conductive paste, after applying the ink containing a metal nanowire, and after coating the electro-conductive polymer composite.

Note that, a temperature for heating after coating the electro-conductive polymer composite is not particularly limited, and may be selected properly according to the kinds of components (A) and (B) used for the electro-conductive polymer composite. For example, a temperature around a range of 50 to 250° C. is preferable.

In the case of using a silver nanowire etc. for the electro-conductive layer, the heating temperature after coating the electro-conductive paste or after coating the ink containing a metal nanowire is in the range of 70 to 600° C., in order to fuse silver each other. At this time, to prevent thermal decomposition of a substrate, it is also possible to use a flash lamp anneal treatment in which intense UV is radiated in a short time.

In the case that heating and radiation of light are combined, these may be carried out at the same time, heating may be carried out after light radiation, or vice versa. Further, air-dry may be carried out to evaporate a solvent before heating after coating.

By putting a waterdrop or spraying steam or mist on a surface of the cured electro-conductive polymer composite layer, affinity with the skin increases, and thus a biological signal can be obtained promptly. In order to fine a size of waterdrop of the steam or the mist, it is possible to use water mixed with alcohol. It is also possible to wet a surface of the electro-conductive polymer composite layer by having them touched with absorbent cotton or cloth containing water.

Water to wet the surface of the cured electro-conductive polymer composite layer may contain a salt. A water-soluble salt to be mixed with water is preferably selected from the group consisting of sodium salts, potassium salts, calcium salts, magnesium salts, and betaine.

Specifically, the water-soluble salts can be salts selected from the group consisting of sodium chloride, potassium chloride, calcium chloride, magnesium chloride, saccharin sodium salts, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaine. Note that, the above dopant polymer (B) is not included in the water-soluble salt.

More specifically, in addition to the above, examples of the water-soluble salts include sodium acetate, sodium propionate, sodium pivalate, sodium glycolate, sodium butyrate, sodium valerate, sodium caproate, sodium enanthate, sodium caprylate, sodium pelargonate, sodium caprate, sodium undecylate, sodium laurate, sodium tridecylate, sodium myristate, sodium pentadecylate, sodium palmitate, sodium margarate, sodium stearate, sodium benzoate, disodium adipate, disodium maleate, disodium phthalate, sodium 2-hydroxybutyrate, sodium 3-hydroxybutyrate, sodium 2-oxobutyrate, sodium gluconate, sodium methanesulfonate, sodium 1-nonanesulfonate, sodium 1-decanesulfonate, sodium 1-dodecanesulfonate, sodium 1-undecanesulfonate, sodium cocoyl isethionate, sodium lauroylmethylalanine, cocoylmethyl sodium taurine, sodium cocoyl glutamate, sodium cocoyl sarcosine, sodium lauroylmethyltaurate, laumidopropyl betaine, potassium isobutyrate, potassium propionate, potassium pivalate, potassium glycolate, potassium gluconate, potassium methanesulfonate, calcium stearate, calcium glycolate, calcium gluconate, calcium 3-methyl-2-oxobutyrate, calcium methanesulfonate. Betaine is a generic term for an internal salt and specifically is a compound in which three methyl groups are added to an amino group of an amino acid, more specifically examples thereof can include trimethylglycine, carnitine and proline betaine.

The water-soluble salts can further contain monohydric or polyhydric alcohols having 1 to 4 carbon atoms. The alcohol is preferably selected from the group consisting of ethanol, isopropyl alcohol, ethylene glycol, diethylene glycol, triethylene glycol, glycerin, polyethylene glycol, polypropylene glycol, polyglycerin, diglycerin, or a silicone compound having a polyglycerin structure. It is more preferable that the silicone compound having a polyglycerin structure is represented by the above general formula (4)'.

As a preprocessing process using solution containing a salt, it is possible to wet bio-electrode film (the cured electro-conductive polymer composite layer) by atomization method, waterdrop dispensing method, etc. It is also possible to wet the layer in hot, humid conditions like in a sauna. After getting wet, the wet layer can be covered by a sheet to prevent drying. Because the sheet has to be removed immediately before attaching the bio-electrode on the skin, the sheet is coated by a release agent or a removable fluororesin film. A dry electrode covered by a removable sheet is sealed in a bag covered with aluminum, etc. for long-term storage. In order to prevent drying in a bag covered by aluminum, it is preferable to seal water in the bag.

It is effective in terms of humidifying skin surface to obtain a biological signal with high sensitivity and high accuracy in a shorter time, to wipe the skin where the bio-electrode is attached with fabric containing water or water-containing alcohol such as ethanol, glycerin, etc., or to spray them onto the skin, immediately before attaching the bio-electrode. Wiping with fabric containing water is effective not only in humidifying the skin but also in removing oil on the skin surface, and also improve sensitivity to a biological signal.

As described above, the inventive method for manufacturing the bio-electrode makes it possible to manufacture, easily at low cost, the inventive bio-electrode which is thin film, highly transparent, highly sensitive to a biological signal, slightly different from skin color, excellent in biocompatibility, light-weight, manufacturable at low cost, capable of preventing significant reduction in electro-conductivity when wetted with water or dried and when attached on the skin for a long time, and comfortable without itching, reddening, or rash of the skin.

Example

Hereinafter, the present invention will be specifically described with reference to Examples and Comparative Examples, but the present invention is not limited thereto. The molecular weight (Mw) and dispersity (Mw/Mn) of the obtained polymers were verified by gel permeation chromatography (GPC) using tetrahydrofuran (THF) as a solvent.

Synthesis of Dopant Polymer 1

Under a nitrogen atmosphere, a solution, in which 54.5 g of Monomer 1 and 4.19 g of dimethyl 2,2'-azobis(isobutyrate) are dissolved in 112.5 g of methanol, was added dropwise over 4 hours to 37.5 g of methanol stirred at 64° C. The mixture was further stirred at 64° C. for 4 hours. After being cooled to room temperature, the mixture was added dropwise to 1,000 g of ethyl acetate under vigorous stirring. The formed solid product was collected by filtration, and dried in a vacuum at 50° C. for 15 hours. As a result, 43.6 g of a white polymer was obtained.

The obtained white polymer was dissolved in 396 g of methanol, and the ammonium salt was converted to a sulfo group by using an ion exchange resin. When the obtained polymer was measured by 19F, 1H-NMR, and GPC, the following analytical results were obtained.

Weight-average molecular weight (Mw)=12,400

Molecular weight distribution (Mw/Mn)=1.51

This compound is referred to as Polymer 1.

Monomer 1

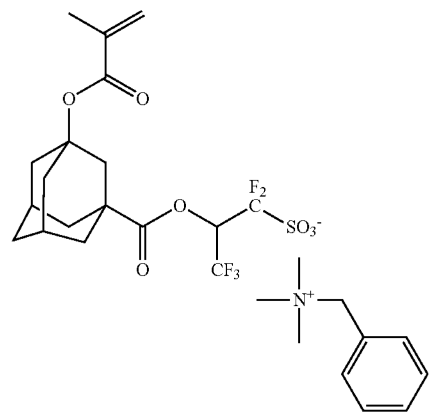

Dopant Polymer 1

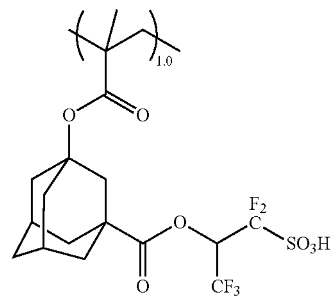

In the same manner, the following Dopant Polymers 2 to 25 were polymerized.

Dopant Polymer 2

Weight-average molecular weight (Mw)=14,000

Molecular weight distribution (Mw/Mn)=1.41

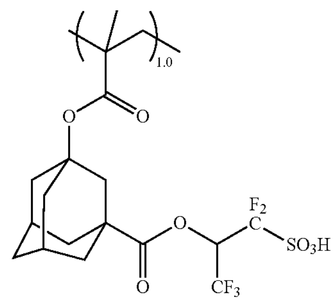

Dopant Polymer 3

Weight-average molecular weight (Mw)=10, 300
Molecular weight distribution (Mw/Mn)=1.48

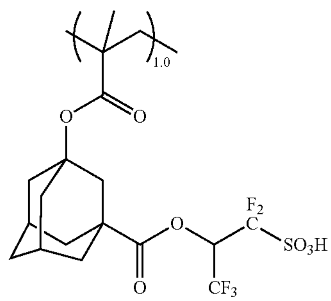

Dopant Polymer 4

Weight-average molecular weight (Mw)=12,500
Molecular weight distribution (Mw/Mn)=1.53

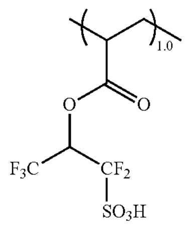

Dopant Polymer 5

Weight-average molecular weight (Mw)=8,500
Molecular weight distribution (Mw/Mn)=1.67

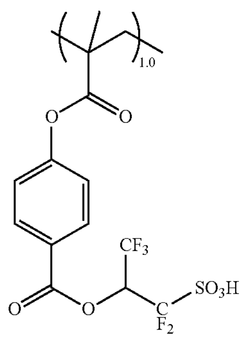

Dopant Polymer 6

Weight-average molecular weight (Mw)=12,500
Molecular weight distribution (Mw/Mn)=1.68

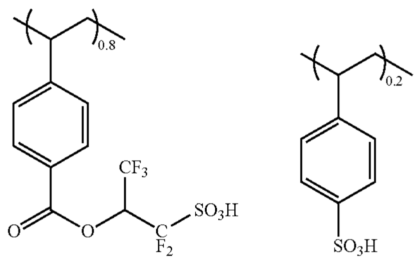

Dopant Polymer 7

Weight-average molecular weight (Mw)=15,500
Molecular weight distribution (Mw/Mn)=1.78

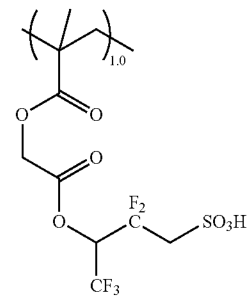

Dopant Polymer 8

Weight-average molecular weight (Mw)=13,500
Molecular weight distribution (Mw/Mn)=1.69

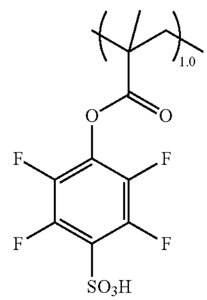

Dopant Polymer 9

Weight-average molecular weight (Mw)=10,500
Molecular weight distribution (Mw/Mn)=1.69

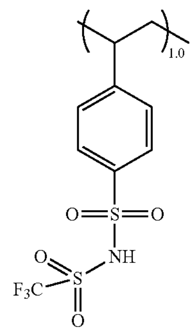

Dopant Polymer 10

Weight-average molecular weight (Mw)=8,500

Molecular weight distribution (Mw/Mn)=1.59

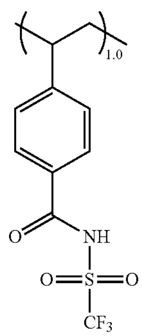

Dopant Polymer 11

Weight-average molecular weight (Mw)=11,000

Molecular weight distribution (Mw/Mn)=1.73

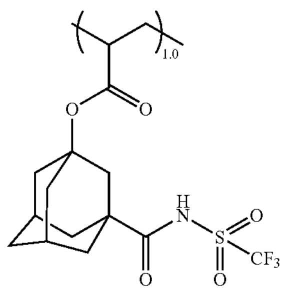

Dopant Polymer 12

Weight-average molecular weight (Mw)=17,100

Molecular weight distribution (Mw/Mn)=1.73

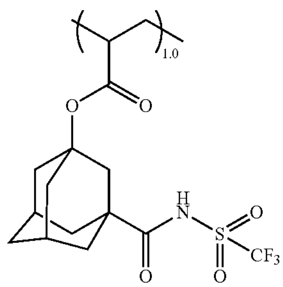

Dopant Polymer 13

Weight-average molecular weight (Mw)=15, 400

Molecular weight distribution (Mw/Mn)=1.74

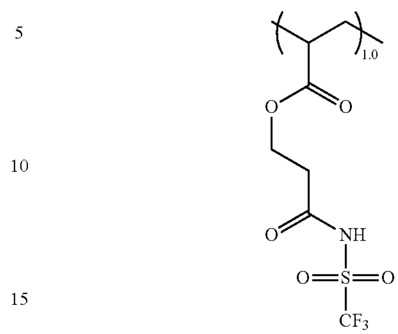

Dopant Polymer 14

Weight-average molecular weight (Mw)=16,800

Molecular weight distribution (Mw/Mn)=1.83

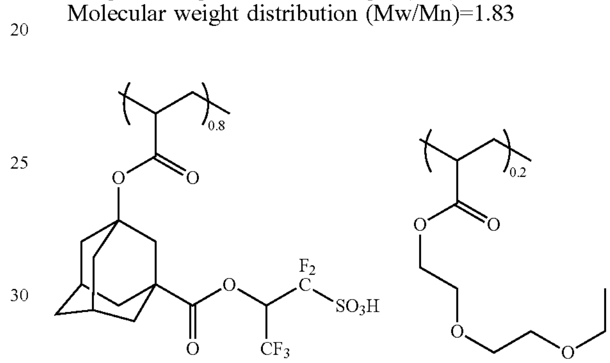

Dopant Polymer 15

Weight-average molecular weight (Mw)=12,900

Molecular weight distribution (Mw/Mn)=1.74

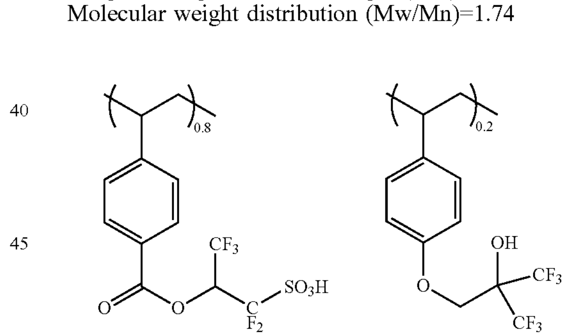

Dopant Polymer 16

Weight-average molecular weight (Mw)=10,400

Molecular weight distribution (Mw/Mn)=1.73

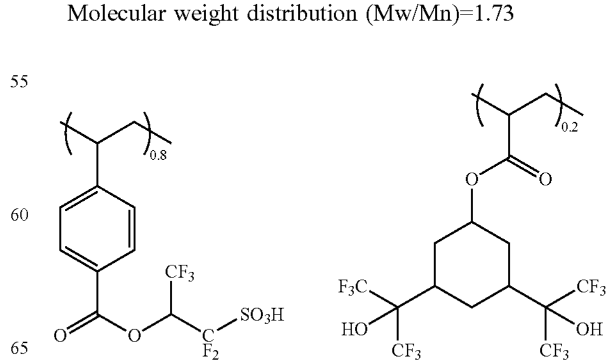

Dopant Polymer 17

Weight-average molecular weight (Mw)=16,500

Molecular weight distribution (Mw/Mn)=1.79

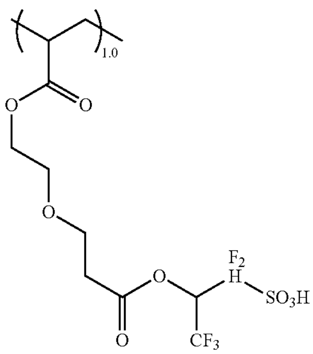

Dopant Polymer 18

Weight-average molecular weight (Mw)=15,700

Molecular weight distribution (Mw/Mn)=1.81

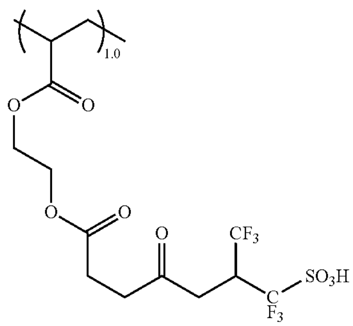

Dopant Polymer 19

Weight-average molecular weight (Mw)=16,100

Molecular weight distribution (Mw/Mn)=1.84

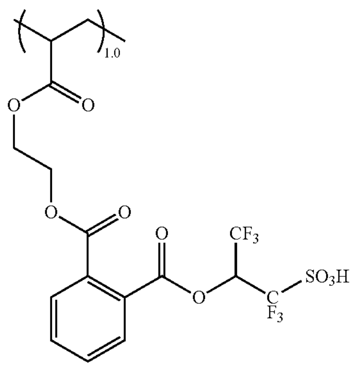

Dopant Polymer 20

Weight-average molecular weight (Mw)=11, 400

Molecular weight distribution (Mw/Mn)=1.65

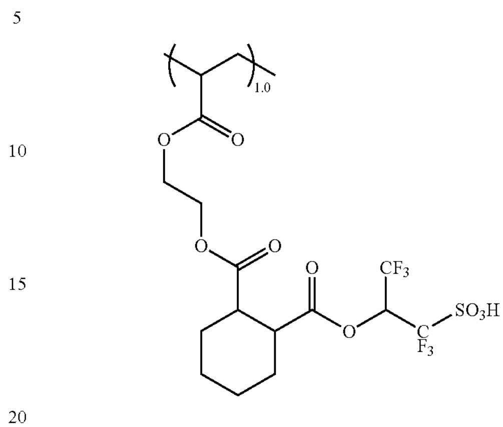

Dopant Polymer 21

Weight-average molecular weight (Mw)=14,400

Molecular weight distribution (Mw/Mn)=1.78

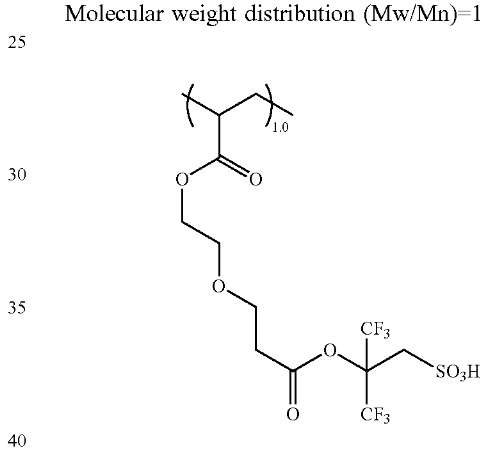

Dopant Polymer 22

Weight-average molecular weight (Mw)=17,400

Molecular weight distribution (Mw/Mn)=1.88

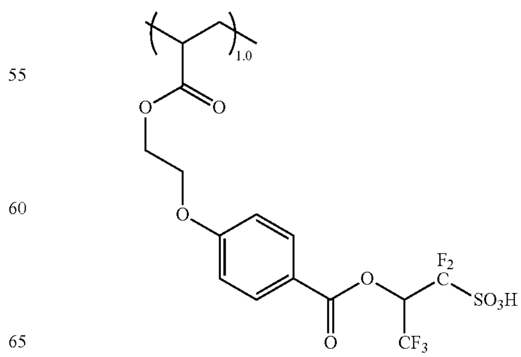

Dopant Polymer 23

Weight-average molecular weight (Mw)=11, 300

Molecular weight distribution (Mw/Mn)=1.59

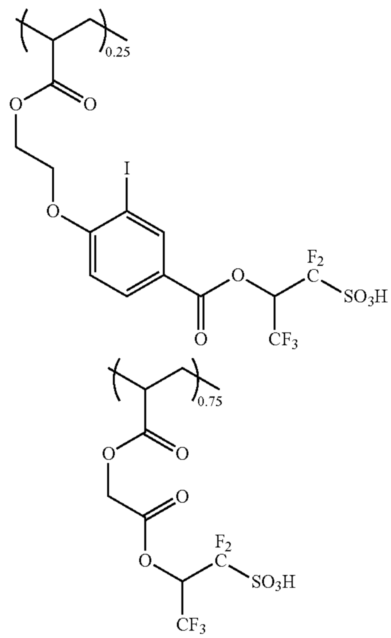

Dopant Polymer 24

Weight-average molecular weight (Mw)=12,100

Molecular weight distribution (Mw/Mn)=1.56

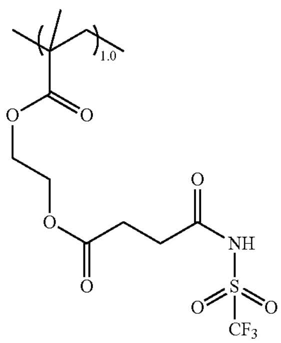

Dopant Polymer 25

Weight-average molecular weight (Mw)=12,900

Molecular weight distribution (Mw/Mn)=1.69

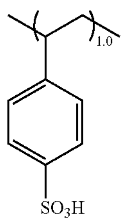

Preparation of Electro-Conductive Polymer Composite Solution Containing Polythiophene as π-Conjugated Polymer Preparation Example 1

3.82 g of 3,4-ethylenedioxythiophene and a solution in which 15.0 g of Dopant Polymer 1 had been dissolved in 1,000 mL of ultrapure water were mixed at 30° C.

The obtained mixture solution was maintained at 30° C., and oxidation catalyst solution of 8.40 g of sodium persulfate and 2.3 g of a ferric sulfate dissolved in 100 mL of ultrapure water were gradually added with stirring the mixture solution. The mixture was reacted with stirring for 4 hours.

To the obtained reaction solution, 1,000 mL of ultrapure water was added, and then about 1,000 mL of the solution was removed by the ultrafiltration method. This operation was repeated three times.

200 mL of sulfuric acid diluted to 10 mass % and 2,000 mL of ion-exchange water were added to the solution subjected to the above filtration treatment; about 2,000 mL of the processed solution was removed by using the ultrafiltration method; 2,000 mL of ion-exchange water was added thereto; and about 2,000 mL of the solution was removed by using the ultrafiltration method. This operation was repeated three times.

The obtained processed solution was refined with cation-exchange resin and anion-exchange resin; 2,000 mL of ion-exchange water was further added thereto; and about 2,000 mL of the processed solution was removed by using the ultrafiltration method. This operation was repeated five times, and 1.0 mass % of Electro-Conductive Polymer Composite Solution 1 was obtained.

The ultrafiltration conditions were as follows.

Molecular weight cutoff of ultrafiltration membrane: 30 K

Cross flow type

Flow amount of supplied liquid: 3,000 mL/minute

Membrane partial pressure: 0.12 Pa

Note that, the ultrafiltration was carried out under the same conditions in the other Preparation Examples.

Preparation Example 2

3.07 g of 3-methoxythiophene and a solution in which 15.0 g of Dopant Polymer 1 had been dissolved in 1,000 mL of pure water were mixed at 30° C.

The obtained mixture solution was maintained at 30° C., and oxidation catalyst solution of 8.40 g of sodium persulfate and 2.3 g of a ferric sulfate dissolved in 100 mL of ultrapure water were gradually added with stirring the mixture solution. The mixture was reacted with stirring for 4 hours.

To the obtained reaction solution, 1,000 mL of ultrapure water was added, and then about 1,000 mL of the solution was removed by the ultrafiltration method. This operation was repeated three times.

200 mL of sulfuric acid diluted to 10 mass % and 2,000 mL of ion-exchange water were added to the solution subjected to the above filtration treatment; about 2,000 mL of the processed solution was removed by using the ultrafiltration method; 2,000 mL of ion-exchange water was added thereto; and about 2,000 mL of the solution was removed by using the ultrafiltration method. This operation was repeated three times.

The obtained processed solution was refined with cation-exchange resin and anion-exchange resin; 2,000 mL of ion-exchange water was further added thereto; and about 2,000 mL of the processed solution was removed by using the ultrafiltration method. This operation was repeated five times, and 1.0 mass % of Electro-Conductive Polymer Composite Solution 2 was obtained.

Preparation Examples 3 to 26

The Dopant Polymer 1 of Preparation Example 1 was changed to Dopant Polymer 2 to 25, and Electro-Conductive Polymer Composite Solutions 3 to 26 were obtained.

(Measurement of Thickness of Living Body Contact Layer)

The electro-conductive polymer composite solutions 1 to 26 were each applied on a Si substrate by spin-coating and baked on a hot plate at 120° C. for 10 minutes, and the film thickness was measured with an optical film thickness meter. Tables 1 and 2 show the results.

Preparation of Bio-Electrode

Electro-conductive paste DOTITE FA-333 (manufactured by Fujikura Kasei Co., Ltd.) was coated on a transparent thermoplastic urethane (TPU) film having a film thickness of 50 μm by screen printing, and baked in an oven at 120° C. for 10 minutes, to print an electro-conductive pattern of 100 lines shown in FIG. 14, in which the lines have a width of 50 μm, a pitch of 200 μm, and a length of 40 mm. A cellophane film, which is in color of 7YR with a value of 8.5 and a chroma of 3 in the Munsell color system and has a transmittance of 80% at a wavelength of 600 nm and a thickness of 30 μm, was adhered on the opposite side of the printed side, to form to a composite film "Electro-conductive base material V" including the electro-conductive layer and the substrate.

As shown in FIG. 25, the fluororesin adhesive masking tape 9 was applied to the half square part of the electro-conductive pattern having an area of 40 mm×20 mm on the printed surface. An electro-conductive polymer composite solution was spin-coated on it and baked with a hot-plate at 120° C. for 10 minutes, and then the fluororesin adhesive tape was removed. An electro-conductive base material on which electro-conductive polymer composite layer 10 was formed was cut out along the printed pattern into a size of 20 mm wide of and 40 mm long, to be made to a bio-electrode.

An aqueous solution of silver nanowire (diameter 60 nm, length 40 μm, concentration 5 mg/mL) manufactured by Sigma-Aldrich Co., LLC. was diluted 10-fold with pure water. The resulting solution was spin-coated on a transparent thermoplastic urethane (TPU) film having a thickness of 50 μm, and baked on a hot plate at 130° C. for 10 minutes, and the silver nanowire was fused and attached to the TPU film. On the opposite side, a cellophane film, which is in color of 2YR with a value of 9 and a chroma of 2 in the Munsell color system and has a transmittance of 84% at a wavelength of 600 nm and a thickness of 30 μm, was attached, to form "Electro-conductive base material W". Electro-conductive polymer composite solution was spin-coated on the silver nanowire layer and baked on a hot plate at 120° C. for 10 minutes. The base material coated with the composite was cut out into a size of 20 mm wide of and 40 mm long, to be made to a bio-electrode.

An aqueous solution of silver nanowire (diameter 60 nm, length 40 μm, concentration 5 mg/mL) manufactured by Sigma-Aldrich Co., LLC. was diluted 10-fold with pure water. The resulting solution was spin-coated on a transparent thermoplastic urethane (TPU) film having a thickness of 50 μm, and baked on a hot plate at 130° C. for 10 minutes, and the silver nanowire was fused and attached to the TPU film. On the opposite side, a cellophane film, which is in color of 5YR with a value of 8.5 and a chroma of 4 in the Munsell color system and has a transmittance of 80% at a wavelength of 600 nm and a thickness of 30 μm, was attached, to form "Electro-conductive base material X". Electro-conductive polymer composite solution was spin-coated on the silver nanowire layer and baked on a hot plate at 120° C. for 10 minutes. The base material coated with the composite was cut out into a size of 20 mm wide of and 40 mm long, to be made to a bio-electrode.

An aqueous solution of silver nanowire (diameter 60 nm, length 40 μm, concentration 5 mg/mL) manufactured by Sigma-Aldrich Co., LLC. was diluted 10-fold with pure water. The resulting solution was spin-coated on a transparent thermoplastic urethane (TPU) film having a thickness of 50 μm, and baked on a hot plate at 130° C. for 10 minutes, and the silver nanowire was fused and attached to the TPU film. On the opposite side, a cellophane film, which is in color of 5YR with a value of 8.5 and a chroma of 4 in the Munsell color system and has a transmittance of 80% at a wavelength of 600 nm and a thickness of 30 μm, was attached. Further, on the cellophane film, a PET film of 20 μm thick, which has triangular moth-eye typed anti-reflective structure of 100 nm high and 200 nm pitch was attached, to form "Electro-conductive base material Y". Electro-conductive polymer composite solution was spin-coated on the silver nanowire layer and baked on a hot plate at 120° C. for 10 minutes. The base material coated with the composite was cut out into a size of 20 mm wide of and 40 mm long, to be made to a bio-electrode.

An aqueous solution of silver nanowire (diameter 60 nm, length 40 μm, concentration 5 mg/mL) manufactured by Sigma-Aldrich Co., LLC. was diluted 10-fold with pure water. The resulting solution was spin-coated on a transparent thermoplastic urethane (TPU) film having a thickness of 50 μm, and baked on a hot plate at 130° C. for 10 minutes, and the silver nanowire was fused and attached to the TPU film. On the opposite side, a PET film, which is in color of 5YR with a value of 8.5 and a chroma of 4 in the Munsell color system and has a transmittance of 80% at a wavelength of 600 nm, a thickness of 30 μm, and triangular moth-eye typed anti-reflective structure of 100 nm high and 200 nm pitch, was attached, to form "Electro-conductive base material Z". Electro-conductive polymer composite solution was spin-coated on the silver nanowire layer and baked on a hot plate at 120° C. for 10 minutes. The base material coated with the composite was cut out into a size of 20 mm wide of and 40 mm long, to be made to a bio-electrode.

An aqueous solution of silver nanowire (diameter 60 nm, length 40 μm, concentration 5 mg/mL) manufactured by Sigma-Aldrich Co., LLC. was diluted 10-fold with pure water. The resulting solution was spin-coated on a transparent thermoplastic urethane (TPU) film having a thickness of 50 μm, and baked on a hot plate at 130° C. for 10 minutes, and the silver nanowire was fused and attached to the TPU film, to form "Comparative electro-conductive base material". Electro-conductive polymer composite solution was spin-coated on the silver nanowire layer and baked on a hot plate at 120° C. for 10 minutes. The base material coated with the composite was cut out into a size of 20 mm wide of and 40 mm long, to be made to a bio-electrode.

(Measurement of Biological Signals)

An electro-conductive polymer composite solution was mixed with a solvent and additives according to the composition shown in Tables 1 and 2 and stirred at room temperature for 2 hours. The mixture was filtered using regenerated cellulose having a pore size of 1.0 μm, and an electro-conductive polymer composite solution was prepared and spin-coated on an electro-conductive base material.

Cellophane tape was attached on the backside of the bio-electrode so that a 20 mm square of the electro-conductive polymer composite layer of the bio-electrode could adhere to the skin. After treated with absorbent cotton wetted with water, the bio-electrodes were attached on the location on the arm shown in FIG. 26. In the case of electrodes with the electro-conductive patterns printed, the exposed area, where conductive wiring had been masked, of the conductive wiring was clipped with a metal clip and connected to the ECG measurement device via electro-conductive wiring. In the case of electrodes using a nanowire, the area, of the bio-electrode, not attached to the skin was clipped with a metal clip and connected to the ECG measurement device via electro-conductive wiring.

For an ECG measuring device, Nexus 10 MARK II manufactured by KISSEI COMTEC Co., Ltd. was used. In FIG. 26, 11 is for a positive electrode, 12 is for a negative electrode, and 13 is for a ground electrode. The results are shown in Tables 1 and 2.

(Measurement of Transparency)

The bio-electrode is placed to face a light receiving surface of a transmissometer, and its transmittance at a wavelength of 600 nm was measured. The results are shown Tables 1 and 2.

(Measurement of Color in Munsell Color System)

Color of the bio-electrode in the Munsell color system was measured using a spectrophotometer/colorimeter CM-600d manufactured by Konica Minolta, Inc. The results are shown in Tables 1 and 2.

Additives

Polyglycerin silicone 1

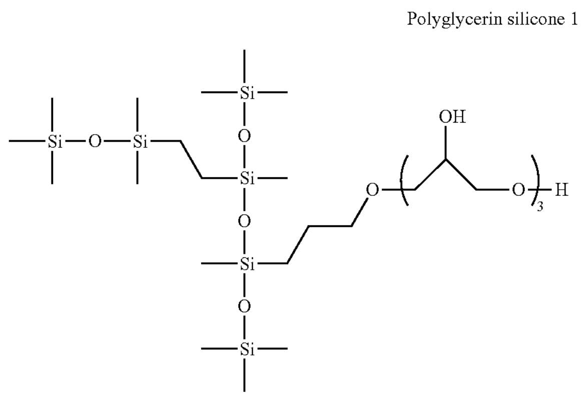

Fluoroalkyl-based nonionic surfactant FS-31 (available from DuPont)

lysine histidine potassium hydroxide

Potassium hydrogen carbonate

Amine 1

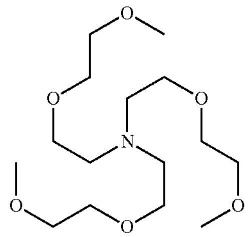 [SMILES: COCCOCCN(CCOCCOC)CCOCCOC]

Amine 2

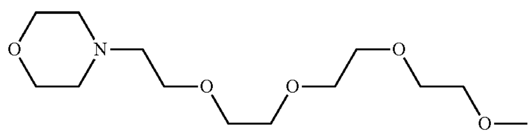 [SMILES: COCCOCCOCCOCCN1CCOCC1]

Salt Compounds 1 to 5

Salt compounds 1

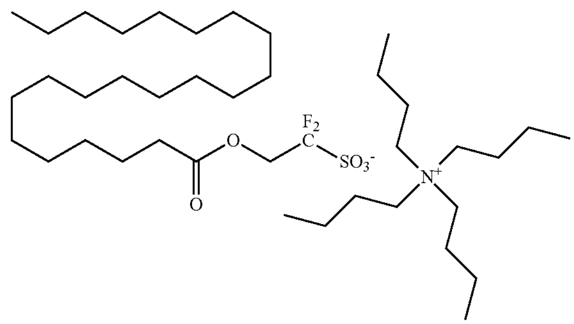

Salt compounds 2

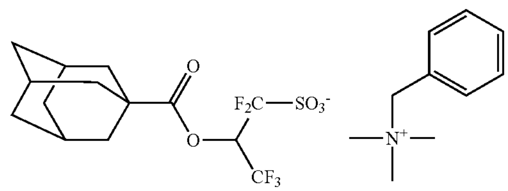

Salt compounds 3

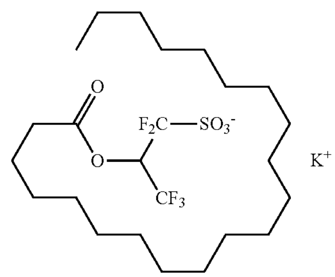

Salt compounds 4

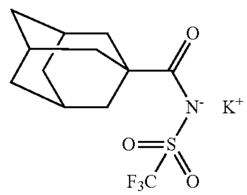

-continued

Salt compounds 5

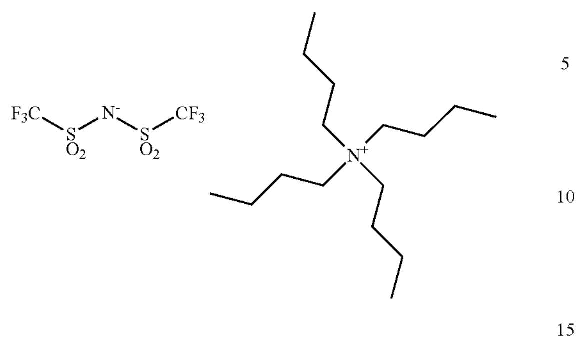

Solvents
Dimethylsulfoxide (DMSO)
Ethylene glycol
Glycerin

TABLE 1

| Example | Electro-conductive polymer composite solution (parts by mass) | Solvent (parts by mass) | Additive (parts by mass) | Thickness (nm) | Base material | TransMittance | Munsell color | ECG signal |
|---|---|---|---|---|---|---|---|---|
| Example 1 | Electro-conductive polymer composite solution 1 (100) | DMSO (5) | FS-31 (0.2) Lysine (0.56) | 110 | Electro-conductive base material V | 60 | 7YR7/2 | Good |
| Example 2 | Electro-conductive polymer composite solution 1 (100) | DMSO (5) | FS-31 (0.2) Lysine (0.56) | 110 | Electro-conductive base material W | 72 | 2YR8/2 | Good |
| Example 3 | Electro-conductive polymer composite solution 1 (100) | DMSO (10) | FS-31 (0.2) Histidine (0.60) | 104 | Electro-conductive base material X | 73 | 4YR8/5 | Good |
| Example 4 | Electro-conductive polymer composite solution 1 (100) | DMSO (5) | FS-31 (0.2) Amine 1 (1.24) | 110 | Electro-conductive base material Y | 79 | 5YR8/5 | Good |
| Example 5 | Electro-conductive polymer composite solution 1 (100) | DMSO (5) | FS-31 (0.2) Amine 2 (1.06) | 109 | Electro-conductive base material X | 72 | 4YR8/5 | Good |
| Example 6 | Electro-conductive polymer composite solution 1 (100) | DMSO (5) | FS-31 (0.2) Potassium hydroxide (0.21) | 96 | Electro-conductive base material X | 71 | 3YR8/4 | Good |
| Example 7 | Electro-conductive polymer composite solution 1 (100) | DMSO (5) | FS-31 (0.2) Potassium hydrogen carbonate (0.38) | 98 | Electro-conductive base material X | 75 | 4YR8/5 | Good |
| Example 8 | Electro-conductive polymer composite solution 1 (100) | DMSO (5) | FS-31 (0.2) | 91 | Electro-conductive base material X | 73 | 4YR8/5 | Good |
| Example 9 | Electro-conductive polymer composite solution 2 (100) | — | — | 110 | Electro-conductive base material X | 72 | 4YR8/4 | Good |
| Example 10 | Electro-conductive polymer composite solution 3 (100) | DMSO (5) | Polyglycerin silicone 1 (5) | 130 | Electro-conductive base material X | 71 | 4YR8/4 | Good |
| Example 11 | Electro-conductive polymer composite solution 4 (100) | DMSO (5) | — | 98 | Electro-conductive base material X | 73 | 5YR7.5/4 | Good |
| Example 12 | Electro-conductive polymer composite solution 5 (100) | Ethylene glycol (5) | Polyglycerin silicone 1 (4) | 102 | Electro-conductive base material X | 73 | 4YR8/5 | Good |
| Example 13 | Electro-conductive polymer composite solution 6 (100) | Glycerin (5) | Salt Compound 1 (2) | 112 | Electro-conductive base material X | 74 | 4YR8/5 | Good |
| Example 14 | Electro-conductive polymer composite solution 7 (100) | DMSO (5) | Salt Compound 2 (2) | 113 | Electro-conductive base material X | 72 | 2YR8/5 | Good |
| Example 15 | Electro-conductive polymer composite solution 8 (100) | DMSO (5) | Salt Compound 3 (2) | 105 | Electro-conductive base material X | 71 | 4YR8/5 | Good |
| Example 16 | Electro-conductive polymer composite solution 9 (100) | Ethylene glycol (5) | Salt Compound 4 (2) | 98 | Electro-conductive base material X | 71 | 4YR7.5/5 | Good |

TABLE 1-continued

| Example | Electro-conductive polymer composite solution (parts by mass) | Solvent (parts by mass) | Additive (parts by mass) | Thickness (nm) | Base material | TransMittance | Munsell color | ECG signal |
|---|---|---|---|---|---|---|---|---|
| Example1 17 | Electro-conductive polymer composite solution 10 (100) | Ethylene glycol (5) | Salt Compound 5 (2) | 105 | Electro-conductive base material X | 73 | 4YR7.5/5 | Good |
| Example 18 | Electro-conductive polymer composite solution 11 (100) | Ethylene glycol (5) | — | 120 | Electro-conductive base material X | 74 | 4YR8/3 | Good |
| Example 19 | Electro-conductive polymer composite solution 12 (100) | Ethylene glycol (5) | — | 122 | Electro-conductive base material X | 76 | 3YR8/3 | Good |
| Example 20 | Electro-conductive polymer composite solution 13 (100) | Ethylene glycol (5) | — | 105 | Electro-conductive base material X | 75 | 4YR7.5/5 | Good |

TABLE 2

| Example | Electro-conductive polymer composite solution (parts by mass) | Solvent (parts by mass) | Additive (parts by mass) | Thickness (nm) | Base material | Transmittance | Munsell color | ECG signal |
|---|---|---|---|---|---|---|---|---|
| Example 21 | Electro-conductive polymer composite solution 14 (100) | DMSO (5) | FS-31 (0.2) Lysine (0.56) | 110 | Electro-conductive base material X | 60 | 3YR8/4 | Good |
| Example 22 | Electro-conductive polymer composite solution 15 (100) | DMSO (5) | FS-31 (0.2) Lysine (0.56) | 110 | Electro-conductive base material X | 72 | 3YR8/4 | Good |
| Example 23 | Electro-conductive polymer composite solution 16 (100) | DMSO (10) | FS-31 (0.2) Histidine (0.60) | 104 | Electro-conductive base material X | 73 | 4YR8/5 | Good |
| Example 24 | Electro-conductive polymer composite solution 17 (100) | DMSO (5) | FS-31 (0.2) Amine 1 (1.24) | 110 | Electro-conductive base material Y | 79 | 5YR8/5 | Good |
| Example 25 | Electro-conductive polymer composite solution 18 (100) | DMSO (5) | FS-31 (0.2) Amine 2 (1.06) | 109 | Electro-conductive base material Z | 78 | 4YR8/5 | Good |
| Example 26 | Electro-conductive polymer composite solution 19 (100) | DMSO (5) | FS-31 (0.2) Potassium hydroxide (0.21) | 96 | Electro-conductive base material X | 71 | 3YR8/4 | Good |
| Example 27 | Electro-conductive polymer composite solution 20 (100) | DMSO (5) | FS-31 (0.2) potassium hydrogen carbonate (0.38) | 98 | Electro-conductive base material X | 75 | 4YR8/5 | Good |
| Example 28 | Electro-conductive polymer composite solution 21 (100) | DMSO (5) | FS-31 (0.2) | 91 | Electro-conductive base material X | 73 | 4YR8/5 | Good |
| Example 29 | Electro-conductive polymer composite solution 22 (100) | — | — | 110 | Electro-conductive base material X | 72 | 4YR8/4 | Good |
| Example 30 | Electro-conductive polymer composite solution 23 (100) | DMSO (5) | Polyglycerin silicone 1 (5) | 130 | Electro-conductive base material X | 71 | 4 YR8/4 | Good |
| Example 31 | Electro-conductive polymer composite solution 24 (100) | DMSO (5) | — | 98 | Electro-conductive base material X | 73 | 5YR7.5/4 | Good |
| Example 32 | Electro-conductive polymer composite solution 25 (100) | Ethylene glycol (5) | Polyglycerin silicone 1 (4) | 102 | Electro-conductive base material X | 73 | 5YR7.5/4 | Good |

TABLE 2-continued

| Example | Electro-conductive polymer composite solution (parts by mass) | Solvent (parts by mass) | Additive (parts by mass) | Thickness (nm) | Base material | Transmittance | Munsell color | ECG signal |
|---|---|---|---|---|---|---|---|---|
| Example 33 | Electro-conductive polymer composite solution 26 (100) | Ethylene glycol (5) | Polyglycerin silicone 1 (4) | 107 | Electro-conductive base material X | 65 | 3YR7/3 | Good |
| Comparative example 1 | Electro-conductive polymer composite solution 25 (100) | Ethylene glycol (5) | Polyglycerin silicone 1 (4) | 102 | Comparative electro-conductive base material | 70 | 7B8/4 | Good |

The ECG signal was judged as good when PQRST waves appeared. The bio-electrodes of the Examples had a light orange color similar to the skin color, and the Comparative Example had a blue color.

As shown in the results of Examples 1-32, the bio-electrode of the present invention using a substrate (D) having a transmittance of 20% or more at a wavelength of 600 nm and being in a yellow-red (YR) color with a value in the range of 1 to 9 and a chroma in the range of 1 to 12 in the Munsell color system, is thin film, highly transparent, slightly different from skin color, highly sensitive to a biological signal, excellent in biocompatibility, light-weight, manufacturable at low cost, capable of preventing significant reduction in electro-conductivity when wetted with water or dried and when attached on the skin for a long time, and comfortable without itching, reddening, or rash of the skin.

On the other hand, as shown in Comparative Example 1, when the substitute (D) in the above is not used, the bio-electrode is blue and the difference from skin color is noticeable.

The present description includes the following embodiments.

[1]: A bio-electrode comprising an electro-conductive polymer composite layer, an electro-conductive layer (C), and a substrate (D), wherein the electro-conductive polymer composite layer consisting of an electro-conductive polymer composite comprises (A) a π-conjugated polymer and (B) a dopant polymer which contains a repeating unit "a" having one or more compounds selected from the group consisting of sulfonic acid, fluorosulfonic acid, fluorosulfonimide, and N-carbonylfluorosulfonamide, and has a weight-average molecular weight of 1,000 to 500,000, and the substrate (D) has a transmittance of 20% or more at a wavelength of 600 nm and is in a yellow-red (YR) color with a value in the range of 1 to 9 and a chroma in the range of 1 to 12 in the Munsell color system.

[2]: The bio-electrode according to the above [1], wherein the electro-conductive layer (C) comprises one or more kinds of substances selected from the group consisting of gold, silver, silver chloride, platinum, aluminum, magnesium, tin, tungsten, iron, copper, nickel, stainless steel, chromium, titanium, and carbon.

[3]: The bio-electrode according to the above [1], wherein the repeating unit "a" has any of partial structure represented by the following general formulae (1)-1 to (1)-4, (1)-1

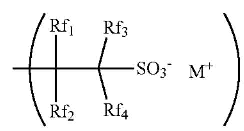

(1)-2

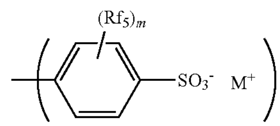

(1)-3

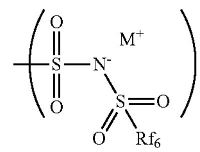

(1)-4

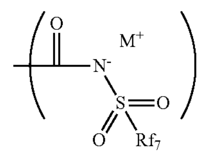

wherein $Rf_1$ and $Rf_2$ each represent a hydrogen atom, a fluorine atom, an oxygen atom, a methyl group, or a trifluoromethyl group, and when $Rf_1$ and $Rf_2$ represent an oxygen atom, $Rf_1$ and $Rf_2$ represent a single oxygen atom bonded to a single carbon atom to form a carbonyl group, $Rf_3$ and $Rf_4$ each represent a hydrogen atom, a fluorine atom, or a trifluoromethyl group, and at least one of $Rf_1$ to $Rf_4$ is a fluorine atom or a trifluoromethyl group; $Rf_5$ represents a hydrogen atom, a fluorine atom, a trifluoromethyl group or a linear or branched alkyl group having 1 to 4 carbon atoms, and "m" represents an integer of 1 to 4; $Rf_6$ and $Rf_7$ each represent a fluorine atom, a trifluoromethyl group or a linear or branched alkyl group having 1 to 4 carbon atoms and at least one fluorine atom; $M^+$ represents an ion selected from the group consisting of a hydrogen ion, an ammonium ion, a sodium ion, and a potassium ion.

[4]: The bio-electrode according to the above [3], wherein the repeating unit "a" has one or more kinds of repeating units selected from the group consisting of A1 to A7 represented by the following general formulae (2), (2)

A1

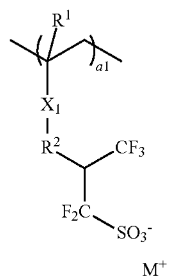

A2

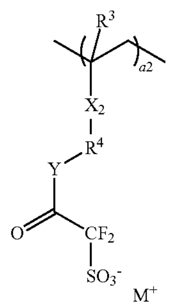

A3

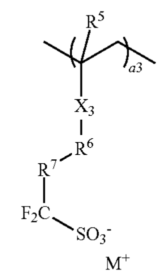

A4

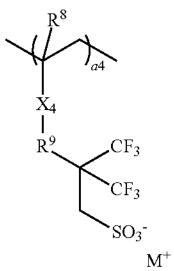

A5

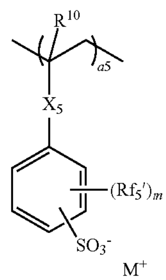

-continued

A6

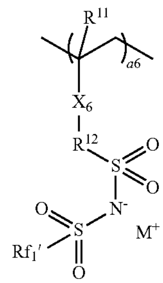

A7

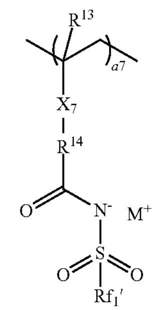

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, $R^{12}$, and $R^{14}$ each independently represent a single bond or a linear, branched, or cyclic hydrocarbon group having 1 to 13 carbon atoms, and the hydrocarbon group optionally having either or both of an ester group and an ether group; $R^7$ represents a linear or branched alkylene group having 1 to 4 carbon atoms, and one or two hydrogen atoms in $R^7$ optionally may be substituted with a fluorine atom; $X_1$, $X_2$, $X_3$, $X_4$, $X_6$, and $X_7$ each independently represent a single bond, a phenylene group, a naphthylene group, an ether group, an ester group, or an amide group; $X_5$ represents a single bond, an ether group, or an ester group; Y represents an oxygen atom or an —$NR^{19}$— group; $R^{19}$ represents a hydrogen atom, a linear, branched or cyclic alkyl group having 1 to 12 carbon atoms, or a phenyl group, and optionally may have one or more kinds of groups selected from the group consisting of an ether group, a carbonyl group, an ester group, and an amide group; Y may optionally form a ring together with $R^4$; $Rf_1'$ and $Rf_5'$ each represent a fluorine atom, a trifluoromethyl group, or a linear or branched alkyl group having 1 to 4 carbon atoms, and have at least one fluorine atom; "m" represents an integer of 1 to 4; a1, a2, a3, a4, a5, a6, and a7 satisfy $0 \le a1 \le 1.0$, $0 \le a2 \le 1.0$, $0 \le a3 \le 1.0$, $0 \le a4 \le 1.0$, $0 \le a5 \le 1.0$, $0 \le a6 \le 1.0$, $0 \le a7 \le 1.0$, and $0 < a1+a2+a3+a4+a5+a6+a7 \le 1.0$; and $M^+$ represents an ion selected from the group consisting of a hydrogen ion, an ammonium ion, a sodium ion, and a potassium ion.

[5]: The bio-electrode according to the above [4], wherein the repeating unit "a" contains an ammonium ion represented by the following general formula (3), as an ammonium ion for forming an ammonium salt, (3)

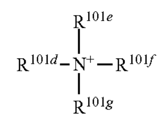

wherein $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, and may optionally have one or more kinds selected from the group consisting of an ether group, a carbonyl group, an ester group, a hydroxy group, a carboxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$ may optionally form a ring together with a nitrogen atom bonded to $R^{101d}$ and $R^{101e}$, or $R^{101d}$, $R^{101e}$, and $R^{101f}$ and when a ring is formed, $R^{101d}$ and $R^{101e}$, or $R^{101d}$, $R^{101e}$, and $R^{101f}$ form an alkylene group having 3 to 10 carbon atoms or a heteroaromatic ring having, in the ring, nitrogen atom in the general formula (3).

[6]: The bio-electrode according to any one of the above [1] to [5], wherein the electro-conductive polymer composite contains, in addition to the components (A) and (B), one or more kinds of resin (E) selected from the group consisting of (meth)acrylate resin, (meth) acrylamide resin, urethane resin, polyvinyl alcohol, polyvinylpyrrolidone, polyoxazoline, polyglycerin, polyglycerin-modified silicone, cellulose, polyethylene glycol, and polypropylene glycol.

[7]: The bio-electrode according to any one of the above [1] to [6], wherein the substrate (D) has a transmittance of 30% or more at a wavelength of 600 nm and a yellow-red (YR) color with a value in the range of 1 to 9 and a chroma in the range of 1 to 12 in the Munsell color system.

[8]: The bio-electrode according to any one of the above [1] to [7], wherein the substrate (D) is attached, on either or both of the sides on which the bio-electrode contacts with the skin and on the opposite side, with a film having a transmittance of 30% or more at a wavelength of 600 nm and being in a yellow-red (YR) color with a value in the range of 1 to 9 and a chroma in the range of 1 to 12 in the Munsell color system.

[9]: The bio-electrode according to any one of the above [1] to [8], wherein the substrate (D) has an anti-reflective structure, on a surface of the opposite side of the side on which the bio-electrode contacts with the skin.

[10]: A method of manufacturing of the bio-electrode according to any one of the above [1] to [9], the method comprising forming the electro-conductive layer (C) by applying a solution containing a metal nanowire or by printing electro-conductive paste containing an electro-conductive particle on the substrate (D) having an transmittance of 20% or more at a wavelength of 600 nm and being in a yellow-red (YR) color with a value in the range of 1 to 9 and a chroma in the range of 1 to 12 in the Munsell color system, to form the electro-conductive polymer composite layer by applying the electro-conductive polymer composite on the electro-conductive layer (C).

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A bio-electrode comprising an electro-conductive polymer composite layer, an electro-conductive layer (C), and a substrate (D), wherein the electro-conductive polymer composite layer consisting of an electro-conductive polymer composite comprises (A) a π-conjugated polymer and (B) a dopant polymer which contains a repeating unit "a" having one or more compounds selected from the group consisting of sulfonic acid, fluorosulfonic acid, fluorosulfonimide, and N-carbonylfluorosulfonamide, and has a weight-average molecular weight of 1,000 to 500,000, and the substrate (D) has a transmittance of 20% or more at a wavelength of 600 nm and is in a yellow-red (YR) color with a value in the range of 1 to 9 and a chroma in the range of 1 to 12 in the Munsell color system.

2. The bio-electrode according to claim 1, wherein the electro-conductive layer (C) comprises one or more kinds of substances selected from the group consisting of gold, silver, silver chloride, platinum, aluminum, magnesium, tin, tungsten, iron, copper, nickel, stainless steel, chromium, titanium, and carbon.

3. The bio-electrode according to claim 2, wherein the repeating unit "a" has any of partial structure represented by the following general formulae (1)-1 to (1)-4,

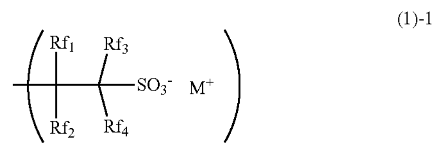

(1)-1

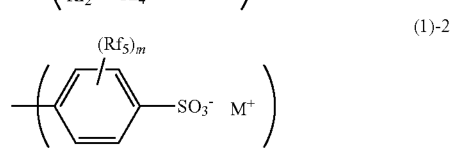

(1)-2

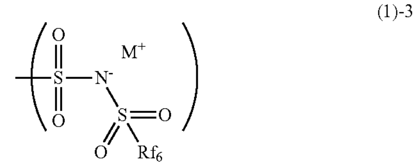

(1)-3

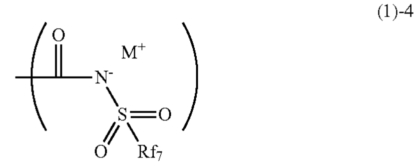

(1)-4 wherein $Rf_1$ and $Rf_2$ each represent a hydrogen atom, a fluorine atom, an oxygen atom, a methyl group, or a trifluoromethyl group, and when $Rf_1$ and $Rf_2$ represent an oxygen atom, $Rf_1$ and $Rf_2$ represent a single oxygen atom bonded to a single carbon atom to form a carbonyl group, $Rf_3$ and $Rf_4$ each represent a hydrogen atom, a fluorine atom, or a trifluoromethyl group, and at least one of Rf1 to Rf4 is a fluorine atom or a trifluoromethyl group; $Rf_5$ represents a hydrogen atom, a fluorine atom, a trifluoromethyl group or a linear or branched alkyl group having 1 to 4 carbon atoms, and "m" represents an integer of 1 to 4; $Rf_6$ and $Rf_7$ each represent a fluorine atom, a trifluoromethyl group or a linear or branched alkyl group having 1 to 4 carbon atoms and at least one fluorine atom; $M^+$ represents an ion selected from the group consisting of a hydrogen ion, an ammonium ion, a sodium ion, and a potassium ion.

4. The bio-electrode according to claim 3, wherein the repeating unit "a" has one or more kinds of repeating units selected from the group consisting of A1 to A7 represented by the following general formulae (2), (2)

A1

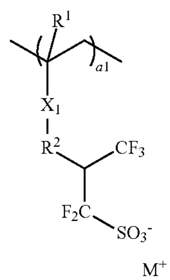

A2

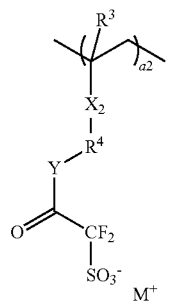

A3

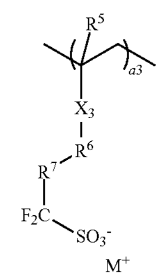

A4

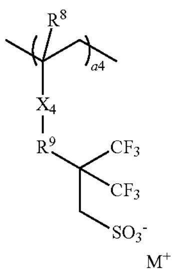

A5

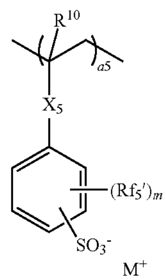

-continued

A6

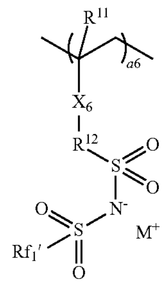

A7

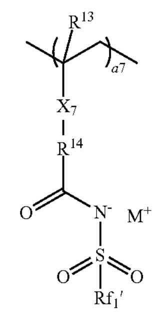

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, $R^{12}$, and $R^{14}$ each independently represent a single bond or a linear, branched, or cyclic hydrocarbon group having 1 to 13 carbon atoms, and the hydrocarbon group optionally having either or both of an ester group and an ether group; $R^7$ represents a linear or branched alkylene group having 1 to 4 carbon atoms, and one or two hydrogen atoms in $R^7$ optionally may be substituted with a fluorine atom; $X_1$, $X_2$, $X_3$, $X_4$, $X_6$, and $X_7$ each independently represent a single bond, a phenylene group, a naphthylene group, an ether group, an ester group, or an amide group; $X_5$ represents a single bond, an ether group, or an ester group; Y represents an oxygen atom or an —$NR^{19}$— group; $R^{19}$ represents a hydrogen atom, a linear, branched or cyclic alkyl group having 1 to 12 carbon atoms, or a phenyl group, and optionally may have one or more kinds of groups selected from the group consisting of an ether group, a carbonyl group, an ester group, and an amide group; Y may optionally form a ring together with $R^4$; $Rf_1'$ and $Rf_5'$ each represent a fluorine atom, a trifluoromethyl group, or a linear or branched alkyl group having 1 to 4 carbon atoms, and have at least one fluorine atom; "m" represents an integer of 1 to 4; a1, a2, a3, a4, a5, a6, and a7 satisfy $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 < a1+a2+a3+a4+a5+a6+a7 \leq 1.0$; and $M^+$ represents an ion selected from the group consisting of a hydrogen ion, an ammonium ion, a sodium ion, and a potassium ion.

5. The bio-electrode according to claim 4, wherein the repeating unit "a" contains an ammonium ion represented by the following general formula (3), as an ammonium ion for forming an ammonium salt, (3)

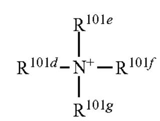

wherein $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, and may optionally have one or more kinds selected from the group consisting of an ether group, a carbonyl group, an ester group, a hydroxy group, a carboxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$ may optionally form a ring together with a nitrogen atom bonded to $R^{101d}$ and $R^{101e}$, or $R^{101d}$, $R^{101e}$, and $R^{101f}$ and when a ring is formed, $R^{101d}$ and $R^{101e}$, or $R^{101d}$, $R^{101e}$, and $R^{101f}$ form an alkylene group having 3 to 10 carbon atoms or a heteroaromatic ring having, in the ring, nitrogen atom in the general formula (3).

6. The bio-electrode according to claim 2, wherein the electro-conductive polymer composite contains, in addition to the components (A) and (B), one or more kinds of resin (E) selected from the group consisting of (meth)acrylate resin, (meth)acrylamide resin, urethane resin, polyvinyl alcohol, polyvinylpyrrolidone, polyoxazoline, polyglycerin, polyglycerin-modified silicone, cellulose, polyethylene glycol, and polypropylene glycol.

7. The bio-electrode according to claim 2, wherein the substrate (D) has a transmittance of 30% or more at a wavelength of 600 nm and a yellow-red (YR) color with a value in the range of 1 to 9 and a chroma in the range of 1 to 12 in the Munsell color system.

8. The bio-electrode according to claim 2, wherein the substrate (D) is attached, on either or both of the sides on which the bio-electrode contacts with the skin and on the opposite side, with a film having a transmittance of 30% or more at a wavelength of 600 nm and being in a yellow-red (YR) color with a value in the range of 1 to 9 and a chroma in the range of 1 to 12 in the Munsell color system.

9. The bio-electrode according to claim 2, wherein the substrate (D) has an anti-reflective structure, on a surface of the opposite side of the side on which the bio-electrode contacts with the skin.

10. A method of manufacturing of the bio-electrode according to claim 2, the method comprising forming the electro-conductive layer (C) by applying a solution containing a metal nanowire or by printing electro-conductive paste containing an electro-conductive particle on the substrate (D) having a transmittance of 20% or more at a wavelength of 600 nm and being in a yellow-red (YR) color with a value in the range of 1 to 9 and a chroma in the range of 1 to 12 in the Munsell color system, to form the electro-conductive polymer composite layer by applying the electro-conductive polymer composite on the electro-conductive layer (C).

11. The bio-electrode according to claim 1, wherein the repeating unit "a" has any of partial structure represented by the following general formulae (1)-1 to (1)-4, (1)-1

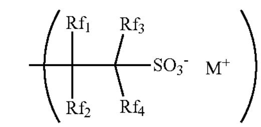

(1)-2

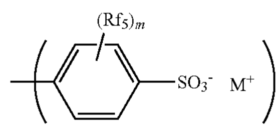

-continued (1)-3

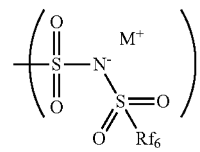

(1)-4

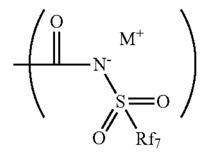

wherein $Rf_1$ and $Rf_2$ each represent a hydrogen atom, a fluorine atom, an oxygen atom, a methyl group, or a trifluoromethyl group, and when $Rf_1$ and $Rf_2$ represent an oxygen atom, $Rf_1$ and $Rf_2$ represent a single oxygen atom bonded to a single carbon atom to form a carbonyl group, $Rf_3$ and $Rf_4$ each represent a hydrogen atom, a fluorine atom, or a trifluoromethyl group, and at least one of Rf1 to Rf4 is a fluorine atom or a trifluoromethyl group; $Rf_5$ represents a hydrogen atom, a fluorine atom, a trifluoromethyl group or a linear or branched alkyl group having 1 to 4 carbon atoms, and "m" represents an integer of 1 to 4; $Rf_6$ and $Rf_7$ each represent a fluorine atom, a trifluoromethyl group or a linear or branched alkyl group having 1 to 4 carbon atoms and at least one fluorine atom; $M^+$ represents an ion selected from the group consisting of a hydrogen ion, an ammonium ion, a sodium ion, and a potassium ion.

12. The bio-electrode according to claim 11, wherein the repeating unit "a" has one or more kinds of repeating units selected from the group consisting of A1 to A7 represented by the following general formulae (2), (2)

A1

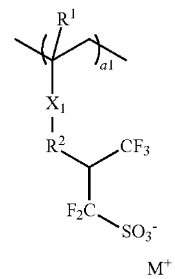

A2

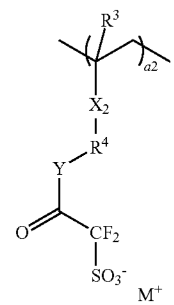

-continued

A3

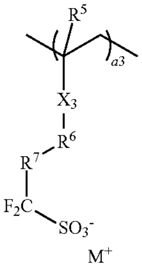

A4

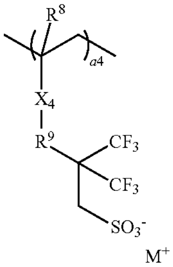

A5

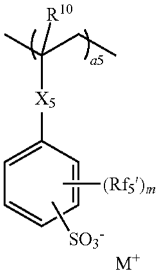

A6

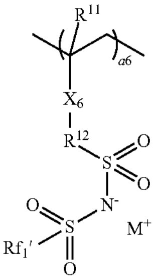

A7

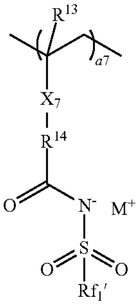

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, $R^{12}$, and $R^{14}$ each independently represent a single bond or a linear, branched, or cyclic hydrocarbon group having 1 to 13 carbon atoms, and the hydrocarbon group optionally having either or both of an ester group and an ether group; $R^7$ represents a linear or branched alkylene group having 1 to 4 carbon atoms, and one or two hydrogen atoms in $R^7$ optionally may be substituted with a fluorine atom; $X_1$, $X_2$, $X_3$, $X_4$, $X_6$, and $X_7$ each independently represent a single bond, a phenylene group, a naphthylene group, an ether group, an ester group, or an amide group; $X_5$ represents a single bond, an ether group, or an ester group; Y represents an oxygen atom or an —$NR^{19}$— group; $R^{19}$ represents a hydrogen atom, a linear, branched or cyclic alkyl group having 1 to 12 carbon atoms, or a phenyl group, and optionally may have one or more kinds of groups selected from the group consisting of an ether group, a carbonyl group, an ester group, and an amide group; Y may optionally form a ring together with $R^4$; $Rf_1'$ and $Rf_5'$ each represent a fluorine atom, a trifluoromethyl group, or a linear or branched alkyl group having 1 to 4 carbon atoms, and have at least one fluorine atom; "m" represents an integer of 1 to 4; a1, a2, a3, a4, a5, a6, and a7 satisfy $0 \le a1 \le 1.0$, $0 \le a2 \le 1.0$, $0 \le a3 \le 1.0$, $0 \le a4 \le 1.0$, $0 \le a5 \le 1.0$, $0 \le a6 \le 1.0$, $0 \le a7 \le 1.0$, and $0 < a1+a2+a3+a4+a5+a6+a7 \le 1.0$; and $M^+$ represents an ion selected from the group consisting of a hydrogen ion, an ammonium ion, a sodium ion, and a potassium ion.

13. The bio-electrode according to claim 12, wherein the repeating unit "a" contains an ammonium ion represented by the following general formula (3), as an ammonium ion for forming an ammonium salt,

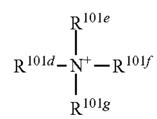

(3)

wherein $R^{101d}$, $R^{101e}$, $R^{101f}$, and $R^{101g}$ each represent a hydrogen atom, a linear, branched, or cyclic alkyl group having 1 to 15 carbon atoms, a linear, branched, or cyclic alkenyl group or alkynyl group having 2 to 12 carbon atoms, or an aromatic group having 4 to 20 carbon atoms, and may optionally have one or more kinds selected from the group consisting of an ether group, a carbonyl group, an ester group, a hydroxy group, a carboxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$ may optionally form a ring together with a nitrogen atom bonded to $R^{101d}$ and $R^{101e}$, or $R^{101d}$, $R^{101e}$, and $R^{101f}$ and when a ring is formed, $R^{101d}$ and $R^{101e}$, or $R^{101d}$, $R^{101e}$, and $R^{101f}$ form an alkylene group having 3 to 10 carbon atoms or a heteroaromatic ring having, in the ring, nitrogen atom in the general formula (3).

14. The bio-electrode according to claim 1, wherein the electro-conductive polymer composite contains, in addition to the components (A) and (B), one or more kinds of resin (E) selected from the group consisting of (meth)acrylate resin, (meth)acrylamide resin, urethane resin, polyvinyl alcohol, polyvinylpyrrolidone, polyoxazoline, polyglycerin, polyglycerin-modified silicone, cellulose, polyethylene glycol, and polypropylene glycol.

15. The bio-electrode according to claim 1, wherein the substrate (D) has a transmittance of 30% or more at a wavelength of 600 nm and a yellow-red (YR) color with a value in the range of 1 to 9 and a chroma in the range of 1 to 12 in the Munsell color system.

16. The bio-electrode according to claim 1, wherein the substrate (D) is attached, on either or both of the sides on which the bio-electrode contacts with the skin and on the opposite side, with a film having a transmittance of 30% or more at a wavelength of 600 nm and being in a yellow-red (YR) color with a value in the range of 1 to 9 and a chroma in the range of 1 to 12 in the Munsell color system.

17. The bio-electrode according to claim 1, wherein the substrate (D) has an anti-reflective structure, on a surface of the opposite side of the side on which the bio-electrode contacts with the skin.

18. A method of manufacturing of the bio-electrode according to claim 1, the method comprising forming the electro-conductive layer (C) by applying a solution containing a metal nanowire or by printing electro-conductive paste containing an electro-conductive particle on the substrate (D) having a transmittance of 20% or more at a wavelength of 600 nm and being in a yellow-red (YR) color with a value in the range of 1 to 9 and a chroma in the range of 1 to 12 in the Munsell color system, to form the electro-conductive polymer composite layer by applying the electro-conductive polymer composite on the electro-conductive layer (C).

* * * * *